United States Patent
Castaigne et al.

(10) Patent No.: US 9,161,988 B2
(45) Date of Patent: *Oct. 20, 2015

(54) MULTIMERIC PEPTIDE CONJUGATES AND USES THEREOF

(75) Inventors: Jean-Paul Castaigne, Mont-Royal (CA); Michel Demeule, Beaconsfield (CA); Christian Che, Longueuil (CA); Carine Thiot, Montreal (CA); Catherine Gagnon, Montreal-Nord (CA); Betty Lawrence, Bolton (CA)

(73) Assignee: Angiochem Inc., Montreal (CA)

( * ) Notice: Subject to any disclaimer, the term of this patent is extended or adjusted under 35 U.S.C. 154(b) by 340 days.

This patent is subject to a terminal disclaimer.

(21) Appl. No.: 13/382,069

(22) PCT Filed: Jun. 30, 2010

(86) PCT No.: PCT/CA2010/001014
§ 371 (c)(1),
(2), (4) Date: Feb. 14, 2012

(87) PCT Pub. No.: WO2011/000095
PCT Pub. Date: Jan. 6, 2011

(65) Prior Publication Data
US 2012/0141416 A1    Jun. 7, 2012

Related U.S. Application Data

(60) Provisional application No. 61/222,785, filed on Jul. 2, 2009, provisional application No. 61/252,024, filed on Oct. 15, 2009.

(51) Int. Cl.
*A61K 38/10* (2006.01)
*A61K 47/48* (2006.01)

(52) U.S. Cl.
CPC ............................. *A61K 47/48246* (2013.01)

(58) Field of Classification Search
CPC ................................................ A61K 47/48246
See application file for complete search history.

(56) References Cited

U.S. PATENT DOCUMENTS

| | | | |
|---|---|---|---|
| 4,671,958 A | 6/1987 | Rodwell et al. |
| 4,801,575 A | 1/1989 | Pardridge |
| 4,902,505 A | 2/1990 | Pardridge et al. |
| 4,942,184 A | 7/1990 | Haugwitz et al. |
| 5,028,697 A | 7/1991 | Johnson et al. |
| 5,041,424 A | 8/1991 | Saulnier et al. |
| 5,118,668 A | 6/1992 | Auerswald et al. |
| 5,126,249 A | 6/1992 | Becker et al. |
| 5,169,933 A | 12/1992 | Anderson et al. |
| 5,204,354 A | 4/1993 | Chakravarty et al. |
| 5,223,409 A | 6/1993 | Ladner et al. |
| 5,258,499 A | 11/1993 | Konigsberg et al. |
| 5,362,831 A | 11/1994 | Mongelli et al. |
| 5,442,043 A | 8/1995 | Fukuta et al. |
| 5,578,451 A | 11/1996 | Nishimoto |
| 5,627,270 A | 5/1997 | Kahne et al. |
| RE35,524 E | 6/1997 | Saulnier et al. |
| 5,683,694 A | 11/1997 | Bagshawe et al. |
| 5,780,265 A | 7/1998 | Dennis et al. |
| 5,807,980 A | 9/1998 | Lasters et al. |
| 5,869,045 A | 2/1999 | Hellstrom et al. |
| 5,922,754 A | 7/1999 | Burchett et al. |
| 5,948,750 A | 9/1999 | Garsky et al. |
| 5,948,888 A | 9/1999 | de la Monte et al. |
| 5,955,444 A | 9/1999 | Ingram et al. |
| 5,962,266 A | 10/1999 | White et al. |
| 5,981,564 A | 11/1999 | Pagé et al. |
| 6,093,692 A | 7/2000 | Shen et al. |
| 6,126,965 A | 10/2000 | Kasid et al. |
| 6,191,290 B1 | 2/2001 | Safavy |
| 6,245,359 B1 | 6/2001 | Milstein et al. |
| 6,306,993 B1 | 10/2001 | Rothbard et al. |
| 6,310,039 B1 | 10/2001 | Kratz |
| 6,316,024 B1 | 11/2001 | Allen et al. |
| 6,348,207 B1 | 2/2002 | Milstein et al. |
| 6,376,648 B2 | 4/2002 | White et al. |
| 6,391,305 B1 | 5/2002 | Feng et al. |
| 6,469,047 B1 | 10/2002 | Jackson et al. |
| 6,475,481 B2 | 11/2002 | Talmadge |
| 6,475,781 B1 | 11/2002 | Mercola et al. |
| 6,495,513 B1 | 12/2002 | Rueger et al. |
| 6,613,890 B2 | 9/2003 | White et al. |
| 6,660,525 B2 | 12/2003 | Martin et al. |

(Continued)

FOREIGN PATENT DOCUMENTS

CA    2283474    9/1998
CA    2525236 A1    1/2005
(Continued)

OTHER PUBLICATIONS

U.S. Appl. No. 61/138,375, Beliveau et al.
Author manuscript of Howes et al., "Rapid induction of therapeutic hypothermia using convective-immersion surface cooling: Safety, efficacy and outcomes," published in final edited form as: Resuscitation. 81(4):388-392 (2010); (13 pages).
Belkin et al., "Matrix-dependent proteolysis of surface transglutaminase by membrane-type metalloproteinase regulates cancer cell adhesion and locomotion," J Biol Chem. 276(21):18415-18422 (2001).
Boado et al., "GDNF fusion protein for targeted-drug delivery across the human blood-brain barrier," Biotechnol Bioeng. 100(2):387-96 (2008).

(Continued)

*Primary Examiner* — Karlheinz R Skowronek
*Assistant Examiner* — Lianko Garyu
(74) *Attorney, Agent, or Firm* — Clark & Elbing LLP

(57) ABSTRACT

The present invention relates to multimeric (e.g., dimeric, trimeric) forms of peptide vectors that are capable of crossing the blood-brain barrier (BBB) or efficiently entering particular cell types. These multimeric peptide vectors, when conjugated to agents (e.g., therapeutic agents) are capable of transporting the agents across the BBB or into particular cell types. These compounds are therefore particularly useful in the treatment of neurological diseases.

14 Claims, 12 Drawing Sheets

(56) References Cited

U.S. PATENT DOCUMENTS

| | | |
|---|---|---|
| 6,689,582 B1 | 2/2004 | Davies et al. |
| 6,713,454 B1 | 3/2004 | Ekwuribe et al. |
| 6,906,033 B2 | 6/2005 | White et al. |
| 6,930,090 B2 | 8/2005 | Ekwuribe et al. |
| 7,019,123 B2 | 3/2006 | Tamburini et al. |
| 7,049,058 B2 | 5/2006 | Singh |
| 7,067,632 B2 | 6/2006 | Elliott |
| 7,101,844 B2 | 9/2006 | Kim et al. |
| 7,115,707 B2 | 10/2006 | Ben-Sasson et al. |
| 7,153,946 B2 | 12/2006 | McChesney et al. |
| 7,192,921 B2 | 3/2007 | Laakkonen et al. |
| 7,208,174 B2 | 4/2007 | Huwyler et al. |
| 7,214,657 B2 | 5/2007 | Kream |
| 7,271,149 B2 | 9/2007 | Glaesner et al. |
| 7,319,090 B2 | 1/2008 | Katz |
| 7,557,182 B2 | 7/2009 | Beliveau et al. |
| 7,569,544 B2 | 8/2009 | Zankel et al. |
| 7,700,554 B2 | 4/2010 | Beliveau et al. |
| 7,902,156 B2 | 3/2011 | Beliveau et al. |
| 8,530,429 B2 | 9/2013 | Robbins et al. |
| 8,569,323 B2 | 10/2013 | Ren et al. |
| 2003/0129186 A1 | 7/2003 | Beliveau et al. |
| 2003/0170891 A1 | 9/2003 | McSwiggen |
| 2004/0058865 A1* | 3/2004 | Danishefsky et al. .......... 514/12 |
| 2004/0077540 A1 | 4/2004 | Quay |
| 2004/0087499 A1 | 5/2004 | Laakkonen et al. |
| 2004/0101904 A1 | 5/2004 | Pardridge et al. |
| 2004/0102369 A1 | 5/2004 | Wu et al. |
| 2004/0146549 A1 | 7/2004 | Ben-Sasson et al. |
| 2004/0162284 A1 | 8/2004 | Harris et al. |
| 2004/0220132 A1 | 11/2004 | Kaemmerer |
| 2005/0026823 A1 | 2/2005 | Zankel et al. |
| 2005/0042227 A1 | 2/2005 | Zankel et al. |
| 2005/0058702 A1 | 3/2005 | Ben-Sasson et al. |
| 2005/0100986 A1 | 5/2005 | Verma et al. |
| 2005/0107325 A1 | 5/2005 | Manoharan et al. |
| 2005/0178395 A1 | 8/2005 | Hunter et al. |
| 2005/0183731 A1 | 8/2005 | Hunter et al. |
| 2006/0019347 A1 | 1/2006 | Cho et al. |
| 2006/0029609 A1 | 2/2006 | Zankel et al. |
| 2006/0135428 A1* | 6/2006 | Bridon et al. ................... 514/12 |
| 2006/0182684 A1 | 8/2006 | Beliveau |
| 2006/0189515 A1 | 8/2006 | Beliveau et al. |
| 2006/0251713 A1 | 11/2006 | Ben-Sasson et al. |
| 2007/0031844 A1 | 2/2007 | Khvorova et al. |
| 2007/0149444 A1 | 6/2007 | Laakkonen et al. |
| 2007/0167365 A1 | 7/2007 | Beliveau et al. |
| 2007/0172462 A1 | 7/2007 | Bohn et al. |
| 2007/0197460 A1 | 8/2007 | Fougerolles et al. |
| 2007/0207958 A1 | 9/2007 | Bridon et al. |
| 2008/0014143 A1 | 1/2008 | Ruoslahti et al. |
| 2008/0199436 A1 | 8/2008 | Sawada |
| 2008/0213185 A1 | 9/2008 | Hong et al. |
| 2008/0299039 A1 | 12/2008 | Beliveau et al. |
| 2009/0016959 A1 | 1/2009 | Beliveau et al. |
| 2009/0021883 A1 | 1/2009 | Delida |
| 2009/0082277 A1 | 3/2009 | Beliveau et al. |
| 2009/0215883 A1 | 8/2009 | Bouzada et al. |
| 2009/0221477 A1 | 9/2009 | Artymiuk et al. |
| 2009/0246211 A1 | 10/2009 | Henri et al. |
| 2010/0209429 A1 | 8/2010 | Erlich et al. |
| 2010/0256055 A1 | 10/2010 | Castaigne et al. |
| 2010/0284921 A1 | 11/2010 | Gordon et al. |
| 2011/0039785 A1* | 2/2011 | Beliveau et al. ............. 514/17.5 |
| 2011/0059187 A1 | 3/2011 | Basu et al. |
| 2011/0171128 A1 | 7/2011 | Beliveau et al. |
| 2011/0218152 A1 | 9/2011 | Beliveau et al. |
| 2011/0305750 A1 | 12/2011 | Beliveau et al. |
| 2012/0015876 A1* | 1/2012 | Castaigne et al. ............. 514/4.9 |
| 2012/0156130 A1 | 6/2012 | Hettmann et al. |
| 2012/0245169 A1 | 9/2012 | Ren et al. |
| 2013/0022546 A1 | 1/2013 | Wall et al. |
| 2013/0029982 A1 | 1/2013 | Castro et al. |
| 2013/0029984 A1 | 1/2013 | Castro et al. |
| 2013/0034572 A1 | 2/2013 | Stanimirovic et al. |
| 2013/0035069 A1 | 2/2013 | Fisher |
| 2013/0045873 A1 | 2/2013 | Hood et al. |
| 2013/0150314 A1 | 6/2013 | Myers et al. |
| 2013/0177499 A1 | 7/2013 | Brahmbhatt et al. |
| 2013/0195761 A1 | 8/2013 | Pereira et al. |

FOREIGN PATENT DOCUMENTS

| | | |
|---|---|---|
| CA | 2637893 | 7/2007 |
| CA | 2638034 | 7/2007 |
| CN | 101262890 A | 9/2008 |
| CN | 102406949 A | 4/2012 |
| CN | 102552928 A | 7/2012 |
| CN | 102614105 A | 8/2012 |
| DE | 19953696 | 5/2001 |
| EA | 005404 B1 | 2/2005 |
| EP | 0393431 | 10/1990 |
| EP | 0393431 A1 | 10/1990 |
| EP | 0495049 B1 | 7/1992 |
| EP | 1982699 A1 | 10/2008 |
| EP | 2333074 A1 | 6/2011 |
| JP | 2007-509977 A | 4/2007 |
| RU | 2172323 C2 | 10/1999 |
| WO | WO 87/05702 | 9/1987 |
| WO | WO 96/31531 | 10/1996 |
| WO | WO 96/35788 | 11/1996 |
| WO | WO-96/39160 A1 | 12/1996 |
| WO | WO 96/39183 | 12/1996 |
| WO | WO 96/40210 | 12/1996 |
| WO | WO 97/33996 | 9/1997 |
| WO | WO 97/40854 | 11/1997 |
| WO | WO 00/01417 | 1/2000 |
| WO | WO 00/71574 | 11/2000 |
| WO | WO 01/30319 | 5/2001 |
| WO | WO 02/33090 | 4/2002 |
| WO | WO-00/24782 A3 | 6/2002 |
| WO | WO-02/43765 A2 | 6/2002 |
| WO | WO-02/085923 A2 | 10/2002 |
| WO | WO 03/009815 | 2/2003 |
| WO | WO-03/102583 A1 | 12/2003 |
| WO | PCT/JP2004/011668 | 6/2004 |
| WO | WO 2004/060403 | 7/2004 |
| WO | WO 2004/091623 | 10/2004 |
| WO | WO-2004/093897 A1 | 11/2004 |
| WO | WO-2004/108071 A2 | 12/2004 |
| WO | WO 2005/002515 | 1/2005 |
| WO | WO-2005/014625 A1 | 2/2005 |
| WO | WO-2005/021579 A2 | 3/2005 |
| WO | WO-2005/042029 A2 | 5/2005 |
| WO | WO 2006/086870 | 8/2006 |
| WO | WO-2006/089290 A1 | 8/2006 |
| WO | WO-2006/108052 A2 | 10/2006 |
| WO | WO-2006/138343 A2 | 12/2006 |
| WO | WO 2007/009229 | 1/2007 |
| WO | WO 2007/020085 | 2/2007 |
| WO | WO 2007/030619 | 3/2007 |
| WO | WO-2007/035716 A2 | 3/2007 |
| WO | WO-2007/044323 A2 | 4/2007 |
| WO | WO-2007/082978 A1 | 7/2007 |
| WO | WO-2007/082979 A1 | 7/2007 |
| WO | WO 2007/103515 | 9/2007 |
| WO | WO 2007/113172 | 10/2007 |
| WO | WO 2008/012629 | 1/2008 |
| WO | WO-2008/036682 A2 | 3/2008 |
| WO | WO 2008/046228 | 4/2008 |
| WO | WO 2008/069876 | 6/2008 |
| WO | WO-2008/116171 A1 | 9/2008 |
| WO | WO 2008/144919 | 12/2008 |
| WO | WO 2009/039188 | 3/2009 |
| WO | WO 2009/046220 | 4/2009 |
| WO | WO 2009/070597 | 6/2009 |
| WO | WO 2009/079790 | 7/2009 |
| WO | WO 2009/105671 | 8/2009 |
| WO | WO 2009/127072 | 10/2009 |
| WO | WO-2010/006239 A2 | 1/2010 |
| WO | WO 2010/043047 | 4/2010 |
| WO | WO 2010/043049 | 4/2010 |
| WO | WO 2010/063122 | 6/2010 |
| WO | WO 2010/063123 | 6/2010 |

(56) References Cited

FOREIGN PATENT DOCUMENTS

| WO | WO 2010/063124 | 6/2010 |
|---|---|---|
| WO | WO 2010/069074 | 6/2010 |
| WO | WO 2010/121379 | 10/2010 |
| WO | WO 2010/142035 | 12/2010 |
| WO | WO-2011/000095 A1 | 1/2011 |
| WO | WO-2011/008823 A2 | 1/2011 |
| WO | WO 2011/041897 | 4/2011 |
| WO | WO-2011/063507 A1 | 6/2011 |
| WO | WO-2011/112635 A1 | 9/2011 |
| WO | WO 2011/153642 | 12/2011 |
| WO | WO 2012/000118 | 1/2012 |
| WO | WO-2012/006239 A1 | 1/2012 |
| WO | WO 2012/037687 | 3/2012 |
| WO | WO-2012/064973 A2 | 5/2012 |
| WO | WO-2012/068531 A2 | 5/2012 |
| WO | WO-2012/097000 A1 | 7/2012 |
| WO | WO-2012/118376 A1 | 9/2012 |
| WO | WO-2012/135025 A2 | 10/2012 |
| WO | WO-2012/138694 A2 | 10/2012 |
| WO | WO-2012/153286 A1 | 11/2012 |
| WO | WO-2012/162807 A1 | 12/2012 |
| WO | WO-2013/004716 A1 | 1/2013 |
| WO | WO-2013/012915 A1 | 1/2013 |
| WO | WO-2013/023184 A1 | 2/2013 |
| WO | WO-2013/032591 A1 | 3/2013 |
| WO | WO-2013/049332 A1 | 4/2013 |
| WO | WO-2013/056096 A1 | 4/2013 |
| WO | WO-2013/063468 A1 | 5/2013 |
| WO | WO-2013/071272 A1 | 5/2013 |
| WO | WO-2013/078562 A2 | 6/2013 |
| WO | WO-2013/078564 A2 | 6/2013 |
| WO | WO-2013/090861 A1 | 6/2013 |
| WO | WO-2013/120107 A1 | 8/2013 |
| WO | WO-2013/131032 A1 | 9/2013 |
| WO | WO-2013/151774 A1 | 10/2013 |
| WO | WO-2013/162757 A1 | 10/2013 |
| WO | WO-2013/185235 A1 | 12/2013 |

OTHER PUBLICATIONS

Brady et al., "Drug design. Refelections on a peptide." Nature. 368(6473):692-693 (1994).
Buvanendran et al., "Recent advances in nonopioid analgesics for acute pain management," Tech Reg Anesth Pain Man. 11(1):19-26 (2007).
Carell et al., "A novel procedure for the synthesis of libraries containing small organic molecules," Angew Chem Int Ed Engl. 33(20):2059-2061 (1994).
Carell et al., "A solution-phase screening procedure for the isolation of active compounds from a library of molecules," Angew Chem Int Ed Engl. 33(20):2061-2064 (1994).
Chen et al., "Synthesis of doxorubicin conjugates through hydrazone bonds to melanotransferrin P97," Synth Commun. 33(14):2377-2390 (2003).
Cho et al., "An unnatural biopolymer," Science. 261:1303-1305 (1993).
Chu et al., "Detection of soluble P-glycoprotein in culture media and extracellular fluids," Biochem Biophys Res Commun. 203(1):506-512 (1994).
Cui et al., "PAMAM-drug complex for delivering anticancer drug across blood-brain barrier in-vitro and in-vivo," Afr J Pharm Pharmacol. 3(5):227-233 (2009).
Cull et al., "Screening for receptor ligands using large libraries of peptides linked to the C terminus of the lac repressor," Proc Natl Acad Sci U S A. 89(5): 1865-1869 (1992).
D'Ortho et al., "Membrane-type matrix metalloproteinases 1 and 2 exhibit broad-spectrum proteolytic capacities comparable to many matrix metalloproteinases," Eur J Biochem. 250(3): 751-757 (1997).
Declaration of Michel Demeule in European Patent Application No. 11010125 dated Sep. 24, 2012 (4 pages).
Demule et al., "ANG2002: A new Angiochem-modified neurotensin with increased brain penetration and analgesic properties," Program No. 374.11/QQ6 2010 Neuroscience Meeting Planner, San Diego, CA: Society for Neuroscience (2010) (5 pages).
DeWitt et al., "'Diversomers': an approach to nonpeptide, nonoligomeric chemical diversity," Proc Natl Acad Sci U S A. 90(15):6909-6913 (1993).
Erb et al., "Recursive deconvolution of combinatorial chemical libraries," Proc Natl Acad Sci U S A. 91(24):11422-11426 (1994).
Evans et al., "Design of nonpeptidal ligands for a peptide receptor: Cholecystokinin antagonists," J Med Chem. 30(7):1229-1239 (1987).
Fauchere et al., "Association with HeLa cells of *Campylobacter jejuni* and *Campylobacter coli* isolated from human feces," Infect Immun. 54(2):283-287 (1986).
Fioretti et al., "Aprotinin-like isoinhibitors in bovine organs," Biol Chem Hoppe Seyler. 369 Suppl:37-42 (1988).
Fodor et al., "Multiplexed biochemical assays with biological chips," Nature. 364(6437):555-556 (1993).
Furuta et al., "Structure-antinociceptive activity studies with neurotensin," Br J Pharmacol. 83(1):43-48 (1984).
Gabathuler, "Approaches to transport therapeutic drugs across the blood-brain barrier to treat brain diseases," Neurobiol Dis. 37(1):48-57 (2010).
Gallop et al., "Applications of combinatorial technologies to drug discovery. 1. Background and peptide combinatorial libraries," J Med Chem. 37(9):1233-1251 (1994).
Halab et al., "Design, synthesis, and conformational analysis of azacycloalkane amino acids as conformationally constrained probes for mimicry of peptide secondary structures," Biopolymers. 55(2):101-122 (2000).
Hanessian et al., "Synthesis of (4$S$)-hydroxymethyl-(2$R$)-(2-propyl)-butyrolactone: A quest for a practical route to an important hydroxyethylene isostere chiron," Tetrahedron. 53(18):6281-6294 (1997).
Hein et al., "Click chemistry, a powerful tool for pharmaceutical sciences," Pharm Res. 25(10):2216-2230 (2008).
Hijova, Matrix metalloproteinases: their biological functions and clinical implications, Bratisl Lek Listy. 106(3):127-132 (2005).
Hiraoka et al., "Matrix metalloproteinases regulate neovascularization by acting as pericellular fibrinolysins," Cell. 95(3):365-377 (1998).
Hong et al., "Coexpression of cyclooxygenase-2 and matrix metalloproteinases in human aortic atherosclerotic lesions," Yonsei Med J. 41(1):82-88 (2000).
Hotary et al., "Membrane type I matrix metalloproteinase usurps tumor growth control imposed by the three-dimensional extracellular matrix," Cell. 114(1):33-45 (2003).
Huang et al., "Production of bioactive human beta-defensin 5 and 6 in *Escherichia coli* by soluble fusion expression," Protein Expr Purif. 61(2):168-174 (2008).
Hudson et al., "Methionine enkephalin and isosteric analogues. I. Synthesis on a phenolic resin support," Int J Pept Protein Res. 14(3):177-185 (1979).
Imai et al., "Expression of membrane-type 1 matrix metalloproteinase and activation of progelatinase A in human osteoarthritic cartilage," Am J Pathol. 151(1):245-256 (1997).
International Preliminary Report on Patentability and Written Opinion for International Application No. PCT/CA2010/001014, mailed Jan. 12, 2012 (12 pages).
Rohl et al., "MT1-MMP: a potent modifier of pericellular microenvironment," J Cell Physiol. 206(1):1-8 (2006).
Jameson et al., "A rationally designed CD4 analogue inhibits experimental allergic encephalomyelitis," Nature. 368(6473):744-746 (1994).
Kajita et al., "Membrane-type 1 matrix metalloproteinase cleaves CD44 and promotes cell migration" J Cell Biol. 153(5):893-904 (2001).
Kamps et al., "Uptake of long-circulating immunoliposomes, directed against colon adenocarcinoma cells, by liver metastases of colon cancer," J Drug Target. 8(4):235-245 (2000).
Kesari et al., "Phase II study of temozolomide, thalidomide, and celecoxib for newly diagnosed glioblastoma in adults," Neuro Oncol. 10(3):300-308 (2008).

(56) References Cited

OTHER PUBLICATIONS

Kirpotin et al., "Sterically stabilized anti-HER2 immunoliposomes: design and targeting to human breast cancer cells in vitro," Biochemistry. 36(1):66-75 (1997).
Konttinen et al., "Analysis of 16 different matrix metalloproteinases (MMP-1 to MMP-20) in the synovial membrane: different profiles in trauma and rheumatoid arthritis" Ann Rheum Dis. 58(11):691-7 (1999).
Kurzrock et al., "ANG1005, an Angiopep-2/paclitaxel conjugate: The first clinical trial in patients with advanced cancer and brain metastases: Preliminary safety and tolerability data," 20th EORTC-NCI-AACR Symposium on "Molecular Targets and Cancer Therapeutics", Euro J of Cancer. 6(12):133, Abstract 424 (2008).
Lachowicz et al., "Analgesic properties of a novel brain-penetrant Angiopep-2-neurotensin derivative (ANG2002) for treating chronic pain," Program No. 173.28/AA9 2012 Neuroscience Meeting Planner, New Orleans, LA: Society for Neuroscience (2012).
Lam et al., A new type of synthetic peptide library for identifying ligand-binding activity, Nature. 354(6348):82-4 (1991).
Lam, "Application of combinatorial library methods in cancer research and drug discovery," Anticancer Drug Des. 12(3):145-67 (1997).
Langer, "New methods of drug delivery," Science. 249(4976):1527-33 (1990).
Mamot et al., "Epidermal growth factor receptor (EGFR)-targeted immunoliposomes mediate specific and efficient drug delivery to EGFR- and EGFRvIII-overexpressing tumor cells," Cancer Res. 63(12):3154-61 (2003).
Markman et al., "Phase II trial of weekly single-agent paclitaxel in platinum/paclitaxel-refractory ovarian cancer," J Clin Oncol. 20(9):2365-9 (2002).
Martinez-Fong et al., "Neurotensin-SPDP-poly-L-lysine conjugate: a nonviral vector for targeted gene delivery to neural cells," Molecular Brain Research 69:249-262 (1999).
Michaud et al., "Risks and benefits of taxanes in breast and ovarian cancer," Drug Saf. 23(5):401-28 (2000).
Moase et al., "Anti-MUC-1 immunoliposomal doxorubicin in the treatment of murine models of metastatic breast cancer," Biochim Biophys Acta. 1510(1-2):43-55 (2001).
Nakada et al., "Expression and tissue localization of membrane-type 1, 2, and 3 matrix metalloproteinases in human astrocytic tumors," Am J Pathol. 154(2):417-28 (1999).
Nam et al., "Sterically stabilized anti-G(M3), anti-Le(x) immunoliposomes: targeting to B16BL6, HRT-18 cancer cells," Oncol Res. 11(1):9-16 (1999).
Notification of Filing Divisional Application and its English Translation for Chinese Patent Application No. 201080038742.3, mailed Aug. 5, 2013 (5 pages).
Nyalendo et al., "Src-dependent phosphorylation of membrane type I matrix metalloproteinase on cytoplasmic tyrosine 573: role in endothelial and tumor cell migration," J Biol Chem. 282(21):15690-9 (2007).
Pardridge et al. "Combined use of carboxyl-directed protein pegylation and vector-mediated blood-brain barrier drug delivery system optimizes brain uptake of brain-derived neurotrophic factor following intravenous administration," Pharm Res. 15(4):576-582 (1998).
Pardridge et al., "Selective transport of an anti-transferrin receptor antibody through the blood-brain barrier in vivo," J Pharmacol Exp Ther. 259(1):66-70 (1991).
Pardridge, "Vector-mediated drug delivery to the brain," Adv Drug Deliv Rev. 36(2-3):299-321 (1999).
Park et al., "Development of anti-p185HER2 immunoliposomes for cancer therapy," Proc Natl Acad Sci U S A. 92(5):1327-31 (1995).
Park et al., "Recombinant expression of biologically active rat leptin in *Escherichia coli*," Protein Expr Purif. 22(1):60-69 (2001).
Pathan et al. "CNS drug delivery systems: novel approaches," Recent Pat Drug Deliv Formul. 3(1):71-89 (2009).
Pei et al., "Transmembrane-deletion mutants of the membrane-type matrix metalloproteinase-1 process progelatinase A and express intrinsic matrix-degrading activity," J Biol Chem. 271(15):9135-9140 (1996).
Powell et al., "Peptide stability in drug development. II. Effect of single amino acid substitution and glycosylation on peptide reactivity in human serum," Pharm Res. 10(9):1268-73 (1993).
Rajavashisth et al., "Membrane type 1 matrix metalloproteinase expression in human atherosclerotic plaques: evidence for activation by proinflammatory mediators," Circulation. 99(24):3103-9 (1999).
Rizo et al. "Constrained peptides: models of bioactive peptides and protein substructures," Annu Rev Biochem. 61:387-418 (1992).
Rose et al., "Metastatic patterns in histologic variants of ovarian cancer. An autopsy study," Cancer. 64(7):1508-13 (1989).
Rudikoff et al., "Single amino acid substitution altering antigen-binding specificity," Proc Natl Acad Sci USA. 79:1979-83 (1982).
Sabeh et al. "Tumor cell traffic through the extracellular matrix is controlled by the membrane-anchored collagenase MT1-MMP," J Cell Biol. 167(4):769-81 (2004).
Sahm et al. "Receptor binding affinities and biological activities of linear and cyclic melanocortins in B16 murine melanoma cells expressing the native MC1 receptor," J Pharm Pharmacol. 48(2):197-200 (1996).
Scott et al. "Searching for peptide ligands with an epitope library," Science. 249(4967):386-90 (1990).
Seiden et al., "A phase II study of the MDR inhibitor biricodar (INCEL, VX-710) and paclitaxel in women with advanced ovarian cancer refractory to paclitaxel therapy," Gynecol Oncol. 86(3):302-10 (2002).
Shao et al., "Angiopep-2 modified PE-PEG based polymeric micelles for amphotericin B delivery targeted to the brain," J Control Release. 147(1):118-26 (2010).
Spatola et al., "Structure-activity relationships of enkephalins containing serially replaced thiomethylene amide bond surrogates," Life Sci. 38(14):1243-9 (1986).
Svenson et al., "Dendrimers in biomedical applications—reflections on the field," Adv Drug Deliv Rev. 57(15):2106-2129 (2005).
UniProt Consortium, "P08183 (MDR1_HUMAN)," <http://www.uniprot.org/uniprot/P08183>, retrieved on Sep. 18, 2013 (16 pages).
Vincent, "Neurotensin receptors: binding properties, transduction pathways, and structure," Cell Mol Neurobiol. 15(5):501-512 (1995).
Wang et al., "Polyamidoamine dendrimers with a modified Pentaerythritol core having high efficiency and low cytotoxicity as gene carriers," Biomacromolecules. 10(3):617-622 (2009).
Wang et al., "Synthesis and antinociceptive effects of endomorphin-1 analogs with C-terminal linked by oligoarginine," Peptides. 32(2):293-9 (2011).
Williamson et al., "Expression and purification of recombinant neurotensin in *Escherichia coli*," Protein Expr Purif. 19(2):271-5 (2000).
Yano et al., "Simultaneous activation of two different receptor systems by enkephalin/neurotensin conjugates having spacer chains of various lengths," Eur J Pharm Sci. 7:41-48 (1998).
Zhai et al. "Expression of membrane type 1 matrix metalloproteinase is associated with cervical carcinoma progression and invasion," Cancer Res. 65(15):6543-6550 (2005).
Zhang et al. "In vitro gene delivery using polyamidoamine dendrimers with a trimesyl core," Biomacromolecules. 6(1):341-350 (2005).
Ballabh et al., "The Blood-Brain Barrier: An Overview Structure, Regulation, and Clinical Implications," *Neurobiol Dis.* 16:1-13 (2004).
Bickel et al., "Delivery of Peptides and Proteins Through the Blood-Brain Barrier," *Adv Drug Deliv Rev.* 46:247-279 (2001).
Boado, "Blood-brain Barrier Transport of Non-viral Gene and RNAi Therapeutics," *Pharm Res.* 24:1772-1787 (2007).
Bork, "Powers and Pitfalls in Sequence Analysis: The 70% Hurdle," *Genome Res.* 10:398-400 (2000).
Bork et al., "Go Hunting in Sequence Databases But Watch Out for the Traps," *Trends Genet.* 12:425-427 (1996).
Brenner, "Errors in Genome Annotation," *Trends Genet.* 15:132-133 (1999).

(56) References Cited

OTHER PUBLICATIONS

Castex et al., "2-Pyrrolinodoxorubicin and Its Peptide-vectorized Form Bypass Multidrug Resistance," *Anticancer Drugs*. 15:609-617 (2004).
Coon et al., "Solutol HS 15, Nontoxic Polyoxyethylene Esters of 12-hydroxystearic Acid, Reverses Multidrug Resistance," *Cancer Res*. 51:897-902 (1991).
D'Onofrio et al., "Glycomimetics as Decorating Motifs for Oligonucleotides: Solid-phase Synthesis, Stability, and Hybridization Properties of Carbopeptoid-oligonucleotide Conjugates," *Bioconjug Chem*. 16:1299-1309 (2005).
Dagenais et al., "Development of an In Situ Mouse Brain Perfusion Model and Its Application to mdr1a P-glycoprotein-deficient Mice," *J Cereb Blood Flow Metab*. 20:381-386 (2000).
Deane et al., "LRP/Amyloid β-Peptide Interaction Mediates Differential Brain Efflux of Aβ Isoforms," *Neuron*. 43:333-344 (2004).
Dehouck et al., "A New Function for the LDL Receptor: Transcytosis of LDL Across the Blood-Brain Barrier," *J Cell Biol*. 138:877-889 (1997).
Dehouck et al., "An Easier, Reproducible, and Mass-production Method to Study the Blood-brain Barrier in Vitro," *J Neurochem*. 54:1798-1801 (1990).
Dehouck et al., "Drug Transfer Across the Blood-Brain Barrier: Correlation Between In Vitro and In Vivo Models," *J Neurochem*. 58:1790-1797 (1992).
Demeule et al., "High Transcytosis of Melanotransferrin (P97) Across the Blood-Brain Barrier," *J Neurochem*. 83:924-933 (2002).
Demeule et al., "Identification and Design of Peptides as a New Drug Delivery System for the Brain," *J Pharmacol Exp Ther*. 324:1064-1072 (2008).
Demeule et al., "Isolation of Endothelial Cells from Brain, Lung, and Kidney: Expression of the Multidrug Resistance P-Glycoprotein Isoforms," *Biochem Biophys Res Commun*. 281:827-834 (2001).
Doerks et al., "Protein Annotation: Detective Work for Function Prediction," *Trends Genet*. 14:248-250 (1998).
Fillebeen et al., "Receptor-Mediated Transcytosis of Lactoferrin Through the Blood-Brain Barrier," *J Biol Chem*. 274:7011-7017 (1999).
Fromm, "P-glycoprotein: A Defense Mechanism Limiting Oral Bioavailability and CNS Accumulation of Drugs," *Int J Clin Pharmacol Ther*. 38:69-74 (2000).
Gelmon, "The Taxoids: Paclitaxel and Docetaxel," *Lancet*. 344:1267-1272 (1994).
Gewirtz, "A Critical Evaluation of the Mechanisms of Action Proposed for the Antitumor Effects of the Anthracycline Antibiotics Adriamycin and Daunorubicin," *Biochem Pharmacol*. 57:727-741 (1999).
Grabb et al., "Neoplastic and Pharmacological Influence on the Permeability of an in vitro Blood-Brain Barrier," *J Neurosurg*. 82:1053-1058 (1995).
Guillot et al., "Angiotensin Peptide Regulation of Bovine Brain Microvessel Endothelial Cell Monolayer Permeability," *J Cardiovasc Pharmacol*. 18:212-218 (1991).
Gumbleton et al., "Progress and Limitations in the Use of in Vitro Cell Cultures to Serve as a Permeability Screen for the Blood-Brain Barrier," *J Pharm Sci*. 90:1681-1698 (2001).
Hawkins et al., "The Blood-Brain Barrier/Neurovascular Unit in Health and Disease," *Pharmacol Rev*. 57:173-185 (2005).
Hussain et al., "The Mammalian Low-Density Lipoprotein Receptor Family," *Annu Rev Nutr*. 19:141-172 (1999).
Ito et al., "Functional Characterization of the Brain-to-Blood Efflux Clearance of Human Amyloid-β Peptide (1-40) Across the Rat Blood-Brain Barrier," *Neurosci Res*. 56:246-252 (2006).
Ke et al., "Gene Delivery Targeted to the Brain Using an Angiopep-conjugated Polyethyleneglycol-modified Polyamidoamine Dendrimer," *Biomaterials*. 30:6976-6985 (2009).
Kiernan et al., "Fluorescent-Labelled Aprotinin: A New Reagent for the Histochemical Detection of Acid Mucosubstances," *Histochemie*. 34: 77-84 (1973).
Kobayashi et al., "The Protease Inhibitor Bikunin, a Novel Anti-Metastatic Agent," *Biol Chem*. 384:749-754 (2003).
Koo et al., "Differential Expression of Amyloid Precursor Protein mRNAs in Cases of Alzheimer's Disease and in Aged Nonhuman Primates," *Neuron*. 2:97-104 (1990).
Kounnas et al, "LDL Receptor-related Protein, a Multifunctional ApoE Receptor, Binds Secreted Beta-amyloid Precursor Protein and Mediates Its Degradation," *Cell*. 82:331-340 (1995).
Koziara et al., "In Situ Blood-brain Barrier Transport of Nanoparticles," *Pharm Res*. 20:1772-1778 (2003).
Kreuter et al., "Apolipoprotein-Mediated Transport of Nanoparticle-Bound Drugs Across the Blood-Brain Barrier," *J Drug Target*. 10:317-325 (2002).
Kreuter et al., "Direct Evidence that Polysorbate-80-coated Poly(Butylcyanoacrylate) Nanoparticles Deliver Drugs to the CNS Via Specific Mechanisms Requiring Prior Binding of Drug to the Nanoparticles," *Pharm Res*. 20:409-416 (2003).
Kreuter, "Nanoparticulate Carriers for Drug Delivery to the Brain," *Nanoparticles as Drug Carriers Torchilin VP*, Imperial College Press, London pp. 527-547 (2006).
Laccabue et al., "A Novel Taxane Active against an Orthotopically Growing Human Glioma Xenograft," *Cancer*. 92:3085-3092 (2001).
Lai et al., "The Critical Component to Establish in vitro BBB Model: Pericyte," *Brain Res Rev*. 50:258-265 (2005).
Larionova et al., "Carbohydrate-Containing Derivatives of the Trypsin-Kallikrein Inhibitor Aprotinin from Bovine Organs II. Inhibitor Coupled to the (Carboxymethyl)dextran Derivatives of D-Galactose," *Biol Chem Hoppe-Seyler*. 366:743-748 (1985).
Larsson, "Megalin, an Endocytotic Receptor With Signalling Potential," *Acta Universitatis Upsaliensis Uppsala* 1-60 (2006).
Ma et al., "Cationic Charge-Dependent Hepatic Delivery of Amidated Serum Albumin," *J Control Release*. 102:583-594 (2005).
Marinò et al., "Megalin-Mediated Transcytosis of Thyroglobulin by Thyroid Cells is a Calmodulin-Dependent Process," *Thyroid*. 10:461-469 (2000).
Marinò et al., "Transcytosis of Retinol-Binding Protein Across Renal Proximal Tubule Cells After Megalin (gp 330)-Mediated Endocytosis," *J Am Soc Nephrol*.12:637-648 (2001).
Martel et al., "Transport of Apolipoproteins E and J at the Blood-Brain Barrier Relevance to Alzheimer's disease," *S.T.P. Pharma Sciences*. 7:28-36 (1997).
Mazel et al., "Doxorubicin-peptide Conjugates Overcome Multidrug Resistance," *Anticancer Drugs*. 12:107-116 (2001).
McCarty, "Cell Biology of the Neurovascular Unit: Implications for Drug Delivery Across the Blood-Brain Barrier," *Assay Drug Dev Technol*. 3:89-95 (2005).
Moestrup et al., "Evidence that Epithelial Glycoprotein 330/Megalin Mediates Uptake of Polybasic Drugs," *J.Clin. Invest*. 96:1404-1413 (1995).
Moore et al., "The Role of Flexible Tethers in Multiple Ligand-receptor Bond Formation Between Curved Surfaces," *Biophys J*. 91:1675-1687 (2006).
Muratovska et al., "Conjugate for Efficient Delivery of Short Interfering RNA (siRNA) Into Mammalian Cells," *FEBS Lett*. 558:63-68 (2004).
Ngo et al., "Computational Complexity; Protein Structure Prediction, and the Levinthal Paradox," *The Protein Folding Problem and Tertiary Structure Prediction Merz*, Jr. and Le Grand, Eds. 491-495 (1994).
Niola et al., "A Plasmid-encoded VEGF siRNA Reduces Glioblastoma Angiogenesis and Its Combination with Interleukin-4 Blocks Tumor Growth in a Xenograft Mouse Model," *Cancer Biol Ther*. 5:174-179 (2006).
Orlando et al., "Identification of the Second Cluster of Ligand-Binding Repeats in Megalin as a Site for Receptor-Ligand Interactions," *Proc Natl Aced Sci*. 94:2368-2373 (1997).
Pan et al., "Efficient Transfer of Receptor-Associated Protein (RAP) Across the Blood-Brain Barrier," *J Cell Sci*. 117:5071-5078 (2004).
Pardridge, "Blood-Brain Barrier Biology and Methodology," *J Neurovirol*. 5:556-569 (1999).
Pardridge, "CNS Drug Design Based on Principles of Blood-Brain Barrier Transport," *J Neurochem*. 70:1781-1792 (1998).

(56) References Cited

OTHER PUBLICATIONS

Pardridge, "Drug Targeting to the Brain," *Pharm Res.* 24:1733-1744 (2007).
Peri et al., "D-Glucose as a Regioselectively Addressable Scaffold for Combinatorial Chemistry on Solid Phase," *J Carbohydr Chem.* 22:57-71 (2003).
Prince et al., "Lipoprotein Receptor Binding, Cellular Uptake, and Lysosomal Delivery of Fusions Between the Receptor-Associated protein (RAP) and α-L-Iduronidase or Acid α-Glucosidase," *J Biol Chem.* 279:35037-35046 (2004).
Qu et al., "Carbohydrate-based Micelle Clusters Which Enhance Hydrophobic Drug Bioavailability by Up to 1 Order of Magnitude," *Biomacromolecules.* 7:3452-3459 (2006).
Ramakrishnan, "The Role of P-glycoprotein in the Blood-Brain Barrier," *Einstein Q J Biol Med.* 19:160-165 (2003).
Rawat et al., "Lipid Carriers: A Versatile Delivery Vehicle for Proteins and Peptides," *Yakugaku Zasshi.* 128:269-280 (2008).
Régina et al., "Antitumour Activity of ANG1005, a Conjugate Between Paclitaxel and the New Brain Delivery Vector Angiopep-2," *Br J Pharmacol.* 155:185-197 (2008).
Régina et al., "Differences in Multidrug Resistance Phenotype and Matrix Metalloproteinases Activity Between Endothelial Cells from Normal Brain and Glioma," *J Neurochem.* 84:316-324 (2003).
Scherrmann, "Drug Delivery to Brain Via the Blood-Brain Barrier," *Vascul Pharmacol.* 38:349-354 (2002).
Schinkel, "P-Glycoprotein, A Gatekeeper in the Blood-Brain Barrier," *Adv Drug Deliv Rev.* 36:179-194 (1999).
Seidel et al., "Effects of Trasylol on the Blood-Brain Barrier in Rats," *Naunyn Schmiedebergs Arch Pharmacol.* 284:R73 (1974).
Shibata et al., "Clearance of Alzheimer's Amyloid-$\beta_{1-40}$ Peptide From Brain by LDL Receptor-Related Protein-1 at the Blood-Brain Barrier," *J Clin Invest.* 106:1489-1499 (2000).
Shiiki et al., "Brain Insulin Impairs Amyloid-$\beta$(1-40) Clearance From the Brain," *J Neurosci.* 24:9632-9637 (2004).
Shimura et al., "Transport Mechanism of a New Behaviorally Highly Potent Adrenocorticotropic Hormone (ACTH) Analog, Ebiratide, through the Blood-Brain Barrier," *J Pharmacol Exp Ther.* 258:459-465 (1991).
Skolnick et al., "From Genes to Protein Structure and Function: Novel Applications of Computational Approaches in the Genomic Era," *Trends Biotechnol.* 18:34-39 (2000).
Smith, "Brain Perfusion Systems for Studies of Drug Uptake and Metabolism in the Central Nervous System," *Pharm Biotechnol.* 285-307 (1996).
Smith et al., "The Challenges of Genome Sequence Annotation or 'The Devil is in the Details'," *Nat Biotechnol.* 15:1222-1223 (1997).
Steiniger et al., "Chemotherapy of Glioblastoma in Rats Using Doxorubicin-loaded Nanoparticles," *Int J Cancer.* 109:759-767 (2004).
Tamai et al., "Structure-Internalization Relationship for Adsorptive-Mediated Endocytosis of Basic Peptides at the Blood-Brain Barrier," *J Pharmacol Exp Ther.* 280:410-415 (1997).
Temsamani et al., "Vector-Mediated Drug Delivery to the Brain," *Expert Opin Biol Ther.* 1:773-782 (2001).
Terasaki et al., "New Approaches to in vitro Models of Blood-Brain Barrier Drug Transport," *Drug Discov Today.* 8:944-954 (2003).
Triguero et al., "Capillary Depletion Method for Quantification of Blood-Brain Barrier Transport of Circulating Peptides and Plasma Proteins," *J Neurochem.* 54:1882-1888 (1990).
Turner et al., "RNA Targeting With Peptide Conjugates of Oligonucleotides, siRNA and PNA," *Blood Cells Mol Dis.* 38:1-7 (2007).
Veronese et al., "PEGylation, Successful Approach to Drug Delivery," *Drug Discov Today.* 10:1451-1458 (2005).
Wang et al., "DNA/dendrimer Complexes Mediate Gene Transfer into Murine Cardiac Transplants ex Vivo," *Mol Ther.* 2:602-608 (2000).
Wells, "Additivity of Mutational Effects in Proteins," *Biochemistry.* 29:8509-8517 (1990).
Witt et al., "Peptide Drug Modifications to Enhance Bioavailability and Blood-Brain Barrier Permeability," *Peptides.* 22:2329-2343 (2001).
Xu et al., "In Vitro and In Vivo Evaluation of Actively Targetable Nanoparticles for Paclitaxel Delivery," *Int J Pharm.* 288:361-368 (2005).
Yepes et al., "Tissue-Type Plasminogen Activator Induces Opening of the Blood-Brain Barrier Via the LDL Receptor-Related Protein," *J Clin Invest.* 112:1533-1540 (2003).
Zhang et al., "Intravenous RNA Interference Gene Therapy Targeting the Human Epidermal Growth Factor Receptor Prolongs Survival in Intracranial Brain Cancer," *Clin Cancer Res.* 10:3667-3677 (2004).
Zhang et al., "Silencing the Epidermal Growth Factor Receptor Gene with RNAi may be Developed as a Potential Therapy for Non Small Cell Lung Cancer," *Genet Vaccines Ther.* 3:5 (2005).
Zhang et al., "siRNA-containing Liposomes Modified with Polyarginine Effectively Silence the Targeted Gene," *J Control Release.* 112:229-239 (2006).
Zlokovic et al., "Glycoprotein 330/Megalin: Probable Role in Receptor-mediated Transport of Apolipoprotein J Alone and in a Complex With Alzheimer Disease Amyloid $\beta$ at the Blood-Brain and Blood-Cerebrospinal Fluid Barriers," *Proc Natl Acad Sci USA.* 93:4229-4234 (1996).
U.S. Appl. No. 12/601,803, filed Nov. 24, 2009, Beliveau et al.
U.S. Appl. No. 12/632,557, filed Dec. 7, 2009, Castaigne et al.
Arpicco et al., "New Coupling Reagents for the Preparation of Disulfide Cross-Linked Conjugates with Increased Stability," *Bioconjugate Chem.* 8:327-337 (1997).
Banks, "Leptin Transport Across the Blood-Brain Barrier: Implications for the Cause and Treatment of Obesity," *Curr. Pharm. Des.* 7:125-133 (2001).
Banks, "The Blood-Brain Barrier as a Cause of Obesity," *Curr. Pharm. Des.* 14:1606-1614 (2008).
Bicamumpaka et al., "In Vitro Cytotoxicity of Paclitaxel-Transferrin Conjugate on H69 Cells," *Oncol. Rep.* 5:1381-1383 (1998).
Demeule et al., "Drug Transport to the Brain: Key Roles for the Efflux Pump P-Glycoprotein in the Blood-Brain Barrier," *Vascul. Pharmacol.* 38:339-348 (2002).
Dooley et al., "An All D-amino Acid Opioid Peptide with Central Analgesic Activity from a Combinatorial Library," *Science* 266: 2019-2022 (1994).
Eigenbrot et al., "X-Ray Structure of Glial Cell-Derived Neurotrophic Factor at 1.9 Å Resolution and Implications for Receptor Binding," *Nat. Struct. Biol.* 4:435-438 (1997).
Gabius et al., "Targeting of Neoglycoprotein-Drug Conjugates to Cultured Human Embryonal Carcinoma Cells,"*J. Cancer Res. Clin. Oncol.* 113:126-130 (1987).
Gottschalk et al., "Protein Self-Association in Solution: The Bovine Pancreatic Trypsin Inhibitor Decamer," *Biophys. J.* 84: 3941-3958 (2003).
Harkavyi et al., "Glucagon-Like Peptide 1 Receptor Stimulation Reverses Key Deficits in Distinct Rodent Models of Parkinson's Disease," *J. Neuroinflammation.* 5:19 (2008) (pp. 1-9).
Kalra, "Central Leptin Insufficiency Syndrome: An Interactive Etiology for Obesity, Metabolic and Neural Diseases and for Designing New Therapeutic Interventions," *Peptides* 29:127-138 (2008).
Karyekar et al., "*Zonula Occludens* Toxin Increases the Permeability of Molecular Weight Markers and Chemotherapeutic Agents Across the Bovine Brain Microvessel Endothelial Cells," *J. Pharm. Sci.* 92:414-423 (2003).
Kirsch et al., "Anti-Angiogenic Treatment Strategies for Malignant Brain Tumors," *J. Neurooncol.* 50:149-163 (2000).
Lewis et al., "Maleimidocysteineamido-DOTA Derivatives: New Reagents for Radiometal Chelate Conjugation to Antibody Sulfhydryl Groups Undergo pH-Dependent Cleavage Reactions," *Bioconjugate Chem.* 9:72-86 (1998).
Saito et al., "Drug Delivery Strategy Utilizing Conjugation Via Reversible Disulfide Linkages: Role and Site of Cellular Reducing Activities," *Adv. Drug. Deliv. Rev.* 55:199-215 (2003).
Samson et al., "Gene Therapy for Diabetes: Metabolic Effects of Helper-Dependent Adenoviral Exendin 4 Expression in a Diet-Induced Obesity Mouse Model," *Mol. Ther.* 16:1805-1812 (2008) (pp. 1-18).

(56) References Cited

OTHER PUBLICATIONS

Uekita et al., "Cytoplasmic Tail-Dependent Internalization of Membrane-Type 1 Matrix Metalloproteinase is Important for its Invasion-Promoting Activity," *J. Cell. Biol.* 155:1345-1356 (2001).
Uekita et al., "Membrane-Type 1 Matrix Metalloproteinase Cytoplasmic Tail-Binding Protein-1 is a New Member of the Cupin Superfamily. A Possible Multifunctional Protein Acting as an Invasion Suppressor Down-Regulated in Tumors," *J. Biol. Chem.* 279:12734-12743 (2004).
Akhtar et al., "Nonviral Delivery of Synthetic siRNAs in Vivo," *J. Clin. Invest.* 117: 3623-3632 (2007).
Anonymous, "Blood-Brain Barrier Tackled," <http:www.ecancermedicalscience.com/news-insider-news.asp?itemId=326> Oct. 22, 2008.
Bertrand et al., "Transport Characteristics of a Novel Peptide Platform for CNS Therapeutics," *J. Cell Mol. Med.* published online Oct. 10, 2009.
Boules et al., "Bioactive Analogs of Neurotensin: Focus on CNS Effects," *Peptides* 27: 2523-2533 (2006).
Chari, "Targeted Cancer Therapy: Conferring Specificity to Cytotoxic Drugs," *Acc. Chem. Res.* 41:98-107 (2008).
Ché et al., "New Angiopep-Modified Doxorubicin (ANG1007) and Etoposide (ANG1009) Chemotherapeutics with Increased Brain Penetration," *J. Med. Chem.* 53: 2814-2824 (2010).
Demeule et al., "Involvement of the Low-Density Lipoprotein Receptor-Related Protein in the Transcytosis of the Brain Delivery Vector Angiopep-2," *J. Neurochem.* 106: 1534-1544 (2008).
Garsky et al., "The Synthesis of a Prodrug of Doxorubicin Designed to Provide Reduced Systemic Toxicity and Greater Target Efficacy," *J. Med. Chem.* 44: 4216-4224 (2001).
Huang et al., "Targeting Delivery of Paclitaxel into Tumor Cells via Somatostatin Receptor Endocytosis," *Chem. Biol.* 7: 453-461 (2000).
Kilic et al., "Intravenous TAT-GDNF is Protective after Focal Cerebral Ischemia in Mice," *Stroke* 34: 1304-1310 (2003).
Kumar et al., "Transvascular Delivery of Small Interfering RNA to the Central Nervous System," *Nature* 448: 39-43 (2007).
Rouselle et al., "New Advances in the Transport of Doxorubicin through the Blood-Brain Barrier by a Peptide Vector-Mediated Strategy," *Mol. Pharmacol.* 57: 679-686 (2000).
Takei et al., "A Small Interfering RNA Targeting Vascular Endothelial Growth Factor as Cancer Therapeutics," *Cancer Res.* 64: 3365-3370 (2004).
Trail et al., "Cure of Xenografted Human Carcinomas by BR96-Doxorubicin Immunoconjugates," *Science* 261:212-215 (1993).
U.S. Appl. No. 61/546,851, filed Oct. 31, 2011, Demeule et al.
Grimm et al., "Ten Year Biochemical Outcomes Following 125-Iodine Monotherapy for Early Stage Prostate Cancer." *Int. J. Rad. Oncol. Biol. Phys.* 48:146-147 (2000).
Kurzrock et al., "ANGI005: Results of a Phase I study in patients with advanced solid tumors and metastatic brain cancer" Poster B168, ACCR/NCI/EORTC Annual Meeting, 2009.
Mathupala, "Delivery of Small-interfering RNA (siRNA) to the Brain," *Exp. Opin. Ther. Pat.* 19: 137-140, (2009).
Nyalendo et al., "Impaired Tyrosine Phosphorylation of Membrane type 1-Matrix Metalloproteinase Reduces Tumor Cell Proliferation in Three-Dimensional Matrices and Abrogates Tumor Growth in Mice," *Carcinogenesis* 29:1655-1664, (2008).
Sadeghi-aliabadi et al., "Solvent optimization on Taxol extraction from *Taxus baccata* L., using HPLC and LC-MS," *DARU* 17:192-198, (2009).
Schiff and Horwitz, "Taxol Stabilizes Microtubules in Mouse Fibroblast Cells," *Proc Natl Acad Sci USA* 77:1561-1565, (1980).
Tilstra et al., "Protein Transduction: Identification, Characterization and Optimization," *Biochem. Soc. Trans.* 35:811-815, (2007).
Zhang et al., "Tat-modified Leptin is more Accessible to Hypothalamus Through Brain-blood Barrier with a Significant Inhibition of Body-weight Gain in High-fat-diet Fed Mice," *Exp. Clin. Endocrin. Diabet.* 118:31-37 (2010).
International Search Report and Written Opinion of the International Searching Authority for Application No. PCT/CA2010/001014, dated Oct. 18, 2010.
Bertrand et al., "Transport characteristics of a novel peptide platform for CNS therapeutics," J Cell Mol Med. 14(12):2827-39 (2010).
Henderson et al., "Terminal amino acid sequences and proteolytic cleavage sites of mouse mammary tumor virus env gene products," J Virol. 48(1):314-9 (1983).
Office Action and its English translation for Chinese Patent Application No. 2010800387423, dated Apr. 22, 2014 (30 pages).
Office Action and its English translation for Russian Patent Application No. 2012103240, dated Aug. 14, 2014 (9 pages).
Skosyrev et al., "The dependence of stability of the green fluorescent protein-obelin hyrbids on the nature of their constituent modules and the structure of the amino acid linker," Bioorg Khim. 27(5):323-329 (2001).
Extended European Search Report for European Patent Application No. 10793472.1, mailed Jan. 13, 2015 (9 pages).
Office Action for Russian Patent Application No. 2012103240, mailed Apr. 10, 2015 (6 pages).

* cited by examiner

| # | RT [min] | Area | Int. Type | Intens. | S/N | Chromatogram | Max. m/z | Area Frac. % |
|---|---|---|---|---|---|---|---|---|
| 1 | 0.93 | 1514.8 | Manual | 1155 | 550.4 | UV Chromatogram, 229 nm | 869.6245 | 100.0 |
| n.a. | 0.94 | n.a. | Average spectrum | n.a. | n.a. | n.a. | 1039.7438 | |

Dimerization of Angiopep-1

TFFYGGCRGKRNNFKTEEY + TFFYGGCRGKRNNFKTEEY
Angiopep-1                    Angiopep-1

↓ 2 hrs at 37°C PBS, pH 8.5

TFFYGGCRGKRNNFKTEEY
|
TFFYGGCRGKRNNFKTEEY

Angiopep-1 dimer

Figure 5

MULTIMERIC PEPTIDE CONJUGATES AND USES THEREOF

CROSS-REFERENCE TO RELATED APPLICATIONS

This Application is a U.S. National Stage Application of international patent application PCT/CA2010/001014, filed Jun. 30, 2010, which, in turn, claims benefit of U.S. Provisional Application No. 61/222,785, filed on Jul. 2, 2009, and U.S. Provisional Application No. 61/252,024, filed on Oct. 15, 2009.

BACKGROUND OF THE INVENTION

The invention relates to compounds including dimeric or multimeric peptide vectors and uses of such compounds.

The brain is shielded against potentially toxic substances by the presence of two barrier systems: the blood-brain barrier (BBB) and the blood-cerebrospinal fluid barrier (BC-SFB). The BBB is considered to be the major route for the uptake of serum ligands since its surface area is approximately 5000-fold greater than that of BCSFB. The brain endothelium, which constitutes the BBB, represents the major obstacle for the use of potential drugs against many disorders of the CNS. As a general rule, only small lipophilic molecules may pass across the BBB, i.e., from circulating systemic blood to brain. Many drugs that have a larger size or higher hydrophobicity show promising results in animal studies for treating CNS disorders. Thus, peptide and protein therapeutics are generally excluded from transport from blood to brain, owing to the negligible permeability of the brain capillary endothelial wall to these drugs.

Therapy of brain diseases can be impaired by the inability of otherwise effective therapeutic agents to cross the BBB. Thus, new strategies for transporting agents into the brain are desired.

SUMMARY OF THE INVENTION

We have now developed compounds containing dimeric or multimeric peptide vectors that are capable of crossing the blood-brain barrier (BBB) or entering particular cell types (e.g., liver, lung, spleen, kidney, and muscle) with enhanced efficiency. When these compounds are joined with (e.g., conjugated to) one or more agents, efficiency of transport across the BBB or into particular cell types is likewise enhanced. Accordingly, the present invention features multimeric peptide vectors optionally conjugated to an agent (e.g., a therapeutic agent), and use of such compounds in treatment and diagnosis of disease.

In a first aspect, the invention features a compound including the formula:

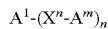

where n is or is at least 1, 2, 3, 4, 5, 6, 7, 8, 9, or 10; m is an integer from 2 to n+1; $A^1$ and each $A^m$ are, independently, a peptide vector, e.g., any described herein such as one that includes an amino acid sequence substantially identical to a sequence selected from the group consisting of SEQ ID NOS: 1-105 and 107-117 or a functional fragment thereof; and each $X^n$ is, independently, a linker joined to the adjacent peptide vectors. The compound may include the formula:

In another aspect, the invention features a compound including the formula:

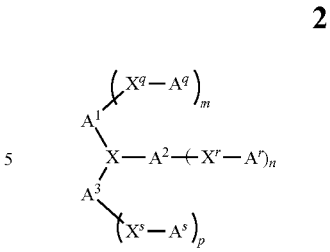

where $A^1$, $A^2$, each $A^q$, each $A^r$, and each $A^s$ are, independently, peptide vector, e.g., any described herein such as one that includes a sequence substantially identical to a sequence selected from the group consisting of SEQ ID NOS:1-105 and 107-117 or a functional fragment thereof; $A^3$ is a peptide vector including a sequence substantially identical to a sequence selected from the group consisting of SEQ ID NOS: 1-105 and 107-117 or a functional fragment thereof or is absent; X, each $X^q$, each $X^r$, and each $X^s$ are, independently, linkers that join peptide vectors; m, n, and p are, independently, 0, 1, 2, 3, 4, 5, 6, 7, 8, 9, or 10; q is an integer from 4 to m+3; r is an integer from m+4 to m+n+3; and s is an integer from m+n+4 to m+n+p+3.

Any of the above compounds may be conjugated to one or more agents (e.g., any described herein), through one or more linkers or through one or more peptide vectors.

In another aspect, the invention features a compound of including the formula:

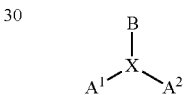

where $A^1$, X, and $A^2$ are as described above and B is an agent and is conjugated to the linker X. The invention also features a compound including the formula:

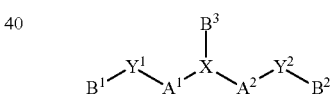

where $A^1$, X, and $A^2$ are as described above; B' is an agent, $B^2$ and $B^3$ are, independently, agents or are absent, $Y^1$ and $Y^2$ are, independently, linkers joining $A^1$ to $B^1$ and $A^2$ to $B^2$, respectively, where $Y^2$ is absent if $B^2$ is absent. The compound may include the formula:

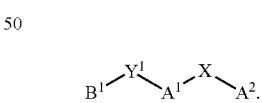

In another aspect, the invention features a compound including (a) at least two peptide vectors, where each peptide vector independently includes an amino acid sequence substantially identical to a sequence selected from the group consisting of SEQ ID NOS:1-105 and 107-117, where the peptide vectors are joined by a linker; and (b) an agent conjugated to at least one of the peptide vectors or to the linker.

Any of the above compounds may include at least one of the peptide vectors including an amino acid sequence at least 70%, 80%, 85%, 90%, 95%, or 100% identical to a sequence selected from the group consisting of SEQ ID NO:1-105 and 107-117 (e.g., Angiopep-1 (SEQ ID NO:67), Angiopep-2 (SEQ ID NO:97), cys-Angiopep-2 (SEQ ID NO:113), Angiopep-2-cys (SEQ ID NO:114), and reversed Angiopep-2 (SEQ ID NO:117)). In compounds including an agent, the agent can be a therapeutic agent (e.g., any described herein, such as an agent selected from the group consisting of an anticancer agent, a therapeutic nucleic acid, a GLP-1 agonist, leptin or a leptin analog, neurotensin or a neurotensin analog, glial-derived neurotrophic factor (GDNF) or a GDNF analog, brain-derived neurotrophic factor (BDNF) or a BDNF analog), or an antibody. The anticancer agent may be paclitaxel (Taxol), vinblastine, vincristine, etoposide, doxorubicin, cyclophosphamide, docetaxel (Taxotere®), melphalan, and chlorambucil, abarelix, aldesleukin, alemtuzumab, alitertinoin, allopurinol, altretamine, amifostine, anakinra, anastrozole, arsenic trioxide, asparaginase, azacitidine, BCG Live, bevacuzimab, bexarotene, bleomycin, bleomycin, bortezombi, bortezomib, busulfan, busulfan, calusterone, capecitabine, carboplatin, carmustine, celecoxib, cetuximab, cisplatin, cladribine, clofarabine, cytarabine, dacarbazine, dactinomycin, actinomycin D, dalteparin, darbepoetin alfa, dasatinib, daunorubicin, daunomycin, decitabine, denileukin, denileukin diftitox, dexrazoxane, dromostanolone propionate, eculizumab, epirubicin , epoetin alfa, erlotinib, estramustine, exemestane, fentany, filgrastim, floxuridine, fludarabine, fluorouracil, 5-FU, fulvestrant, gefitinib, gemcitabine, gemtuzumab ozogamicin, goserelin, histrelin, hydroxyurea, ibritumomab tiuxetan, idarubicin, ifosfamide, imatinib, Interferon alfa-2b, irinotecan, lapatinib ditosylate, lenalidomide, letrozole, leucovorin, leuprolide, levamisole, lomustine, CCNU, meclorethamine (nitrogen mustard), megestrol, mercaptopurine (6-MP), mesna, methotrexate, methoxsalen, mitomycin C, mitotane, mitoxantrone, nandrolone phenpropionate, nelarabine, nofetumomab, oprelvekin, oxaliplatin, palifermin, pamidronate, panitumumab, pegademase, pegaspargase, pegfilgrastim, peginterferon alfa-2b, pemeterxed, pentostatin, pipobroman, plicamycin (mithramycin), porfimer, procarbazine, quinacrine, rasburicase, rituximab, sargramostim, sorafenib, streptozocin, sunitinib, talc, tamoxifen, temozolomide, teniposide (VM-26), testolactone, thalidomide, thioguanine (6-TG), thiotepa, thiotepa, thiotepa, topotecan, toremifene, Tositumomab/I-131 (tositumomab), trastuzumab, trastuzumab, tretinoin (ATRA), uracil mustard, vairubicin, vinorelbine, vorinostat, zoledronate, and zoledronic acid; or a pharmaceutically acceptable salt thereof. In particular embodiments, the anticancer agent is paclitaxel, etoposide, or doxorubicin, or an analog thereof. The agent may be an RNAi agent (e.g., any RNAi agent described herein such as an RNAi agent is capable of silencing EGFR or VEGF expression). The agent may be a GLP-1 agonist (e.g., any described herein, such as exendin-4 (SEQ ID NO: 132), or an analog or fragment thereof having GLP-1 agonist activity, exendin-4 (SEQ ID NO: 132), [Lys$^{39}$]exendin-4 (SEQ ID NO: 134), or [Cys$^{32}$]exendin-4 (SEQ ID NO: 133)). The agent may be leptin or a leptin analog (e.g., any described herein, such as leptin or leptin analog is full-length human leptin, mature human leptin (amino acids 22-167 of the full length human leptin), or leptin$_{116-130}$. The agent may be neurotensin or a neurotensin analog (e.g., any described herein, such as human neurotensin, human neurotensin(8-13), or pELYENKPRRPYIL-OH, where pE represents L-pyroglutamic acid). The agent may be GDNF, BDNF, or an analog thereof (e.g., a full length GDNF or BDNF sequence or a mature form of GDNF or BDNF or is human GDNF$^{78-211}$). The antibody may be a monoclonal antibody such as an antibody directed against the amyloid-βprotein. The antibody may be selected from the group consisting of R1450 (Roche), bapineuzumab, solanezumab (LY2062430; Eli Lilly), BAN2401, PF-04360365 (Pfizer), and GSK933776A (GlaxoSmithKline). In a specific embodiment, the compound has the structure shown in FIG. 9A, or a pharmaceutically acceptable salt thereof (e.g., a TFA salt).

The compounds of the invention (e.g., those described above and in the detailed description) can be used in the treatment of disease and conditions. Such methods are as follows.

The invention also features a method of treating or treating prophylactically a subject having a cancer. The method includes administering to the patient a compound including an anticancer agent or a RNAi capable of inhibiting a gene whose expression is associated with or causes cancer (e.g., EGFR or VEGF). The cancer may be selected from the group consisting of brain cancer, hepatocellular carcinoma, breast cancer, cancers of the head and neck including various lymphomas such as mantle cell lymphoma, non-Hodgkin's lymphoma, adenoma, squamous cell carcinoma, laryngeal carcinoma, cancers of the retina, cancers of the esophagus, multiple myeloma, ovarian cancer, uterine cancer, melanoma, colorectal cancer, bladder cancer, prostate cancer, lung cancer (including non-small cell lung carcinoma), pancreatic cancer, cervical cancer, head and neck cancer, skin cancers, nasopharyngeal carcinoma, liposarcoma, epithelial carcinoma, renal cell carcinoma, gallbladder adenocarcinoma, parotid adenocarcinoma, endometrial sarcoma, and multidrug resistant cancers. The brain cancer may be selected from the group consisting of astrocytoma, pilocytic astrocytoma, dysembryoplastic neuroepithelial tumor, oligodendrogliomas, ependymoma, glioblastoma multiforme, mixed gliomas, oligoastrocytomas, medulloblastoma, retinoblastoma, neuroblastoma, germinoma, and teratoma.

The invention also features a method of treating or treating prophylactically a subject having a metabolic disorder by administering a compound including GLP-1 agonist, leptin, a leptin analog, neurotensin, or a neurotensin analog in an amount sufficient to treat the disorder. The metabolic disorder may be diabetes (e.g., type I or type II diabetes), obesity, diabetes as a consequence of obesity, hyperglycemia, dyslipidemia, hypertriglyceridemia, syndrome X, insulin resistance, impaired glucose tolerance (IGT), diabetic dyslipidemia, hyperlipidemia, a cardiovascular disease, or hypertension.

The invention also features a method of reducing food intake by, or reducing body weight of, a subject by administering a compound including GLP-1 agonist, leptin, or a leptin analog to a subject in an amount sufficient to reduce food intake or reduce body weight. The subject may be overweight, obese, or bulimic.

The invention also features a method of treating or treating prophylactically a disorder selected from the group consisting of anxiety, movement disorder, aggression, psychosis, seizures, panic attacks, hysteria, sleep disorders, Alzheimer's disease, and Parkinson's disease by administering a compound including a GLP-1 agonist to a subject in an amount sufficient to treat or prevent the disorder.

The invention also features a method of increasing neurogenesis in a subject by administering to the subject and effective amount of a compound including a GLP-1 agonist to the subject. The subject may be suffering from Parkinson's Disease, Alzheimer's Disease, Huntington's Disease, ALS, stroke, ADD, or a neuropsychiatric syndrome. The increase in neurogenesis may improve learning or enhances neuroprotection in the subject.

The invention also features a method for converting liver stem/progenitor cells into functional pancreatic cells; preventing beta-cell deterioration and stimulation of beta-cell proliferation; treating obesity; suppressing appetite and inducing satiety; treating irritable bowel syndrome; reducing the morbidity and/or mortality associated with myocardial infarction and stroke; treating acute coronary syndrome characterized by an absence of Q-wave myocardial infarction; attenuating post-surgical catabolic changes; treating hibernating myocardium or diabetic cardiomyopathy; suppressing plasma blood levels of norepinepherine; increasing urinary sodium excretion, decreasing urinary potassium concentration; treating conditions or disorders associated with toxic hypervolemia, renal failure, congestive heart failure, nephrotic syndrome, cirrhosis, pulmonary edema, and hypertension; inducing an inotropic response and increasing cardiac contractility; treating polycystic ovary syndrome; treating respiratory distress; improving nutrition via a non-alimentary route, i.e., via intravenous, subcutaneous, intramuscular, peritoneal, or other injection or infusion; treating nephropathy; treating left ventricular systolic dysfunction (e.g., with abnormal left ventricular ejection fraction); inhibiting antroduodenal motility (e.g., for the treatment or prevention of gastrointestinal disorders such as diarrhea, postoperative dumping syndrome and irritable bowel syndrome, and as premedication in endoscopic procedures; treating critical illness polyneuropathy (CIPN) and systemic inflammatory response syndrome (SIRS; modulating triglyceride levels and treating dyslipidemia; treating organ tissue injury caused by reperfusion of blood flow following ischemia; or treating coronary heart disease risk factor (CHDRF) syndrome in a subject by administering and effective amount of a compound including a GLP-1 agonist to the subject.

The invention also features a method of increasing GLP-1 receptor activity in a subject by administering a compound including a GLP-1 agonist to a subject in an amount sufficient to increase GLP-1 receptor activity.

The invention also features a method of reducing body temperature of a subject, the method including administering a compound including neurotensin or a neurotensin analog in a sufficient amount to reduce body temperature. The subject may be suffering from or has suffered from cerebral ischemia, cardiac ischemia, or a nerve injury. The nerve injury may be a spinal cord injury.

The invention also features a method of treating pain or prophylactically treating pain in a subject, the method including administering a compound of including neurotensin or a neurotensin analog in an amount sufficient to treat the pain. The pain may be an acute pain selected from the group consisting of mechanical pain, heat pain, cold pain, ischemic pain, and chemical-induced pain. The pain may be peripheral or central neuropathic pain, inflammatory pain, migraine-related pain, headache-related pain, irritable bowel syndrome-related pain, fibromyalgia-related pain, arthritic pain, skeletal pain, joint pain, gastrointestinal pain, muscle pain, angina pain, facial pain, pelvic pain, claudication, postoperative pain, post traumatic pain, tension-type headache, obstetric pain, gynecological pain, or chemotherapy-induced pain.

The invention also features a method of treating or treating prophylactically a subject having a psychotic disorder (e.g., schizophrenia), the method including administering a compound including neurotensin or a neurotensin analog in an amount sufficient to treat the disorder.

The invention also features a method of treating drug addiction or drug abuse in a subject, the method including administering to the subject a compound including neurotensin or a neurotensin analog in an amount sufficient to treat the addiction or abuse. The drug may be a psychostimulant (e.g., amphetamine, methamphetamine, 3,4-methylenedioxymethamphetamine, nicotine, cocaine, methylphenidate, and arecoline)

The invention also features a method of treating or treating prophylactically a neurological disorder in a subject, the method including administering to the subject in an amount sufficient to treat or prevent the disorder (e.g., schizophrenia).

The invention also features a method of treating or treating prophylactically a subject having a neurodegenerative disorder, the method including administering to the subject an effective amount of a compound including GDNF, BDNF, or an analog thereof. The neurodegenerative disorder may be selected from the group consisting of a polyglutamine expansion disorder, fragile X syndrome, fragile XE mental retardation, Friedreich's ataxia, myotonic dystrophy, spinocerebellar ataxia type 8, and spinocerebellar ataxia type 12, Alexander disease, Alper's disease, Alzheimer's disease, amyotrophic lateral sclerosis (ALS), ataxia telangiectasia, Batten disease (Spielmeyer-Vogt-Sjogren-Batten disease), Canavan disease, Cockayne syndrome, corticobasal degeneration, Creutzfeldt-Jakob disease, ischemia stroke, Krabbe disease, Lewy body dementia, multiple sclerosis, multiple system atrophy, Parkinson's disease, Pelizaeus-Merzbacher disease, Pick's disease, primary lateral sclerosis, Refsum's disease, Sandhoff disease, Schilder's disease, spinal cord injury, spinal muscular atrophy, Steele-Richardson-Olszewski disease, and Tabes dorsalis. In certain embodiments, the polyglutamine repeat disease is Huntington's disease (HD), dentatorubropallidoluysian atrophy, Kennedy's disease (also referred to as spinobulbar muscular atrophy), or a spinocerebellar ataxia selected from the group consisting of type 1, type 2, type 3 (Machado-Joseph disease), type 6, type 7, and type 17).

The invention also features a method of treating a subject having a neuronal damage, the method including administering to the subject an effective amount of a compound including GDNF, BDNF, or an analog thereof. The neuronal damage may be caused by an ischemic stroke, a hemorrhagic stroke, or a spinal cord injury.

The invention also features a method of treating a subject having depression or schizophrenia, the method including administering to the subject an effective amount of a compound including GDNF, BDNF, or an analog thereof.

The invention also features a method of treating a subject having a disease related to the amyloid-β protein (e.g., Alzheimer's disease or cerebral amyloid angiopathy) by administering to said patient an effective amount of a therapeutic antibody (e.g., an antibody that specifically binds amyloid-β or a fragment thereof).

In any of the above methods, the subject may be a human.

In the treatment methods of the invention, in certain embodiments, the compound is administered at a lower (e.g., less than 95%, 75%, 60%, 50%, 40%, 30%, 25%, 10%, 5%, or 1%) equivalent dosage as compared to the recommended dosage of the unconjugated agent. In other embodiments, the compound is administered at a higher (1.5×, 2×, 2.5×, 3.0×, 5×, 8×, 10×, 15×, 20×, 25×) equivalent dosage than a dosage recommended for the unconjugated agent.

In any of the above aspects, the peptide vector may be a polypeptide substantially identical to any of the sequences set Table 1, or a fragment thereof. In certain embodiments, the peptide vector has a sequence of Angiopep-1 (SEQ ID NO:67), Angiopep-2 (SEQ ID NO:97), Angiopep-3 (SEQ ID NO:107), Angiopep-4a (SEQ ID NO:108), Angiopep-4b (SEQ ID NO:109), Angiopep-5 (SEQ ID NO:110), Angiopep-6 (SEQ ID NO:111), Angiopep-7 (SEQ ID NO:112) or reversed Angiopep-2 (SEQ ID NO:117)). The peptide vector or compound of the invention may be efficiently transported into a particular cell type (e.g., any one, two, three, four, or five of liver, lung, kidney, spleen, and muscle) or may cross the mammalian BBB efficiently (e.g., Angiopep-1, -2, -3, -4a, -4b, -5, and -6). In another embodiment, the peptide vector or compound is able to enter a particular cell type (e.g., any one, two, three, four, or five of liver, lung, kidney, spleen, and muscle) but does not cross the BBB efficiently (e.g., a conjugate including Angiopep-7). The peptide vector may be of any length, for example, at least 6, 7, 8, 9, 10, 11, 12, 13, 14, 15, 16, 17, 18, 19, 20, 21, 25, 35, 50, 75, 100, 200, or 500 amino acids, or any range between these numbers. In certain embodiments, the peptide vector is 10 to 50 amino acids in length. The polypeptide may be produced by recombinant genetic technology or chemical synthesis.

TABLE 1

Exemplary Peptide Vectors

| SEQ ID NO: | Sequence |
|---|---|
| 1 | T F V Y G G C R A K R N N F K S A E D |
| 2 | T F Q Y G G C M G N G N N F V T E K E |
| 3 | P F F Y G G C G G N R N N F D T E E Y |
| 4 | S F Y Y G G C L G N K N N Y L R E E E |
| 5 | T F F Y G G C R A K R N N F K R A K Y |
| 6 | T F F Y G G C R G K R N N F K R A K Y |
| 7 | T F F Y G G C R A K K N N Y K R A K Y |
| 8 | T F F Y G G C R G K K N N F K R A K Y |
| 9 | T F Q Y G G C R A K R N N F K R A K Y |
| 10 | T F Q Y G G C R G K K N N F K R A K Y |
| 11 | T F F Y G G C L G K R N N F K R A K Y |
| 12 | T F F Y G G S L G K R N N F K R A K Y |
| 13 | P F F Y G G C G G K K N N F K R A K Y |
| 14 | T F F Y G G C R G K G N N Y K R A K Y |
| 15 | P F F Y G G C R G K R N N F L R A K Y |
| 16 | T F F Y G G C R G K R N N F K R E K Y |
| 17 | P F F Y G G C R A K K N N F K R A K E |
| 18 | T F F Y G G C R G K R N N F K R A K D |
| 19 | T F F Y G G C R A K R N N F D R A K Y |
| 20 | T F F Y G G C R G K K N N F K R A E Y |
| 21 | P F F Y G G C G A N R N N F K R A K Y |
| 22 | T F F Y G G C G G K K N N F K T A K Y |
| 23 | T F F Y G G C R G N R N N F L R A K Y |
| 24 | T F F Y G G C R G N R N N F K T A K Y |
| 25 | T F F Y G G S R G N R N N F K T A K Y |
| 26 | T F F Y G G C L G N G N N F K R A K Y |
| 27 | T F F Y G G C L G N R N N F L R A K Y |
| 28 | T F F Y G G C L G N R N N F K T A K Y |
| 29 | T F F Y G G C R G N G N N F K S A K Y |
| 30 | T F F Y G G C R G K K N N F D R E K Y |
| 31 | T F F Y G G C R G K R N N F L R E K E |
| 32 | T F F Y G G C R G K G N N F D R A K Y |
| 33 | T F F Y G G S R G K G N N F D R A K Y |
| 34 | T F F Y G G C R G N G N N F V T A K Y |
| 35 | P F F Y G G C G G K G N N Y V T A K Y |
| 36 | T F F Y G G C L G K G N N F L T A K Y |
| 37 | S F F Y G G C L G N K N N F L T A K Y |
| 38 | T F F Y G G C G G N K N N F V R E K Y |
| 39 | T F F Y G G C M G N K N N F V R E K Y |
| 40 | T F F Y G G S M G N K N N F V R E K Y |
| 41 | P F F Y G G C L G N R N N Y V R E K Y |
| 42 | T F F Y G G C L G N R N N F V R E K Y |
| 43 | T F F Y G G C L G N K N N Y V R E K Y |
| 44 | T F F Y G G C G G N G N N F L T A K Y |
| 45 | T F F Y G G C R G N R N N F L T A E Y |
| 46 | T F F Y G G C R G N G N N F K S A E Y |
| 47 | P F F Y G G C L G N K N N F K T A E Y |
| 48 | T F F Y G G C R G N R N N F K T E E Y |
| 49 | T F F Y G G C R G K R N N F K T E E D |
| 50 | P F F Y G G C G G N G N N F V R E K Y |
| 51 | S F F Y G G C M G N G N N F V R E K Y |
| 52 | P F F Y G G C G G N G N N F L R E K Y |
| 53 | T F F Y G G C L G N G N N F V R E K Y |
| 54 | S F F Y G G C L G N G N N Y L R E K Y |
| 55 | T F F Y G G S L G N G N N F V R E K Y |
| 56 | T F F Y G G C R G N G N N F V T A E Y |
| 57 | T F F Y G G C L G K G N N F V S A E Y |
| 58 | T F F Y G G C L G N R N N F D R A E Y |
| 59 | T F F Y G G C L G N R N N F L R E E Y |
| 60 | T F F Y G G C L G N K N N Y L R E E Y |
| 61 | P F F Y G G C G G N R N N Y L R E E Y |
| 62 | P F F Y G G S G G N R N N Y L R E E Y |
| 63 | M R P D F C L E P P Y T G P C V A R I |
| 64 | A R I I R Y F Y N A K A G L C Q T F V Y G |
| 65 | Y G G C R A K R N N Y K S A E D C M R T C G |
| 66 | P D F C L E P P Y T G P C V A R I I R Y F Y |
| 67 | T F F Y G G C R G K R N N F K T E E Y |

TABLE 1 -continued

Exemplary Peptide Vectors

| SEQ ID NO: | |
|---|---|
| 68 | K F F Y G G C R G K R N N F K T E E Y |
| 69 | T F Y Y G G C R G K R N N Y K T E E Y |
| 70 | T F F Y G G S R G K R N N F K T E E Y |
| 71 | C T F F Y G C C R G K R N N F K T E E Y |
| 72 | T F F Y G G C R G K R N N F K T E E Y C |
| 73 | C T F F Y G S C R G K R N N F K T E E Y |
| 74 | T F F Y G G S R G K R N N F K T E E Y C |
| 75 | P F F Y G G C R G K R N N F K T E E Y |
| 76 | T F F Y G G C R G K R N N F K T K E Y |
| 77 | T F F Y G G K R G K R N N F K T E E Y |
| 78 | T F F Y G G C R G K R N N F K T K R Y |
| 79 | T F F Y G G K R G K R N N F K T A E Y |
| 80 | T F F Y G G K R G K R N N F K T A G Y |
| 81 | T F F Y G G K R G K R N N F K R E K Y |
| 82 | T F F Y G G K R G K R N N F K R A K Y |
| 83 | T F F Y G G C L G N R N N F K T E E Y |
| 84 | T F F Y G C G R G K R N N F K T E E Y |
| 85 | T F F Y G G R C G K R N N F K T E E Y |
| 86 | T F F Y G G C L G N G N N F D T E E E |
| 87 | T F Q Y G G C R G K R N N F K T E E Y |
| 88 | Y N K E F G T F N T K G C E R G Y R F |
| 89 | R F K Y G G C L G N M N N F E T L E E |
| 90 | R F K Y G G C L G N K N N F L R L K Y |
| 91 | R F K Y G G C L G N K N N Y L R L K Y |
| 92 | K T K R K R K K Q R V K I A Y E E I F K N Y |
| 93 | K T K R K R K K Q R V K I A Y |
| 94 | R G G R L S Y S R R F S T S T G R |
| 95 | R R L S Y S R R R F |
| 96 | R Q I K I W F Q N R R M K W K K |
| 97 | T F F Y G G S R G K R N N F K T E E Y |
| 98 | M R P D F C L E P P Y T G P C V A R I I R Y F Y N A K A G L C Q T F V Y G G C R A K R N N F K S A E D C M R T C G G A |
| 99 | T F F Y G G C R G K R N N F K T K E Y |
| 100 | R F K Y G G C L G N K N N Y L R L K Y |
| 101 | T F F Y G G C R A K R N N F K R A K Y |
| 102 | N A K A G L C Q T F V Y G G C L A K R N N F E S A E D C M R T C G G A |
| 103 | Y G G C R A K R N N F K S A E D C M R T C G G A |

TABLE 1 -continued

Exemplary Peptide Vectors

| SEQ ID NO: | |
|---|---|
| 104 | G L C Q T F V Y G G C R A K R N N F K S A E |
| 105 | L C Q T F V Y G G C E A K R N N F K S A |
| 107 | T F F Y G G S R G K R N N F K T E E Y |
| 108 | R F F Y G G S R G K R N N F K T E E Y |
| 109 | R F F Y G G S R G K R N N F K T E E Y |
| 110 | R F F Y G G S R G K R N N F R T E E Y |
| 111 | T F F Y G G S R G K R N N F R T E E Y |
| 112 | T F F Y G G S R G R R N N F R T E E Y |
| 113 | C T F F Y G G S R G K R N N F K T E E Y |
| 114 | T F F Y G G S R G K R N N F K T E E Y C |
| 115 | C T F F Y G G S R G R R N N F R T E E Y |
| 116 | T F F Y G G S R G R R N N F R T E E Y C |
| 117 | Y E E T K F N N R K G R S G G Y F F T |

Polypeptides Nos. 5, 67, 76, and 91, include the sequences of SEQ ID NOS: 5, 67, 76, and 91, respectively, and are amidated at the C-terminus.
Polypeptides Nos. 107, 109, and 110 include the sequences of SEQ ID NOS: 97, 109, and 110, respectively, and are acetylated at the N-terminus.

In any of the above aspects, the peptide vector may include an amino acid sequence having the formula:

X1-X2-X3-X4-X5-X6-X7-X8-X9-X10-X11-X12-X13-X14-X15-X16-X17-X18-X19 where each of X1-X19 (e.g., X1-X6, X8, X9, X11-X14, and X16-X19) is, independently, any amino acid (e.g., a naturally occurring amino acid such as Ala, Arg, Asn, Asp, Cys, Gln, Glu, Gly, His, Ile, Leu, Lys, Met, Phe, Pro, Ser, Thr, Trp, Tyr, and Val) or absent and at least one (e.g., 2 or 3) of X1, X10, and X15 is arginine. In some embodiments, X7 is Ser or Cys; or X10 and X15 each are independently Arg or Lys. In some embodiments, the residues from X1 through X19, inclusive, are substantially identical to any of the amino acid sequences of any one of SEQ ID NOS:1-105 and 107-117 (e.g., Angiopep-1, Angiopep-2, Angiopep-3, Angiopep-4a, Angiopep-4b, Angiopep-5, Angiopep-6, Angiopep-7, and reversed Angiopep-2). In some embodiments, at least one (e.g., 2, 3, 4, or 5) of the amino acids X1-X19 is Arg. In some embodiments, the polypeptide has one or more additional cysteine residues at the N-terminal of the polypeptide, the C-terminal of the polypeptide, or both.

In certain embodiments of any of the above aspects, the peptide vector or a peptide therapeutic described herein is modified (e.g., as described herein). The peptide or polypeptide may be amidated, acetylated, or both. Such modifications may be at the amino or carboxy terminus of the polypeptide. The peptide or polypeptide may also include peptidomimetics (e.g., those described herein) of any of the polypeptides described herein.

In certain embodiments, the peptide vector or a peptide therapeutic described herein has an amino acid sequence described herein with at least one amino acid substitution (e.g., 2, 3, 4, 5, 6, 7, 8, 9, 10, 11, or 12 substitutions), insertion, or deletion or is substantially identical to an amino acid sequence described herein. The peptide or polypeptide may contain, for example, 1 to 12, 1 to 10, 1 to 5, or 1 to 3 amino acid substitutions, for example, 1 to 10 (e.g., to 9, 8, 7, 6, 5, 4, 3, 2) amino acid substitutions. The amino acid substitution(s) may be conservative or non-conservative. For example, the peptide vector may have an arginine at one, two, or three of the positions corresponding to positions 1, 10, and 15 of the amino acid sequence of any of SEQ ID NO:1, Angiopep-1, Angiopep-2, Angiopep-3, Angiopep-4a, Angiopep-4b, Angiopep-5, Angiopep-6, Angiopep-7, and reversed Angiopep-2. In certain embodiments, the BDNF, GDNF, or related molecule may have a cysteine or lysine substitution or addition at any position (e.g., a lysine substitution at the N- or C-terminal position).

In any of the above aspects, the compound may specifically exclude a polypeptide including or consisting of any of SEQ ID NOS:1-105 and 107-117 (e.g., Angiopep-1, Angiopep-2, Angiopep-3, Angiopep-4a, Angiopep-4b, Angiopep-5, Angiopep-6, Angiopep-7, and reversed Angiopep-2). In some embodiments, the polypeptides and compounds of the invention exclude the polypeptides of SEQ ID NOs:102, 103, 104, and 105.

By "fragment" is meant a portion of a full-length amino acid or nucleic acid sequence (e.g., any sequence described herein). Fragments may include at least 4, 5, 6, 8, 10, 15, 20, 25, 30, 35, 40, 45, 50, 60, 70, 75, 80, 90, 100, 125, 150, 200, 500, 1000, 1500, 2000, or 5000 amino acids or nucleic acids of the full length sequence. A fragment may retain at least one of the biological activities of the full length protein.

By "substantially identical" is meant a polypeptide or nucleic acid exhibiting at least 35%, 40%, 50%, 55%, 60%, 65%, 70%, 75%, 85%, 90%, 95%, or even 99% identity to a reference amino acid or nucleic acid sequence. For polypeptides, the length of comparison sequences will generally be at least 4 (e.g., at least 5, 6, 7, 8, 9, 10, 11, 12, 13, 14, 15, 16, 17, 18, 19, 20, 25, 50, or 100) amino acids. For nucleic acids, the length of comparison sequences will generally be at least 60 nucleotides, preferably at least 90 nucleotides, and more preferably at least 120 nucleotides, or full length. It is to be understood herein that gaps may be found between the amino acids of sequences that are identical or similar to amino acids of the original polypeptide. The gaps may include no amino acids, one or more amino acids that are not identical or similar to the original polypeptide. Percent identity may be determined, for example, with n algorithm GAP, BESTFIT, or FASTA in the Wisconsin Genetics Software Package Release 7.0, using default gap weights.

By "peptide vector" is meant a compound or molecule such as a polypeptide or a peptidomimetic that can be transported into a particular cell type (e.g., liver, lungs, kidney, spleen, or muscle) or across the BBB. The vector may be attached to (covalently or not) or conjugated to an agent and thereby may be able to transport the agent into a particular cell type or across the BBB. In certain embodiments, the vector may bind to receptors present on cancer cells or brain endothelial cells and thereby be transported into the cancer cell or across the BBB by transcytosis. The vector may be a molecule for which high levels of transendothelial transport may be obtained, without affecting the cell or BBB integrity. The vector may be a polypeptide or a peptidomimetic and may be naturally occurring or produced by chemical synthesis or recombinant genetic technology.

By "agent" is meant any compound having at least one biological activity. Agents include both diagnostic and therapeutic agents.

By "therapeutic agent" is meant an agent that is capable of being used in the treatment or prophylactic treatment of a disease or condition.

By "RNAi agent" is meant any agent or compound that exerts a gene silencing effect by way of an RNA interference pathway. RNAi agents include any nucleic acid molecules that are capable of mediating sequence-specific RNAi, for example, a short interfering RNA (siRNA), double-stranded RNA (dsRNA), microRNA (miRNA), short hairpin RNA (shRNA), short interfering oligonucleotide, short interfering nucleic acid, short interfering modified oligonucleotide, chemically-modified siRNA, and post-transcriptional gene silencing RNA (ptgsRNA).

By "treating" a disease, disorder, or condition in a subject is meant reducing at least one symptom of the disease, disorder, or condition by administrating a therapeutic agent to the subject.

By "treating prophylactically" a disease, disorder, or condition in a subject is meant reducing the frequency of occurrence or severity of (e.g., preventing) a disease, disorder or condition by administering to the subject a therapeutic agent to the subject prior to the appearance of a disease symptom or symptoms.

By "subject" is meant a human or non-human animal (e.g., a mammal).

By "equivalent dosage" is meant the amount of a compound of the invention required to achieve the same molar amount of agent in the compound of the invention, as compared to the unconjugated molecule.

By a polypeptide which is "efficiently transported across the BBB" is meant a polypeptide that is able to cross the BBB at least as efficiently as Angiopep-6 (i.e., greater than 38.5% that of Angiopep-1 (250 nM) in the in situ brain perfusion assay described in U.S. patent application Ser. No. 11/807, 597, filed May 29, 2007, hereby incorporated by reference). Accordingly, a polypeptide which is "not efficiently transported across the BBB" is transported to the brain at lower levels (e.g., transported less efficiently than Angiopep-6).

By a polypeptide or compound which is "efficiently transported to a particular cell type" is meant that the polypeptide or compound is able to accumulate (e.g., either due to increased transport into the cell, decreased efflux from the cell, or a combination thereof) in that cell type to at least a 10% (e.g., 25%, 50%, 100%, 200%, 500%, 1,000%, 5,000%, or 10,000%) greater extent than either a control substance, or, in the case of a conjugate, as compared to the unconjugated agent. Such activities are described in detail in International Application Publication No. WO 2007/009229, hereby incorporated by reference.

Other features and advantages of the invention will be apparent from the following Detailed Description, the drawings, and the claims.

BRIEF DESCRIPTION OF THE DRAWINGS

FIG. 5 is a schematic diagram showing formation of the Angiopep-1 (SEQ ID NO: 67) dimmer formed through disulfide bonds.

DETAILED DESCRIPTION

Figure 1:
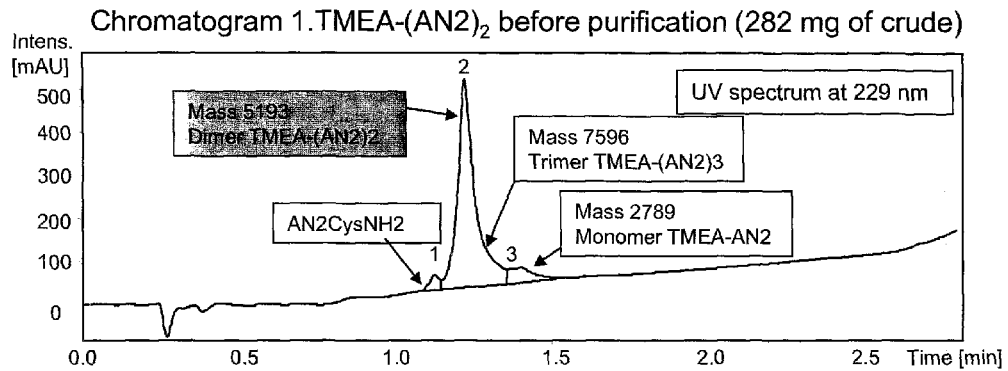
FIG. 1 is a set of graphs showing the TMEA-(Angiopep-2)$_2$ conjugate before (Chromatogram 1) and after (Chromatogram 2) purification.
Figure 1:
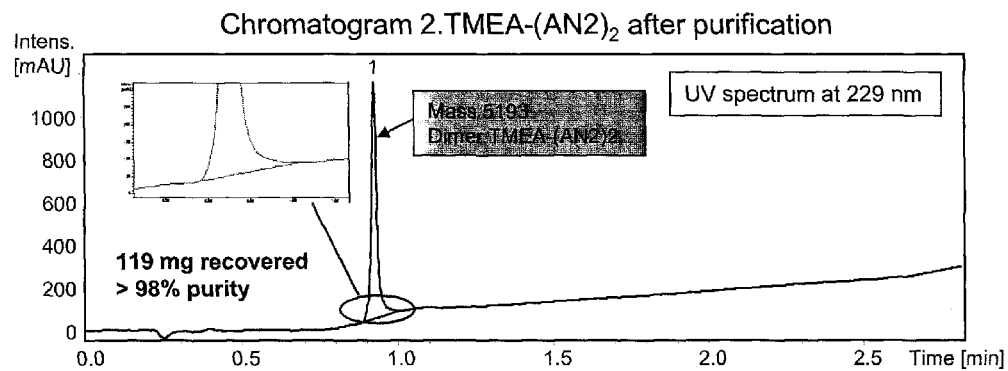

We have now developed multimeric forms of peptide vectors that are able to cross the blood-brain barrier (BBB) or are able to enter particular cell types (e.g., liver, spleen, kidney, muscle, ovary) with enhanced efficiency. These multimeric forms, when conjugated to a therapeutic agent, can transport the agent across the BBB or into particular cells. In some cases, the multimeric (e.g., dimeric) form of the peptide vector is capable of crossing the BBB or entering particular cell types more efficiently, and in certain cases as described herein, far more efficiently, than the monomeric form of the peptide vector. This increased efficiency in transport may allow for lower dosages of the therapeutic as compared either to the unconjugated agent or to the agent conjugated to a monomeric form of the peptide vector. In other cases, by directing the agent more efficiently to its target tissue(s), the compounds of the invention may administered in higher dosages than either the unconjugated agent or the agent conjugated to a monomeric form of the peptide vector, as the greater targeting efficiency can reduce side effects. Compounds including such multimers and their use in treatment of disease are described in detail below.

Multimeric Peptide Vectors

The compounds of the invention feature a multimeric (e.g., dimeric) form of the peptide vectors described herein. The peptide vectors are joined by a chemical bond either directly (e.g., a covalent bond such as a disulfide or a peptide bond) or indirectly (e.g., through a linker such as those described herein). Exemplary multimeric peptides are described below.

Peptides Joined by Linkers

In some embodiments, the peptide vectors described herein are joined by a chemical linker. Such chemical linkers are known in the art and are described herein. Any appropriate linker can be used to produce a multimer of the invention. Exemplary chemical linkers include those described below.

In certain embodiments, the multimeric peptide vector is a dimer having the formula:

$$A^1\text{-}X\text{-}A^2$$

where $A^1$ and $A^2$ are each, independently, a peptide vector (e.g., any peptide vector described herein) and X is a linker. The linker may be any linker described herein. In particular embodiments, the linker contains a maleimido moiety and binds to a cysteine present in the peptide vector (e.g., a peptide vector to which an N-terminal or C-terminal cysteine residue has been added).

In other embodiments, the multimeric peptide vector has or includes a formula selected from the group consisting of:

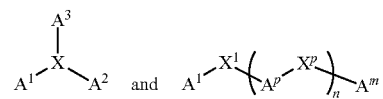

where $A^1$, $A^2$, $A^3$, $A^m$, and each $A^p$ are, independently, a peptide vector (e.g., any peptide vector described herein); X, $X^1$, and each $X^p$ are, independently, a linker (e.g., any linker described herein) that joins together two peptide vectors; n is 0, 1, 2, 3, 4, 5, 6, 7, 8, 9, or 10; m is n+2; and p is an integer from 2 to n+1. In particular embodiments, n is 1, and the compound has the formula:

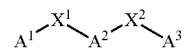

Higher order multimers can also be described by the formula:

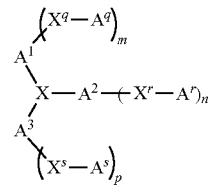

where $A^1$, $A^2$, each $A^q$, each $A^r$, and each $A^s$ are, independently, peptide vectors (e.g., any of those described herein); $A^3$ is a peptide vector or is absent; X, each $X^q$, each $X^r$, and each $X^s$ are, independently, linkers that join peptide vectors; m, n, and p are each, independently, 0, 1, 2, 3, 4, 5, 6, 7, 8, 9, or 10; q is an integer from 4 to m+3; r is an integer from m+4 to m+n+3; and s is an integer from m+n+4 to m+n+p+3.

Fusion Protein Multimers

In other embodiments, the multimeric peptide is in the form of a fusion protein. The fusion protein may contain 2, 3, 4, 5, or more peptide vectors, either joined directly by a peptide bond, or through peptide linkers. In one example, fusion protein dimers are described by the formula:

where $A^1$ and $A^2$ are, independently, a peptide vector (e.g., an amino acid sequence substantially identical to a sequence selected from the group consisting of SEQ ID NO:1-105 and 107-117, or a functional fragment thereof) and X is either (a) a peptide bond that joins $A^1$ and $A^2$ or (b) one or more amino acids joined to $A^1$ and $A^2$ by peptide bonds. In certain embodiments, the peptide is a single amino acid (e.g., a naturally occurring amino acid), a flexible linker, a rigid linker, or an a-helical linker. Exemplary peptide linkers that can be used in the invention are described in the section entitled "peptide linkers" below. In certain embodiments $A^1$ and $A^2$ are the same peptide vector.

Fusion protein multimers can be described by the formula:

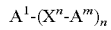

where n is or is at least 1, 2, 3, 4, 5, 6, 7, 8, 9, or 10; m is an integer from 2 to n+1; $A^1$ and each $A^m$ are, independently, a peptide vector (e.g., an amino acid sequence substantially identical to a sequence selected from the group consisting of SEQ ID NO:1-105 and 107-117, or a functional fragment thereof); and each $X^n$ is, independently, either (a) a peptide bond that joins $A^1$ and $A^2$ or (b) one or more amino acids joined to the adjacent peptide vector ($A^1$ or $A^n$) by peptide bonds.

The peptide vectors forming the multimer, in certain embodiments, may each be fewer than 100, 50, 40, 35, 30, 25, 24, 23, 22, 21, 20, 19, 18, 17, 16, or 15 amino acids in length. The fusion protein may be fewer than 1,000, 500, 250, 150, 100, 90, 80, 75, 70, 65, 60, 55, 50, 45, 40, or 35 amino acids in length.

Linkers

The peptide vectors may be bound to each other or to a therapeutic agent either directly (e.g., through a covalent bond such as a peptide bond) or may be bound through a linker. Linkers include chemical linking agents (e.g., cleavable linkers) and peptides. Any of the linkers described below may be used in the compounds of the invention.

Chemical Linking Agents

In some embodiments, the linker is a chemical linking agent. The peptide vector may be conjugated through sulfhydryl groups, amino groups (amines), or any appropriate reactive group. Homobifunctional and heterobifunctional cross-linkers (conjugation agents) are available from many commercial sources. Sites available for cross-linking may be found on the peptides and agents described herein. The cross-linker may comprise a flexible arm, e.g., 2, 3, 4, 5, 6, 7, 8, 9, 10, 11, 12, 13, 14, or 15 carbon atoms. Exemplary cross-linkers include $BS^3$ ([Bis(sulfosuccinimidyl)suberate]; $BS^3$ is a homobifunctional N-hydroxysuccinimide ester that targets accessible primary amines), NHS/EDC (N-hydroxysuccinimide and 1-ethyl-3-(3-dimethylaminopropyl)carbodiimide; NHS/EDC allows for the conjugation of primary amine groups with carboxyl groups), sulfo-EMCS ([N-ε-maleimidocaproic acid]hydrazide; sulfo-EMCS are heterobifunctional reactive groups (maleimide and NHS-ester) that are reactive toward sulfhydryl and amino groups), hydrazide (most proteins contain exposed carbohydrates and hydrazide is a useful reagent for linking carboxyl groups to primary amines), SATA (N-succinimidyl-S-acetylthioacetate; SATA is reactive towards amines and adds protected sulfhydryls groups), and BMOE (bis-maleimidoethane).

To form covalent bonds, one can use as a chemically reactive group a wide variety of active carboxyl groups (e.g., esters) where the hydroxyl moiety is physiologically acceptable at the levels required to modify the peptide. Particular agents include N-hydroxysuccinimide (NHS), N-hydroxysulfosuccinimide (sulfo-NHS), maleimide-benzoyl-succinimide (MBS), gamma-maleimido-butyryloxy succinimide ester (GMBS), maleimido propionic acid (MPA), maleimido hexanoic acid (MHA), and maleimido undecanoic acid (MUA).

Primary amines are the principal targets for NHS esters. Accessible α-amine groups present on the N-termini of proteins and the ε-amine of lysine react with NHS esters. Thus, compounds of the invention can include a linker having a NHS ester conjugated to an N-terminal amino of a peptide or to an ε-amine of lysine. An amide bond is formed when the NHS ester conjugation reaction reacts with primary amines releasing N-hydroxysuccinimide. These succinimide containing reactive groups are herein referred to as succinimidyl groups. In certain embodiments of the invention, the functional group on the protein will be a thiol group and the chemically reactive group will be a maleimido-containing group such as gamma-maleimide-butrylamide (GMBA or MPA). Such maleimide containing groups are referred to herein as maleido groups.

The maleimido group is most selective for sulfhydryl groups on peptides when the pH of the reaction mixture is 6.5-7.4. At pH 7.0, the rate of reaction of maleimido groups with sulfhydryls (e.g., thiol groups on proteins such as serum albumin or IgG) is 1000-fold faster than with amines. Thus, a stable thioether linkage between the maleimido group and the sulfhydryl can be formed. Accordingly, a compound of the invention can include a linker having a maleimido group conjugated to a sulfhydryl group of a peptide vector or of an agent.

Amine-to-amine linkers include NHS esters and imidoesters. Exemplary NHS esters are DSG (disuccinimidyl glutarate), DSS (disuccinimidyl suberate), $BS^3$ (bis[sulfosuccinimidyl]suberate), TSAT (tris-succinimidyl aminotriacetate), variants of bis-succinimide ester-activated compounds that include a polyethylene glycol spacer such as $BS(PEG)_n$, where n is 1-20 (e.g., $BS(PEG)_5$ and $BS(PEG)_9$), DSP (Dithiobis[succinimidyl propionate]), DTSSP (3,3'-dithiobis [sulfosuccinimidylpropionate]), DST (disuccinimidyl tartarate), BSOCOES (bis[2-(succinimidooxycarbonyloxy) ethyl]sulfone), EGS (ethylene glycol bis [succinimidylsuccinate]), and sulfo-EGS (ethylene glycol bis [sulfosuccinimidylsuccinate]). Imidoesters include DMA (dimethyl adipimidate.2 HCl), DMP (dimethyl pimelimidate.2HCl), DMS (dimethyl suberimidate.2HCl), and DTBP (dimethyl 3,3'-dithiobispropionimidate.2HCl). Other amine-to-amine linkers include DFDNB (1,5-difluoro-2,4-dinitrobenzene) and THPP (β-[tris(hydroxymethyl)phosphino]propionic acid (betaine)).

The linker may be a sulfhydryl-to-sulfhydry linker. Such linkers include maleimides and pyridyldithiols. Exemplary maleimides include BMOE (bis-maleimidoethane), BMB (1,4-bismaleimidobutane), BMH (bismaleimidohexane), TMEA (tris[2-maleimidoethyl]amine), BM(PEG)2 1,8-bis-maleimidodiethyleneglycol) or $BM(PEG)_n$, where n is 1 to 20 (e.g., 2 or 3), BMDB (1,4 bismaleimidyl-2,3-dihydroxybutane), and DTME (dithio-bismaleimidoethane). Exemplary pyridyldithiols include DPDPB (1,4-di-[3'-(2'-pyridyldithio)-propionamido]butane). Other sulfhydryl linkers include HBVS (1,6-hexane-bis-vinylsulfone).

The linker may be an amine-to-sulfhydryl linker, which includes NHS ester/maliemide compounds. Examples of these compounds are AMAS (N-(α-maleimidoacetoxy)succinimide ester), BMPS(N-[β-maleimidopropyloxy]succinimide ester), GMBS (N-[γ-maleimidobutyryloxy]succinimide ester), sulfo-GMBS (N-[γ-maleimidobutyryloxy]sulfosuccinimide ester), MBS (m-maleimidobenzoyl-N-hydroxysuccinimide ester), sulfo-MBS (m-maleimidobenzoyl-N-hydroxysulfosuccinimide ester), SMCC (succinimidyl 4-[N-maleimidomethyl]cyclohexane-1-carboxylate), sulfo-SMCC (Sulfosuccinimidyl 4-[N-maleimidomethyl]cyclohexane-1-carboxylate), EMCS ([N-ε-maleimidocaproyloxy]succinimide ester), Sulfo-EMCS ([N-ε-maleimidocaproyloxy]sulfosuccinimide ester), SMPB (succinimidyl 4-[p-maleimidophenyl]butyrate), sulfo-SMPB (sulfosuccinimidyl 4-[p-maleimidophenyl]butyrate), SMPH (succinimidyl-6-[β-maleimidopropionamido]hexanoate), LC-SMCC (succinimidyl-4-[N-maleimidomethyl]cyclohexane-1-carboxy-[6-amidocaproate]), sulfo-KMUS (N-[κ-maleimidoundecanoyloxy]sulfosuccinimide ester), SM(PEG)$_n$ (succinimidyl-([N-maleimidopropionamido-polyethyleneglycol) ester), where n is 1 to 30 (e.g., 2, 4, 6, 8, 12, or 24), SPDP(N-succinimidyl 3-(2-pyridyldithio)-propionate), LC-SPDP (succinimidyl 6-(3-[2-pyridyldithio]-propionamido)hexanoate), sulfo-LC-SPDP (sulfosuccinimidyl 6-(3'-[2-pyridyldithio]-propionamido)hexanoate), SMPT (4-succinimidyloxycarbonyl-α-methyl-α-[2-pyridyldithio] toluene), Sulfo-LC-SMPT (4-sulfosuccinimidyl-6-[α-methyl-α-(2-pyridyldithio)toluamido]hexanoate), SIA (N-succinimidyl iodoacetate), SBAP (succinimidyl 3-[bromoacetamido]propionate), SIAB (N-succinimidyl[4-iodoacetyl]aminobenzoate), and sulfo-SIAB (N-sulfosuccinimidyl[4-iodoacetyl]aminobenzoate).

In other embodiments, the linker is an amino-to-nonselective linker. Examples of such linkers include NHS ester/aryl azide and NHS ester/diazirine linkers. NHS ester/aryl azide linkers include NHS-ASA (N-hydroxysuccinimidyl-4-azidosalicylic acid), ANB-NOS(N-5-azido-2-nitrobenzoyloxysuccinimide), sulfo-HSAB (N-hydroxysulfosuccinimidyl-4-azidobenzoate), sulfo-NHS-LC-ASA (sulfosuccinimidyl [4-azidosalicylamido]hexanoate), SANPAH (N-succinimidyl-6-(4'-azido-2'-nitrophenylamino)hexanoate), sulfo-SANPAH (N-sulfosuccinimidyl-6-(4'-azido-2'-nitrophenylamino)hexanoate), sulfo-SFAD (sulfosuccinimidyl-(perfluoroazidobenzamido)-ethyl-1,3'-dithioproprionate), sulfo-SAND (sulfosuecinimidyl-2-(m-azido-o-nitrobenzamido)-ethyl-1,3'-proprionate), and sulfo-SAED (sulfosuccinimidyl 2-[7-amino-4-methylcoumarin-3-acetamido]ethyl-1,3'dithiopropionate). NHS ester/diazirine linkers include SDA (succinimidyl 4,4'-azipentanoate), LC-SDA (succinimidyl 6-(4,4'-azipentanamido)hexanoate), SDAD (succinimidyl 2-([4,4'-azipentanamido]ethyl)-1,3'-dithioproprionate), sulfo-SDA (sulfosuccinimidyl 4,4'-azipentanoate), sulfo-LC-SDA (sulfosuccinimidyl 6-(4,4'-azipentanamido)hexanoate), and sulfo-SDAD (sulfosuccinimidyl 2-([4,4'-azipentanamido]ethyl)-1,3'-dithioproprionate).

Exemplary amine-to-carboxyl linkers include carbodiimide compounds (e.g., DCC(N,N-dicyclohexylcarbodimide) and EDC (1-ethyl-3-[3-dimethylaminopropyl]carbodiimide)). Exemplary sulfhydryl-to-nonselective linkers include pyridyldithiol/aryl azide compounds (e.g., APDP((N-[4-(p-azidosalicylamido)butyl]-3'-(2'-pyridyldithio)propionamide)). Exemplary sulfhydryl-to-carbohydrate linkers include maleimide/hydrazide compounds (e.g., BMPH(N-[β-maleimidopropionic acid]hydrazide), EMCH ([N-ε-maleimidocaproic acid]hydrazide), MPBH 4-(4-N-maleimidophenyl)butyric acid hydrazide), and KMUH(N-[κ-maleimidoundecanoic acid]hydrazide)) and pyridyldithiol/hydrazide compounds (e.g., PDPH (3-(2-pyridyldithio) propionyl hydrazide)). Exemplary carbohydrate-to-nonselective linkers include hydrazide/aryl azide compounds (e.g., ABH (p-azidobenzoyl hydrazide)). Exemplary hydroxyl-to-sulfhydryl linkers include isocyanate/maleimide compounds (e.g., (N-[p-maleimidophenyl]isocyanate)). Exemplary amine-to-DNA linkers include NHS ester/psoralen compounds (e.g., SPB (succinimidyl-[4-(psoralen-8-yloxy)]-butyrate)).

In other embodiments, the linker is a trifunctional, tetrafunctional, or greater linking agent. Exemplary trifunctional linkers include TMEA, THPP, TSAT, LC-TSAT (tris-succinimidyl (6-aminocaproyl)aminotriacetate), tris-succinimidyl-1,3,5-benzenetricarboxylate, MDSI (maleimido-3,5-disuccinimidyl isophthalate), SDMB (succinimidyl-3,5-dimaleimidophenyl benzoate, Mal-4 (tetrakis-(3-maleimidopropyl)pentaerythritol, NHS-4 (tetrakis-(N-succinimidylcarboxypropyl)pentaerythritol)).

TMEA has the structure:

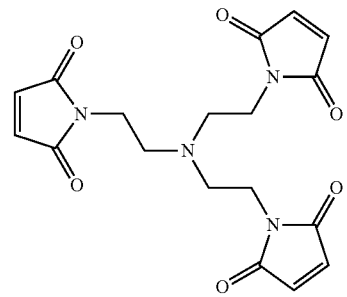 [SMILES: O=C1C=CC(=O)N1CCN(CCN1C(=O)C=CC1=O)CCN1C(=O)C=CC1=O]

TMEA, through its maleimide groups, can react with sulfhydryl groups (e.g., through cysteine amino acid side chains).

THPP has the structure:

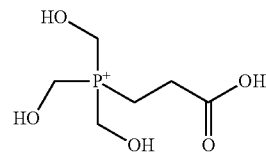

The hydroxyl groups and carboxy group of THPP can react with primary or secondary amines.

Linkers are also described in U.S. Pat. No. 4,680,338 having the formula Y=C=N-Q-A-C(O)—Z, where Q is a homoaromatic or heteroaromatic ring system; A is a single bond or an unsubstituted or substituted divalent $C_{1-30}$ bridging group, Y is O or S; and Z is Cl, Br, I, $N_3$, N-succinimidyloxy, imidazolyl, 1-benzotriazolyloxy, OAr where Ar is an electron-deficient activating aryl group, or OC(O)R where R is -A-Q-N=C=Y or $C_4$-20 tertiary-alkyl.

Linkers are also described in U.S. Pat. No. 5,306,809, which describes linkers having the formula

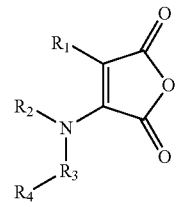

where $R_1$ is H, $C_{1-6}$ alkyl, $C_{2-6}$ alkenyl, $C_{6-12}$ aryl or aralkyl or these coupled with a divalent organic —O—, —S—, or

where R' is $C_{1-6}$ alkyl, linking moiety; $R_2$ is H, $C_{1-12}$ alkyl, $C_{6-12}$ aryl, or $C_{6-12}$ aralkyl, $R_3$ is

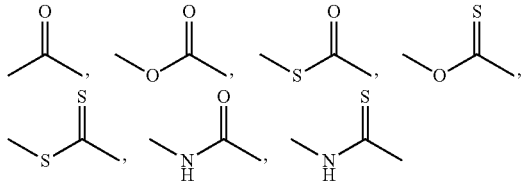

or another chemical structure which is able to delocalize the lone pair electrons of the adjacent nitrogen and $R_4$ is a pendant reactive group capable of linking $R_3$ to a peptide vector or to an agent.

Amino Acid and Peptide Linkers

In other embodiments, the linker includes at least one amino acid (e.g., a peptide of at least 2, 3, 4, 5, 6, 7, 10, 15, 20, 25, 40, or 50 amino acids). In certain embodiments, the linker is a single amino acid (e.g., any naturally occurring amino acid such as Cys). In other embodiments, a glycine-rich peptide such as a peptide having the sequence [Gly-Gly-Gly-Gly-Ser]$_n$ (SEQ ID NO: 124) where n is 1, 2, 3, 4, 5 or 6 is used, as described in U.S. Pat. No. 7,271,149. In other embodiments, a serine-rich peptide linker is used, as described in U.S. Pat. No. 5,525,491. Serine rich peptide linkers include those of the formula [X-X-X-X-Gly]$_y$ (SEQ ID NO: 125) where up to two of the X are Thr, and the remaining X are Ser, and y is 1 to 5 (e.g., Ser-Ser-Ser-Ser-Gly, (SEQ ID NO: 126) where y is greater than 1). In some cases, the linker is a single amino acid (e.g., any amino acid, such as Gly or Cys).

Amino acid linkers may be selected for flexibility (e.g., flexible or rigid) or may be selected on the basis of charge (e.g., positive, negative, or neutral). Flexible linkers typically include those with Gly resides (e.g., [Gly-Gly-Gly-Gly-Ser]$_n$ (SEQ ID NO : 124) where n is 1, 2, 3, 4, 5 or 6). Other linkers include rigid linkers (e.g., PAPAP (SEQ ID NO: 127) and (PT)$_n$P (SEQ ID NO : 128), where n is 2, 3, 4, 5, 6, or 7) and α-helical linkers (e.g., A(EAAAK)$_n$ A (SEQ ID NO : 129), where n is 1, 2, 3, 4, or 5).

Examples of suitable linkers are succinic acid, Lys, Glu, and Asp, or a dipeptide such as Gly-Lys. When the linker is succinic acid, one carboxyl group thereof may form an amide bond with an amino group of the amino acid residue, and the other carboxyl group thereof may, for example, form an amide bond with an amino group of the peptide or substituent. When the linker is Lys, Glu, or Asp, the carboxyl group thereof may form an amide bond with an amino group of the amino acid residue, and the amino group thereof may, for example, form an amide bond with a carboxyl group of the substituent. When Lys is used as the linker, a further linker may be inserted between the ε-amino group of Lys and the substituent. In one particular embodiment, the further linker is succinic acid, which can form an amide bond with the ε-amino group of Lys and with an amino group present in the substituent. In one embodiment, the further linker is Glu or Asp (e.g., which forms an amide bond with the ε-amino group of Lys and another amide bond with a carboxyl group present in the substituent), that is, the substituent is a $N^\epsilon$-acylated lysine residue.

In other embodiments, the peptide linker is a branched polypeptide. Exemplary branched peptide linkers are described in U.S. Pat. No. 6,759,509. Such linkers includes those of the formula:

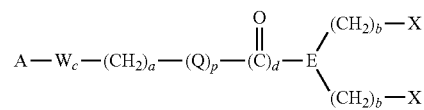

where A is a thiol acceptor; W is a bridging moiety; c is an integer of 0 to 1; a is an integer of 2 to 12; Q is O, NH, or N-lower alkyl; p is an integer of 0 or 1; d is an integer of 0 or 1; E is a polyvalent atom; each b is an integer of 1 to 10; each X is of the formula:

where Y is two amino acid residues in the L form; Z is one or two amino acid residues; m is an integer of 0 or 1; G is a self-immolative spacer; and n is a integer of 0 or 1; provided that when n is 0 then —Y—$Z_m$ is Ala-Leu-Ala-Leu or Gly-Phe-Leu-Gly; or each X is of the formula:

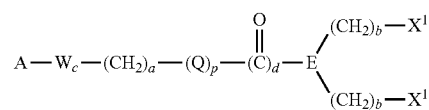

where each $X^1$ is of the formula —CO—Y—$Z_m$-$G_n$; and where Y, Z, Q, E, G, m, d, p, a, b, and n are as defined above; or each $X^1$ is of the formula:

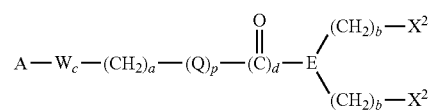

where each $X^2$ is of the formula —CO—Y—$Z_m$-$G_n$; and where Y, Z, G, Q, E, m, d, p, a, b, and n are as defined above; or each $X^2$ is of the formula:

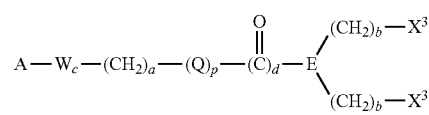

where each $X^3$ is of the formula —CO—Y—$Z_m$-$G_n$; and wherein Y, Z, G, Q, E, m, d, p, a, b, and n are as defined above; or each $X^3$ is of the formula

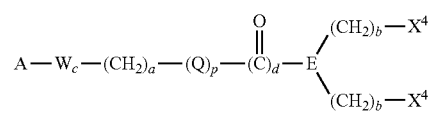

where each $X^4$ is of the formula —CO—Y—$Z_m$-$G_n$; and where Y, Z, G, Q, E, m, d, p, a, b, and n are as defined above.

The branched linker may employ an intermediate self-immolative spacer moiety (G), which covalently links together the agent or peptide vector and the branched peptide linker. A self-immolative spacer can be a bifunctional chemical moiety capable of covalently linking together two chemical moieties and releasing one of said spaced chemical moieties from the tripartate molecule by means of enzymatic cleavage (e.g., any appropriate linker described herein. In certain embodiments, G is a self-immolative spacer moiety which spaces and covalently links together the agent or peptide vector and the peptide linker, where the spacer is linked to the peptide vector or agent via the T moiety (as used in the following formulas "T" represents a nucleophilic atom which is already contained in the agent or peptide vector), and which may be represented by

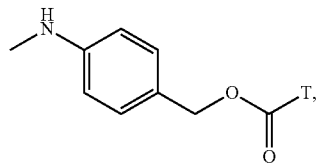

where T is O, N or S; —HN—$R^1$—COT, where T is O, N or S, and $R^1$ is $C_{1-5}$ alkyl;

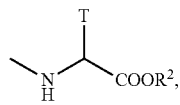

where T is O, N, or S, and $R^2$ is H or $C_{1-5}$ alkyl;

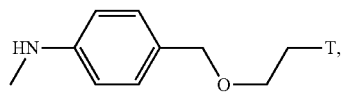

where T is O, N or S; or

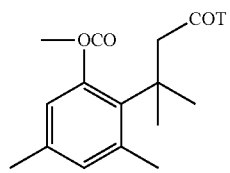

where T is O, N, or S. Preferred Gs include PABC (p-aminobenzyl-carbamoyl), GABA (γ-aminobutyric acid), α,α-dimethyl GABA, and β,β-dimethyl GABA.

In the branched linker, the thiol acceptor "A" is linked to a peptide vector or agent by a sulfur atom derived from the peptide vector or agent. The thiol acceptor can be, for example, an α-substituted acetyl group. Such a group has the formula:

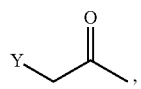

where Y is a leaving group such as Cl, Br, I, mesylate, tosylate, and the like. If the thiol acceptor is an alpha-substituted acetyl group, the thiol adduct after linkage to the ligand forms the bond —S—$CH_2$—. Preferably, the thiol acceptor is a Michael Addition acceptor. A representative Michael Addition acceptor of this invention has the formula

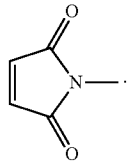

After linkage the thiol group of the ligand, the Michael Addition acceptor becomes a Michael Addition adduct, e.g.,

where L is an agent or peptide vector.

The bridging group "W" is a bifunctional chemical moiety capable of covalently linking together two spaced chemical moieties into a stable tripartate molecule. Examples of bridging groups are described in S. S. Wong, *Chemistry of Protein Conjugation and Crosslinking*. CRC Press, Florida, (1991); and G. E. Means and R. E. Feeney, *Bioconjugate Chemistry*, vol. 1, pp. 2-12, (1990), the disclosures of which are incorporated herein by reference. W can covalently link the thiol acceptor to a keto moiety. An exemplary a bridging group has the formula —$(CH_2)_f$—$(Z)_g$—$(CH_2)_h$—, where f is 0 to 10; h is 0 to 10; g is 0 or 1, provided that when g is 0, then f+h is 1 to 10; Z is S, O, NH, $SO_2$, phenyl, naphthyl, a polyethylene glycol, a cycloaliphatic hydrocarbon ring containing 3 to 10 carbon atoms, or a heteroaromatic hydrocarbon ring containing 3 to 6 carbon atoms and 1 or 2 heteroatoms selected from O, N, or S. Preferred cycloaliphatic moieties include cyclopropyl, cyclobutyl, cyclopentyl, cyclohexyl, and the like. Preferred heteroaromatic moieties include pyridyl, polyethylene glycol (1-20 repeating units), furanyl, pyranyl, pyrimidinyl, pyrazinyl, pyridazinyl, oxazinyl, pyrrolyl, thiazolyl, morpholinyl, and the like. In the bridging group, it is preferred that when g is 0, f+h is an integer of 2 to 6 (e.g., 2 to 4 such as 2). When g is 1, it is preferred that f is 0, 1 or 2; and that h is 0, 1 or 2. Preferred bridging groups coupled to thiol acceptors are shown in the Pierce Catalog, pp. E-12, E-13, E-14, E-15, E-16, and E-17 (1992).

Joining of the Peptide Vector Multimer to an Agent

In addition to the multimeric peptide vectors described above, the invention features compounds where the multimeric peptide vector is joined (e.g., by a covalent bond) to one or more agents (e.g., a diagnostic or therapeutic agent, such as any of those described herein). The agent may be joined to the peptide vector directly through a covalent bond such as a peptide bond or disulfide bond, or may be joined to the peptide vector through a linker (e.g., any linker described herein). The agent may be joined to the peptide vector through any appropriate reactive moiety on the vector, e.g., through a primary amine such as an N-terminal amine or a ε-amino group on a lysine side chain, through a thiol bond (e.g., through a cysteine side chain), or through a carboxyl group (e.g., a C-terminal carboxyl group or a aspartic acid or glutamic acid side chain). In embodiments where the agent is a peptide or polypeptide, the agent may be joined to the peptide vector by a peptide bond (e.g., produced synthetically or recombinantly as a fusion protein).

Dimeric Conjugates

Compounds including an agent and dimeric peptide vector can be conjugated either through the peptide vector portion of the molecule or through the linker portion of the molecule.

Compounds of the invention in which the agent is joined (e.g., through a linker where the linker is a chemical linker, peptide, or a covalent bond such as a peptide bond) to the peptide vector can be represented by the formula:

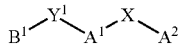

where $A^1$ and $A^2$ are each, independently, peptide vectors (e.g., any described herein); X is a linker (e.g., chemical linker, peptide, or covalent bond) that joins $A^1$ and $A^2$; $B^1$ is an agent; and $Y^1$ is a linker that joins $B^1$ and $A^1$. In certain embodiments, two or more (e.g., 3, 4, 5, 6, 7, 8, 9, or 10) agents are joined to one or both of the peptide vectors. Such compounds can be represented by the formula:

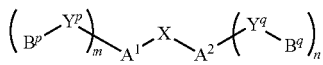

where $A^1$, $A^2$, and X are as defined above; m is 1, 2, 3, 4, 5, 6, 7, 8, 9, or 10; n is 0, 1, 2, 3, 4, 5, 6, 7, 8, 9, or 10; p is an integer from 1 to m; q is an integer from m+1 to m+n; each $B^p$ and each $B^q$ are, independently, an agent (e.g., any described herein); and each $Y^p$ and each $Y^q$ are, independently, a linker that joins each $B^p$ or each $B^q$ to $A^1$ or $A^2$, respectively.

In other embodiments, the agent is joined (e.g., through a covalent bond or a chemical linker such as those described herein) to the dimer through the linker that joins the peptide vectors forming the dimer. Such compounds can have the formula:

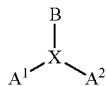

where $A^1$ and $A^2$ are peptide vectors (e.g., any described herein); B is an agent; and X is a linker that joins $A^1$, $A^2$, and B.

In other embodiments, agents can be joined to both the linker and a peptide vector. Such compounds can be represented by the formula:

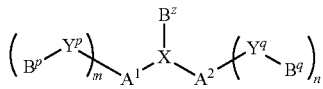

where $A^1$ and $A^2$ are, independently, peptide vectors; $B^z$ is an agent or is absent; m is 0, 1, 2, 3, 4, 5, 6, 7, 8, 9, or 10; n is 0, 1, 2, 3, 4, 5, 6, 7, 8, 9, or 10; p is an integer from 1 to m; q is an integer from m+1 to m+n; Each $B^p$ and $B^q$ is, independently, an agent (e.g., any described herein); and each $Y^p$ and $Y^q$ is, independently, a linker that joins each $B^p$ or each $B^q$ to $A^1$ or $A^2$, respectively, where at least one (e.g., at least two) of the following is true (i) B1 is present; (ii) m is at least 1; and (iii) n is at least 1.

Trimeric Conjugates

Compounds of the invention can also include a trimeric peptide vector. Where the trimeric peptide vector is joined to a single agent through one of the peptide vectors, the compound can have one of the following formulas:

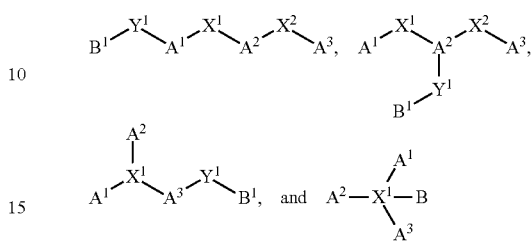

where $A^1$, $A^2$, and $A^3$ are each, independently, a peptide vector (e.g., any described herein); $X^1$ and $X^2$ are linkers; $B^1$ is an agent; and $Y^1$ is a linker that joins $B^1$ to a peptide vector (e.g., $A^1$, $A^2$, and $A^3$) or to the linker $X^1$.

In other embodiments, the trimeric peptide vector is conjugated to one or more than one agent. Such conjugation can be through either the peptide vector, or through the linker(s). Such compounds can include one of the following formulas:

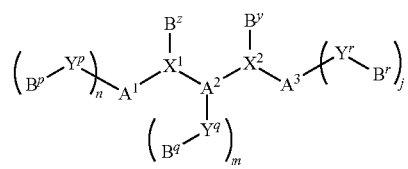

where $A^1$, $A^2$, and $A^3$ are peptide vectors; n, m, and j are 0, 1, 2, 3, 4, 5, 6, 7, 8, 9, or 10; Each $B^p$, each $B^q$, and each $B^r$ are, independently, agents (e.g., any agent described herein); $B^z$ and $B^y$ are, independently, agents or are absent; $X^1$ is a linker joining $A^1$, $A^2$, and $B^z$, if present; $X^2$ is a linker joining $A^2$, $A^3$, and $B^y$, if present. In certain embodiments, at least one of n, m, or j is at least one, $B^z$ is present, or $B^y$ is present. In other embodiments, at least two (e.g., at least 3, 4, 5, 6, 7, 8, 9, 10, 15, 20, 25, or 30) of $B^p$, $B^q$, $B^r$, $B^y$, and $B^z$ are present.

Higher Order Multimer Conjugates

The compounds of the invention can also include peptide multimers of a higher order (e.g., quatromers, pentomers, etc.). Such multimers can be described by the formula:

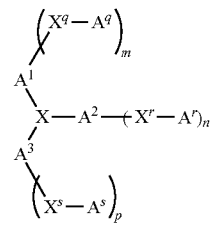

where $A^1$, $A^2$, each $A^q$, each $A^r$, and each $A^s$ are, independently, peptide vectors; $A^3$ is a peptide vector or is absent; X, each $X^q$, $X^r$, and $X^s$ are, independently, linkers that join peptide vectors; m, n, and p are each, independently, 0, 1, 2, 3, 4, 5, 6, 7, 8, 9, or 10; q is an integer from 4 to m+3; r is an integer from m+4 to m+n+3; and s is an integer from m+n+4 to m+n+p+3. One or more agents can be joined to either the linkers (X, any $X^q$, $X^r$, or $X^s$) or the peptide vectors ($A^1$, $A^2$, $A^3$, each $A^q$, each $A^r$, and each $A^s$) of this formula in order to form higher order multimer conjugates.

Peptide Vectors

The compounds of the invention can feature any of polypeptides described herein, for example, any of the peptides described in Table 1 (e.g., Angiopep-1, Angiopep-2, Angiopep-7, or reversed Angiopep-2), or a fragment or analog thereof. In certain embodiments, the polypeptide may have at least 35%, 40%, 50%, 60%, 70%, 80%, 90%, 95%, 99%, or even 100% identity to a polypeptide described herein. The polypeptide may have one or more (e.g., 2, 3, 4, 5, 6, 7, 8, 9, 10, 11, 12, 13, 14, or 15) substitutions relative to one of the sequences described herein. Other modifications are described in greater detail below.

The invention also features fragments of these polypeptides (e.g., a functional fragment). In certain embodiments, the fragments are capable of efficiently being transported to or accumulating in a particular cell type (e.g., liver, eye, lung, kidney, or spleen) or are efficiently transported across the BBB. Truncations of the polypeptide may be 1, 2, 3, 4, 5, 6, 7, 8, 9, 10, 11, 12, or more amino acids from either the N-terminus of the polypeptide, the C-terminus of the polypeptide, or a combination thereof. Other fragments include sequences where internal portions of the polypeptide are deleted.

Additional polypeptides may be identified by using one of the assays or methods described herein. For example, a candidate polypeptide may be produced by conventional peptide synthesis, conjugated with paclitaxel and administered to a laboratory animal. A biologically-active polypeptide conjugate may be identified, for example, based on its ability to increase survival of an animal injected with tumor cells and treated with the conjugate as compared to a control which has not been treated with a conjugate (e.g., treated with the unconjugated agent). For example, a biologically active polypeptide may be identified based on its location in the parenchyma in an in situ cerebral perfusion assay.

Assays to determine accumulation in other tissues may be performed as well. Labeled conjugates of a polypeptide can be administered to an animal, and accumulation in different organs can be measured. For example, a polypeptide conjugated to a detectable label (e.g., a near-IR fluorescence spectroscopy label such as Cy5.5) allows live in vivo visualization. Such a polypeptide can be administered to an animal, and the presence of the polypeptide in an organ can be detected, thus allowing determination of the rate and amount of accumulation of the polypeptide in the desired organ. In other embodiments, the polypeptide can be labelled with a radioactive isotope (e.g., $^{125}I$). The polypeptide is then administered to an animal. After a period of time, the animal is sacrificed and the organs are extracted. The amount of radioisotope in each organ can then be measured using any means known in the art. By comparing the amount of a labeled candidate polypeptide in a particular organ relative to the amount of a labeled control polypeptide, the ability of the candidate polypeptide to access and accumulate in a particular tissue can be ascertained. Appropriate negative controls include any peptide or polypeptide known not to be efficiently transported into a particular cell type (e.g., a peptide related to Angiopep that does not cross the BBB, or any other peptide).

Additional sequences are described in U.S. Pat. No. 5,807,980 (e.g., SEQ ID NO:102 herein), U.S. Pat. No. 5,780,265 (e.g., SEQ ID NO:103), U.S. Pat. No. 5,118,668 (e.g., SEQ ID NO:105). An exemplary nucleotide sequence encoding an aprotinin analog atgagaccag atttctgcct cgagccgccg tacactgggc cctgcaaagc tcgtatcatc cgttacttct acaatgcaaa ggcaggcctg tgtcagacct tcgtatacgg cggctgcaga gctaagcgta acaacttcaa atccgcggaa gactgcatgc gtacttgcgg tggtgcttag; SEQ ID NO:6; Genbank accession No. X04666). Other examples of aprotinin analogs may be found by performing a protein BLAST (Genbank: www.ncbi.nlm.nih.gov/BLAST/) using the synthetic aprotinin sequence (or portion thereof) disclosed in International Application No. PCT/CA2004/000011. Exemplary aprotinin analogs are also found under accession Nos. CAA37967 (GI:58005) and 1405218C (GI:3604747).

Agents

Any therapeutic or diagnostic agent may be conjugated to a multimer (e.g., a dimer) of the invention. Such agents may be chemically conjugated to one or more of the peptide vectors, or may be conjugated to a linker that joins two (or more) of the peptide vectors (e.g., a trifunetional linker). Agents of particular interest include anticancer agents (e.g., paclitaxel, etoposide, doxorubicin and analogs thereof), RNAi agents, and peptide and polypeptide therapeutics (e.g., GLP-1 agonists, neurotensin and neurotensin receptor agonists, leptin and OB receptor agonists, GDNF, BDNF, and analogs thereof).

In certain embodiments, the agent is a small molecule drug, an antibiotic, a medicine, a detectable label, a protein (e.g., an enzyme), protein-based compound (e.g., a protein complex comprising one or polypeptide chain) and a peptide or polypeptide. Exemplary peptide and polypeptide therapeutics that can be used in the present invention are described, for example in U.S. Provisional Application No. 61/200,947, filed Dec. 5, 2008, which is hereby incorporated by reference. The agent may be more particularly, a molecule which is active at the level of the central nervous system. The agent may be any agent for treating or detecting a neurological disease.

The agent may be a small molecule drug, an antibiotic, a medicine, a detectable label, a protein (e.g., an enzyme), protein-based compound (e.g., a protein complex comprising one or polypeptide chain) and a peptide or polypeptide. The agent may be more particularly, a molecule that is active at the level of the central nervous system. The agent may be any agent for treating or detecting a neurological disease.

The detectable label may be a radioimaging agent. Other label include an isotope, a fluorescent label (e.g., rhodamine), a reporter molecule (e.g., biotin), etc. Other examples of detectable labels include, for example, a green fluorescent protein, biotin, a histag protein and β-galactosidase.

Protein or protein-based compound which may be conjugated to a multimer of the invention include an antibody, an antibody fragment (e.g., an antibody binding fragment such as Fv fragment, F(ab)$_2$, F(ab)$_2$' and Fab and the like), a peptidic- or protein-based drug (e.g., a positive pharmacological modulator (agonist) or an pharmacological inhibitor (antagonist)). Other examples of agents are cellular toxins (e.g., monomethyl auristatin E (MMAE), toxins from bacteria endotoxins and exotoxins; diphtheria toxins, botunilum toxins, tetanus toxins, perussis toxins, staphylococcus enterotoxins, toxin shock syndrome toxin TSST-1, adenylate cyclase toxin, shiga toxin, cholera enterotoxin, and others) and anti-angiogenic compounds (endostatin, catechins, nutriceuticals, chemokine IP-10, inhibitors of matrix metalloproteinase (MMPIs), anastellin, vironectin, antithrombin, tyrosine kinase inhibitors, VEGF inhibitors, antibodies against receptor, trastuzumab (Herceptin®), Bevacizumab (Avastin®), and panitumumab and others).

Particular agents are described in greater detail below.

Anticancer Agents

Also in accordance with the present invention, the agent may be an anticancer drug. An anticancer drug encompassed by the present invention may include, for example, a drug having a group allowing its conjugation to the carrier of the invention. Particular anticancer drugs include those selected from the group consisting of paclitaxel (Taxol), vinblastine, vincristine, etoposide, doxorubicin, cyclophosphamide, docetaxel (Taxotere®), melphalan, and chlorambucil; pharmaceutically acceptable salts thereof; or a combination thereof. In particular embodiments, the anticancer agent is paclitaxel, etoposide, or doxorubicin; a pharmaceutically acceptable salt thereof; or a derivative thereof.

Other exemplary agents include abarelix, aldesleukin, alemtuzumab, alitertinoin, allopurinol, altretamine, amifostine, anakinra, anastrozole, arsenic trioxide, asparaginase, azacitidine, BCG Live, bevacuzimab, bexarotene, bleomycin, bleomycin, bortezombi, bortezomib, busulfan, busulfan, calusterone, capecitabine, carboplatin, carmustine, celecoxib, cetuximab, cisplatin, cladribine, clofarabine, cytarabine, dacarbazine, dactinomycin, actinomycin D, dalteparin (e.g., sodium), darbepoetin alfa, dasatinib, daunorubicin, daunomycin, decitabine, denileukin, denileukin diftitox, dexrazoxane, dromostanolone propionate, eculizumab, epirubicin (e.g., HCl), epoetin alfa, erlotinib, estramustine, exemestane, fentanyl (e.g., citrate), filgrastim, floxuridine, fludarabine, fluorouracil, 5-FU, fulvestrant, gefitinib, gemcitabine (e.g., HCl), gemtuzumab ozogamicin, goserelin (e.g., acetate), histrelin (e.g., acetate), hydroxyurea, ibritumomab tiuxetan, idarubicin, ifosfamide, imatinib (e.g., mesylate), Interferon alfa-2b, irinotecan, lapatinib ditosylate, lenalidomide, letrozole, leucovorin, leuprolide (e.g., acetate), levamisole, lomustine, CCNU, meclorethamine (nitrogen mustard), megestrol, mercaptopurine (6-MP), mesna, methotrexate, methoxsalen, mitomycin C, mitotane, mitoxantrone, nandrolone phenpropionate, nelarabine, nofetumomab, oprelvekin, oxaliplatin, palifermin, pamidronate, panitumumab, pegademase, pegaspargase, pegfilgrastim, peginterferon alfa-2b, pemeterxed (e.g., disodium), pentostatin, pipobroman, plicamycin (mithramycin), porfimer (e.g., sodium), procarbazine, quinacrine, rasburicase, rituximab, sargramostim, sorafenib, streptozocin, sunitinib (e.g., maleate), talc, tamoxifen, temozolomide, teniposide (VM-26), testolactone, thalidomide, thioguanine (6-TG), thiotepa, thiotepa, thiotepa, topotecan (e.g., hcl), toremifene, Tositumomab/1-131 (tositumomab), trastuzumab, trastuzumab, tretinoin (ATRA), uracil mustard, vairubicin, vinorelbine, vorinostat, zoledronate, and zoledronic acid.

Paclitaxel Derivatives

In certain embodiments, the agent is a derivative of paclitaxel. Structural analogs of paclitaxel are disclosed in U.S. Pat. No. 6,911,549 and can be described by the formula:

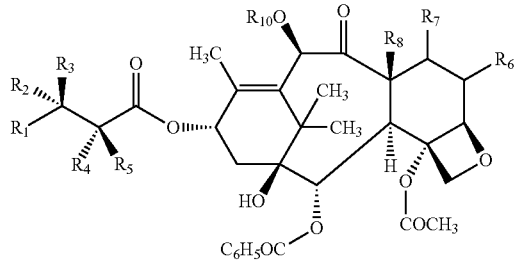

where $R_1$ is selected from the group consisting of —$CH_3$; —$C_6H_5$, or phenyl substituted with one, 2 or 3 $C_1$-$C_4$ alkyl, $C_1$-$C_3$ alkoxy, halo, $C_1$-$C_3$ alkylthio, trifluoromethyl, $C_2$-$C_6$, dialkylamino, hydroxyl, or nitro; and -2-furyl, 2-thienyl, 1-naphthyl, 2-naphthyl or 3,4-methylenedioxyphenyl; $R_2$ is selected from the group consisting of —H, —NHC(O)H, —NHC(O)$C_1$-$C_{10}$ alkyl (preferably —NHC(O)$C_4$-$C_6$ alkyl), —NHC(O)phenyl, —NHC(O)phenyl substituted with one, 2, or 3 $C_1$-$C_4$ alkyl, $C_1$-$C_3$ alkoxy, halo, $C_1$-$C_3$ alkylthio, trifluoromethyl, $C_2$-$C_6$ dialkylamino, hydroxy or nitro, —NHC(O)C($CH_3$)=$CHCH_3$, —NHC(O)OC($CH_3$)$_3$, —NHC(O)OCH$_2$phenyl, —NH$_2$, —NHSO$_2$-4-methylphenyl, —NHC(O)(CH$_2$)$_3$COOH, —NHC(O)-4-(SO$_3$H)phenyl, —OH, —NHC(O)O-1-adamantyl, —NHC(O)O-3-tetrahydrofuranyl, —NHC(O)O-4-tetrahydropyranyl, —NHC(O)CH$_2$C(CH$_3$)$_3$, —NHC(O)C(CH$_3$)$_3$, —NHC(O)OC$_1$-$C_{10}$ alkyl, —NHC(O)NHC$_1$-$C_{10}$ alkyl, —NHC(O)NHPh, —NHC(O)NHPh substituted with one, 2, or 3 $C_1$-$C_4$ alkyl, $C_1$-$C_3$ alkoxy, halo, $C_1$-$C_3$ alkylthio, trifluoromethyl, $C_2$-$C_6$ dialkylamino, or nitro, —NHC(O)$C_3$-$C_8$ cycloalkyl, —NHC(O)C(CH$_2$CH$_3$)$_2$CH$_3$, —NHC(O)C(CH$_3$)$_2$CH$_2$Cl, —NHC(O)C(CH$_3$)$_2$CH$_2$CH$_3$, phthalimido, —NHC(O)-1-phenyl-1-cyclopentyl, —NHC(O)-1-methyl-1-cyclohexyl, —NHC(S)NHC(CH$_3$)$_3$, —NHC(O)NHCC(CH$_3$)$_3$ or —NHC(O)NHPh; $R_3$ is selected from the group consisting of —H, —NHC(O)phenyl or —NHC(O)OC(CH$_3$)$_3$, with the overall proviso that one of $R_2$ and $R_3$ is —H but $R_2$ and $R_3$ are not both —H; $R_4$ is —H or selected from the group consisting of —OH, —OAc (—OC(O)CH$_3$), —OC(O)OCH$_2$C(Cl)$_3$, —OCOCH$_2$CH$_2$ NH$_3^+$ HCOO$^-$, —NHC(O)phenyl, —NHC(O)OC(CH$_3$)$_3$, —OCOCH$_2$CH$_2$ COOH and pharmaceutically acceptable salts thereof, —OCO(CH$_2$)$_3$COOH and pharmaceutically acceptable salts thereof, and —OC(O)—Z—C(O)—R' [where Z is ethylene (—CH$_2$CH$_2$), propylene (—CH$_2$CH$_2$CH$_2$—), —CH=CH—, 1,2-cyclohexane or 1,2-phenylene, R' s —OH, —OH base, —NR'$_2$R'$_3$, —OR'$_3$, —SR'$_3$, —OCH$_2$C(O)NR'$_4$R'$_5$ where R'$_2$ is —H or —CH$_3$, R'$_3$ s —(CH$_2$)$_n$NR'$_6$R'$_7$ or (CH$_2$)$_n$N$^+$R'$_6$R'$_7$R'$_8$X$^-$ where n is 1-3, R'$_4$ is —H or —C$_1$-$C_4$ alkyl, R'$_5$ is —H. —C$_1$-$C_4$ alkyl, benzyl, hydroxyethyl, —CH$_2$CO$_2$H or dimethylaminoethyl, R'$_6$ and R'$_7$ are —CH$_3$, —CH$_2$CH$_3$, benzyl or R'$_6$ and R'$_7$ together with the nitrogen of NR'$_6$R'$_7$ form a pyrrolidino, piperidino, morpholino, or N-methylpiperizino group; R'$_8$ s —CH$_3$, —CH$_2$CH$_3$ or benzyl, X$^-$ is halide, and base is NH$_3$, (HOC$_2$H$_4$)$_3$N,N(CH$_3$)$_3$, CH$_3$N(C$_2$H$_4$)$_2$NH, NH$_2$(CH$_2$)$_6$NH$_2$, N-methylglucamine, NaOH or KOH], —OC(O)(CH$_2$)$_n$NR$^2$R$^3$ [where n is 1-3, R$^2$ is —H or —C$_1$-$C_3$ alkyl and R$^3$ is —H or —C$_1$-$C_3$ alkyl], —OC(O)CH(R'')NH$_2$ [where R'' is selected from the group consisting of —H, —CH$_3$, —CH$_2$CH(CH$_3$)$_2$, —CH(CH$_3$)CH$_2$CH$_3$, —CH(CH$_3$)$_2$, —CH$_2$ phenyl, —(CH$_2$)$_4$NH$_2$, —CH$_2$CH$_2$COON, —(CH$_2$)$_3$NHC(=NH)NH$_2$], the residue of the amino acid proline, —OC(O)CH=CH$_2$, —C(O)CH$_2$CH$_2$C(O)NHCH$_2$CH$_2$SO$_3^-$Y$^+$, —OC(O)CH$_2$CH$_2$C(O)NHCH$_2$CH$_2$CH$_2$SO$_3^-$Y$^+$ wherein Y$^+$ is Na$^+$ or N$^+$(Bu)$_4$, —OC(O)CH$_2$CH$_2$C(O)OCH$_2$CH$_2$OH; $R_5$ is —H or —OH, with the overall proviso that when $R_5$ s —OH, $R_4$ is —H and with the further proviso that when $R_5$ is —H, $R_4$ is not —H; $R_6$ is —H:—H when $R_7$ is α-$R_{71}$:β-$R_{72}$ where one of $R_{71}$ and $R_{72}$ is —H and the other of $R_{71}$ and $R_{72}$ s —X where X is halo and $R_8$ s —CH$_3$; $R_6$ is —H:—H when $R_7$ is α-H: β-$R_{74}$ where $R_{74}$ and $R_8$ are taken together to form a cyclopropyl ring; $R_{10}$ is —H or —C(O)CH$_3$; and pharmaceutically acceptable salts thereof when the compound contains either an acidic or basic functional group.

Particular paclitaxel analogs include ((azidophenyl)ureido)taxoid, (2α,5α,7β,9α,10β,13α)-5,10,13,20-tetraacetoxytax-11-ene-2,7,9-triol, (2α,5α,9α,10β)-2,9,10-triacetoxy-5-(β-D-glucopyranosyl)oxy)-3,11-cyclotax-11-en-13-one, 1β-hydroxybaccatin I, 1,7-dihydroxytaxinine, 1-acety-5,7,10-deacetyl-baccatin I, 1-dehydroxybaccatin VI, 1-hydroxy-2-deacetoxy-5-decinnamoyl-taxinine j, 1-hydroxy-7,9-dideacetylbaccatin I, 1-hydroxybaccatin I, 10-acetyl-4-deacetyltaxotere, 10-deacetoxypaclitaxel, 10-Deacetyl baccatin III dimethyl sulfoxide disolvate, 10-deacetyl-10-(3-aminobenzoyl)paclitaxel, 10-deacetyl-10-(7-(diethylamino) coumarin-3-carbonyl)paclitaxel, 10-deacetyl-9-dihydrotaxol, 10-deacetylbaccatine III, 10-deacetylpaclitaxel, 10-deacetyltaxinine, 10-deacetyltaxol, 10-deoxy-10-C-morpholinoethyl docetaxel, 10-O-acetyl-2-O-(cyclohexylcarbonyl)-2-debenzoyltaxotere, 10-O-sec-aminoethyl docetaxel, 11-desmethyllaulimalide, 13-deoxo-13-acetyloxy-7,9-diacetyl-1,2-dideoxytaxine, 13-deoxybaccatin III, 14-hydroxy-10-deacetyl-2-O-debenzoylbacatin III, 14-hydroxy-10-deacetylbaccatin III, 14β-benzoyloxy-13-deacetylbaccatin IV, 14β-benzoyloxy-2-deacetylbaccatin VI, 14β-benzoyloxybaccatin IV, 19-hydroxybaccatin III, 2',2"-methylenedocetaxel, 2',2"-methylenepaclitaxel, 2'-(valyl-leucyl-lysyl-PABC)paclitaxel, 2'-acetyltaxol, 2'-O-acetyl-7-O—(N-(4'-fluoresceincarbonyl)alanyl)taxol, 2,10,13-triacetoxy-taxa-4(20),11-diene-5,7,9-triol, 2,20-O-diacetyltaxumairol N, 2-(4-azidobenzoyl)taxol, 2-deacetoxytaxinine J, 2-debenzoyl-2-m-methoxybenozyl-7-triethylsilyl-13-oxo-14-hydroxybaccatin III 1,14-carbonate, 2-O-(cyclohexylcarbonyl)-2-debenzoylbaccatin III 13-O—(N-(cyclohexylcarbonyl)-3-cyclohexylisoserinate), 2α, 7β,9α,10β,13α-pentaacetoxyltaxa-4 (20), 11-dien-5-ol, 2α,5α,7β,9α,13α-pentahydroxy-10β-acetoxytaxa-4(20),11-diene, 2α,7β,9α,10β,13-pentaacetoxy-11β-hydroxy-5α-(3'-N,N-dimethylamino-3'-phenyl)-propionyloxytaxa-4(20),12-diene, 2α,7β-diacetoxy-5α,10β,13β-trihydroxy-2(3-20)abeotaxa-4(20),11-dien-9-one, 2α,9α-dihydroxy-10β,13α-diacetoxy-5α-(3'-methylamino-3'-phenyl)-propionyloxytaxa-4(20),11-diene, 2α-hydroxy-7β,9α,10β,13α-tetraacetoxy-5α-(2'-hydroxy-3'-N,N-dimethylamino-3'-phenyl)-propionyloxytaxa-4(20),11-diene, 3'-(4-azidobenzamido)taxol, 3'-N-(4-benzoyldihydrocinnamoyl)-3'-N-debenzoylpaclitaxel, 3'-N-m-aminobenzamido-3'-debenzamidopaclitaxel, 3'-p-hydroxypaclitaxel, 3,11-cyclotaxinine N,N-2,4-deacetyltaxol, 5,13-diacetoxy-taxa-4 (20),11-diene-9,10-diol, 5-O-benzoylated taxinine K, 5-O-phenylpropionyloxytaxinine A, 5α,13α-diacetoxy-10β-cinnamoyloxy-4(20),11-taxadien-9α-ol, 6,3'-p-dihydroxypaclitaxel, 6-α-hydroxy-7-deoxy-10-deacetylbaccatin-III, 6-fluoro-10-acetyldocetaxel, 6-hydroxytaxol, 7,13-diacetoxy-5-climamyloxy-2(3-20)-abeo-taxa-4(20),11-diene-2,10-diol, 7,9-dideacetylbaccatin VI, 7-(5'Biotinylamidopropanoyl)paclitaxel, 7-acetyltaxol, 7-deoxy-10-deacetylbaccatin-III, 7-deoxy-9-dihydropaclitaxel, 7-epipaclitaxel, 7-methylthiomethylpaclitaxel, 7-O-(4-benzoyldihydrocinnamoyl)paclitaxel, 7-O—(N-(4'-fluoresceincarbonyl)alanyetaxol, 7-xylosyl-10-deacetyltaxol, 8,9-single-epoxy brevifolin, 9-dihydrobaccatin III, 9-dihydrotaxol, 9α-hydroxy-2α,10β,13α-triacetoxy-5α-(3'-N,N-dimethylamino-3'-phenyl)-propionyloxytaxa-4(20),11-diene, baccatin III, baccatin III 13-O-(N-benzoyl-3-cyclohexylisoserinate), BAY59, benzoyltaxol, BMS 181339, BMS185660, BMS188797, brevifoliol, butitaxel, cephalomannine, dantaxusin A, dantaxusin B, dantaxusin C, dantaxusin D, dibromo-10-deacetylcephalomannine, DJ927, docetaxel, Flutax 2, glutarylpaclitaxel 6-aminohexanol glucuronide, IDN 5109, IDN 5111, IDN 5127, IDN 5390, isolaulimalide, laulimalide, MST 997, N-(paclitaxel-2'-O-(2-amino)phenylpropionate)-O-(β-glucuronyl)carbamate, N-(paclitaxel-2'-O-3,3-dimethyl butanoate)-O-(β-glucuronyl)carbamate, N-debenzoyl-N-(3-(dimethylamino)benzoyl)paclitaxel, nonataxel, octreotide-conjugated paclitaxel, Paclitaxel, paclitaxel-transferrin, PNU 166945, poly(ethylene glycol)-conjugated paclitaxel-2'-glycinate, polyglutamic acid-paclitaxel, protax, protaxel, RPR 109881A, SB T-101187, SB T-1102, SB T-1213, SB T-1214, SB T-1250, SB T-12843, tasumatrol E, tasumatrol F, tasumatrol G, taxa-4 (20),11(12)-dien-5-yl acetate, taxa-4(20),11(12)-diene-5-ol, taxane, taxchinin N, taxcultine, taxezopidine M, taxezopidine N, taxine, taxinine, taxinine A, taxinine M, taxinine NN-1, taxinine N,N-7, taxol C-7-xylose, taxol-sialyl conjugate, taxumairol A, taxumairol B, taxumairol G, taxumairol H, taxumairol I, taxumairol K, taxumairol M, taxumairol N, taxumairol 0, taxumairol U, taxumairol V, taxumairol W, taxumairol-X, taxumairol-Y, taxumairol-Z, taxusin, taxuspinanane A, taxuspinanane B, taxuspine C, taxuspine D, taxuspine F, taxuyunnanine C, taxuyunnanine S, taxuyunnanine T, taxuyunnanine U, taxuyunnanine V, tRA-96023, and wallifoliol. Other paclitaxel analogs include 1-deoxypaclitaxel, 10-deacetoxy-7-deoxypaclitaxel, 10-O-deacetylpaclitaxel 10-monosuccinyl ester, 10-succinyl paclitaxel, 12b-acetyloxy-2a,3,4,4a,5,6,9,10,11,12,12a,12b-dodecahydro-4,11-dihydroxy-12-(2,5-dimethoxybenzyloxy)-4a,8,13,13-tetramethyl-5-oxo-7,11-methano-1H-cyclodeca(3,4)benz(1,2-b)oxet-9-yl 3-(tert-butyloxycarbonyl)amino-2-hydroxy-5-methyl-4-hexaenoate, 130-nm albumin-bound paclitaxel, 2'-paclitaxel methyl 2-glucopyranosyl succinate, 3'-(4-azidophenyl)-3'-dephenylpaclitaxel, 4-fluoropaclitaxel, 6,6,8-trimethyl-4,4a,5,6,7,7a,8,9-octahydrocyclopenta(4,5)cyclohepta(1,2-c)-furan-4,8-diol 4-(N-acetyl-3-phenylisoserinate), 6,6,8-trimethyl-4,4a,5,6,7,7a,8,9-octahydrocyclopenta(4,5)cyclohepta(1,2-c)-furan-4,8-diol 4-(N-tert-butoxycarbonyl-3-phenylisoserinate), 7-(3-methyl-3-nitrosothiobutyryl)paclitaxel, 7-deoxypaclitaxel, 7-succinylpaclitaxel, A-Z-CINN 310, AI-850, albumin-bound paclitaxel, AZ 10992,isotaxel, MAC321, MBT-0206, NK105, Pacliex, paclitaxel poliglumex, paclitaxel-EC-1 conjugate, polilactofate, and TXD 258. Other paclitaxel analogs are described in U.S. Pat. Nos. 4,814,470, 4,857,653, 4,942, 184, 4,924,011, 4,924,012, 4,960,790; 5,015,744; 5,157,049; 5,059,699; 5,136,060; 4,876,399; and 5,227,400

Etoposide Derivatives

Etoposide derivatives may also be used in the compounds of the invention. In some embodiments, the podophyllotoxin derivative is a compound having a structure according to the formula:

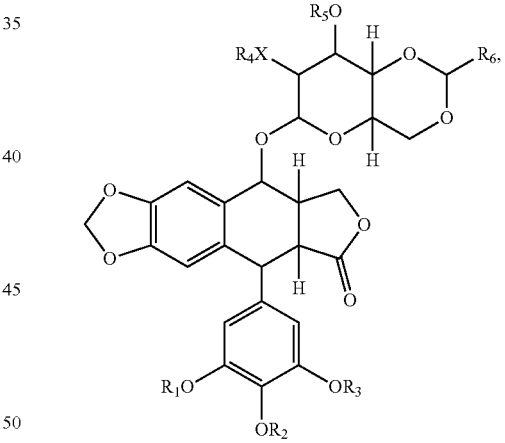

or a stereoisomer thereof; where each $R_1$, $R_2$, and $R_3$ is selected, independently, from H, optionally substituted $C_{1-6}$ alkyl, $C(O)R_8$, $P(O)(OR_9)(OR_{10})$, $S(O)_2(OR_9)$, or a hydrolyzable linker Y that comprises a covalent bond to an amino acid of the polypeptide; X is O or $NR_7$; each $R_4$, $R_5$, and $R_7$ is selected, independently, from H, optionally substituted $C_{1-6}$ alkyl, $C(O)R_8$, or a hydrolyzable linker Y that comprises a covalent bond to an amino acid of the polypeptide; $R_6$ is H, optionally substituted $C_{1-6}$ alkyl, optionally substituted aryl, optionally substituted heteroaryl; $R_8$ is selected from optionally substituted $C_{1-6}$ alkyl or optionally substituted aryl; each $R_9$ and $R_{10}$ is selected, independently, from H, optionally substituted $C_{1-6}$ alkyl, or optionally substituted aryl; and n is 1, 2, 3, 4, 5, 6, 7, or 8. In certain embodiments, the etoposide derivative is conjugated at the 2' or 3' hydroxyl group. Further examples of such conjugation strategies are described in U.S.

Provisional Application Nos. 61/105,654, filed Oct. 15, 2008, and 61/171,010, filed Apr. 20, 2009.

Other derivatives of etoposide include etoposide phosphate (ETOPOPHOS®), where the phenolic —OH is replaced with —OP(O)(OH)$_2$, or any pharmaceutically acceptable salt thereof (e.g., —OP(O)(ONa)$_2$). Etoposide phosphate has improved water solubility compared to etoposide.

Other etoposide derivatives include those where the phenolic —OH is replaced with an acyloxy group (e.g., —OC(O)R$_8$, as described herein) such as the following compound:

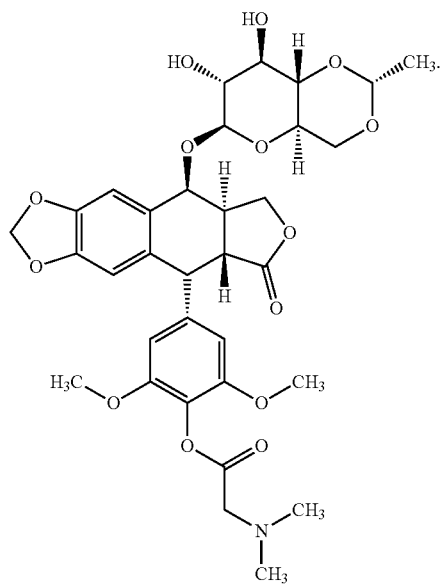

("etoposide 4'-dimethylglycine" or "etoposide$_{DMG}$")

These acylated etoposide derivatives can also show improved water solubility relative to etoposide when covalently attached to any of the polypeptides described herein.

Other exemplary podophyllotoxin derivatives include teniposide and NK611.

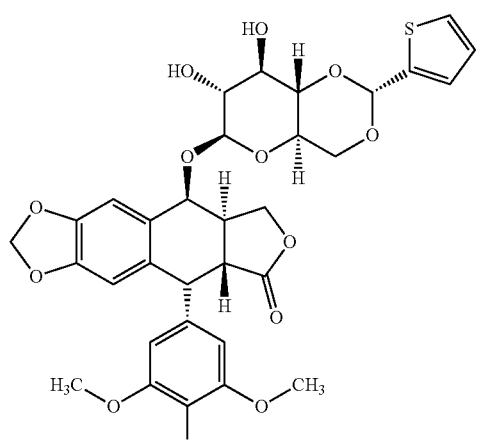

TENIPOSIDE

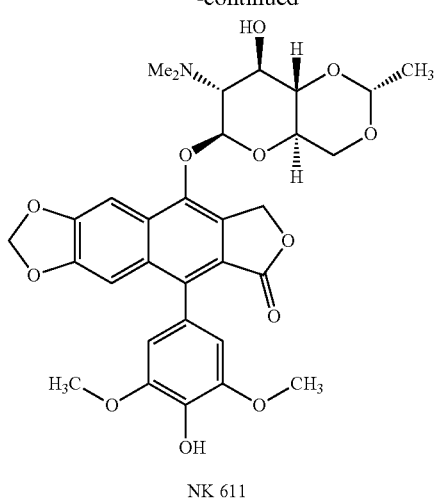

NK 611

Still other podophyllotoxin derivatives suitable for use in the invention are described in U.S. Pat. Nos. 4,567,253; 4,609,644; 4,900,814; 4,958,010; 5,489,698; 5,536,847; 5,571,914; 6,051,721; 6,107,284; 6,475,486; 6,610,299; 6,878,746; 6,894,075; 7,087,641; 7,176,236; 7,241,595; 7,342,114; and 7,378,419; and in U.S. Patent Publication Nos. 20030064482, 20030162722, 20040044058, 20060148728, and 20070249651, each of which is hereby incorporated by reference.

Doxorubicin Derivatives

In some embodiments, the anti-cancer agent is doxorubicin (hydroxydaunorubicin or Adriamycin®) or a doxorubicin derivative such as epirubicin (Ellence® or Pharmorubicie®). The structures of these exemplary compounds are shown below. Doxorubicin and doxorubicin derivatives can be covalently attached to an amino acid in any of the polypeptides described herein through a hydrolyzable covalent linker bonded to, for example, the 14-hydroxyl group.

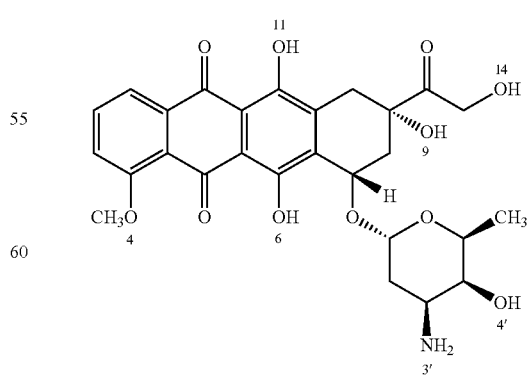

Doxorubicin

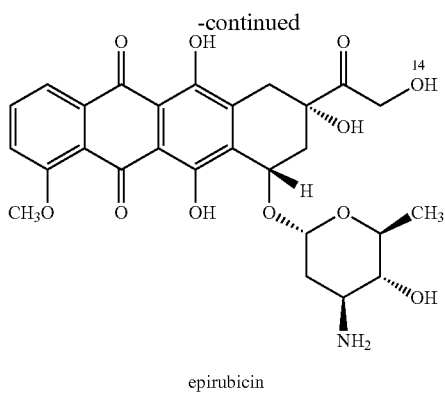

epirubicin

Doxorubicin derivatives can be described generally by the following formula:

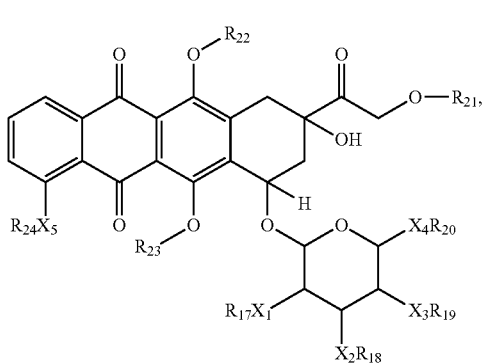

(II)

where each $X_1$, $X_2$, $X_3$, $X_4$, and $X_5$ is selected, independently, from a covalent bond, O, or $NR_{25}$; each $R_{17}$, $R_{18}$, $R_{19}$, $R_{20}$, $R_{20}$, $R_{21}$, $R_{22}$, $R_{23}$, $R_{24}$, and $R_{25}$, is selected, independently, from H, optionally substituted $C_{1-6}$ alkyl, optionally substituted $C_{2-6}$ alkenyl, optionally substituted $C_{2-6}$ alkynyl, optionally substituted cycloalkyl, optionally substituted heterocyclyl, or is a hydrolyzable linker Y as defined herein.

When a compound of Formula (II) is attached to any of the polypeptides described herein, one of $R_{17}$, $R_{18}$, $R_{19}$, $R_{20}$, $R_{20}$, $R_{21}$, $R_{22}$, $R_{23}$, $R_{24}$, and $R_{25}$ is Y. In certain embodiments, $R_{21}$ is Y.

Other doxorubicin derivatives can be found in U.S. Pat. Nos. 4,098,884, 4,301,277, 4,314,054, 4,464,529, 4,585,859, 4,672,057, 4,684,629, 4,826,964, 5,200,513, 5,304,687, 5,594,158, 5,625,043, and 5,874,412, each of which is hereby incorporated by reference.

Nucleic Acids

The multimeric peptide vectors may be conjugated to any nucleic acid, including expression vectors (e.g., a plasmid) and therapeutic nucleic acids (e.g., RNAi agents). The expression vector may encode a polypeptide (e.g., a therapeutic polypeptide such as an interferon, a therapeutic cytokine (e.g., IL-12), or FGF-2) or may encode a therapeutic nucleic acid (e.g., an RNAi agent such as those described herein).

Nucleic acids include any type known in the art, such as double and single-stranded DNA and RNA molecules of any length, conformation, charge, or shape (i.e., linear, concatemer, circular (e.g., a plasmid), nicked circular, coiled, supercoiled, or charged. Additionally, the nucleic acid can contain 5' and 3' terminal modifications and include blunt and overhanging nucleotides at these termini, or combinations thereof. In certain embodiments of the invention the nucleic acid is or encodes an RNA interference sequence (e.g., an siRNA, shRNA, miRNA, or dsRNA nucleotide sequence) that can silence a targeted gene product. The nucleic acid can be, for example, a DNA molecule, an RNA molecule, or a modified form thereof.

Exemplary RNAi targets include growth factors (e.g., epidermal growth factor (EGF), vascular endothelial growth factor (VEGF), transforming growth factor-β (TGF-β)), growth factor receptors, including receptor tyrosine kinases (e.g., EGF receptor (EGFR), including Her2/neu (ErbB), VEGF receptor (VEGFR), platelet-derived growth factor receptor (PDGFR), cytokines, chemokines, kinases, including cytoplasmic tyrosine and serine/threonine kinases (e.g., focal adhesion kinase, cyclin-dependent kinase, SRC kinases, syk-ZAP70 kinases, BTK kinases, RAF kinase, MAP kinases (including ERIC), and Wnt kinases), phosphatases, regulatory GTPases (e.g., Ras protein), transcription factors (e.g., MYC), hormones and hormone receptors (e.g., estrogen and estrogen receptor), anti-apoptotic molecules (e.g., survivin, Bcl-2, Bcl-xL), oncogenes (e.g., tumor suppressor regulators such as mdm2), enzymes (e.g., superoxide dismutase 1 (SOD-1), α, β (BACE), and γ secretases, alpha-L-iduronidase, iduronate sulfatase, heparan N-sulfatase, alpha-N-acetylglucosaminidase, acetyl-CoAlpha-glucosaminide acetyltransferase, N-acetylglucosamine 6-sulfatase, N-acetylgalactosamine 4-sulfatase, beta-galactosidase, sphingomyelinase, glucocerebrosidase, alpha-galactosidase-A, ceramidase, galactosylceramidase, arylsulfatase A, aspartoacylase, phytanoyl-CoA hydroxylase, peroxin-7, beta-hexosaminidase A, aspartylglucosaminidase, fucosidase, and alpha-mannosidase, sialidase), and other proteins (e.g., Huntingtin (Htt protein), amyloid precursor protein (APP), sorting nexins (including SNX6), α-synuclein, LINGO-1, Nogo-A, and Nogo receptor 1 (NgR-1)), and glial fibrillary acidic protein. Table 2 illustrates the relationship between exemplary RNAi targets and diseases.

Exemplary RNAi sequences to silence EGFR are SEQ ID NO:117 (GGAGCUGCCCAUGAGAAAU) and SEQ ID NO:118 (AUUUCUCAUGGGCAGCUCC). Likewise, VEGF can be silenced with an RNAi molecule having the sequence, for example, set forth in SEQ ID NO:119 (GGAGTACCCTGATGAGATC). Additional RNAi sequences for use in the agents of the invention may be either commercially available (e.g., Dharmacon, Ambion) or the practitioner may use one of several publicly available software tools for the construction of viable RNAi sequences (e.g., The siRNA Selection Server, maintained by MIT/Whitehead; available at: http://jura.wi.mit.edu/bioc/siRNAext/). Examples of diseases or conditions, and RNAi target that may be useful in treatment of such diseases, are shown in Table 3.

TABLE 2

Exemplary Diseases and Target Molecules

| Disease/Condition | RNAi Target Molecules |
|---|---|
| Cancer | |
| Glioblastoma | Epidermal growth factor receptor (EGFR), Vascular endothelial growth factor (VEGF) |
| Glioma | EGFR, VEGF |
| Astrocytoma | EGFR, VEGF |

TABLE 2-continued

Exemplary Diseases and Target Molecules

| Disease/Condition | RNAi Target Molecules |
|---|---|
| Neuroblastoma | EGFR, VEGF |
| Lung cancer | EGFR, VEGF |
| Breast cancer | EGFR, VEGF |
| Hepatocellular carcinoma | EGFR, VEGF |
| Neurodegenerative Disease | |
| Huntington's disease | Huntingtin (Htt) |
| Parkinson's disease | Alpha-synuclein |
| Alzheimer's disease | Amyloid precursor protein (APP), Presenilin-1 or -2, Apolipoprotein E (ApoE) |
| Amyotropic lateral schlerosis | Superoxide dismutase 1 (SOD-1) |
| Multiple schlerosis | Sorting nexin-6 (SNX6), LINGO-1, Nogo-A, NgR-1, APP |
| Lysosomal Storage Disease | |
| MPS-I (Hurler, Scheie diseases) | Alpha-L-iduronidase |
| MPS-II (Hunter syndrome) | Iduronate sulfatase |
| MPS-IIIA (Sanfilippo syndrome A) | Heparan N-sulfatase |
| MPS-IIIB (Sanfilippo syndrome B) | Alpha-N-acetylglucosaminidase |
| MPS-IIIC (Sanfilippo syndrome C) | Acetyl-CoAlpha-glucosaminide acetyltransferase |
| MPS-IIID (Sanfilippo syndrome D) | N-acetylglucosamine 6-sulfatase |
| MPS-VI (Maroteaux-Lamy syndrome) | N-acetylgalactosamine 4-sulfatase |
| MPS-VII (Sly syndrome) | Beta-glucuronidase |
| Niemann-Pick disease | Sphingomyelinase |
| Gaucher's disease | Glucocerebrosidase |
| Fabry disease | Alpha-galactosidase-A |
| Farber's disease | Ceramidase |
| Krabbé disease | Galactosylceramidase |
| Metachromatic leukodystrophy | Arylsulfatase A |
| Alexander disease | Glial fibrillary acidic protein |
| Canavan disease | Aspartoacylase |
| Refsum's disease | Phytanoyl-CoA hydroxylase or peroxin-7 |
| GM1 gangliosidoses | Beta-galactosidase |
| GM2 gangliosidoses (e.g., Tay-Sachs, Sandhoff diseases) | Beta-hexosaminidase A |
| Aspartylglucosaminuria | Aspartylglucosaminidase (AGA). |
| Fucosidosis | Fucosidase |
| Mannosidosis | Alpha-mannosidase |
| Mucolipodosis (sialidosis) | Sialidase |

GLP-1 Agonists

The multimers described herein can be conjugated to GLP-1 agonist known in the art. Particular GLP-1 agonists include GLP-1, exendin-4, and analogs thereof. Exemplary analogs are described below.

Exendin-4 and exendin-4 analogs. Exendin-4 and exendin-4 analogs can also be used in the compositions, methods, and kits of the invention. The compounds of the invention can include fragments of the exendin-4 sequence. Exendin-4 has the sequence.

His-Gly-Glu-Gly-Thr-Phe-Thr-Ser-Asp-Leu-Ser-Lys-
Gln-Met-Glu-Glu-Glu-Ala-Val-Arg-Leu-Phe-Ile-
Glu-Trp-Leu-Lys-Asn-Gly-Gly-Pro-Ser-Ser-Gly-
Ala-Pro-Pro-Pro-Ser-NH$_2$ (SEQ ID NO: 132)

Particular exendin-4 analogs include those having a cysteine substitution (e.g., [Cys$^{32}$]exendin-4 (SEQ ID NO: 133)) or a lysine substitution (e.g., [Lys$^{39}$]exendin-4 (SEQ ID NO: 134)).

Exendin analogs are also described in U.S. Pat. No. 7,157,555 and include those of the formula:

$X_1$-$X_2$-$X_3$-Gly-Thr-$X_4$-$X_5$-$X_6$-$X_7$-$X_8$-Ser-Lys-Gln-
$X_9$-Glu-Glu-Glu-Ala-Val-Arg-Leu-$X_{10}$-$X_{11}$-$X_{12}$-
$X_{13}$-Leu-Lys-Asn-Gly-Gly-$X_{14}$-Ser-Ser-Gly-Ala-
$X_{15}$-$X_{16}$-$X_{17}$-$X_{18}$-Z (SEQ ID NO: 135)

where $X_1$ is His, Arg or Tyr; $X_2$ is Ser, Gly, Ala or Thr; $X_3$ is Asp or Glu; $X_4$ is Phe, Tyr or NaI; $X_5$ is Thr or Ser; $X_6$ is Ser or Thr; $X_7$ is Asp or Glu; $X_8$ is Leu, Ile, Val, pGly or Met; $X_9$ is Leu, Ile, pGly, Val or Met; $X_{10}$ is Phe, Tyr, or NaI; $X_{11}$ is Ile, Val, Leu, pGly, t-BuG or Met; $X_{12}$ is Glu or Asp; $X_{13}$ is Trp, Phe, Tyr, or NaI; $X_{14}$, $X_{15}$, $X_{16}$ and $X_{17}$ are independently Pro, HPro, 3Hyp, 4Hyp, TPro, N-alkylglycine, N-alkyl-pGly or N-alkylalanine; $X_{18}$ is Ser, Thr, or Tyr; and Z s —OH or —NH$_2$ (e.g., with the proviso that the compound is not exendin-3 or exindin-4.)

Preferred N-alkyl groups for N-alkylglycine, N-alkyl-pGly and N-alkylalanine include lower alkyl groups (e.g., $C_{1-6}$ alkyl or $C_{1-4}$ alkyl).

In certain embodiments, $X_1$ is His or Tyr (e.g., His). $X_2$ can be Gly. $X_9$ can be Leu, pGly, or Met. $X_{13}$ can be Trp or Phe. $X_4$ can be Phe or NaI; $X_{11}$ can be Ile or Val, and $X_{14}$, $X_{15}$, $X_{16}$ and $X_{17}$ can be independently selected from Pro, HPro, TPro, or N-alkylalanine (e.g., where N-alkylalanine has a N-alkyl group of 1 to about 6 carbon atoms). In one aspect, $X_{15}$, $X_{16}$, and $X_{17}$ are the same amino acid residue. $X_{18}$ may be Ser or Tyr (e.g., Ser). Z can be —NH$_2$.

In other embodiments, $X_1$ is His or Tyr (e.g., His); $X_2$ is Gly; $X_4$ is Phe or NaI; $X_9$ is Leu, pGly, or Met; $X_{10}$ is Phe or NaI; $X_{11}$ is Ile or Val; $X_{14}$, $X_{15}$, $X_{16}$, and $X_{17}$ are independently selected from Pro, HPro, TPro, or N-alkylalanine; and $X_{18}$ is Ser or Tyr, (e.g., Ser). Z can be —NH$_2$.

In other embodiments, $X_1$ is His or Arg; $X_2$ is Gly; $X_3$ is Asp or Glu; $X_4$ is Phe or napthylalanine; $X_5$ is Thr or Ser; $X_6$ is Ser or Thr; $X_7$ is Asp or Glu; $X_8$ is Leu or pGly; $X_9$ is Leu or pGly; $X_{10}$ is Phe or NaI; $X_{11}$ is Ile, Val, or t-butyltylglycine; $X_{12}$ is Glu or Asp; $X_{13}$ is Trp or Phe; $X_{14}$, $X_{15}$, $X_{16}$, and $X_{17}$ are independently Pro, HPro, TPro, or N-methylalanine; $X_{18}$ is Ser or Tyr: and Z s —OH or —NH$_2$ (e.g., where the compound is not exendin-3 or exendin-4). Z can be —NH$_2$.

In another embodiment, $X_9$ is Leu, Ile, Val, or pGly (e.g., Leu or pGly) and $X_{13}$ is Phe, Tyr, or NaI (e.g., Phe or NaI). These compounds can exhibit advantageous duration of action and be less subject to oxidative degradation, both in vitro and in vivo, as well as during synthesis of the compound.

Other exendin analogs also described in U.S. Pat. Nos. 7,157,555 and 7,223,725, include compounds of the formula:

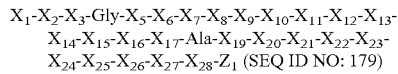

where $X_1$ is His, Arg, or Tyr; $X_2$ is Ser, Gly, Ala, or Thr; $X_3$ is Asp or Glu; $X_5$ is Ala or Thr; $X_6$ is Ala, Phe, Tyr, or NaI; $X_7$ is Thr or Ser; $X_8$ is Ala, Ser, or Thr; $X_9$ is Asp or Glu; $X_{10}$ is Ala, Leu, Ile, Val, pGly, or Met; $X_{11}$ is Ala or Ser; $X_{12}$ is Ala or Lys; $X_{13}$ is Ala or Gln; $X_{14}$ is Ala, Leu, Ile, pGly, Val, or Met; $X_{15}$ is Ala or Glu; $X_{16}$ is Ala or Glu; $X_{17}$ is Ala or Glu; $X_{19}$ is Ala or Val; $X_{20}$ is Ala or Arg; $X_{21}$ is Ala or Leu; $X_{22}$ is Phe, Tyr, or NaI; $X_{23}$ is Ile, Val, Leu, pGly, t-BuG, or Met; $X_{24}$ is Ala, Glu, or Asp; $X_{25}$ is Ala, Trp, Phe, Tyr, or NaI; $X_{26}$ is Ala or Leu; $X_{27}$ is Ala or Lys; $X_{28}$ is Ala or Asn; $Z_1$ s —OH, —NH$_2$, Gly-$Z_2$, Gly-Gly-$Z_2$, Gly-Gly-$X_{31}$-$Z_2$, Gly-Gly-$X_{31}$-Ser-$Z_2$, Gly-Gly-$X_{31}$-Ser-Ser-$Z_2$, Gly-Gly-$X_{31}$-Ser-Ser-Gly-$Z_2$, Gly-Gly-$X_{31}$-Ser-Ser-Gly-Ala-$Z_2$, Gly-Gly-$X_{31}$-Ser-Ser-Gly-Ala-$X_{36}$-$Z_2$, Gly-Gly-$X_{31}$-Ser-Ser-Gly-Ala-$X_{36}$-$X_{37}$-$Z_2$ Or Gly-Gly-$X_{31}$-Ser-Ser-Gly-Ala-$X_{36}$-$X_{37}$-$X_{38}$-$Z_2$; $X_{31}$, $X_{36}$, $X_{37}$, and $X_{38}$ are independently Pro, HPro, 3Hyp, 4Hyp, TPro, N-alkylglycine, N-alkyl-pGly or N-alkylalanine; and $Z_2$ s —OH or —NH$_2$ (e.g., provided that no more than three of $X_5$, $X_6$, $X_8$, $X_{10}$, $X_{11}$, $X_{12}$, $X_{13}$, $X_{14}$, $X_{15}$, $X_{16}$, $X_{17}$, $X_{19}$, $X_{20}$, $X_{21}$, $X_{24}$, $X_{25}$, $X_{26}$, $X_{27}$ and $X_{28}$ are Ala). Preferred N-alkyl groups for N-alkylglycine, N-alkyl-pGly and N-alkylalanine include lower alkyl groups of 1 to about 6 carbon atoms (e.g., 1 to 4 carbon atoms).

In certain embodiments, $X_1$ is His or Tyr (e.g., His). $X_2$ can be Gly. $X_{14}$ can be Leu, pGly, or Met. $X_{25}$ can be Trp or Phe. In some embodiments, $X_6$ is Phe or NaI, $X_{22}$ is Phe or NaI, and $X_{23}$ is Ile or Val. $X_{31}$, $X_{36}$, $X_{37}$, and $X_{38}$ can be independently selected from Pro, HPro, TPro, and N-alkylalanine. In certain embodiments, $Z_1$ s —NH$_2$ or $Z_2$ s —NH$_2$.

In another embodiment, $X_1$ is His or Tyr (e.g., His); $X_2$ is Gly; $X_6$ is Phe or NaI; $X_{14}$ is Leu, pGly, or Met; $X_{22}$ is Phe or NaI; $X_{23}$ is Ile or Val; $X_{31}$, $X_{36}$, $X_{37}$, and $X_{38}$ are independently selected from Pro, HPro, TPro, or N-alkylalanine. In particular embodiments, $Z_1$ s —NH$_2$.

In another embodiment, $X_1$ is His or Arg; $X_2$ is Gly or Ala; $X_3$ is Asp or Glu; $X_5$ is Ala or Thr; $X_6$ is Ala, Phe, or naphthylalanine; $X_7$ is Thr or Ser; $X_8$ is Ala, Ser, or Thr; $X_9$ is Asp or Glu; $X_{10}$ is Ala, Leu, or pGly; $X_{11}$ is Ala or Ser; $X_{12}$ is Ala or Lys; $X_{13}$ is Ala or Gln; $X_{14}$ is Ala, Leu, or pGly; $X_{15}$ is Ala or Glu; $X_{16}$ is Ala or Glu; $X_{17}$ is Ala or Glu; $X_{19}$ is Ala or Val; $X_{20}$ is Ala or Arg; $X_{21}$ is Ala or Len; $X_{22}$ is Phe or NaI; $X_{23}$ is Ile, Val or t-BuG; $X_{24}$ is Ala, Glu or Asp; $X_{25}$ is Ala, Trp or Phe; $X_{26}$ is Ala or Leu; $X_{27}$ is Ala or Lys; $X_{28}$ is Ala or Asn; $Z_1$ s —OH, —NH$_2$, Gly-$Z_2$, Gly-Gly-$Z_2$, Gly-Gly-$X_{31}$-$Z_2$, Gly-Gly $X_{31}$-Ser-$Z_2$, Gly-Gly-$X_{31}$ Ser-Ser-$Z_2$, Gly-Gly-$X_{31}$ Ser-Ser-Gly-$Z_2$, Gly-Gly-$X_{31}$ Ser-Ser-Gly Ala-$Z_2$, Gly-Gly-$X_{31}$ Ser-Ser-Gly-Ala-$X_{36}$-$Z_2$, Gly-Gly-$X_{31}$-Ser-Ser-Gly-Ala-$X_{36}$-$X_{37}$-$Z_2$, Gly-Gly-$X_{31}$-Ser-Ser-Gly-Ala-$X_{36}$-$X_{37}$-$X_{38}$-$Z_2$; $X_{31}$, $X_{36}$, $X_{37}$ and $X_{38}$ being independently Pro HPro, TPro or N-methylalanine; and $Z_2$ being —OH or —NH$_2$ (e.g., provided that no more than three of $X_3$, $X_5$, $X_6$, $X_8$, $X_{10}$, $X_{11}$, $X_{12}$, $X_{13}$, $X_{14}$, $X_{15}$, $X_{16}$, $X_{17}$, $X_{19}$, $X_{20}$, $X_{21}$, $X_{24}$, $X_{25}$, $X_{26}$, $X_{27}$ and $X_{28}$ are Ala).

In yet another embodiment, $X_{14}$ is Leu, Ile, Val, or pGly (e.g., Leu or pGly), and $X_{25}$ is Phe, Tyr or NaI (e.g., Phe or NaI).

Exendin analogs described in U.S. Pat. No. 7,220,721 include compounds of the formula:

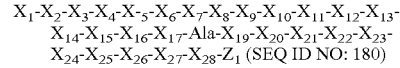

where $X_1$ is His, Arg, Tyr, Ala, Norval, Val, or Norleu; $X_2$ is Ser, Gly, Ala, or Thr; $X_3$ is Ala, Asp, or Glu; $X_4$ is Ala, Norval, Val, Norleu, or Gly; $X_5$ is Ala or Thr; $X_6$ is Phe, Tyr or NaI; $X_7$ is Thr or Ser; $X_8$ is Ala, Ser or Thr; $X_9$ is Ala, Norval, Val, Norleu, Asp, or Glu; $X_{10}$ is Ala, Leu, Ile, Val, pGly, or Met; $X_{11}$ is Ala or Ser; $X_{12}$ is Ala or Lys; $X_{13}$ is Ala or Gln; $X_{14}$ is Ala, Leu, Ile, pGly, Val, or Met; $X_{15}$ is Ala or Glu; $X_{16}$ is Ala or Glu; $X_{17}$ is Ala or Glu; $X_{19}$ is Ala or Val; $X_{20}$ is Ala or Arg; $X_{21}$ is Ala or Leu; $X_{22}$ is Phe, Tyr, or NaI; $X_{23}$ is Ile, Val, Leu, pGly, t-BuG, or Met; $X_{24}$ is Ala, Glu, or Asp; $X_{25}$ is Ala, Trp, Phe, Tyr, or NaI; $X_{26}$ is Ala or Leu; $X_{27}$ is Ala or Lys; $X_{28}$ is Ala or Asn; $Z_1$ s —OH, —NH$_2$, Gly-$Z_2$, Gly-Gly-$Z_2$, Gly-Gly-$X_{31}$-$Z_2$, Gly-Gly-$X_{31}$-Ser-$Z_2$, Gly-Gly-$X_{31}$-Ser-Ser-$Z_2$, Gly-Gly-$X_{31}$-Ser-Ser-Gly-$Z_2$, Gly-Gly-$X_{31}$ Ser-Ser-Gly-Ala-$Z_2$, Gly-Gly-$X_{31}$-Ser-Ser-Gly-Ala-$X_{13}$-$Z_2$, Gly-Gly-$X_{31}$, Ser-Ser-Gly-Ala-$X_{36}$-$X_{37}$-$Z_2$, Gly-Gly $X_{31}$ Ser Ser Gly Ala $X_{36}X_{37}$ $X_{31}$-$Z_2$ or Gly Gly $X_{31}$ Ser Ser Gly Ala $X_{36}$ $X_{37}X_{38}$ $X_{39}$-$Z_2$; where $X_{31}$, $X_{36}$, $X_{37}$, and $X_{38}$ are independently Pro, HPro, 3Hyp, 4Hyp, TPro, N-alkylglycine, N-alkyl-pGly, or N-alkylalanine; and $Z_2$ is —OH or —NH$_2$ (e.g., provided that no more than three of $X_3$, $X_4$, $X_5$, $X_8$, $X_9$, $X_{10}$, $X_{11}$, $X_{12}$, $X_{13}$, $X_{14}$, $X_{15}$, $X_{16}$, $X_{17}$, $X_{19}$, $X_{20}$, $X_{21}$, $X_{24}$, $X_{25}$, $X_{26}$, $X_{27}$ and $X_{28}$ are Ala and/or provided also that, if $X_1$ is His, Arg, or Tyr, then at least one of $X_3$, $X_4$ and $X_9$ is Ala).

U.S. Pat. No. 7,329,646 describes exendin-4 analogs having the general formula:

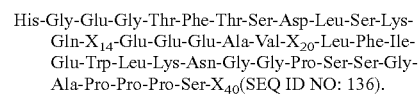

where $X_{14}$ is Arg, Leu, Ile, or Met; $X_{20}$ is His, Arg, or Lys; $X_{40}$ is Arg-OH, —OH, —NH$_2$ or Lys-OH. In certain embodiments, when $X_{14}$ is Met and $X_{20}$ is Arg, $X_{40}$ cannot be —NH$_2$. Other exendin-4 derivatives include [(Ile/Leu/Met)$^{14}$,(His/Lys)$^{20}$,Arg$^{40}$]exendin-4; [(not Lys/not Arg)$^{12}$,(not Lys/not Arg)$^{20}$,(not Lys/not Arg)$^{27}$,Arg$^{40}$]exendin-4; and [(not Lys/not Arg)$^{20}$,Arg$^{40}$]exendin-4. Particular exendin-4 analogs include [Lys$^{20}$,Arg$^{40}$]exendin-4,[His$^{20}$,Arg$^{40}$]exendin-4; and [Leu$^{14}$,Lys$^{20}$,Arg$^{40}$]exendin-4.

The invention may also use truncated forms of exendin-4 or any of the exendin analogs described herein. The truncated forms may include deletions of 1, 2, 3, 4, 5, 6, 7, 8, 9, 10, 11, 12, 13, 14, 15, 16, 17, 18, 19, or 20 amino acids from the N-terminus, from the C-terminus, or a combination thereof. Particular exendin-4 fragments include Exendin-4(1-31). Other fragments of exendin-4 are described in U.S. Patent Application Publication No. 2007/0037747 and have the formula:

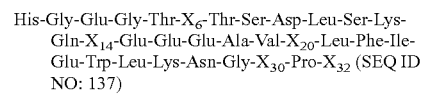

where $X_6$ is Phe or Tyr, $X_{14}$ is Met, Ile or Leu, $X_{20}$ is Lys; $X_{30}$ is Gly or is absent; and $X_{32}$ is Arg or is absent.

GLP-1 and GLP-1 analogs. The GLP-1 agonist used in the compositions, methods, and kits of the invention can be GLP-1 or a GLP-1 analog. In certain embodiments, the GLP-1 analog is a peptide, which can be truncated, may have one or more substitutions of the wild type sequence (e.g., the human wild type sequence), or may have other chemical modifications. GLP-1 agonists can also be non-peptide compounds, for example, as described in U.S. Pat. No. 6,927,214. Particular analogs include LY548806, CJC-1131, and Liraglutide.

The GLP-1 analog can be truncated form of GLP-1. The GLP-1 peptide may be truncated by 1, 2, 3, 4, 5, 6, 7, 8, 9, 10, 11, 12, 13, 15, 20, or more residues from its N-terminus, its C-terminus, or a combination thereof. In certain embodiments, the truncated GLP-1 analog is the GLP-1(7-34), GLP-1(7-35), GLP-1(7-36), or GLP-1(7-37) human peptide or the C-terminal amidated forms thereof.

In other embodiments of the invention, modified forms of truncated GLP-1 peptides are used. Exemplary analogs are described in U.S. Pat. No. 5,545,618 and have the amino acid sequence:

His-Ala-Glu-Gly-Thr-Phe-Thr-Ser-Asp-Val-Ser-Ser-
Tyr-Leu-Glu-Gly-Gln-Ala-Ala-Lys-Glu-Phe-Ile-
Ala-Trp-Leu-Val-Lys-(Gly)-(Arg)-(Gly) (SEQ ID
NO: 138)

where (Gly), (Arg), and (Gly) are present or absent depending on indicated chain length, with at least one modification selected from the group consisting of (a) substitution of a neutral amino acid, Arg, or a D form of Lys for Lys at position 26 and/or 34 and/or a neutral amino acid, Lys, or a D form of Arg for Arg at position 36; (b) substitution of an oxidation-resistant amino acid for Trp at position 31; (c) substitution according to at least one of Tyr for Val at position 16; Lys for Ser at position 18; Asp for Glu at position 21; Ser for Gly at position 22; Arg for Gln at position 23; Arg for Ala at position 24; and Gln for Lys at position 26; (d) a substitution comprising at least one of an alternative small neutral amino acid for Ala at position 8; an alternative acidic amino acid or neutral amino acid for Glu at position 9; an alternative neutral amino acid for Gly at position 10; and an alternative acidic amino acid for Asp at position 15; and (e) substitution of an alternative neutral amino acid or the Asp or N-acylated or alkylated form of His for His at position 7. With respect to modifications (a), (b), (d), and (e), the substituted amino acids may be in the D form. The amino acids substituted at position 7 can also be the N-acylated or N-alkylated amino acids. Exemplary GLP-1 analogs include [D-His$^7$]GLP-1(7-37), [Tyr$^7$]GLP-1(7-37), [N-acetyl-His$^7$]GLP-1 (7-37), [N-isopropyl-His$^7$]GLP-1(7-37), [D-Ala$^8$]GLP-1(7-37), [D-Glu$^9$]GLP-1 (7-37), [Asp$^9$]GLP-1(7-37), [D-Asp$^9$]GLP-1(7-37), [D-Phe$^{10}$]GLP-1(7-37), [Ser$^{22}$,Arg$^{23}$,Arg$^{24}$,Gln$^{26}$]GLP-1(7-37), and [Ser$^8$,Gln$^9$, Tyr$^{16}$,Lys$^{18}$,Asp$^{21}$]GLP-1(7-37).

Other GLP-1 fragments are described in U.S. Pat. No. 5,574,008 have the formula:

R$_1$-Ser-Tyr-Leu-Glu-Gly-Gln-Ala-Ala-Lys-Glu-Phe-
Ile-Ala-Trp-Leu-Val-X-Gly-Arg-R$_2$ (SEQ ID
NO: 181)

where R$_1$ is H$_2$N; H$_2$N-Ser; H$_2$N-Val-Ser; H$_2$N-Asp-Val-Ser; H$_2$N-Ser-Asp-Val-Ser; H$_2$N-Thr-Ser-Asp-Val-Ser; H$_2$N-Phe-Thr-Ser-Asp-Val-Ser; H$_2$N-Thr-Phe-Thr-Ser-Asp-Val-Ser; H$_2$N-Gly-Thr-Phe-Thr-Ser-Asp-Val-Ser; H$_2$N-Glu-Gly-Thr-Phe-Thr-Ser-Asp-Val-Ser; or H$_2$N-Ala-Glu-Gly-Thr-Phe-Thr-Ser-Asp-Val-Ser; X is Lys or Arg; and R$_2$ is NH$_2$, OH, Gly-NH$_2$, or Gly-OH.

Other GLP-1 analogs, described in U.S. Pat. No. 5,118,666, include the sequence His-Ala-Glu-Gly-Thr-Phe-Thr-Ser-Asp-Val-Ser-Ser-Tyr-Leu-Glu-Gly-Gln-Ala-Ala-Lys-Glu-Phe-Ile-Ala-Trp-Leu-Val-X (SEQ ID NO: 139), where X is Lys, Lys-Gly, or Lys-Gly-Arg.

GLP-1 analogs also include peptides of the formula: H$_2$N—X—CO—R$_1$, where R$_1$ is OH, OM, or —NR$_2$R$_3$; M is a pharmaceutically acceptable cation or a lower branched or unbranched alkyl group (e.g., C$_{1-6}$ alkyl); R$_2$ and R$_3$ are independently selected from the group consisting of hydrogen and a lower branched or unbranched alkyl group (e.g., C$_{1-6}$ alkyl); X is a peptide comprising the sequence His-Ala-Glu-Gly-Thr-Phe-Thr-Ser-Asp-Val-Ser-Ser-Tyr-Leu-Glu-Gly-Gln-Ala-Ala-Lys-Glu-Phe-Ile-Ala-Trp-Leu-Val-Lys-Gly-Arg; (SEQ ID NO: 203); NH$_2$ is the amine group of the amino terminus of X; and CO is the carbonyl group of the carboxy terminus of X; acid addition salts thereof; and the protected or partially protected derivatives thereof. These compounds may have insulinotropic activity exceeding that of GLP-1(1-36) or GLP-1(1-37).

Other GLP-1 analogs are described in U.S. Pat. No. 5,981,488 and have the formula:

R$_1$-X-Glu-Gly-Thr-Phe-Thr-Ser-Asp-Val-Ser-Ser-Tyr-
Leu-Y-Gly-Gln-Ala-Ala-Lys-Z-Phe-Ile-Ala-Trp-
Leu-Val-Lys-Gly-Arg-R$_2$ (SEQ ID NO: 142)

where R$_1$ is His, D-His, desamino-His, 2-amino-His, β-hydroxy-His, homohistidine, α-fluoromethyl-His, or α-methyl-His; X is Met, Asp, Lys, Thr, Leu, Asn, Gln, Phe, Val, or Tyr; Y and Z are independently selected from Glu, Gln, Ala, Thr, Ser, and Gly; and R$_2$ is selected from NH$_2$ and Gly-OH (e.g., provided that, if R$_1$ is His, X is Val, Y is Glu, and Z is Glu, then R$_2$ is NH$_2$).

Other GLP-1 analogs are described in U.S. Pat. No. 5,512,549 and have the formula:

R$_1$-Ala-Glu-Gly-Thr-Phe-Thr-Ser-Asp-Val-Ser-Ser-
Tyr-Leu-Glu-Gly-Gln-Ala-Ala-Xaa-Glu-Phe-Ile-
Ala-Trp-Leu-Val-Lys(R$_2$)-Gly-Arg-R$_3$ (SEQ ID
NO: 143)

where R$_1$ is 4-imidazopropionyl (des-amino-histidyl), 4-imidazoacetyl, or 4-imidazo-α, adimethyl-acetyl; R$_2$, which is bound to the side chain of the Lys (e.g., through the ε amino group), is C$_{6-10}$ unbranched acyl or is absent; R$_3$ is Gly-OH or NH$_2$; and Xaa is Lys or Arg.

Still other GLP-1 analogs are described in U.S. Pat. No. 7,084,243. In one embodiment, the GLP-1 analog has the formula:

His-X$_8$-Glu-Gly-X$_{11}$-X$_{12}$-Thr-Ser-Asp-X$_{16}$-Ser-Ser-
Tyr-Leu-Glu-X$_{22}$-X$_{23}$-X$_{24}$-Ala-X$_{26}$-X$_{27}$-Phe-Ile-
Ala-X$_{31}$-Leu-X$_{33}$-X$_{34}$-X$_{35}$-X$_{36}$-R (SEQ ID NO: 144)

where X$_8$ is Gly, Ala, Val, Leu, Ile, Ser, or Thr; X$_{11}$ is Asp, Glu, Arg, Thr, Ala, Lys, or His; X$_{12}$ is His, Trp, Phe, or Tyr; X$_{16}$ is Leu, Ser Thr, Trp, His, Phe, Asp, Val, Tyr, Glu, or Ala; X$_{22}$ is Gly, Asp, Glu, Gln, Asn, Lys, Arg, Cys, or Cya; X$_{23}$ is His, Asp, Lys, Glu, or Gln; X$_{24}$ is Glu, His, Ala, or Lys; X$_{26}$ is Asp, Lys, Glu, or His; X$_{27}$ is Ala, Glu, His, Phe, Tyr, Trp, Arg, or Lys; X$_{30}$ is Ala, Glu, Asp, Ser, or His; X$_{33}$ is Asp, Arg, Val, Lys, Ala, Gly, or Glu; X$_{34}$ is Glu, Lys, or Asp; X$_{35}$ is Thr, Ser, Lys, Arg, Trp, Tyr, Phe, Asp, Gly, Pro, His, or Glu; X$_{36}$ is Arg, Glu, or His; R is Lys, Arg, Thr, Ser, Glu, Asp, Trp, Tyr, Phe, His, —NH$_2$, Gly, Gly-Pro, or Gly-Pro-NH$_2$, or is deleted (e.g., provided that the polypeptide does not have the sequence of GLP-1(7-37)OH or GLP-1(7-36)-NH$_2$ and provided that the polypeptide is not Gly$^8$-GLP-1(7-37)OH, Gly$^8$-GLP-1(7-36)NH$_2$, Val$^8$-GLP-1(7-37)OH, Val$^8$-GLP-1 (7-36)NH$_2$, Leu$^8$-GLP-1(7-37)OH, Leu$^8$-GLP-1(7-36)NH$_2$, Ile$^8$-GLP-1(7-37)OH, Ile$^8$-GLP-1(7-36)NH$_2$, Ser$^8$-GLP-1 (7-37)OH, Ser$^8$-GLP-1(7-36)NH$_2$, Thr$^8$-GLP-1(7-37)OH, or Thr$^8$-GLP-1(7-36)NH$_2$, Ala$^{11}$-Glp-1(7-37)OH, Ala$^{16}$-Glp-1 (7-36)NH$_2$, Ala$^{16}$-Glp-1(7-37)OH, Ala$^{16}$-Glp-1(7-36)NH$_2$, Ala²⁷-Glp-1(7-37)OH, Ala²⁷-Glp-1(7-36)NH₂, Ala²⁷-Glp-1 (7-37)OH, Ala²⁷-Glp-1(7-36)NH₂, Ala³³-Glp-1 (7-37)OH, or Ala³³-Glp-1(7-36)NH₂).

In another embodiment, the polypeptide has the amino acid sequence:

His-X₈-Glu-Gly-Thr-X₁₂-Thr-Ser-Asp-X₁₆-Ser-Ser-
Tyr-Leu-Glu-X₂₂-X₂₃-Ala-Ala-X₂₆-Glu-Phe-Ile-
X₃₀-Trp-Leu-Val-Lys-X₃₅-Arg-R (SEQ ID NO: 145)

where X₈ is Gly, Ala, Val, Leu, Ile, Ser, or Thr; X₁₂ is His, Trp, Phe, or Tyr; X₁₆ is Leu, Ser, Thr, Trp, His, Phe, Asp, Val, Glu, or Ala; X₂₂ is Gly, Asp, Glu, Gln, Asn, Lys, Arg, Cys, or Cya; X₂₃ is His, Asp, Lys, Glu, or Gln; X₂₆ is Asp, Lys, Glu, or His; X₃₀ is Ala, Glu, Asp, Ser, or His; X₃₅ is Thr, Ser, Lys, Arg, Trp, Tyr, Phe, Asp, Gly, Pro, His, or Glu; R is Lys, Arg, Thr, Ser, Glu, Asp, Trp, Tyr, Phe, His, —NH₂, Gly, Gly-Pro, Gly-Pro-NH₂, or is deleted, (e.g., provided that the polypeptide does not have the sequence of GLP-1 (7-37)OH or GLP-1(7-36)-NH₂ and provided that the polypeptide is not Gly⁸GLP-1(7-37)OH, Gly⁸-GLP-1(7-36)NH₂, Val⁸-GLP-1(7-37)OH, Val⁸-GLP-1(7-36)NH₂, Leu⁸-GLP-1(7-37)OH, Leu⁸-GLP-1(7-36)NH₂, Ile⁸-GLP-1(7-37)OH, Ile⁸-GLP-1(7-36)NH₂, Ser⁸-GLP-1(7-37)OH, Ser⁸-GLP-1(7-36)NH₂, Thr⁸-GLP-1(7-37) OH, Thr⁸-GLP-1(7-36)NH₂, Ala¹⁶-GLP(7-37)OH, or Ala¹⁶-GLP-1(7-36)NH₂).

In another embodiment, the polypeptide has the amino acid sequence:

His-X₈-Glu-Gly-Thr-Phe-Thr-Ser-Asp-Val-Ser-Ser-
Tyr-Leu-Glu-X₂₂-X₂₃-Ala-Ala-Lys-X₂₇-Phe-Ile-
X₃₀-Trp-Leu-Val-Lys-Gly-Arg-R (SEQ ID NO: 146)

where X₈ is Gly, Ala, Val, Leu, Ile, Ser, or Thr; X₂₂ is Gly, Asp, Glu, Gln, Asn, Lys, Arg, Cys, or Cya; X₂₃ is His, Asp, Lys, Glu, or Gln; X₂₇ is Ala, Glu, His, Phe, Tyr, Trp, Arg, or Lys X₃₀ is Ala, Glu, Asp, Ser, or His; R is Lys, Arg, Thr, Ser, Glu, Asp, Trp, Tyr, Phe, His, —NH₂, Gly, Gly-Pro, or Gly-Pro-NH₂, or is deleted (e.g., provided that the polypeptide does not have the sequence of GLP-1(7-37)OH or GLP-1(7-36) NH₂ and provided that the polypeptide is not Gly⁸-GLP-1(7-37)OH, Gly⁸-GLP-1(7-36)NH₂, Val⁸-GLP-1(7-37)OH, Val⁸-GLP-1(7-36)NH₂, Leu⁸-GLP-1(7-37)OH, Leu⁸-GLP-1(7-36)NH₂, Ile⁸-GLP-1(7-37)OH, Ile⁸-GLP-1(7-36)NH₂, Ser⁸-GLP-1(7-37)OH, Ser⁶-GLP-1(7-36)NH₂, Thr⁸-GLP-1(7-37) OH, Thr⁸-GLP-1(7-36)NH₂, Ala¹⁶-GLP-1(7-37)OH, Ala¹⁶-Glp-1(7-36) NH₂, Glu²⁷-Glp-1(7-37)OH, or Glu²⁷-Glp-1(7-36)NH₂.

In another embodiment, the polypeptide has the amino acid sequence:

X₇-X₈-Glu-Gly-Thr-Phe-Thr-Ser-Asp-Val-Ser-Ser-
Tyr-Leu-Glu-X₂₂-Gln-Ala-Ala-Lys-Glu-Phe-Ile-
Ala-Trp-Leu-Val-Lys-Gly-Arg-R (SEQ ID NO: 147)

where X₇ is L-His, D-His, desamino-His, 2-amino-His, β-hydroxy-His, homo-His, α-fluoromethyl-His or α-methyl-His; X₈ is Gly, Ala, Val, Leu, Ile, Ser or Thr (e.g., Gly, Val, Leu, Ile, Ser, or Thr); X₂₂ is Asp, Glu, Gln, Asn, Lys, Arg, Cys, or Cya, and R is —NH₂ or Gly(OH).

In another embodiment, the GLP-1 compound has an amino acid other than alanine at position 8 and an amino acid other than glycine at position 22. Specific examples of GLP-1 compounds include [Glu²²]GLP-1(7-37)OH, [Asp²²]GLP-1(7-37)OH, [Arg²²]GLP-1(7-37)OH, [Lys²²]GLP-1(7-37) OH, [Cya²²]GLP-1(7-37)OH, [Val⁸,Glu²²]GLP-1(7-37)OH, [Val⁸,Asp²²]GLP-1(7-37)OH, [Val⁸,Arg²²]GLP-1(7-37)OH, [Val⁸,Lys²²]GLP-1(7-37)OH, [Val⁸,Cya²²]GLP-1(7-37)OH, [Gly⁸,Glu²²]GLP-1(7-37)OH, [Gly⁸,Asp²²]GLP-1(7-37) OH, [Gly⁸,Arg²²]GLP-1(7-37)OH, [Gly⁸,Lys²²]GLP-1(7-37)OH, [Gly⁸,Cya²²]GLP-1(7-37)OH, [Glu²²]GLP-1(7-36)NH₂, [Asp²²]GLP-1(7-36)NH₂, [Arg²²]GLP-1(7-36) NH₂, [Lys²²]GLP-1(7-36)NH₂, [Cya²²]GLP-1(7-36)NH₂, [Val⁸,Glu²²]GLP-1(7-36)NH₂, [Val⁸,Asp²²]GLP-1(7-36) NH₂, [Val⁸,Arg²²]GLP-1(7-36)NH₂, [Val⁸,Lys²²]GLP-1(7-36)NH₂, [Val⁸,Cya²²]GLP-1(7-36)NH₂, [Gly⁸,Glu²²]GLP-1(7-36)NH₂, [Gly⁸,Asp²²]GLP-1(7-36)NH₂, [Gly⁸,Arg²²]GLP-1(7-36)NH₂, [Gly⁸,Lys²²]GLP-1(7-36)NH₂, [Gly⁸,Cya²²]GLP-1(7-36)NH₂, [Val⁸,Lys²³]GLP-1(7-37)OH, [Val⁸,Ala²⁷]GLP-1(7-37)OH, [Val⁸,Glu³⁰]GLP-1(7-37)OH, [Gly⁸,Glu³⁰]GLP-1(7-37)OH, [Val⁸,His³⁵]GLP-1(7-37)OH, [Val⁸,His³⁷]GLP-1(7-37)OH, [Val⁸,Glu²²,Lys²³]GLP-1(7-37)OH, [Val⁸,Glu²²,Glu²]GLP-1(7-37)OH, [Val⁸,Glu²², Ala²⁷]GLP-1(7-37)OH, [Val⁸,Gly³⁴,Lys³⁵]GLP-1(7-37)OH, [Val⁸,His³⁷]GLP-1(7-37)OH, [Gly⁸,His³⁷]GLP-1(7-37)OH.

Other GLP-1 analogs are described in U.S. Pat. No. 7,101,843 and include those having the formula:

X₇-X₈-Glu-Gly-Thr-X₁₂-Thr-Ser-Asp-X₁₆-Ser-X₁₈-
X₁₉-X₂₀-Glu-X₂₂-Gln-Ala-Ala-X₂₅-Lys-X₂₇-Phe-Ile-
X₃₀-Trp-Leu-X₃₃-Lys-Gly-Arg-X₃₇ (SEQ ID NO: 148)

wherein: X₇ is L-His, D-His, desamino-His, 2-amino-His, β-hydroxy-His, homohistidine, α-fluoromethyl-His, or α-methyl-His; X₈ is Ala, Gly, Val, Leu, Ile, Ser, or Thr; X₁₂ is Phe, Trp, or Tyr; X₁₆ is Val, Trp, Ile, Leu, Phe, or Tyr; X₁₈ is Ser, Trp, Tyr, Phe, Lys, Ile, Leu, or Val; X₁₉ is Tyr, Trp, or Phe; X₂₀ is Leu, Phe, Tyr, or Trp; X₂₂ is Gly, Glu, Asp, or Lys; X₂₅ is Ala, Val, Ile, or Leu; X₂₇ is Glu, Ile, or Ala; X₃₀ is Ala or Glu X₃₃ is Val, or Ile; and X₃₇ is Gly, His, NH₂, or is absent (e.g., provided that the compound does not have the sequence GLP-1(7-37)OH, GLP-1(7-36)—NH₂, [Gly⁸]GLP-1(7-37)OH, [Gly⁸]GLP-1 (7-36)NH₂, [Val⁸]GLP-1(7-37)OH, [Val⁸] GLP-1(7-36)NH₂, [Leu⁸]GLP-1(7-37)OH, [Leu⁸]GLP-1(7-36)NH₂, [Ile]GLP-1(7-37)OH, [Ile⁸]GLP-1(7-36)NH₂, [Ser⁸]GLP-1(7-37)OH, [Ser⁸]GLP-1(7-36)NH₂, [Thr⁸] GLP-1(7-37)OH, [Thr⁸]GLP-1(7-36)NH₂, [Val⁸,Tyr¹²] GLP-1(7-37)OH, [Val⁸,Tyr¹²]GLP-1(7-36)NH₂, [Val⁸,Tyr¹⁶]GLP-1(7-37)OH, [Val⁸,Tyr¹⁶]GLP-1(7-36)NH₂, [Val⁸,Glu²²]GLP-1(7-37)OH, [Val⁸,Glu²²]GLP-1(7-36) NH₂, [Gly⁸,Glu²²]GLP-1(7-37)OH, [Gly⁸,Glu²²]GLP-1(7-36)NH₂, [Val⁸,Asp²²]GLP-1(7-37)OH, [Val⁸,Asp²²]GLP-1(7-36)NH₂, [Gly⁸,Asp²²]GLP-1(7-37)OH, [Gly⁸,Asp²²] GLP-1(7-36)NH₂, [Val⁸,Lys²²]GLP-1(7-37)OH, [Val⁸,Lys²²]GLP-1(7-36)NH₂, [Gly⁸,Lys²²]GLP-1(7-37)OH, [Gly⁸,Lys²²]GLP-1(7-36)NH₂, [Leu⁸,Glu²²]GLP-1(7-37) OH, [Leu⁸,Glu²²]GLP-1(7-36)NH₂, [Ile⁸,Glu²²]GLP-1(7-37)OH, [Ile⁸,Glu²²]GLP-1(7-36)NH₂, [Leu⁸,Asp²²]GLP-1(7-37)OH, [Leu⁸,Asp²²]GLP-1(7-36)NH₂, [Ile⁸,Asp²²] GLP-1(7-37)OH, [Ile⁸,Asp²²]GLP-1(7-36)NH₂, [Leu⁸,Lys²²]GLP-1(7-37)OH, [Leu⁸,Lys²²]GLP 1(7-36)NH₂, [Ile⁸,Lys²²]GLP-1(7-37)OH, [Ile⁸,Lys²²]GLP-1(7-36)NH₂, [Ser⁸,Glu²²]GLP-1(7-37)OH, [Ser⁸,Glu²²]GLP-1(7-36)NH₂, [Thr⁸,Glu²²]GLP-1(7-37)OH, [Thr⁸,Glu²²]GLP-1(7-36) NH₂, [Ser⁸,Asp²²]GLP-1(7-37)OH, [Ser⁸,Asp²²]GLP-1(7-36)NH₂, [Thr⁸,Asp²²]GLP-1(7-37)OH, [Thr⁸,Asp²²]GLP-1(7-36)NH₂, [Ser⁸,Lys²²]GLP-1(7-37)OH, [Ser⁸,Lys²²]GLP-1(7-36)NH₂, [Thr⁸,Lys²²]GLP-1(7-37)OH, [Thr⁸,Lys²²] GLP-1(7-36)NH₂, [Glu²²]GLP-1(7-37)OH, [Glu²]GLP-1(7-36)NH₂, [Asp²²]GLP-1(7-37)OH, [Asp²²]GLP-1(7-36) NH₂, [Lys²²]GLP-1(7-37)OH, [Lys²²]GLP-1(7-36)NH₂, [Val⁸,Ala²⁷]GLP-1(7-37)OH, [Val⁸,Glu²²,Ala²⁷]GLP-1(7-37)OH, [Val⁸,Glu³⁰]GLP-1(7-37)OH, [Val⁸,Glu³⁰]GLP-1(7-36)NH₂, [Gly⁸,Glu³⁰]GLP-1(7-37)OH, [Gly⁸,Glu³⁰]GLP-1 (7-36)NH₂, [Leu⁸,Glu³⁰]GLP-1(7-37)OH, [Leu⁸,Glu³⁰] GLP-1(7-36)NH₂, [Ile⁸,Glu³⁰]GLP-1(7-37)OH, [Ile⁸,Glu³⁰] GLP-1(7-36)NH₂, [Ser⁸,Glu³⁰]GLP-1 (7-37)OH, [Ser⁸, Glu$^{30}$]GLP-1(7-36)NH$_2$, [Thr$^8$,Glu$^{30}$]GLP-1(7-37)OH, [Thr$^8$,Glu$^{30}$]GLP-1(7-36)NH$_2$, [Val$^8$,His$^{37}$]GLP-1(7-37) OH, [Val$^8$,His$^{37}$]GLP-1(7-36)NH$_2$, [Gly$^8$,His$^{37}$]GLP-1(7-37)OH, [Gly$^8$,His$^{37}$]GLP-1(7-36)NH$_2$, [Leu$^8$,His$^{37}$]GLP-1(7-37)OH, [Leu$^8$,His$^{37}$]GLP-1(7-36)NH$_2$, [Ile$^8$,His$^{37}$]GLP-1(7-37)OH, [Ile$^8$,His$^{37}$]GLP-1(7-36)NH$_2$, [Ser$^8$,His$^{37}$]GLP-1(7-37)OH, [Ser$^8$,His$^{37}$]GLP-1(7-36)NH$_2$, [Thr$^8$,His$^{37}$]GLP-1(7-37)OH, [Thr$^8$,His$^{37}$]GLP-1(7-36)NH$_2$).

Other GLP-1 analogs described in U.S. Pat. No. 7,101,843 have the formula:

X$_7$-X$_8$-Glu-Gly-Thr-Phe-Thr-Ser-Asp-X$_{16}$-Ser-X$_{18}$-
Tyr-Leu-Glu-X$_{22}$-Gln-Ala-X$_{25}$-Lys-Glu-Phe-Ile-
Ala-Trp-Leu-X$_{33}$-Lys-Gly-Arg-X$_{37}$ (SEQ ID
NO: 149)

wherein: X$_7$ is L-His, D-His, desamino-His, 2-amino-His, β-hydroxy-His, homohistidine, α-fluoromethyl-His, or α-methyl-His; X$_8$ is Gly, Ala, Val, Leu, Ile, Ser, or Thr; X$_{16}$ is Val, Phe, Tyr, or Trp; X$_{18}$ is Ser, Tyr, Trp, Phe, Lys, Ile, Leu, or Val; X$_{22}$ is Gly, Glu, Asp, or Lys; X$_{25}$ is Ala, Val, Ile, or Leu; X$_{33}$ is Val or Ile; and X$_{37}$ is Gly, NH$_2$, or is absent (e.g., provided that the GLP-1 compound does not have the sequence of GLP-1(7-37)OH, GLP-1(7-36)-NH$_2$, [Gly$^8$]GLP-1(7-37)OH, [Gly$^8$]GLP-1(7-36)NH$_2$, [Val$^8$]GLP-1(7-37)OH, [Val$^8$]GLP-1(7-36)NH$_2$, [Leu$^8$]GLP-1(7-37)OH, [Leu$^8$]GLP-1(7-36)NH$_2$, [Ile$^8$]GLP-1(7-37)OH, [Ile$^8$]GLP-1(7-36)NH$_2$, [Ser$^8$]GLP-1(7-37)OH, [Ser$^8$]GLP-1(7-36)NH$_2$, [Thr$^8$]GLP-1(7-37)OH, [Thr$^8$]GLP-1(7-36)NH$_2$, [Val$^8$-Tyr$^{16}$]GLP-1(7-37)OH, [Val$^8$-Tyr$^{16}$]GLP 1(7-36)NH$_2$, [Val$^8$,Glu$^{22}$]GLP-1(7-37)OH, [Val$^8$,Glu$^{22}$]GLP-1(7-36)NH$_2$, [Gly$^8$,Glu$^{22}$]GLP-1(7-37)OH, [Gly$^8$,Glu$^{22}$]GLP-1(7-36)NH$_2$, [Val$^8$,Asp$^{22}$]GLP-1(7-37)OH, [Val$^8$,Asp$^{22}$]GLP-1(7-36)NH$_2$, [Gly$^8$,Asp22]GLP-1(7-37)OH, [Gly$^8$,Asp$^{22}$]GLP-1(7-36)NH$_2$, [Val$^8$,Lys$^{22}$]GLP-1(7-37)OH, [Val$^8$,Lys$^{22}$]GLP-1(7-36)NH$_2$, [Gly$^8$,Lys$^{22}$]GLP-1(7-37)OH, [Gly$^8$,Lys$^{22}$]GLP-1(7-36)NH$_2$, [Leu$^8$,Glu$^{22}$]GLP-1(7-37)OH, [Leu$^8$,Glu$^{22}$]GLP-1(7-36)NH$_2$, [Ile$^8$,Glu$^{22}$]GLP-1(7-37)OH, [Ile$^8$,Glu$^{22}$]GLP-1(7-36)NH$_2$, [Leu$^8$,Asp$^{22}$]GLP1 (7-37)OH, [Leu$^8$,Asp$^{22}$]GLP-1(7-36)NH$_2$, [Ile$^8$,Asp$^{22}$]GLP-1(7-37)OH, [Ile$^8$,Asp$^{22}$]GLP-1(7-36)NH$_2$, [Leu$^8$,Lys$^{22}$]GLP-1(7-37)OH, [Leu$^8$,Lys$^{22}$]GLP-1(7-36)NH$_2$, [Ile$^8$,Lys$^{22}$]GLP-1(7-37)OH, [Ile$^8$,Lys$^{22}$]GLP-1(7-36)NH$_2$, [Ser$^8$,Glu$^{22}$]GLP-1(7-37)OH, [Ser$^8$,Glu$^{22}$]GLP-1(7-36)NH$_2$, [Thr$^8$,Glu$^{22}$]GLP-1(7-37)OH, [Thr$^8$,Glu$^{22}$]GLP-1(7-36)NH$_2$, [Ser$_8$,Asp$^{22}$]GLP-1(7-37)OH, [Ser$^8$, Asp$^{22}$]GLP-1(7-36)NH$_2$, [Thr$^8$,Asp$^{22}$]GLP-1(7-37)OH, [Thr$^8$,Asp$^{22}$]GLP-1(7-36)NH$_2$, [Ser$^8$,Lys$^{22}$]GLP-1(7-37)OH, [Ser$^8$,Lys$^{22}$]GLP-1(7-36)NH$_2$, [Thr$^8$,Lys$^{22}$]GLP-1(7-37)OH, [Thr$^8$,Lys$^{22}$]GLP-1(7-36)NH$_2$, [Glu$^{22}$]GLP-1(7-37)OH, [Glu$^{22}$]GLP-1(7-36)NH$_2$, [Asp$^{22}$]GLP-1(7-37)OH, [Asp$^{22}$]GLP-1(7-36)NH$_2$, [Lys$^{22}$]GLP-1(7-37)OH, [Lys$^{22}$]GLP-1(7-36)NH$_2$).

GLP-1 analogs are also described in U.S. Pat. No. 7,238,670 and have the structure:

A-X$_1$-X$_2$-X$_3$-X$_4$-X$_5$-X$_6$-X$_7$-X$_8$-X$_9$-Y-Z-B where each of X$_{1-9}$ is a naturally or nonnaturally occurring amino acid residue; Y and Z are amino acid residues; and one of the substitutions at the α-carbon atoms of Y and Z may each independently be substituted with a primary substituent group selected from the group consisting of hydrogen, alkyl, cycloalkyl, cycloalkylalkyl, heterocyclylalkyl, arylalkyl and heteroarylalkyl, heterocyclylalkyl said primary substituent optionally being substituted with a secondary substituent selected from a cycloalkyl, heterocyclyl, aryl, or heteroaryl group; any of said primary or secondary substituents may further be substituted with one or more of H, alkyl, cycloalkyl, arylalkyl, aryl, heterocyclyl, heteroaryl, alkenyl, alkynyl, halo, hydroxy, mercapto, nitro, cyano, amino, acylamino, azido, guanidino, amidino, carboxyl, carboxamido, carboxamido alkyl, formyl, acyl, carboxyl alkyl, alkoxy, aryloxy, arylalkyloxy, heteroaryloxy, heterocycleoxy, acyloxy, mercapto, mercapto alkyl, mercaptoaryl, mercapto acyl, halo, cyano, nitro, azido, amino, guanidino alkyl, guanidino acyl, sulfonic, sulfonamido, alkyl sulfonyl, aryl sulfonyl or phosphonic group; wherein, the primary or secondary substitutents may optionally be bridged by covalent bonds to form one or more fused cyclic or heterocyclic systems with each other; where, the other substitution at the alpha-carbon of Y may be substituted with H, C$_{1-6}$ alkyl, aminoalkyl, hydroxyalkyl or carboxyalkyl; where the other substitution at the alpha-carbon of Z may be substituted with hydrogen, C$_{1-12}$ alkyl, aminoalkyl, hydroxyalkyl, or carboxyalkyl;

A and B are optionally present, where A is present and A is H, an amino acid or peptide containing from about 1-15 amino acid residues, an R group, an R—C(O) (amide) group, a carbamate group RO—C(O), a urea R$_4$R$_5$N—C(O), a sulfonamido R—SO$_2$, or R$_4$R$_5$N—SO$_2$; where R is selected from the group consisting of hydrogen, C$_{1-12}$ alkyl, C$_{3-10}$ cycloalkyl, cycloalkylalkyl, heterocyclyl, heterocycloalkyl, aryl, heteroaryl, arylalkyl, aryloxyalkyl, heteroarylalkyl, and heteroaryloxyalkyl; R$_4$ and R$_5$ are each independently selected from the group consisting of H, alkyl, cycloalkyl, cycloalkylalkyl, heterocyclyl, heterocycloalkyl, aryl, heteroaryl, arylalkyl, aryloxyalkyl, heteroarylalkyl, and heteroaryloxyalky; where the α-amino group of X$_1$ is substituted with H or an alkyl group, said alkyl group may optionally form a ring with A; where B is present and B is OR$_1$, NR$_1$R$_2$, or an amino acid or peptide containing from 1 to 15 amino acid residues (e.g., 1 to 10 or 1 to 5) terminating at the C-terminus as a carboxamide, substituted carboxamide, an ester, a free carboxylic acid, or an amino-alcohol; where R$_1$ and R$_2$ are independently chosen from H, C$_{1-12}$ alkyl, C$_{3-10}$ cycloalkyl, cycloalkylalkyl, heterocyclyl, heterocycloalkyl, aryl, heteroaryl, arylalkyl, aryloxyalkyl, heteroarylalkyl or heteroaryloxyalkyl.

Exemplary substitutions on the α-carbon atoms of Y and Z include heteroarylarylmethyl, arylheteroarylmethyl, and biphenylmethyl forming biphenylalanine residues, any of which is also optionally substituted with one or more, hydrogen, alkyl, cycloalkyl, arylalkyl, aryl, heterocyclyl, heteroaryl, alkenyl, alkynyl, halo, hydroxy, mercapto, nitro, cyano, amino, acylamino, azido, guanidino, amidino, carboxyl, carboxamido, carboxamido alkyl, formyl, acyl, carboxyl alkyl, alkoxy, aryloxy, arylalkyloxy, heteroaryloxy, heterocycleoxy, acyloxy, mercapto, mercapto alkyl, mercaptoaryl, mercapto acyl, halo, cyano, nitro, azido, amino, guanidino alkyl, guanidino acyl, sulfonic, sulfonamido, alkyl sulfonyl, aryl sulfonyl and phosphonic group.

Other embodiments include isolated polypeptides where the other substitution at the α-carbon of Y is substituted with H, methyl, or ethyl; and where the other substitution at the α-carbon of Z is substituted with H, methyl, or ethyl.

Further embodiments include isolated polypeptides as described above where X$_1$ is naturally or non-naturally occurring amino acid residue in which one of the substitutions at the α-carbon is a primary substituent selected from the group consisting of heterocyclylalkyl, heteroaryl, heteroarylkalkyl and arylalkyl, said primary substituent optionally being substituted with secondary substituent selected from heteroaryl or heterocyclyl; and in which the other substitution at the α-carbon is H or alkyl; X$_2$ is naturally or nonnaturally occurring amino acid residue in which one of the substitutions at the α-carbon is an alkyl or cycloalkyl where the alkyl group may optionally form a ring with the nitrogen of X$_2$; and wherein the other substitution at the α-carbon is H or alkyl; $X_3$ is a naturally or nonnaturally occurring amino acid residue in which one of the substitutions at the α-carbon is a carboxyalkyl, bis-carboxyalkyl, sulfonylalkyl, heteroalkyl, or mercaptoalkyl; and where the other substitution at the α-carbon is hydrogen or alkyl; $X_4$ is a naturally or nonnaturally occurring amino acid residue in which the α-carbon is not substituted, or in which one of the substitutions at the α-carbon is aminoalkyl, carboxyalkyl heteroarylalkyl, or heterocyclylalkyl; $X_5$ is a naturally or nonnaturally occurring amino acid residue in which one of the substitutions at the α-carbon is an alkyl or hydroxyalkyl, and in which the other substitution at the α-carbon is hydrogen or alkyl; $X_6$ is a naturally or nonnaturally occurring amino acid residue in which one of the substitutions at the α-carbon is $C_{1-12}$ alkyl, aryl, heteroaryl, heterocyclyl, cycloalkylalkyl, heterocyclylalkyl, arylalkyl, or heteroarylalkyl group, and the other substitution at the α-carbon is H or alkyl; $X_7$ is a naturally or nonnaturally occurring amino acid residue in which one of the substitutions at the α-carbon is a hydroxyalkyl group; $X_8$ is a naturally or nonnaturally occurring amino acid residue in which one of the substitutions at the α-carbon is $C_{1-12}$ alkyl, hydroxyalkyl, heteroarylalkyl, or carboxamidoalkyl, and the other substitution at the α-carbon is H or alkyl; $X_9$ is a naturally or nonnaturally occurring amino acid residue in which one of the substitutions at α-carbon is carboxylalkyl, bis-carboxylalkyl, carboxylaryl, sulfonylalkyl, carboxylamidoalkyl, or heteroarylalkyl; and where A is H, an amino acid or peptide containing from about 1 to about 5 amino acid residues, an R group, an R—C(O) amide group, a carbamate group RO—C(O), a urea $R_4R_5N$—C(O), a sulfonamido R—$SO_2$ or a $R_4R_5N$—$SO_2$.

In certain embodiments, $X_1$ is His, D-His, N-Methyl-His, D-N-Methyl-His, 4-ThiazolylAla, or D-4-ThiazolylAla; $X_2$ is Ala, D-Ala, Pro, Gly, D-Ser, D-Asn, Nma, D-Nma, 4-Thio-Pro, 4-Hyp, L-2-Pip, L-2-Azt, Aib, S- or R-Iva and Acc3; $X_3$ is Glu, N-Methyl-Glu, Asp, D-Asp, His, Gla, Adp, Cys, or 4-ThiazolyAla; $X_4$ is Gly, His, Lys, or Asp; $X_5$ is Thr, D-Thr, Nle, Met, Nva, or L-Aoc; $X_6$ is Phe, Tyr, Tyr(Bzl), Tyr(3-$NO_2$), Nle, Trp, Phe(penta-fluoro), D-Phe(penta-fluoro), Phe (2-fluoro), Phe(3-fluoro), Phe(4-fluoro), Phe(2,3-di-fluoro), Phe(3,4-di-fluoro), Phe(3,5-di-fluoro), Phe(2,6-di-fluoro), Phe(3,4,5-tri-fluoro), Phe(2-iodo), Phe(2-OH), Phe(2-OMe), Phe(3-OMe), Phe(3-cyano), Phe(2-chloro), Phe(2-$NH_2$), Phe(3-$NH_2$), Phe(4-$NH_2$), Phe(4-$NO_2$), Phe(4-Me), Phe(4-allyl), Phe(n-butyl), Phe(4-cyclohexyl), Phe(4-cyclohexyloxy), Phe (4-phenyloxy), 2-NaI, 2-pyridylAla, 4-thiazolylAla, 2-Thi, α-Me-Phe, D-α-Me-Phe, α-Et-Phe, D-α-Et-Phe, α-Me-Phe (2-fluoro), D-α-Me-Phe(2-fluoro), α-Me-Phe(2,3-di-fluoro), D-α-Me-Phe(2,3-di-fluoro), α-Me-Phe(2,6-di-fluoro), D-α-Me-Phe(2,6-di-fluoro), α-Me-Phe(penta-fluoro) and D-α-Me-Phe(penta-fluoro); $X_7$ is Thr, D-Thr, Ser, or hSer; $X_8$ is Ser, hSer, His, Asn, or α-Me-Ser; and $X_9$ is Asp, Glu, Gla, Adp, Asn, or His.

Additional embodiments include those where Y is Bip, D-Bip, L-Bip(2-Me), D-Bip(2-Me), L-Bip(2'-Me), L-Bip(2-Et), D-Bip(2-Et), L-Bip(3-Et), L-Bip(4-Et), L-Bip(2-n-propyl), L-Bip(2-n-propyl, 4-OMe), L-Bip(2-n-propyl,2'-Me), L-Bip(3-Me), L-Bip(4-Me), L-Bip(2,3-di-Me), L-Bip(2,4-di-Me), L-Bip(2,6-di-Me), L-Bip(2,4-di-Et), L-Bip(2-Me, 2'-Me), L-Bip(2-Et, 2'-Me), L-Bip(2-Et, 2'-Et), L-Bip(2-Me, 4-OMe), L-Bip(2-Et,4-OMe), D-Bip(2-Et,4-OMe), L-Bip(3-OMe), L-Bip(4-OMe), L-Bip(2,4,6-tri-Me), L-Bip(2,3-di-OMe), L-Bip(2,4-di-OMe), L-Bip(2,5-di-OMe), L-Bip(3,4-di-OMe), L-Bip(2-Et,4,5-di-OMe), L-Bip(3,4-Methylene-di-oxy), L-Bip(2-Et, 4,5-Methylene-di-oxy), L-Bip(2-$CH_2OH$, 4-OMe), L-Bip(2-Ac), L-Bip(3-NH—Ac), L-Bip (4-NH—Ac), L-Bip(2,3-di-chloro), L-Bip(2,4-di-chloro), L-Bip(2,5-di-chloro), L-Bip(3,4-di-chloro), L-Bip(4-fluoro), L-Bip(3,4-di-fluoro), L-Bip(2,5-di-fluoro), L-Bip(3-n-propyl), L-Bip(4-n-propyl), L-Bip(2-iso-propyl), L-Bip(3-iso-propyl), L-Bip(4-iso-propyl), L-Bip(4-tert-butyl), L-Bip(3-phenyl), L-Bip(2-chloro), L-Bip(3-chloro), L-Bip(2-fluoro), L-Bip(3-fluoro), L-Bip(2-$CF_3$), L-Bip(3-$CF_3$), L-Bip(4-$CF_3$), L-Bip(3-$NO_2$), L-Bip(3-$OCF_3$), L-Bip(4-$OCF_3$), L-Bip(2-OEt), L-Bip(3-OEt), L-Bip(4-OEt), L-Bip(4-SMe), L-Bip(2-OH), L-Bip(3-OH), L-Bip(4-OH), L-Bip(2-$CH_2$—COOH), L-Bip(3-$CH_2$—COOH), L-Bip(4-$CH_2$—COOH), L-Bip(2-$CH_2$—$NH_2$), L-Bip(3-$CH_2$—$NH_2$), L-Bip(4-$CH_2$—$NH_2$), L-Bip(2-$CH_2$—OH), L-Bip(3-$CH_2$—OH), L-Bip(4-$CH_2$—OH), L-Phe[4-(1-propargyl)], L-Phe[4-(1-propenyl)], L-Phe[4-n-butyl], L-Phe[4-cyclohexyl], Phe(4-phenyloxy), L-Phe(penta-fluoro), L-2-(9,10-dihydrophenanthrenyl)-Ala, 4-(2-benzo(b)furan-Phe, 4-(4-Dibenzofuran)-Phe, 4-(4-phenoxathiin)-Phe, 4-(2-Benzo(b)thiophene)-Phe, 4-(3-thiophene)-Phe, 4-(3-Quinoline)-Phe, 4-(2-naphthyl)-Phe, 4-(1-Naphthyl)-Phe, 4-(4-(3,5-dimethylisoxazole))-Phe, 4-(2,4-dimethoxypyrimidine)-Phe, homoPhe, Tyr(Bzl), Phe(3,4-di-chloro), Phe(4-Iodo), 2-Naphthyl-Ala, L-α-Me-Bip, or D-α-Me-Bip; Z is L-Bip, D-Bip, L-Bip(2-Me), D-Bip (2-Me), L-Bip(2'-Me), L-Bip(2-Et), D-Bip(2-Et), L-Bip(3-Me), L-Bip(4-Me), L-Bip(3-OMe), L-Bip(4-OMe), L-Bip(4-Et), L-Bip(2-n-propyl,2'-Me), L-Bip(2,4-di-Me), L-Bip(2-Me, 2'-Me), L-Bip(2-Me,4-OMe), L-Bip(2-Et, 4-OMe), D-Bip(2-Et,4-OMe), L-Bip(2,6-di-Me), L-Bip(2,4,6-tri-Me), L-Bip(2,3,4,5,-tetra-Me), L-Bip(3,4-di-OMe), L-Bip(2,5-di-OMe), L-Bip(3,4-Methylene-di-oxy), L-Bip(3-NH—Ac), L-Bip(2-iso-propyl), L-Bip(4-iso-propyl), L-Bip(2-Phenyl), L-Bip(4-Phenyl), L-Bip(2-fluoro), L-Bip(4-$CF_3$), L-Bip(4-$OCF_3$), L-Bip(2-OEt), L-Bip(4-OEt), L-Bip(4-SMe), L-Bip(2-$CH_2$—COOH), D-Bip(2-$CH_2$—COOH), L-Bip(T-$CH_2$—COOH), L-Bip(3-$CH_2$—COOH), L-Bip(4-$CH_2$—COOH), L-Bip(2-$CH_2$—$NH_2$), L-Bip(3-$CH_2$—$NH_2$), L-Bip(4-$CH_2$—$NH_2$), L-Bip(2-$CH_2$—OH), L-Bip(3-$CH_2$—OH), L-Bip(4-$CH_2$—OH), L-Phe(3-Phenyl), L-Phe[4-n-Butyl], L-Phe[4-cyclohexyl], Phe(4-Phenyloxy), L-Phe(penta-fluoro), L-2-(9,10-Dihydrophenanthrenyl)-Ala, 4-(3-Pyridyl)-Phe, 4-(2-Naphthyl)-Phe, 4-(1-naphthyl)-Phe, 2-naphthyl-Ala, 2-fluorenyl-Ala, L-α-Me-Bip, D-α-Me-Bip, L-Phe(4-$NO_2$), or L-Phe(4-Iodo); A is H, acetyl, 13-Ala, Ahx, Gly, Asp, Glu, Phe, Lys, Nva, Asn, Arg, Ser, Thr, Val, Trp, Tyr, caprolactam, Bip, Ser(Bzl), 3-pyridylAla, Phe(4-Me), Phe (penta-fluoro), 4-methylbenzyl, 4-fluorobenzyl, n-propyl, n-hexyl, cyclohexylmethyl, 6-hydroxypentyl, 2-thienylmethyl, 3-thienylmethyl, penta-fluorobenzyl, 2-naphthylmethyl, 4-biphenylmethyl, 9-anthracenylmethyl, benzyl, (S)-(2-amino-3-phenyl)propyl, methyl, 2-aminoethyl, or (S)-2-aminopropyl; and B is OH, $NH_2$, Trp-$NH_2$, 2-naphthylAla-$NH_2$, Phe(penta-fluoro)-$NH_2$, Ser(Bzl)-$NH_2$, Phe(4-$NO_2$)—$NH_2$, 3-pyridylAla-$NH_2$, Nva-$NH_2$, Lys-$NH_2$, Asp-$NH_2$, Ser-$NH_2$, His-$NH_2$, Tyr-$NH_2$, Phe-$NH_2$, L-Bip-$NH_2$, D-Ser-$NH_2$, Gly-OH, beta.-Ala-OH, GABA-OH, or APA-OH.

In certain embodiments, when A is not present, and $X_1$ is an R group, an R—C(O) (amide) group, a carbamate group RO—C(O), a urea $R_4R_5N$—C(O), a sulfonamido R—$SO_2$, or a $R_4R_5N$—$SO_2$; wherein R is H, $C_{1-12}$ alkyl, $C_{3-10}$ cycloalkyl, cycloalkylalkyl, heterocyclyl, heterocycloalkyl, aryl, heteroaryl, arylalkyl, aryloxyalkyl, heteroarylalkyl, heteroaryloxyalkyl, or heteroarylalkoxyalkyl; and where $R_4$ and $R_5$ are each independently H, $C_{1-12}$ alkyl, $C_{3-10}$ cycloalkyl, cycloalkylalkyl, heterocyclyl, heterocycloalkyl, aryl, heteroaryl, arylalkyl, aryloxyalkyl, heteroarylalkyl, or heteroaryloxyalky.

In certain embodiments, when B is not present and Z is $OR_1$, $NR_1R_2$, or an amino-alcohol; where $R_1$ and $R_2$ are independently H, $C_{1-12}$ alkyl, $C_{3-10}$ cycloalkyl, cycloalkylalkyl, heterocycle, heterocycloalkyl, aryl, heteroaryl, arylalkyl, aryloxyalkyl, heteroarylalkyl, or heteroaryloxyalkyl. In certain embodiments, $X_1$ (where applicable), $X_2$, and $X_3$ are N—H or N-alkylated, (e.g., N-methylated) amino acid residues. The polypeptide may be a 10-mer to 15-mer and capable of binding to and activating the GLP-1 receptor.

The following abbreviations are used above. NaI=naphthylalanine; pGly=pentylglycine; t-BuG=t-butylglycine; TPro=thioproline; HPro=homoproline; NmA=N-methylalanine; Cya=cysteic acid; Thi=β2-Thienyl-Ala; hSer=homoserine; Aib=α-aminoisobutyric acid; Bip=biphenylalanine; Nle=norleucine; Ahx=2-aminohexanoic acid; Nva=norvaline.

Leptin and Leptin Derivatives

The compounds of the invention can include leptin and leptin derivatives. Leptin is an adipokine, and thus the proteins or peptides used in the invention can include an adipokine or an analog thereof. Adipokines include adiponectin, leptin, and resistin. Adiponectins include human, mouse, and rat adiponectin. Leptins include leptin (116-130), leptin (22-56), leptin (57-92), leptin (93-105), LY396623, meterleptin, murine leptin analog, pegylated leptin, and methionyl human leptin. Resistins include human, mouse, and rat resistin. The leptin may be a cleaved sequence or the full length protein. The polypeptide used in the invention may be any of these peptides or proteins or may be substantially identical to any of these peptides or proteins.

Neurotensin and Neurotensin Derivatives

Neurotensin (NT) is a 13 amino acid peptide found in the central nervous system and in the gastrointestinal tract. In brain, NT is associated with dopaminergic receptors and other neurotransmitter system. Peripheral NT acts as a paracrine and endocrine peptide on both the digestive and cardiovascular systems. To exert its biological effects in the brain NT has to be injected or delivered directly to the brain because NT does not cross the BBB and is rapidly degraded by peptidases following systematic administration. Preclinical pharmacological studies, most of which involve direct injection of NT into the brain, strongly suggest that an agonist of NT receptors would be clinically useful for the treatment of neuropsychiatric conditions including psychosis, schizophrenia, Parkinson's disease, pain, and the abuse of psychostimulants. In particular, in various animal studies, intraventricular injection of NT led to hypothermia and analgesia in antinociception experiments.

The peptide therapeutic may be neurotensin or analog thereof. Human neurotensin is a thirteen amino acid peptide having the sequence QLYENKPRRPYIL. Exemplary neurotensin analogs include (VIP-neurotensin) hybrid antagonist, acetylneurotensin(8-13), JMV 1193, KK13 peptide, neuromedin N, neuromedin N precursor, neurotensin(1-10), neurotensin(1-11), neurotensin(1-13), neurotensin(1-6), neurotensin(1-8), neurotensin(8-13), Asp(12)-neurotensin(8-13), Asp(13)-neurotensin(8-13), Lys(8)-neurotensin(8-13), N-methyl-Arg(8)-Lys(9)-neo-Trp(11)-neo-Leu(12)-neurotensin(8-13), neurotensin(9-13), neurotensin 69 L, Arg(9)-neurotensin, azidobenzoyl-Lys(6)-Trp(11)-neurotensin, Gln (4)-neurotensin, iodo-Tyr(11)-neurotensin, iodo-Tyr(3)-neurotensin, N-α-(fluoresceinylthiocarbamyl)glutamyl(1)-neurotensin, Phe(11)-neurotensin, Ser(7)-neurotensin, Trp (11)-neurotensin, Tyr(11)-neurotensin, rat NT77, PD 149163, proneurotensin, stearyl-Nle(17)-neurotensin(6-11) VIP(7-28), $^{99m}$Tc-NT-XI, TJN 950, and vasoactive intestinal peptide-neurotensin hybrid.

Other neurotensin analogs include NT64L [L-neo-Trp11] NT(8-13), NT72D [D-Lys9,D-neo-Trp11,tert-Leu12]NT(9-13), NT64D [D-neo-Trp11]NT(8-13), NT73L [D-Lys9,L-neo-Trp11]NT(9-13), NT65L [L-neo-Trp11, tert-Leu12]NT (8-13), NT73D [D-Lys9,D-neo-Trp11]NT(9-13), NT65D [D-neo-Trp11, tert-Leu12]NT(8-13), NT74L [DAB9,L-neo-Trp11,tert-Leu12]NT(9-13), NT66L [D-Lys8, L-neo-Trp11, tert-Leu12]NT(8-13), NT74D [DAB9,Pro,D-neo-Trp11,tert-Leu12]NT(9-13), NT66D [D-Lys8, D-neo-Trp11, tert-Leu12]NT(8-13), NT75L [DAB8 L-neo-Trp11]NT(8-13), NT67L [D-Lys8, L-neo-Trp11]NT(8-13), NT75D [DAB8,D-neo-Trp11]NT(8-13), NT67D [D-Lys8, D-neo-Trp11]NT(8-13), NT76L [D-Orn9,L-neo-Trp11]NT(8-13), NT69L [N-methyl-Arg8,L-Lys9 L-neo-Trp11,tert-Leu12]NT(8-13), NT76D [D-Orn9,D-neo-Trp11]NT(8-13), NT69D [N-methyl-Arg8 L-Lys9,D-neo-Trp11,tert-Leu12]NT(8-13), NT71L [D-Orn9,L-neo-Trp11,tert-Leu12]NT(8-13), NT71L [N-methyl-Arg8,DAB9 L-neo-Trp11,tert-leu12]NT(8-13), NT77D [D-Orn9,D-neo-Trp11,tert-Leu12]NT(8-13), NT71D [N-methyl-Arg8,DAB9,D-neo-Trp11,tert-leu12]NT (8-13), NT78L [N-methyl-Arg8,D-Orn9 L-neo-Trp11,tert-Leu12]NT(8-13), NT72L [D-Lys9,L-neo-Trp11,tert-Leu12] NT(9-13), and NT78D [N-methyl-Arg8,D-Orn9,D-neo-Trp11,tert-Leu12]NT(8-13), where neo-Trp is (2-amino-3-[1H-indolyl]propanoic acid). Other neurotensin analogs include Beta-lactotensin (NTR2 selective), JMV-449, and PD-149 or PD-163 (NTR1 selective; reduced amide bond 8-13 fragment of neurotensin).

Other neurotensin analogs include those with modified amino acids (e.g., any of those described herein). The neurotensin analog may be selective for NTR1, NTR2, or NTR3 (e.g., may bind to or activate one of NTR1, NTR2, or NTR3 at least 2, 5, 10, 50, 100, 500, 1000, 5000, 10,000, 50,000, or 100,000 greater) as compared to at least one of the other NTR receptors or both.

GDNF and GDNF Derivatives

In certain embodiments, the peptide vector is attached to GDNF, a GDNF analog, a GDNF fragment, or a modified form thereof. In certain embodiments, the GDNF analog is a sequence substantially identical (e.g., at least 60%, 70%, 80%, 85%, 90%, 95%, 98%, 99% identical) to GDNF, a GDNF analog, or to a fragment thereof.

GDNF is secreted as a disulfide-linked homodimer, and is able to support survival of dopaminergic neurons, Purkinje cells, motoneurons, and sympathetic neurons. GDNF analogs or fragments having one or more of these activities may be used in the present invention, and activity of such analogs and fragments can be tested using any means known in the art.

Human GDNF is expressed as a 211 amino acid protein (isoform 1); a 185 amino acid protein (isoform 2), and a 133 amino acid protein. Mature GDNF is a 134 amino acid sequence that includes amino acids 118-211 of isoform 1, amino acids 92-185 of isoform 2. Isoform 3 includes a transforming growth factor like domain from amino acids 40-133.

In certain embodiments, the GDNF analog is a splice variant of GDNF. Such proteins are described in PCT Publication No. WO 2009/053536, and include the pre-(α)pro-GDNF, pre-(β)pro-GDNF, and pre-(γ)pro-GDNF splice variant, as well as the variants lacking the pre-pro region: (α)pro-GDNF, (β)pro-GDNF, and pre-(γ)pro-GDNF.

GDNF analogs are also described in U.S. Patent Application Publication No. 2009/0069230, which include a GDNF analog having the sequence:

$Xaa_1$-Pro-$Xaa_3$-Pro-$Xaa_5$-$Xaa_6$-$Xaa_7$-$Xaa_8$ (SEQ ID NO: 182)

where Xaa$_1$ is Phe, Trp, or Tyr; Xaa$_3$ is Leu, Ala, Ile, or Val; Xaa$_5$ is Ala, Leu, Ile, or Val; Xaa$_6$ is Gly, is any amino acid residue of the D configuration or is absent; Xaa$_7$ is Lys, Arg, or His or is absent; and Xaa$_8$ is Arg, Lys, or His or is absent. Xaa represents an amino acid, which we may also refer to as an amino acid residue. The subscripts (here, the subscripts 1-8) represent the positions of each amino acid in the peptide sequence. Thus, Xaa$_1$ represents the first amino acid residue in a fragment of a GDNF precursor protein.

In specific embodiments, the fragments of a GDNF precursor protein can have a sequence represented by (1) Phe-Pro-Xaa$_3$-Pro-Xaa$_5$-Xaa$_6$-Xaa$_7$-Xaa$_8$ (SEQ ID NO: 183), (e.g., Phe-Pro-Leu-Pro-Ala-Gly-Lys-Arg (SEQ ID NO: 151); (2) Xaa$_1$-Pro-Leu-Pro-Xaa$_5$-Xaa$_6$-Xaa$_7$-Xaa$_8$ (SEQ ID NO: 184); (3) Phe-Pro-Leu-Pro-Xaa$_5$-Xaa$_6$-Xaa$_7$-Xaa$_8$ (SEQ ID NO: 152); (4) Xaa$_1$-Pro-Xaa$_3$-Pro-Ala-Xaa$_6$-Xaa$_7$-Xaa$_8$ (SEQ ID NO: 185); (5) Phe-Pro-Xaa$_3$-Pro-Ala-Xaa$_6$-Xaa$_7$-Xaa$_8$ (SEQ ID NO: 153); (6) Phe-Pro-Leu-Pro-Ala-Xaa$_7$-Xaa$_7$-Xaa$_8$ (SEQ ID NO: 154); (7) Xaa$_1$-Pro-Xaa$_3$-Pro-Xaa$_5$-Gly Xaa$_7$-Xaa$_8$ SEQ ID NO: 186); (8) Phe-Pro-Xaa$_3$-Pro-Xaa$_5$-Gly-Xaa$_7$-Xaa$_8$ (SEQ ID NO: 155); (9) Phe-Pro-Leu-Pro-Xaa$_5$-Gly-Xaa$_7$-Xaa$_8$ (SEQ ID NO: 156); (10) Phe-Pro-Leu-Pro-Ala-Gly-Xaa$_7$-Xaa$_8$ (SEQ ID NO: 157); (11) Xaa$_1$-Pro-Xaa$_3$-Pro-Xaa$_5$-Xaa$_6$-Lys-Xaa$_8$ (SEQ ID NO: 187); (12) Phe-Pro-Xaa$_3$-Pro-Xaa$_5$-Xaa$_6$-Lys-Xaa$_8$ (SEQ ID NO: 158); (13) Phe-Pro-Leu-Pro-Xaa$_5$-Xaa$_6$-Lys-Xaa$_8$ (SEQ ID NO: 159); (14) Phe-Pro-Leu-Pro-Ala-Xaa$_6$-Lys-Xaa$_8$ (SEQ ID NO: 160); (15) Phe-Pro-Leu-Pro-Ala-Gly-Lys-Xaa$_8$ (SEQ ID NO: 161); (16) Xaa$_1$-Pro-Xaa$_3$-Pro-Xaa$_5$-Xaa$_6$-Xaa$_7$-Arg (SEQ ID NO: 188); (17) Phe-Pro-Xaa$_3$-Pro-Xaa$_5$-Xaa$_6$-Xaa$_7$-Arg (SEQ ID NO: 162); (18) Phe-Pro-Leu-Pro-Xaa$_5$-Xaa$_6$-Xaa$_7$-Arg (SEQ ID NO: 163); (19) Phe-Pro-Leu-Pro-Ala-Xaa$_6$-Xaa$_7$-Arg (SEQ ID NO: 164); and (20) Phe-Pro-Leu-Pro-Ala-Gly-Xaa$_7$-Arg (SEQ ID NO: 165).

In another embodiment, the fragment of a GDNF precursor protein can be a fragment or portion of a GDNF precursor protein conforming to Formula I, where Xaa$_1$ is Phe, Xaa$_3$ is Leu, Xaa$_5$ is Ala, Xaa$_6$ is Gly, Xaa$_7$ is Lys and Xaa$_8$ is Arg (i.e., Phe-Pro-Leu-Pro-Ala-Gly-Lys-Arg). At least one (e.g., one, two, or three) of the amino acid residues represented by Formula I can be absent. For example, Xaa$_6$, Xaa$_7$, and/or Xaa$_8$ can be absent.

In another embodiment, the fragment of a GDNF precursor protein or the biologically active variants can have, or can include, a sequence of amino acid residues conforming to the amino acid sequence:

Pro-Pro-Xaa$_3$-Xaa$_4$-Pro-Xaa$_6$-Xaa$_7$-Xaa$_8$-Xaa$_9$-Xa-a$_{10}$-Xaa$_{11}$-Xaa$_{12}$-Xaa$_{13}$-Xaa$_{14}$ (SEQ ID NO: 189) where Xaa$_3$ is Glu or Asp; Xaa$_4$ is Ala, Gly, Ile, Leu, Met, or Val; Xaa$_6$ is Ala, Gly, Ile, Leu, Met, or Val; Xaa$_7$ is Glu or Asp; Xaa$_8$ is Asp or Glu; Xaa$_9$ is Arg, His, or Lys; Xaa$_{10}$ is Ser, Asn, Gln, or Thr; Xaa$_{11}$ is Leu, Ala, Gly, Ile, Leu, Met or Val; Xaa$_{12}$ is Gly, is any amino acid residue of the D-configuration, or is not present; Xaa$_{13}$ is Arg, His, or Lys or is not present; Xaa$_{14}$ is Arg, His, or Lys or is not present. An exemplary peptide conforming to Formula II can have the sequence Pro-Pro-Glu-Ala-Pro-Ala-Glu-Asp-Arg-Ser-Leu-Gly-Arg-Arg (SEQ ID NO: 190).

In another embodiment, the fragments of a GDNF precursor protein or the biologically active variants can have, or can include, a sequence of amino acid residues conforming to the amino acid sequence of Formula III:

Xaa$_1$-Xaa$_2$-Xaa$_3$-Xaa$_4$-Xaa$_5$-Xaa$_6$-Xaa$_7$-Xaa$_8$-Xaa$_9$-
Xaa$_{10}$-Xaa$_{11}$-Xaa$_{12}$-Xaa$_{13}$-Xaa$_{14}$-Xaa$_{15}$-Xaa$_{16}$-
Xaa$_{17}$-Xaa$_{18}$-Xaa$_{19}$-Xaa$_{20}$-Xaa$_{21}$-Xaa$_{22}$(SEQ ID
NO: 191)     (III).

where Xaa$_1$ and Xaa$_2$ are, independently, Arg, Lys, or His or are absent; Xaa$_3$ is Glu or Asp; Xaa$_4$ is Arg, Lys, or His; Xaa$_5$ is Asn, Gln, Ser, or Thr; Xaa$_6$ is Arg, Lys, or His; Xaa$_7$ is Gln, Asn, Ser, or Thr; Xaa$_8$, Xaa$_9$, Xaa$_{10}$, and Xaa$_{11}$ are, independently, Ala, Gly, Ile, Leu, Met, or Val; Xaa$_{12}$ is Asn, Gln, Ser, or Thr; Xaa$_{13}$ is Pro or Ser; Xaa$_{14}$ is Glu or Asp; Xaa$_{15}$ is Asn, Gln, Ser, or Thr; Xaa$_{16}$ is Ser, Asn, Gln, or Thr; Xaa$_{17}$ is Lys, Arg, or His; Xaa$_{18}$ is Gly, Ala, Ile, Leu, Met, or Val; Xaa$_{19}$ is Lys, Arg, or His; Xaa$_{20}$ is Gly, is any amino acid residue of the D-configuration, or is not present; and Xaa$_{21}$ and Xaa$_{22}$ are, independently, Arg, Lys, His, or are not present. An exemplary peptide conforming to Formula III can have the sequence Arg-Arg-Glu-Arg-Asn-Arg-Gln-Ala-Ala-Ala-Ala-Asn-Pro-Glu-Asn-Ser-Arg-Gly-Lys-Gly-Arg-Arg (SEQ ID NO: 192).

Other GDNF analogs are described in PCT Publication No. WO 2008/069876. These analogs include ERNRQAAAAN-PENSRGK-amide (SEQ ID NO: 200); FPLPA-amide (SEQ ID NO: 194); and PPEAPAEDRSL-amide (SEQ ID NO: 195).

Still other GDNF analogs are described in PCT Publication No. WO 2007/019860. The analogs include those having the formula:

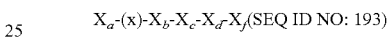
$X_a$-(x)-$X_b$-$X_c$-$X_d$-$X_f$(SEQ ID NO: 193)

where $X_a$ is D, E, A or G, (x) is a sequence of 2-3 amino acid residues or a single amino acid residue selected from the group consisting of amino acid residues A, D, E, G, I, K, L, P, Q, S, T and V, $X_b$ is amino acid residue Y or H, or a hydrophobic amino acid residue, and at least one of $X_c$, $X_d$, or $X_f$ is a charged or hydrophobic amino acid residue. The analog may be 6-22 amino acids in length.

Further GDNF analogs are described in U.S. Patent Application Publication No. 2006/0258576. These analogs include FPLPA-amide, (SEQ ID NO: 194), PPEAPAEDRSL-amide (SEQ ID NO: 195), LLEAPAEDHSL-amide (SEQ ID NO: 196), SPDKQMAVLP (SEQ ID NO: 197), SPDKQAAALP (SEQ ID NO: 198), SPDKQTPIFS (SEQ ID NO: 199), ERN-RQAAAANPENSRGK-amide (SEQ ID NO: 200), ERN-RQAAAASPENSRGK-amide (SEQ ID NO: 201), and ERN-RQSAATNVENSSKK-amide (SEQ ID NO: 202).

Additional GDNF analogs can include functional fragments (e.g., any of the fragments described herein), peptides having any of the modifications described herein, or peptidomimetics thereof. Activity of such analogs and fragments can be tested using any means known in the art.

Brain-Derived Neurotrophic Factor (BDNF) and BDNF Derivatives

The compounds of the invention may be or may include BDNF, BDNF analogs, or BDNF fragments. BDNF is glycoprotein of the nerve growth factor family of proteins. The protein is encoded as a 247 amino acid polypeptide (isoform A), a 255 amino acid polypeptide (isoform B), a 262 amino acid polypeptide (isoform C), a 276 amino acid polypeptide (isoform D), a 329 amino acid polylpeptide (isoform E). The mature 119 amino acid glycoprotein is processed from the larger precursor to yield a neutrophic factor that promotes the survival of neuronal cell populations. The mature protein includes amino acids 129-247 of the isoform A preprotein, amino acids 137-255 of the isoform B preprotein, amino acids 144-162 of isoform C preprotein, amino acids 158-276 of the isoform D preprotein, or amino acids 211 (or 212)-329 of the isoform E preprotein. BDNF acts at the TrkB receptor and at low affinity nerve growth factor receptor (LNGFR or p75). BDNF is capable of supporting neuronal survival of existing neurons and can also promote growth and differentiation of new neurons. The BDNF fragments or analogs of the invention may have any of the aforementioned activities. Activity of such analogs and fragments can be tested using any means known in the art.

BDNF analogs are described in U.S. Patent Application Publication No. 2004/0072291, which include those having a substitution of A, C, D, E, G, H, K, N P, Q R, S, or T at one more positions selected from the group consisting of 10, 16, 20, 29, 31, 36, 38, 39, 42, 44, 49, 52, 53, 54, 61, 63, 71, 76, 86, 87, 90, 92, 98, 100, 102, 103, and 105. Additional substitutions are described in Table 3 below.

TABLE 3

| Residue # | WT Residue | Possible substitutions |
|---|---|---|
| 9 | E | A C F G I L M P V W Y |
| 10 | L | I M F V W Y |
| 11 | S | A C F G I L M P V W Y |
| 13 | C | D E F H I K N P Q R S T V Y |
| 14 | D | A C F G I L M P V W Y |
| 15 | S | D F H I L N P Q W Y |
| 16 | I | W M Y |
| 17 | S | A C G P |
| 18 | E | T F H I P Q S |
| 19 | W | A C D E G H K N P Q R S T |
| 20 | V | W Y |
| 21 | T | D F H I L P W Y |
| 22 | A | D E H K N P Q R S T |
| 23 | A | H T |
| 24 | D | H P T |
| 28 | A | H T |
| 31 | M | W Y |
| 32 | S | A C G P |
| 34 | G | T D E H K N P Q R S |
| 35 | T | A C G P |
| 36 | V | F I L M W Y |
| 38 | V | W Y F I M |
| 39 | L | F I M V W Y |
| 41 | K | A C G H P S |
| 42 | V | I |
| 44 | V | F L M W Y |
| 45 | S | A C F P V Y |
| 46 | K | A C G P Q S T |
| 47 | G | D E H N P Q R S T |
| 48 | Q | A C G P |
| 49 | L | F I M V W Y |
| 50 | K | I P T |

TABLE 3 -continued

| Residue # | WT Residue | Possible substitutions |
|---|---|---|
| 51 | Q | A C G P |
| 52 | Y | I M V W |
| 53 | F | M W Y |
| 55 | E | A C G H N P Q S T |
| 56 | T | A C G P |
| 57 | K | A C G H P Q S T |
| 58 | C | D E G H K N P Q R S T |
| 59 | N | A C G P T |
| 60 | P | T |
| 61 | M | I V W Y |
| 87 | V | F I M W Y |
| 88 | R | A C G P |
| 89 | A | D E H K N Q R T |
| 90 | L | F I M V W Y |
| 91 | T | A C P G P |
| 92 | H | I W Y |
| 93 | D | P T |
| 94 | S | A C G P |
| 95 | K | H P |
| 96 | K | P |
| 97 | R | A C G P |
| 98 | I | H W |
| 101 | R | P T |
| 102 | F | I M V W Y |
| 103 | I | F M W Y |
| 104 | R | A C G P T |
| 105 | I | M W |
| 106 | D | A C G H I M P T |
| 107 | T | A C D E G H K N P Q S |
| 108 | S | A C D G H P |
| 109 | C | D E H K N P Q R S T |
| 110 | V | T |
| 111 | C | D E F H I K N P Q R S T V W Y |
| 112 | T | A C F G I L H P V W Y |
| 113 | L | Any amino acid |

BDNF analogs are also described in U.S. Pat. No. 6,800,607, which describes BDNF modified with 1-acyl-glycerol. These analogs include a modified BDNF, where is the compound of the formula:

$$A(X{-}B)_n$$

where A is a residue of brain-derived neurotrophic factor, B is a residue of a 1-acyl-glycerol derivative having a hydroxyl group at the 2-position of the glycerol moiety, which is prepared by removing a hydrogen atom from the hydroxyl group, X is a chemical cross-linkage, and m is an average number of the introduction and is not less than about 0.5; (3) A modified BDNF according to the above (2), wherein X is a group of the formula (2):

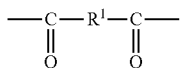

where $R^1$ is an alkylene group, or a group of the formula (3):

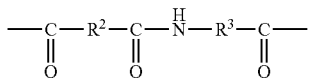

where $R^2$ and $R^3$ are independently an alkylene group; (4) A modified BDNF according to the above (2), wherein the 1-acyl-glycerol derivative is 1-acyl-glycero-3-phosphoryl choline, 1-acyl-glycero-3-phosphoryl serine, or 1-acyl-grycero-3-phosphoryl ethylamine; (5) A modified BDNF according to the above (2), wherein B is a 1-acyl-glycero-3-phosphoryl choline residue of the formula (4):

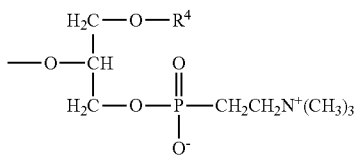

where $R^4$ is an acyl group, a 1-acyl-glycero-3-phosphoryl serine residue of the formula (5):

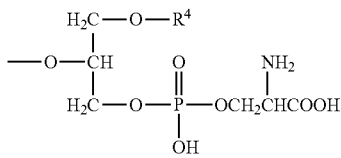

where $R^4$ is an acyl group, or a 1-acyl-glycero-phosphoryl ethylamine residue of the formula (6):

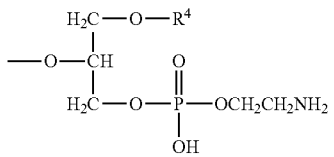

where $R^4$ is an acyl group; (6) A modified BDNF according to the above (2) or (3), where B is a group of the formula (4):

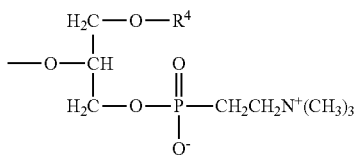

where $R^4$ is an acyl group; (7) A modified BDNF according to any one of the above (2), (3), (4), (5) and (6), where the acyl group is an alkanoyl group having 8 to 30 carbon atoms; (8) A modified BDNF according to any one of the above (2), (3), (4), (5), (6) and (7), where the acyl group is palmitoyl group; (9) A modified BDNF according to any one of the above (2), (3), (4), (5), (6), (7) and (8), where m is in the range of from about 1 to about 6; (11) A modified BDNF according to the above (10), where $R^1$ is a straight chain alkylene group having 2 to 10 carbon atoms; (12) A modified BDNF according to the above (10), where $R^1$ is trimethylene.

Other BDNF analogs include those described in PCT Publication No. WO 96/15146, which described conjugates of BDNF to water soluble polymers such as polyethylene glycol. Additional BDNF analogs can include functional fragments (e.g., any of the fragments described herein), peptides having any of the modifications described herein, or peptidomimetics thereof. Activity of such analogs can be tested using any method known in the art.

Modified Polypeptides

The peptide vectors and peptide/polypeptide agents used in the invention may have a modified amino acid sequence. In certain embodiments, the modification does not destroy significantly a desired biological activity (e.g., ability to cross the BBB or agonist activity). The modification may reduce (e.g., by at least 5%, 10%, 20%, 25%, 35%, 50%, 60%, 70%, 75%, 80%, 90%, or 95%), may have no effect, or may increase (e.g., by at least 5%, 10%, 25%, 50%, 100%, 200%, 500%, or 1000%) the biological activity of the original polypeptide. The modified peptide or polypeptide may have or may optimize a characteristic of a polypeptide, such as in vivo stability, bioavailability, toxicity, immunological activity, immunological identity, and conjugation properties.

Modifications include those by natural processes, such as posttranslational processing, or by chemical modification techniques known in the art. Modifications may occur anywhere in a polypeptide including the polypeptide backbone, the amino acid side chains and the amino- or carboxy-terminus. The same type of modification may be present in the same or varying degrees at several sites in a given polypeptide, and a polypeptide may contain more than one type of modification. Polypeptides may be branched as a result of ubiquitination, and they may be cyclic, with or without branching. Cyclic, branched, and branched cyclic polypeptides may result from posttranslational natural processes or may be made synthetically. Other modifications include pegylation, acetylation, acylation, addition of acetomidomethyl (Acm) group, ADP-ribosylation, alkylation, amidation, biotinylation, carbamoylation, carboxyethylation, esterification, covalent attachment to flavin, covalent attachment to a heme moiety, covalent attachment of a nucleotide or nucleotide derivative, covalent attachment of drug, covalent attachment of a marker (e.g., fluorescent or radioactive), covalent attachment of a lipid or lipid derivative, covalent attachment of phosphatidylinositol, cross-linking, cyclization, disulfide bond formation, demethylation, formation of covalent crosslinks, formation of cystine, formation of pyroglutamate, formylation, gamma-carboxylation, glycosylation, GPI anchor formation, hydroxylation, iodination, methylation, myristoylation, oxidation, proteolytic processing, phosphorylation, prenylation, racemization, selenoylation, sulfation, transfer-RNA mediated addition of amino acids to proteins such as arginylation and ubiquitination.

A modified polypeptide can also include an amino acid insertion, deletion, or substitution, either conservative or non-conservative (e.g., D-amino acids, desamino acids) in the polypeptide sequence (e.g., where such changes do not substantially alter the biological activity of the polypeptide). In particular, the addition of one or more cysteine residues to the amino or carboxy terminus of any of the polypeptides of the invention can facilitate conjugation of these polypeptides by, e.g., disulfide bonding. For example, Angiopep-1 (SEQ ID NO:67), Angiopep-2 (SEQ ID NO:97), or Angiopep-7 (SEQ ID NO:112) can be modified to include a single cysteine residue at the amino-terminus (SEQ ID NOS: 71, 113, and 115, respectively) or a single cysteine residue at the carboxy-terminus (SEQ ID NOS: 72, 114, and 116, respectively). Amino acid substitutions can be conservative (i.e., wherein a residue is replaced by another of the same general type or group) or non-conservative (i.e., wherein a residue is replaced by an amino acid of another type). In addition, a non-naturally occurring amino acid can be substituted for a naturally occurring amino acid (i.e., non-naturally occurring conservative amino acid substitution or a non-naturally occurring non-conservative amino acid substitution).

Polypeptides made synthetically can include substitutions of amino acids not naturally encoded by DNA (e.g., non-naturally occurring or unnatural amino acid). Examples of non-naturally occurring amino acids include D-amino acids, an amino acid having an acetylaminomethyl group attached to a sulfur atom of a cysteine, a pegylated amino acid, the omega amino acids of the formula $NH_2(CH_2)_nCOOH$ wherein n is 2-6, neutral nonpolar amino acids, such as sarcosine, t-butyl alanine, t-butyl glycine, N-methyl isoleucine, and norleucine. Phenylglycine may substitute for Trp, Tyr, or Phe; citrulline and methionine sulfoxide are neutral nonpolar, cysteic acid is acidic, and ornithine is basic. Proline may be substituted with hydroxyproline and retain the conformation conferring properties.

Analogs may be generated by substitutional mutagenesis and retain the biological activity of the original polypeptide. Examples of substitutions identified as "conservative substitutions" are shown in Table 4. If such substitutions result in a change not desired, then other type of substitutions, denominated "exemplary substitutions" in Table 4, or as further described herein in reference to amino acid classes, are introduced and the products screened.

Substantial modifications in function or immunological identity are accomplished by selecting substitutions that differ significantly in their effect on maintaining (a) the structure of the polypeptide backbone in the area of the substitution, for example, as a sheet or helical conformation. (b) the charge or hydrophobicity of the molecule at the target site, or (c) the bulk of the side chain. Naturally occurring residues are divided into groups based on common side chain properties:

(1) hydrophobic: norleucine, methionine (Met), Alanine (Ala), Valine (Val), Leucine (Leu), Isoleucine (Ile), Histidine (His), Tryptophan (Trp), Tyrosine (Tyr), Phenylalanine (Phe), (2) neutral hydrophilic: Cysteine (Cys), Serine (Ser), Threonine (Thr)

(3) acidic/negatively charged: Aspartic acid (Asp), Glutamic acid (Glu)

(4) basic: Asparagine (Asn), Glutamine (Gln), Histidine (His), Lysine (Lys), Arginine (Arg)

(5) residues that influence chain orientation: Glycine (Gly), Proline (Pro);

(6) aromatic: Tryptophan (Trp), Tyrosine (Tyr), Phenylalanine (Phe), Histidine (His), (7) polar: Ser, Thr, Asn, Gln (8) basic positively charged: Arg, Lys, His, and;

(9) charged: Asp, Glu, Arg, Lys, His

Other amino acid substitutions are listed in Table 4.

TABLE 4

| Amino acid substitutions | | |
|---|---|---|
| Original residue | Exemplary substitution | Conservative substitution |
| Ala (A) | Val, Leu, Ile | Val |
| Arg (R) | Lys, Gln, Asn | Lys |
| Asn (N) | Gln, His, Lys, Arg | Gln |

TABLE 4 -continued

| Amino acid substitutions | | |
|---|---|---|
| Original residue | Exemplary substitution | Conservative substitution |
| Asp (D) | Glu | Glu |
| Cys (C) | Ser | Ser |
| Gln (Q) | Asn | Asn |
| Glu (E) | Asp | Asp |
| Gly (G) | Pro | Pro |
| His (H) | Asn, Gln, Lys, Arg | Arg |
| Ile (I) | Leu, Val, Met, Ala, Phe, norleucine | Leu |
| Leu (L) | Norleucine, Ile, Val, Met, Ala, Phe | Ile |
| Lys (K) | Arg, Gln, Asn | Arg |
| Met (M) | Leu, Phe, Ile | Leu |
| Phe (F) | Leu, Val, Ile, Ala | Leu |
| Pro (P) | Gly | Gly |
| Ser (S) | Thr | Thr |
| Thr (T) | Ser | Ser |
| Trp (W) | Tyr | Tyr |
| Tyr (Y) | Trp, Phe, Thr, Ser | Phe |
| Val (V) | Ile, Leu, Met, Phe, Ala, norleucine | Leu |

Polypeptide Derivatives and Peptidomimetics

In addition to polypeptides consisting of naturally occurring amino acids, peptidomimetics or polypeptide analogs are also encompassed by the present invention and can form the peptide vectors or peptide/polypeptide agents used in the compounds of the invention. Polypeptide analogs are commonly used in the pharmaceutical industry as non-peptide drugs with properties analogous to those of the template polypeptide. The non-peptide compounds are termed "peptide mimetics" or peptidomimetics (Fauchere et al., *Infect. Immun.* 54:283-287, 1986 and Evans et al., *J. Med. Chem.* 30:1229-1239, 1987). Peptide mimetics that are structurally related to therapeutically useful peptides or polypeptides may be used to produce an equivalent or enhanced therapeutic or prophylactic effect. Generally, peptidomimetics are structurally similar to the paradigm polypeptide (i.e., a polypeptide that has a biological or pharmacological activity) such as naturally-occurring receptor-binding polypeptides, but have one or more peptide linkages optionally replaced by linkages such as $-CH_2NH-$, $-CH_2S-$, $-CH_2-CH_2-$, $-CH=CH-$(cis and trans), $-CH_2SO-$, $-CH(OH)CH_2-$, $-COCH_2-$ etc., by methods well known in the art (Spatola, *Peptide Backbone Modifications, Vega Data*, 1:267, 1983; Spatola et al., *Life Sci.* 38:1243-1249, 1986; Hudson et al., *Int. J. Pept. Res.* 14:177-185, 1979; and Weinstein, 1983, Chemistry and Biochemistry, of Amino Acids, Peptides and Proteins, Weinstein eds., Marcel Dekker, New York). Such polypeptide mimetics may have significant advantages over naturally occurring polypeptides including more economical production, greater chemical stability, enhanced pharmacological properties (e.g., half-life, absorption, potency, efficiency), reduced antigenicity, and others.

While the peptide vectors described herein may efficiently cross the BBB or target particular cell types (e.g., those described herein), their effectiveness may be reduced by the presence of proteases. Likewise, the effectiveness of the peptide/polypeptide agents used in the invention may be similarly reduced. Serum proteases have specific substrate requirements, including L-amino acids and peptide bonds for cleavage. Furthermore, exopeptidases, which represent the most prominent component of the protease activity in serum, usually act on the first peptide bond of the polypeptide and require a free N-terminus (Powell et al., *Pharm. Res.* 10:1268-1273, 1993). In light of this, it is often advantageous to use modified versions of polypeptides. The modified polypeptides retain the structural characteristics of the original L-amino acid polypeptides, but advantageously are not readily susceptible to cleavage by protease and/or exopeptidases.

Systematic substitution of one or more amino acids of a consensus sequence with D-amino acid of the same type (e.g., an enantiomer; D-lysine in place of L-lysine) may be used to generate more stable polypeptides. Thus, a polypeptide derivative or peptidomimetic as described herein may be all L-, all D-, or mixed D, L polypeptides. The presence of an N-terminal or C-terminal D-amino acid increases the in vivo stability of a polypeptide because peptidases cannot utilize a D-amino acid as a substrate (Powell et al., *Pharm. Res.* 10:1268-1273, 1993). Reverse-D polypeptides are polypeptides containing D-amino acids, arranged in a reverse sequence relative to a polypeptide containing L-amino acids. Thus, the C-terminal residue of an L-amino acid polypeptide becomes N-terminal for the D-amino acid polypeptide, and so forth. Reverse D-polypeptides retain the same tertiary conformation and therefore the same activity, as the L-amino acid polypeptides, but are more stable to enzymatic degradation in vitro and in vivo, and thus have greater therapeutic efficacy than the original polypeptide (Brady and Dodson, *Nature* 368:692-693, 1994 and Jameson et al., *Nature* 368:744-746, 1994). In addition to reverse-D-polypeptides, constrained polypeptides including a consensus sequence or a substantially identical consensus sequence variation may be generated by methods well known in the art (Rizo et al., *Ann. Rev. Biochem.* 61:387-418, 1992). For example, constrained polypeptides may be generated by adding cysteine residues capable of forming disulfide bridges and, thereby, resulting in a cyclic polypeptide. Cyclic polypeptides have no free N- or C-termini. Accordingly, they are not susceptible to proteolysis by exopeptidases, although they are, of course, susceptible to endopeptidases, which do not cleave at polypeptide termini. The amino acid sequences of the polypeptides with N-terminal or C-terminal D-amino acids and of the cyclic polypeptides are usually identical to the sequences of the polypeptides to which they correspond, except for the presence of N-terminal or C-terminal D-amino acid residue, or their circular structure, respectively.

A cyclic derivative containing an intramolecular disulfide bond may be prepared by conventional solid phase synthesis while incorporating suitable S-protected cysteine or homocysteine residues at the positions selected for cyclization such as the amino and carboxy termini (Sah et al., *J. Pharm. Pharmacol.* 48:197, 1996). Following completion of the chain assembly, cyclization can be performed either (1) by selective removal of the S-protecting group with a consequent on-support oxidation of the corresponding two free SH-functions, to form a S—S bonds, followed by conventional removal of the product from the support and appropriate purification procedure or (2) by removal of the polypeptide from the support along with complete side chain de-protection, followed by oxidation of the free SH-functions in highly dilute aqueous solution.

The cyclic derivative containing an intramolecular amide bond may be prepared by conventional solid phase synthesis while incorporating suitable amino and carboxyl side chain protected amino acid derivatives, at the position selected for cyclization. The cyclic derivatives containing intramolecular —S-alkyl bonds can be prepared by conventional solid phase chemistry while incorporating an amino acid residue with a suitable amino-protected side chain, and a suitable S-protected cysteine or homocysteine residue at the position selected for cyclization.

Another effective approach to confer resistance to peptidases acting on the N-terminal or C-terminal residues of a polypeptide is to add chemical groups at the polypeptide termini, such that the modified polypeptide is no longer a substrate for the peptidase. One such chemical modification is glycosylation of the polypeptides at either or both termini. Certain chemical modifications, in particular N-terminal glycosylation, have been shown to increase the stability of polypeptides in human serum (Powell et al., *Pharm. Res.* 10:1268-1273, 1993). Other chemical modifications which enhance serum stability include, but are not limited to, the addition of an N-terminal alkyl group, consisting of a lower alkyl of from one to twenty carbons, such as an acetyl group, and/or the addition of a C-terminal amide or substituted amide group. In particular, the present invention includes modified polypeptides consisting of polypeptides bearing an N-terminal acetyl group and/or a C-terminal amide group.

Also included by the present invention are other types of polypeptide derivatives containing additional chemical moieties not normally part of the polypeptide, provided that the derivative retains the desired functional activity of the polypeptide. Examples of such derivatives include (1) N-acyl derivatives of the amino terminal or of another free amino group, wherein the acyl group may be an alkanoyl group (e.g., acetyl, hexanoyl, octanoyl) an aroyl group (e.g., benzoyl) or a blocking group such as F-moc (fluorenylmethyl-O—CO—); (2) esters of the carboxy terminal or of another free carboxy or hydroxyl group; (3) amide of the carboxy-terminal or of another free carboxyl group produced by reaction with ammonia or with a suitable amine; (4) phosphorylated derivatives; (5) derivatives conjugated to an antibody or other biological ligand and other types of derivatives.

Longer polypeptide sequences which result from the addition of additional amino acid residues to the polypeptides described herein are also encompassed in the present invention. Such longer polypeptide sequences can be expected to have the same biological activity and specificity (e.g., cell tropism) as the polypeptides described above. While polypeptides having a substantial number of additional amino acids are not excluded, it is recognized that some large polypeptides may assume a configuration that masks the effective sequence, thereby preventing binding to a target (e.g., a member of the LRP receptor family such as LRP or LRP2). These derivatives could act as competitive antagonists. Thus, while the present invention encompasses polypeptides or derivatives of the polypeptides described herein having an extension, desirably the extension does not destroy the cell targeting activity of the polypeptides or its derivatives.

Other derivatives included in the present invention are dual polypeptides consisting of two of the same, or two different polypeptides, as described herein, covalently linked to one another either directly or through a spacer, such as by a short stretch of alanine residues or by a putative site for proteolysis (e.g., by cathepsin, see e.g., U.S. Pat. No. 5,126,249 and European Patent No. 495 049): Multimers of the polypeptides described herein consist of a polymer of molecules formed from the same or different polypeptides or derivatives thereof.

The present invention also encompasses polypeptide derivatives that are chimeric or fusion proteins containing a polypeptide described herein, or fragment thereof, linked at its amino- or carboxy-terminal end, or both, to an amino acid sequence of a different protein. Such a chimeric or fusion protein may be produced by recombinant expression of a nucleic acid encoding the protein. For example, a chimeric or fusion protein may contain at least 6 amino acids shared with one of the described polypeptides which desirably results in a chimeric or fusion protein that has an equivalent or greater functional activity.

Assays to Identify Peptidomimetics

As described above, non-peptidyl compounds generated to replicate the backbone geometry and pharmacophore display (peptidomimetics) of the polypeptides described herein often possess attributes of greater metabolic stability, higher potency, longer duration of action, and better bioavailability.

Peptidomimetics compounds can be obtained using any of the numerous approaches in combinatorial library methods known in the art, including biological libraries, spatially addressable parallel solid phase or solution phase libraries, synthetic library methods requiring deconvolution, the 'one-bead one-compound' library method, and synthetic library methods using affinity chromatography selection. The biological library approach is limited to peptide libraries, while the other four approaches are applicable to peptide, non-peptide oligomer, or small molecule libraries of compounds (Lam, *Anticancer Drug Des.* 12:145, 1997). Examples of methods for the synthesis of molecular libraries can be found in the art, for example, in: DeWitt et al. (*Proc. Natl. Acad. Sci. USA* 90:6909, 1993); Erb et al. (*Proc. Natl. Acad. Sci. USA* 91:11422, 1994); Zuckermann et al. (*J. Med. Chem.* 37:2678, 1994); Cho et al. (*Science* 261:1303, 1993); Carell et al. (*Angew. Chem, Int. Ed. Engl.* 33:2059, 1994 and ibid 2061); and in Gallop et al. (*Med. Chem.* 37:1233, 1994). Libraries of compounds may be presented in solution (e.g., Houghten, *Biotechniques* 13:412-421, 1992) or on beads (Lam, *Nature* 354:82-84, 1991), chips (Fodor, *Nature* 364:555-556, 1993), bacteria or spores (U.S. Pat. No. 5,223,409), plasmids (Cull et al., *Proc. Natl. Acad. Sci. USA* 89:1865-1869, 1992) or on phage (Scott and Smith, *Science* 249:386-390, 1990), or luciferase, and the enzymatic label detected by determination of conversion of an appropriate substrate to product.

Once a polypeptide as described herein is identified, it can be isolated and purified by any number of standard methods including, but not limited to, differential solubility (e.g., precipitation), centrifugation, chromatography (e.g., affinity, ion exchange, and size exclusion), or by any other standard techniques used for the purification of peptides, peptidomimetics, or proteins. The functional properties of an identified polypeptide of interest may be evaluated using any functional assay known in the art. Desirably, assays for evaluating downstream receptor function in intracellular signaling are used (e.g., cell proliferation).

For example, the peptidomimetics compounds of the present invention may be obtained using the following three-phase process: (1) scanning the polypeptides described herein to identify regions of secondary structure necessary for targeting the particular cell types described herein; (2) using conformationally constrained dipeptide surrogates to refine the backbone geometry and provide organic platforms corresponding to these surrogates; and (3) using the best organic platforms to display organic pharmocophores in libraries of candidates designed to mimic the desired activity of the native polypeptide. In more detail the three phases are as follows. In phase 1, the lead candidate polypeptides are scanned and their structure abridged to identify the requirements for their activity. A series of polypeptide analogs of the original are synthesized. In phase 2, the best polypeptide analogs are investigated using the conformationally constrained dipeptide surrogates. Indolizidin-2-one, indolizidin-9-one and quinolizidinone amino acids ($I^2aa$, $I^9aa$ and Qaa respectively) are used as platforms for studying backbone geometry of the best peptide candidates. These and related platforms (reviewed in Halab et al., *Biopolymers* 55:101-122, 2000 and Hanessian et al., *Tetrahedron* 53:12789-12854, 1997) may be introduced at specific regions of the polypeptide to orient the pharmacophores in different directions. Biological evaluation of these analogs identifies improved lead polypeptides that mimic the geometric requirements for activity. In phase 3, the platforms from the most active lead polypeptides are used to display organic surrogates of the pharmacophores responsible for activity of the native peptide. The pharmacophores and scaffolds are combined in a parallel synthesis format. Derivation of polypeptides and the above phases can be accomplished by other means using methods known in the art.

Structure function relationships determined from the polypeptides, polypeptide derivatives, peptidomimetics or other small molecules described herein may be used to refine and prepare analogous molecular structures having similar or better properties. Accordingly, the compounds of the present invention also include molecules that share the structure, polarity, charge characteristics and side chain properties of the polypeptides described herein.

In summary, based on the disclosure herein, those skilled in the art can develop peptides and peptidomimetics screening assays which are useful for identifying compounds for targeting an agent to particular cell types (e.g., those described herein). The assays of this invention may be developed for low-throughput, high-throughput, or ultra-high throughput screening formats. Assays of the present invention include assays amenable to automation.

Diseases and Conditions

The compounds of the invention can be used to treat a variety of diseases and conditions. Because the compounds of the invention are able to cross the BBB or enter particular cell types, treatments of neurological disorders, including neurodegenerative diseases and cancer, can be enhanced using the multimers of the invention.

Cancer Therapy

Compounds of the invention including anticancer agents may be used to treat any brain or central nervous system disease (e.g., a brain cancer such as glioblastoma, astrocytoma, glioma, meduloblastoma, and oligodendroma, neuroglioma, ependymoma, and meningioma). Compounds that are efficiently transported to the liver, lung, kidney, spleen or muscle (e.g., AngioPep-1 through AngioPep-7) and therefore may also be used, in conjunction with an appropriate therapeutic agent, to treat a disease associated with these tissues (e.g., a cancer such as hepatocellular carcinoma, liver cancer, small cell carcinoma (e.g., oat cell cancer), mixed small cell/large cell carcinoma, combined small cell carcinoma, and metastatic tumors. Metastatic tumors can originate from cancer of any tissue, including breast cancer, colon cancer, prostate cancer, sarcoma, bladder cancer, neuroblastoma, Wilm's tumor, lymphoma, non-Hodgkin's lymphoma, and certain T-cell lymphomas). Additional exemplary cancers that may be treated using a composition of the invention include hepatocellular carcinoma, breast cancer, cancers of the head and neck including various lymphomas such as mantle cell lymphoma, non-Hodgkin's lymphoma, adenoma, squamous cell carcinoma, laryngeal carcinoma, cancers of the retina, cancers of the esophagus, multiple myeloma, ovarian cancer, uterine cancer, melanoma, colorectal cancer, bladder cancer, prostate cancer, lung cancer (including non-small cell lung carcinoma), pancreatic cancer, cervical cancer, head and neck cancer, skin cancers, nasopharyngeal carcinoma, liposarcoma, epithelial carcinoma, renal cell carcinoma, gallbladder adenocarcinoma, parotid adenocarcinoma, endometrial sarcoma, multidrug resistant cancers; and proliferative diseases and conditions, such as neovascularization associated with tumor angiogenesis, macular degeneration (e.g., wet/dry AMD), corneal neovascularization, diabetic retinopathy, neovascular glaucoma, myopic degeneration and other proliferative diseases and conditions such as restenosis and polycystic kidney disease. Brain cancers that may be treated with vector that is transported efficiently across the BBB include astrocytoma, pilocytic astrocytoma, dysembryoplastic neuroepithelial tumor, oligodendrogliomas, ependymoma, glioblastoma multiforme, mixed gliomas, oligoastrocytomas, medulloblastoma, retinoblastoma, neuroblastoma, germinoma, and teratoma.

GLP-1-Based Therapy

The compounds of the invention including a GLP-1 agoinst can be used in any therapeutic application where a GLP-1 agonist activity in the brain, or in a particular tissues, is desired. GLP-1 agonist activity is associated with stimulation of insulin secretion (i.e., to act as an incretin hormone) and inhibition glucagon secretion, thereby contributing to limit postprandial glucose excursions. GLP-1 agonists can also inhibit gastrointestinal motility and secretion, thus acting as an enterogastrone and part of the "ileal brake" mechanism. GLP-1 also appears to be a physiological regulator of appetite and food intake. Because of these actions, GLP-1 and GLP-1 receptor agonists can be used for therapy of metabolic disorders, as reviewed in, e.g., Kinzig et al., J Neurosci 23:6163-6170, 2003. Such disorders include obesity, hyperglycemia, dyslipidemia, hypertriglyceridemia, syndrome X, insulin resistance, IGT, diabetic dyslipidemia, hyperlipidemia, a cardiovascular disease, and hypertension.

GLP-1 is also has neurological effects including sedative or anti-anxiolytic effects, as described in U.S. Pat. No. 5,846, 937. Thus, GLP-1 agonists can be used in the treatment of anxiety, aggression, psychosis, seizures, panic attacks, hysteria, or sleep disorders. GLP-1 agonists can also be used to treat Alzheimer's disease, as GLP-1 agonists have been shown to protect neurons against amyloid-β peptide and glutamate-induced apoptosis (Perry et al., Curr Alzheimer Res 2:377-85, 2005).

Other therapeutic uses for GLP-1 agonists include improving learning, enhancing neuroprotection, and alleviating a symptom of a disease or disorder of the central nervous system, e.g., through modulation of neurogenesis, and e.g., Parkinson's Disease, Alzheimer's Disease, Huntington's Disease, ALS, stroke, ADD, and neuropsychiatric syndromes (U.S. Pat. No. 6,969,702 and U.S. Patent Application No. 2002/0115605). Stimulation of neurogenesis using GLP-1 agonists has been described, for example, in Bertilsson et al., J Neurosci Res 86:326-338, 2008.

Still other therapeutic uses include converting liver stem/progenitor cells into functional pancreatic cells (U.S. Patent Application Publication No. 2005/0053588); preventing beta-cell deterioration (U.S. Pat. Nos. 7,259,233 and 6,569, 832) and stimulation of beta-cell proliferation (U.S. Patent Application Publication No. 2003/0224983); treating obesity (U.S. Pat. No. 7,211,557); suppressing appetite and inducing satiety (U.S. Patent Application Publication No. 2003/0232754); treating irritable bowel syndrome (U.S. Pat. No. 6,348,447); reducing the morbidity and/or mortality associated with myocardial infarction (U.S. Pat. No. 6,747,006) and stroke (PCT Publication No. WO 00/16797); treating acute coronary syndrome characterized by an absence of Q-wave myocardial infarction (U.S. Pat. No. 7,056,887); attenuating post-surgical catabolic changes (U.S. Pat. No. 6,006,753); treating hibernating myocardium or diabetic cardiomyopathy (U.S. Pat. No. 6,894,024); suppressing plasma blood levels of norepinepherine (U.S. Pat. No. 6,894,024); increasing urinary sodium excretion, decreasing urinary potassium concentration (U.S. Pat. No. 6,703,359); treating conditions or disorders associated with toxic hypervolemia, e.g., renal failure, congestive heart failure, nephrotic syndrome, cirrhosis, pulmonary edema, and hypertension (U.S. Pat. No. 6,703,359); inducing an inotropic response and increasing cardiac contractility (U.S. Pat. No. 6,703,359); treating polycystic ovary syndrome (U.S. Pat. No. 7,105,489); treating respiratory distress (U.S. Patent Application Publication No. 2004/0235726); improving nutrition via a non-alimentary route, i.e., via intravenous, subcutaneous, intramuscular, peritoneal, or other injection or infusion (U.S. Pat. No. 6,852,690); treating nephropathy (U.S. Patent Application Publication No. 2004/0209803); treating left ventricular systolic dysfunction, e.g., with abnormal left ventricular ejection fraction (U.S. Pat. No. 7,192,922); inhibiting antro-duodenal motility, e.g., for the treatment or prevention of gastrointestinal disorders such as diarrhea, postoperative dumping syndrome and irritable bowel syndrome, and as premedication in endoscopic procedures (U.S. Pat. No. 6,579,851); treating critical illness polyneuropathy (CIPN) and systemic inflammatory response syndrome (SIRS) (U.S. Patent Application Publication No. 2003/0199445); modulating triglyceride levels and treating dyslipidemia (U.S. Patent Application Publication Nos. 2003/0036504 and 2003/0143183); treating organ tissue injury caused by reperfusion of blood flow following ischemia (U.S. Pat. No. 6,284,725); treating coronary heart disease risk factor (CHDRF) syndrome (U.S. Pat. No. 6,528, 520); and others.

Leptin-Based Therapy

Compounds of the invention that include leptin or a related molecule can be used to treat metabolic disorders, neurological diseases, as well as other indications.

In certain embodiments, the compound of the invention is used to treat a metabolic disorder. Such disorders include diabetes (type I or type II), obesity, hyperglycemia, dyslipidemia, hypertriglyceridemia, syndrome X, insulin resistance, IGT, diabetic dyslipidemia, hyperlipidemia, a cardiovascular disease, and hypertension. Leptin decreases food intake and thus can be used to reduce weight and to treat diseases where reduced food intake or weight loss is beneficial.

Because peptide vectors described herein are capable of transporting an agent across the BBB, the compounds of the invention are also useful for the treatment of neurological diseases such as neurodegenerative diseases or other conditions of the central nervous system (CNS), the peripheral nervous system, or the autonomous nervous system (e.g., where neurons are lost or deteriorate). Many neurodegenerative diseases are characterized by ataxia (i.e., uncoordinated muscle movements) and/or memory loss. Neurodegenerative diseases include Alexander disease, Alper disease, Alzheimer's disease, amyotrophic lateral sclerosis (ALS; i.e., Lou Gehrig's disease), ataxia telangiectasia, Batten disease (Spielmeyer-Vogt-Sjogren-Batten disease), bovine spongiform encephalopathy (BSE), Canavan disease, Cockayne syndrome, corticobasal degeneration, Creutzfeldt-Jakob disease, Huntington's disease, HIV-associated dementia, Kennedy's disease, Krabbé disease, Lewy body dementia, Machado-Joseph disease (Spinocerebellar ataxia type 3), multiple sclerosis, multiple system atrophy, narcolepsy, neuroborreliosis, Parkinson's disease, Pelizaeus-Merzbacher disease, Pick's disease, primary lateral sclerosis, prion diseases, Refsum's disease, Schilder's disease (i.e., adrenoleukodystrophy), schizophrenia, spinocerebellar ataxia, spinal muscular atrophy, Steele-Richardson, Olszewski disease, and tabes dorsalis.

The compounds of the invention can also be used to treat diseases found in other organs or tissues. For example, Angiopep-7 (SEQ ID NO:112) is efficiently transported into liver, lung, kidney, spleen, and muscle cells, allowing for the preferential treatment of diseases associated with these tissues (e.g., hepatocellular carcinoma and lung cancer). The compounds of the presents invention may also be used to treat genetic disorders, such as Down syndrome (i.e., trisomy 21), where down-regulation of particular gene transcripts may be useful.

Neurotensin-based Therapies

The compounds of the invention can be used in any appropriate therapeutic application where the activity of neurotensin activity is beneficial. In brain, NT is associated with dopaminergic receptors and other neurotransmitter systems. Peripheral NT acts as a paracrine and endocrine peptide on both the digestive and cardiovascular systems. Various therapeutic applications have been suggested for neurotensin, including psychiatric disorders, metabolic disorder, and pain. Because neurotensin has been shown to modulate neurotransmission in areas of the brain associated with schizophrenia, neurotensin and neurotensin receptor agonists have been proposed as antipsychotic agents.

Because polypeptides described herein are capable of transporting an agent across the BBB, the compounds of the invention are also useful for the treatment of neurological diseases such as neurodegenerative diseases or other conditions of the central nervous system (CNS), the peripheral nervous system, or the autonomous nervous system (e.g., where neurons are lost or deteriorate). Neurotensin has been suggested an antipsychotic therapy, and thus may be useful in the treatment of diseases such as schizophrenia and bipolar disorder. Many neurodegenerative diseases are characterized by ataxia (i.e., uncoordinated muscle movements) and/or memory loss. Neurodegenerative diseases include Alexander disease, Alper disease, Alzheimer's disease, amyotrophic lateral sclerosis (ALS; i.e., Lou Gehrig's disease), ataxia telangiectasia, Batten disease (Spielmeyer-Vogt-Sjogren-Batten disease), bovine spongiform encephalopathy (BSE), Canavan disease, Cockayne syndrome, corticobasal degeneration, Creutzfeldt-Jakob disease, Huntington's disease, HIV-associated dementia, Kennedy's disease, Krabbé disease, Lewy body dementia, Machado-Joseph disease (Spinocerebellar ataxia type 3), multiple sclerosis, multiple system atrophy, narcolepsy, neuroborreliosis, Parkinson's disease, Pelizaeus-Merzbacher disease, Pick's disease, primary lateral sclerosis, prion diseases, Refsum's disease, Schilder's disease (i.e., adrenoleukodystrophy), schizophrenia, spinocerebellar ataxia, spinal muscular atrophy, Steele-Richardson, Olszewski disease, and tabes dorsalis.

The compounds of the invention may be used to reduce the body temperature of a subject. Because reduction in body temperature has been shown to be beneficial in subjects who may be suffering from, or may have recently suffered from, a stroke, cerebral ischemia, cardiac ischemia, or a nerve injury such as a spinal cord injury, such a treatment would therefore be useful in reducing complications of these conditions.

Neurotensin is also known to have analgesic effects. Thus the compounds of the invention may be used to reduce pain in a subject. The subject may be suffering from an acute pain (e.g., selected from the group consisting of mechanical pain, heat pain, cold pain, ischemic pain, and chemical-induced pain). Other types of pain include peripheral or central neuropathic pain, inflammatory pain, migraine-related pain, headache-related pain, irritable bowel syndrome-related pain, fibromyalgia-related pain, arthritic pain, skeletal pain, joint pain, gastrointestinal pain, muscle pain, angina pain, facial pain, pelvic pain, claudication, postoperative pain, post traumatic pain, tension-type headache, obstetric pain, gynecological pain, or chemotherapy-induced pain.

There is evidence that neurotensin can be used to treat metabolic disorders; see, e.g., U.S. Patent Application No. 2001/0046956. Thus the compounds of the invention may be used to treat such disorders. The metabolic disorder may be diabetes (e.g., Type I or Type II), obesity, diabetes as a consequence of obesity, hyperglycemia, dyslipidemia, hypertriglyceridemia, syndrome X, insulin resistance, impaired glucose tolerance (IGT), diabetic dyslipidemia, hyperlipidemia, a cardiovascular disease, or hypertension. The subject may be overweight, obese, or bulimic.

Neurotensin has also been suggested to be able to treat drug addiction or reduce drug abuse in subjects, particularly with psychostimulant. Thus the compounds of the invention may be useful in treating addiction to or abuse of drugs such as amphetamine, methamphetamine, 3,4-methylenedioxymethamphetamine, nicotine, cocaine, methylphenidate, and arecoline.

GDNF/BDNF-based Therapy

GDNF and BDNF-based compounds may be used to treat any disease or condition where enhancing neuronal survival (e.g., decreasing neuronal death rate) or increasing the rate of neuronal formation is beneficial. Such conditions include neurodegenerative disorders, e.g., a disorder selected from the group consisting of a polyglutamine expansion disorder (e.g., Huntington's disease (HD), dentatorubropallidoluysian atrophy, Kennedy's disease (also referred to as spinobulbar muscular atrophy), and spinocerebellar ataxia (e.g., type 1, type 2, type 3 (also referred to as Machado-Joseph disease), type 6, type 7, and type 17)), another trinucleotide repeat expansion disorder (e.g., fragile X syndrome, fragile XE mental retardation, Friedreich's ataxia, myotonic dystrophy, spinocerebellar ataxia type 8, and spinocerebellar ataxia type 12), Alexander disease, Alper's disease, Alzheimer's disease, amyotrophic lateral sclerosis (ALS), ataxia telangiectasia, Batten disease (also referred to as Spielmeyer-Vogt-Sjogren-Batten disease), Canavan disease, Cockayne syndrome, corticobasal degeneration, Creutzfeldt-Jakob disease, ischemia stroke, Krabbe disease, Lewy body dementia, multiple sclerosis, multiple system atrophy, Parkinson's disease, Pelizaeus-Merzbacher disease, Pick's disease, primary lateral sclerosis, Refsum's disease, Sandhoff disease, Schilder's disease, spinal cord injury, spinal muscular atrophy, Steele-Richardson-Olszewski disease, and Tabes dorsalis. Other conditions include injury (e.g., spinal cord injury), concussion, ischemic stroke, and hemorrhagic stroke.

Administration and Dosage

The present invention also features pharmaceutical compositions that contain a therapeutically effective amount of a compound of the invention. The composition can be formulated for use in a variety of drug delivery systems. One or more physiologically acceptable excipients or carriers can also be included in the composition for proper formulation. Suitable formulations for use in the present invention are found in *Remington's Pharmaceutical Sciences*, Mack Publishing Company, Philadelphia, Pa., 17th ed., 1985. For a brief review of methods for drug delivery, see, e.g., Langer (*Science* 249:1527-1533, 1990).

The pharmaceutical compositions are intended for parenteral, intranasal, topical, oral, or local administration, such as by a transdermal means, for prophylactic and/or therapeutic treatment. The pharmaceutical compositions can be administered parenterally (e.g., by intravenous, intramuscular, or subcutaneous injection), or by oral ingestion, or by topical application or intraarticular injection at areas affected by the vascular or cancer condition. Additional routes of administration include intravascular, intra-arterial, intratumor, intraperitoneal, intraventricular, intraepidural, as well as nasal, ophthalmic, intrascleral, intraorbital, rectal, topical, or aerosol inhalation administration. Sustained release administration is also specifically included in the invention, by such means as depot injections or erodible implants or components. Thus, the invention provides compositions for parenteral administration that include the above mention agents dissolved or suspended in an acceptable carrier, preferably an aqueous carrier, e.g., water, buffered water, saline, PBS, and the like. The compositions may contain pharmaceutically acceptable auxiliary substances as required to approximate physiological conditions, such as pH adjusting and buffering agents, tonicity adjusting agents, wetting agents, detergents and the like. The invention also provides compositions for oral delivery, which may contain inert ingredients such as binders or fillers for the formulation of a tablet, a capsule, and the like. Furthermore, this invention provides compositions for local administration, which may contain inert ingredients such as solvents or emulsifiers for the formulation of a cream, an ointment, and the like.

These compositions may be sterilized by conventional sterilization techniques, or may be sterile filtered. The resulting aqueous solutions may be packaged for use as is, or lyophilized, the lyophilized preparation being combined with a sterile aqueous carrier prior to administration. The pH of the preparations typically will be between 3 and 11, more preferably between 5 and 9 or between 6 and 8, and most preferably between 7 and 8, such as 7 to 7.5. The resulting compositions in solid form may be packaged in multiple single dose units, each containing a fixed amount of the above-mentioned agent or agents, such as in a sealed package of tablets or capsules. The composition in solid form can also be packaged in a container for a flexible quantity, such as in a squeezable tube designed for a topically applicable cream or ointment.

The compositions containing an effective amount can be administered for prophylactic or therapeutic treatments. In prophylactic applications, compositions can be administered to a subject with a clinically determined predisposition or increased susceptibility to a neurological or neurodegenerative disease. Compositions of the invention can be administered to the subject (e.g., a human) in an amount sufficient to delay, reduce, or preferably prevent the onset of clinical disease. In therapeutic applications, compositions are administered to a subject (e.g., a human) already suffering from disease (e.g., a neurological condition or neurodegenerative disease) in an amount sufficient to cure or at least partially arrest the symptoms of the condition and its complications. An amount adequate to accomplish this purpose is defined as a "therapeutically effective amount," an amount of a compound sufficient to substantially improve some symptom associated with a disease or a medical condition. For example, in the treatment of a neurodegenerative disease (e.g., those described herein), an agent or compound that decreases, prevents, delays, suppresses, or arrests any symptom of the disease or condition would be therapeutically effective. A therapeutically effective amount of an agent or compound is not required to cure a disease or condition but will provide a treatment for a disease or condition such that the onset of the disease or condition is delayed, hindered, or prevented, or the disease or condition symptoms are ameliorated, or the term of the disease or condition is changed or, for example, is less severe or recovery is accelerated in an individual.

Amounts effective for this use may depend on the severity of the disease or condition and the weight and general state of the subject, but generally range from about 0.05 µg to about 1000 µg (e.g., 0.5-100 µg) of an equivalent amount of the agent per dose per subject. Suitable regimes for initial administration and booster administrations are typified by an initial administration followed by repeated doses at one or more hourly, daily, weekly, or monthly intervals by a subsequent administration. The total effective amount of an agent present in the compositions of the invention can be administered to a mammal as a single dose, either as a bolus or by infusion over a relatively short period of time, or can be administered using a fractionated treatment protocol, in which multiple doses are administered over a more prolonged period of time (e.g., a dose every 4-6, 8-12, 14-16, or 18-24 hours, or every 2-4 days, 1-2 weeks, once a month). Alternatively, continuous intravenous infusion sufficient to maintain therapeutically effective concentrations in the blood are contemplated.

The therapeutically effective amount of one or more agents present within the compositions of the invention and used in the methods of this invention applied to mammals (e.g., humans) can be determined by the ordinarily-skilled artisan with consideration of individual differences in age, weight, and the condition of the mammal. Because certain compounds of the invention exhibit an enhanced ability to cross the BBB, the dosage of the compounds of the invention can be lower than (e.g., less than or equal to about 90%, 75%, 50%, 40%, 30%, 20%, 15%, 12%, 10%, 8%, 7%, 6%, 5%, 4%, 3%, 2%, 1%, 0.5%, or 0.1% of) the equivalent dose of required for a therapeutic effect of the unconjugated agonist. The agents of the invention are administered to a subject (e.g. a mammal, such as a human) in an effective amount, which is an amount that produces a desirable result in a treated subject (e.g., preservation of neurons, new neuronal growth). Therapeutically effective amounts can also be determined empirically by those of skill in the art.

The subject may also receive an agent in the range of about 0.05 to 1,000 µg equivalent dose as compared to unconjugated agent per dose one or more times per week (e.g., 2, 3, 4, 5, 6, or 7 or more times per week), 0.1 to 2,500 (e.g., 2,000, 1,500, 1,000, 500, 100, 10, 1, 0.5, or 0.1) µg dose per week. A subject may also receive an agent of the composition in the range of 0.1 to 3,000 µg per dose once every two or three weeks.

Single or multiple administrations of the compositions of the invention including an effective amount can be carried out with dose levels and pattern being selected by the treating physician. The dose and administration schedule can be determined and adjusted based on the severity of the disease or condition in the subject, which may be monitored throughout the course of treatment according to the methods commonly practiced by clinicians or those described herein.

The compounds of the present invention may be used in combination with either conventional methods of treatment or therapy or may be used separately from conventional methods of treatment or therapy.

When the compounds of this invention are administered in combination therapies with other agents, they may be administered sequentially or concurrently to an individual. Alternatively, pharmaceutical compositions according to the present invention may be comprised of a combination of a compound of the present invention in association with a pharmaceutically acceptable excipient, as described herein, and another therapeutic or prophylactic agent known in the art.

EXAMPLE 1

Synthesis of Dimeric Angiopep-2 Using a TMEA Linker

The following scheme was used produce a dimeric form of Angiopep-2 joined by a TMEA linker.

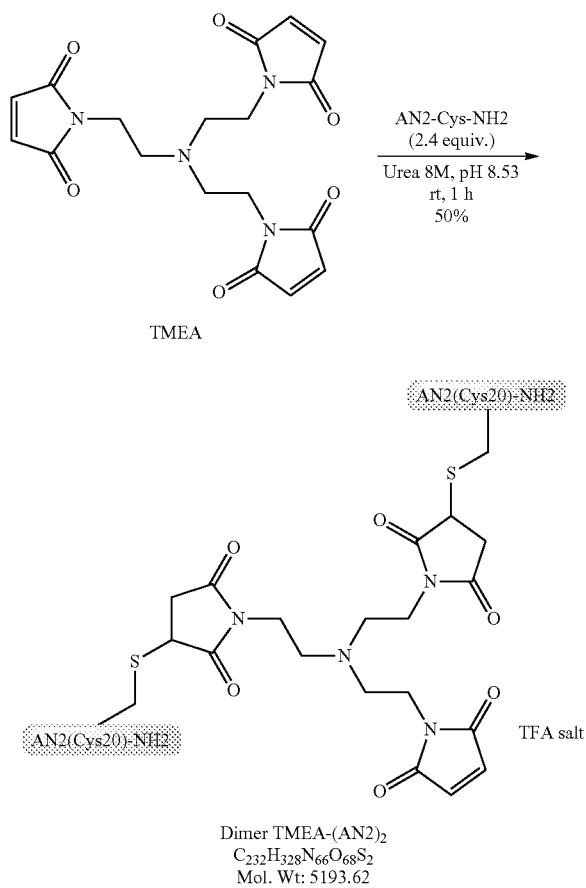

C-terminally amidated Angiopep-2 with an additional C-terminal cysteine (Angiopep-2-Cys; SEQ ID NO:114) (264.2 mg, 109.9 umol, 2.4 eq.) was dissolved in urea 8 M (18 ml). This solution was added dropwise to a solution of TMEA (tris-(2-maleimidoethyl)amine) (Pierce Biotechnology) (17.7 mg, 45.8 umol, 1 eq. in 9 ml of urea 8 M). Monitoring of the reaction was done using the analytical methods 1 and 2 (which are described in chromatograms 1-2 of FIG. 1). The reaction (1.7 mM, pH 8.53) allowed to proceed at room temperature for 1 hour, and the mixture was purified by RP-HPLC chromatography (Waters PrepLC 4000; see chromatogram 3, Table 5).

TABLE 5

| | Purification | | |
|---|---|---|---|
| Time (min) | Column Volume (C.V.) | Flow Rate (ml/min) | % Solvent B |
| 0.00 | 0.00 | 13.00 | 20.0 |
| 5.12 | 1.52 | 13.00 | 20.0 |
| 28.75 | 7.01 | 13.00 | 40.0 (over 23.63 min) |
| 33.30 | 1.35 | 13.00 | 95.0 (over 4.6 min) |
| 38.00 | 1.39 | 13.00 | 95.0 |

1 CV = 43 ml

After coupling, ESI-TOF MS analysis showed the presence of TMEA cross-linked monomer, dimer, and trimer in solution. After evaporation of methanol and lyophilization, the dimer TMEA-(AN2)$_2$ was obtained as a pure white solid (119 mg, 50%, purity>98%). The mass was checked by ESI-TOF MS (Bruker Daltonics).

In addition to the information in FIG. 1, the following apparatus was used in the analytic methods. A Waters Acquity HPLC Column BEH phenyl, 1.7 μm, 2.1×50 mm was used. Detection was performed at 229 nm. Solution A was 0.1% FA in H$_2$O; Solution B was 0.1% FA in MeOH. A flow rate of 0.5 ml/min was used. The gradient settings are shown in Table 6 below.

TABLE 6

| Time | Flow | | Method 1 | | Method 2 | |
|---|---|---|---|---|---|---|
| (min) | (mL/min) | Curve | % A | % B | % A | % B |
| | 0.5 | | 90 | 10 | 80 | 20 |
| 0.40 | 0.5 | 6 | 90 | 10 | 80 | 20 |
| 0.70 | 0.5 | 6 | 70 | 30 | 50 | 50 |
| 2.20 | 0.5 | 6 | 30 | 70 | 15 | 85 |
| 2.40 | 0.5 | 6 | 10 | 90 | 5 | 95 |
| 2.70 | 0.5 | 6 | 10 | 90 | 5 | 95 |
| 2.80 | 0.5 | 6 | 90 | 10 | 80 | 20 |
| 2.81 | 0.5 | 6 | 90 | 10 | 80 | 20 |

Using ESI-TOF MS (Bruker Daltonics) the following m/z values were calculated and identified: calculated 5193.62. found 5193.68, m/z 866.62 (+6), 1039.74 (+5), 1299.42 (+4), 1732.21 (+3).

Purification was performed as follows, using a Waters PrepLC 4000 with a Phenyl OBD column (Waters X-Bridge) 5 μm, 19×150 mm, 135 Å, Sample load: 282 mg, Urea 8 M (27 ml), 20% MeOH in H$_2$O (2 ml), FA, Solution A was 0.1% FA in H$_2$O, Solution B was 0.1% FA in MeOH A flow rate of 13 ml/min was employed with a gradient: 20-40% B. Purification of the crude was performed in 2 batches successively.

Possible side reactions include hydrolysis of TMEA-(AN2)$_2$ (≤5%, Mw=5211.63) might occur. Conjugate is then stored under nitrogen atmosphere, below −20° C.

EXAMPLE 2

Synthesis of Dimeric Angiopep-2

The following synthetic scheme was used to produce dimeric Angiopep-2 having an SATP linker.

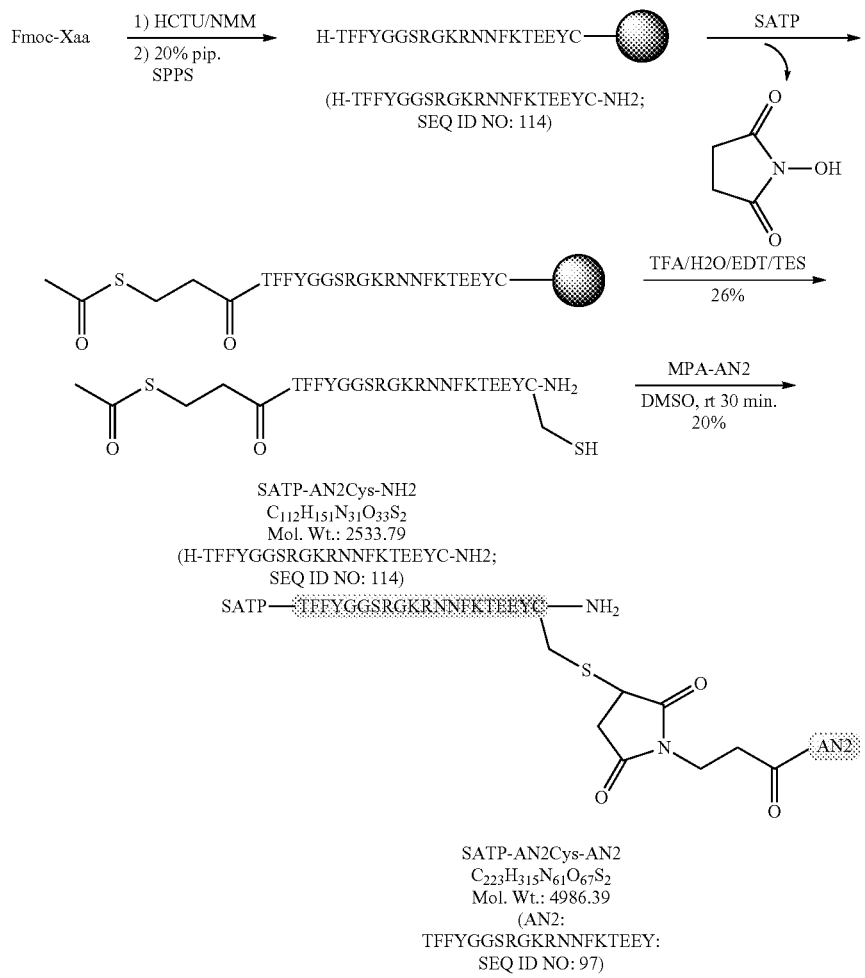

Angiopep-2-Cys-NH₂ (H-TFFYGGSRGKRNNFK-TEEYC-NH₂; SEQ ID NO:114) was synthesized using solid phase peptide synthesis (SPPS). G⁶S⁷ is coupled using pseudoproline dipeptide GS to optimize the synthesis. SPPS was carried out on a Protein Technologies, Inc. Symphony® peptide synthesizer using Fmoc (9-fluorenylmethyloxycarbonyl)amino-terminus protection. Angiopep-2-Cys-NH₂ (H-TFFYGGSRGKRNNFKTEECY-NH₂; SEQ ID NO:114) was synthesized on a 100-μmol scale using a 5-fold excess of Fmoc-amino acids (200 mM) relative to the resin. Coupling was performed from a Rink amide MBHA resin (with Nle) (0.40 mmol/g) for carboxyl-terminus amides using 1:1:2 amino acid/activator/NMM in DMF with HCTU (2-(1H-6-chlorobenzotriazol-1-yl)-1,1,3,3-tetramethyluronium hexafluorophosphate) and NMM (N-methylmorpholine). Deprotection was carried out using 20% piperidine/DMF.

Rink amide MBHA resin (with Nle) (0.40 mmol/g), Fmoc-amino acids and HCTU were purchased from ChemImpex, and the pseudoproline dipeptide GS was purchased from Novabiochem. Side protecting groups for amino acids were trityl (Trt) for cysteine and aspargine, (tBu) for glutamic acid, tyrosine, serine, and threonine, pentamethyldihydrobenzofuran-5-sulfonyl (Pbf) for arginine, and tButyloxycarbonyl (tBoc) for lysine.

Figure 2:
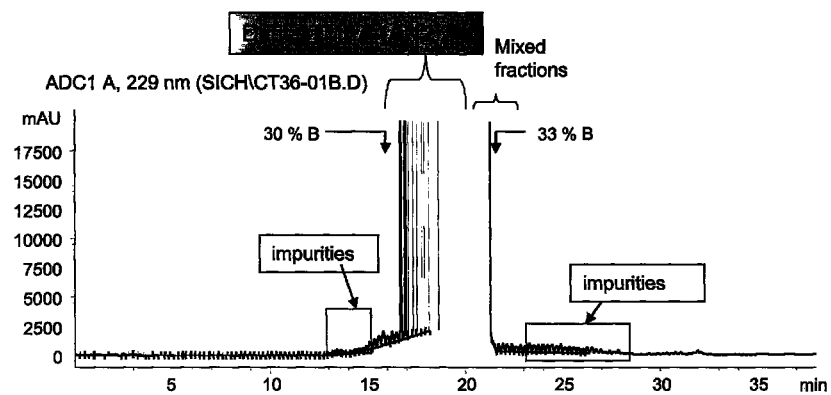
FIG. 2 is a graph showing purification of the TMEA-(Angiopep-2)$_2$ conjugate.

The SATP-AN2Cys-NH₂ was generated as follows. After deprotection of the last threonine residue, N-terminal S-acetylthiopropionic acyl groups were introduced by treating the free N-terminal amino peptide bound to the resin with a solution of SATP (N-succinimidyl S-acetylthiopropionate) (Pierce Biotechnology) (24.5 mg, 100 μmol, 1 eq. in 4 ml of DMF, 25 mM) for one hour at room temperature. The modification with SATP solution was repeated once for 1 h 30. Cleavage of the resin-bound product was carried out using TFA/water/EDT/TES (94/2.5/2.5/1) for two hours at room temperature. The crude modified peptide was precipitated using ice-cold ether and purified by RP-HPLC chromatography (Waters PrepLC 4000, See chromatograms 1-3 in FIGS. 1 and 2, Table 9).

Methanol was evaporated from the collected fractions and lyophilized to give SATP-AN2Cys-NH₂ as a pure white solid (736 mg, 26%, purity>95%). The mass was confirmed by ESI-TOF MS (Bruker Daltonics): calculated 2533.79. found 2533.18, m/z 1267.59 (+2), 845.41 (+3).

Figure 3:
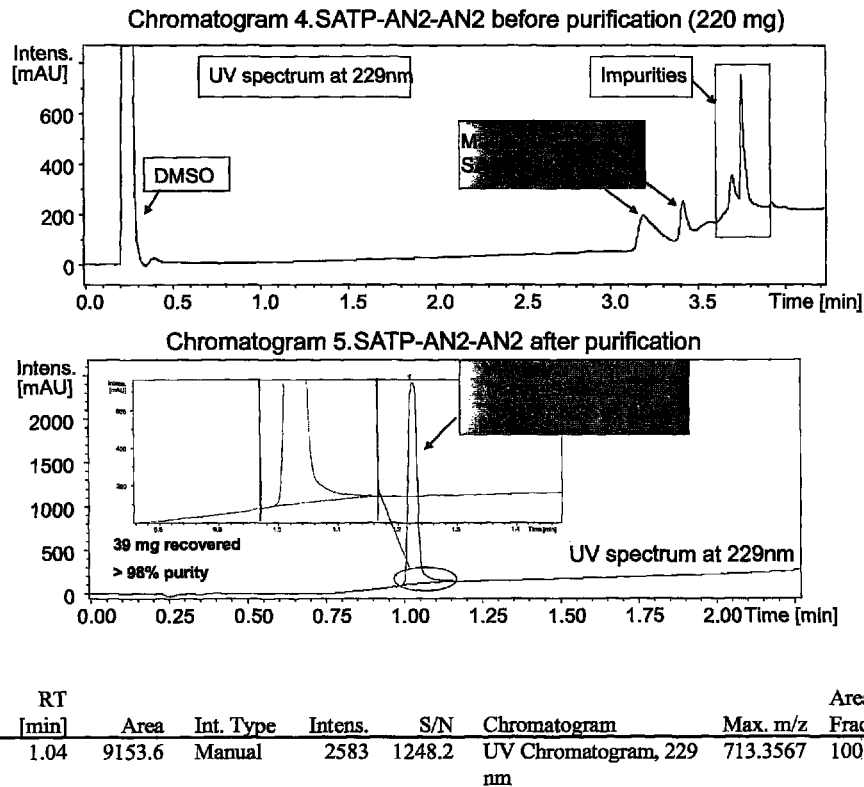
FIG. 3 is a set of graphs showing the SATP-Angiopep-2-Angiopep-2 conjugate before (Chromatogram 4) and after (Chromatogram 5) purification.
Figure 4:
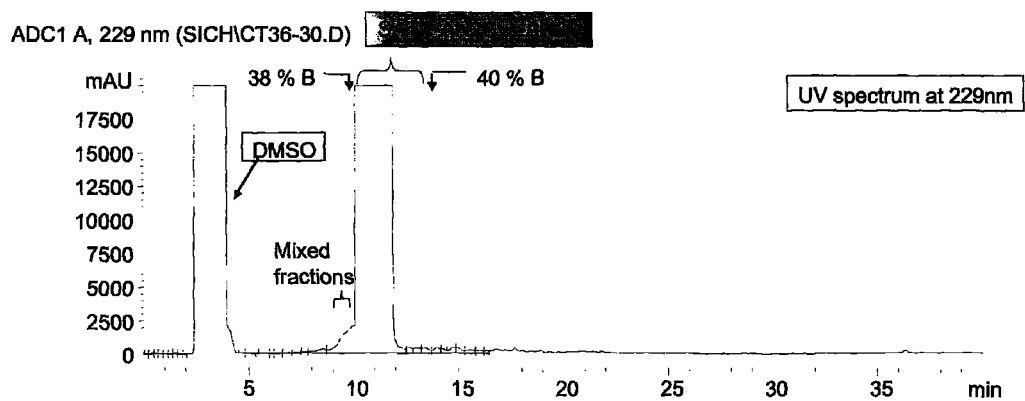
FIG. 4 is a graph showing purification of the SATP-Angiopep-2-Angiopep-2 conjugate.

Dimeric SATP-AN2-AN2 was produced as follows. MPA-AN2, AN2 vector activated by BMPS(N-[β-Maleimidopropyloxy]succinimide ester), (120 mg, 39.4 umol, 1 eq., 80.25% peptide content) was dissolved in DMSO (2 ml). This solution was added to a solution of SATP-AN2-CysNH2 (100 mg, 39.4 μmol, 1 eq. in 2.5 ml of DMSO). Monitoring of the reaction was done with the analytical methods 1 and 2 (See chromatograms 4-5 in FIG. 3). The reaction (8.8 mM) allowed to proceed at room temperature for 30 minutes and filtered. The mixture was purified by RP-HPLC chromatography (Waters PrepLC 4000, See chromatograms 4-6 in FIGS. 3 and 4 and Table 9).

After evaporation of methanol and lyophilization, the dimer SATP-AN2-AN2 was obtained as a pure white solid (39 mg, 20%, purity>98%). The mass was confirmed by ESI-TOF MS (Bruker Daltonics): calculated 4986.39. found 4986.42, m/z 1247.60 (+4), 998.08 (+5), 832.07 (+6), 713.35 (+7).

Analytical methods 1 and 2 were performed as follows. Both methods used a Waters Acquity HPLC system with a Waters Acquity HPLC BEH phenyl column (1.7 µm, 2.1×50 mm). Detection was performed at 229 nm. Solution A was 0.1% FA in $H_2O$: Solution B was 0.1% FA in MeOH, with a flow rate of 0.5 ml/min. Flow gradients are shown in the Tables 7 and 8 below for each method.

TABLE 7

Method 1

| Time (min) | Flow (mL/min) | % A | % B | Curve |
|---|---|---|---|---|
|  | 0.5 | 90 | 10 |  |
| 0.40 | 0.5 | 90 | 10 | 6 |
| 0.70 | 0.5 | 70 | 30 | 6 |
| 2.20 | 0.5 | 30 | 70 | 6 |
| 2.40 | 0.5 | 10 | 90 | 6 |
| 2.70 | 0.5 | 10 | 90 | 6 |
| 2.80 | 0.5 | 90 | 10 | 6 |
| 2.81 | 0.5 | 90 | 10 | 6 |

TABLE 8

Method 2:

| Time (min) | Flow (mL/min) | % A | % B | Curve |
|---|---|---|---|---|
|  | 0.5 | 80 | 20 |  |
| 0.40 | 0.5 | 80 | 20 | 6 |
| 3.00 | 0.5 | 60 | 40 | 6 |
| 3.30 | 0.5 | 5 | 95 | 6 |
| 3.80 | 0.5 | 5 | 95 | 6 |
| 4.00 | 0.5 | 80 | 20 | 6 |
| 4.20 | 0.5 | 80 | 20 | 6 |
| 4.21 | 0.5 | 80 | 20 | 6 |

Purification of SATP-AN2Cys-$NH_2$ was performed as follows using a Waters PrepLC 4000 with a Kromasil column (C18, 10 µm, 50×250 mm, 100 Å). Solution A was 0.1% FA in $H_2O$; Solution B was 0.1% FA in MeOH, with a flow rate of 48 ml/min and gradient of 20-45% B. Purification results are shown in Table 9.

TABLE 9

Purification of SATP-AN2-Cys-$NH_2$

| Time (min) | Column Volume (C.V.) | Flow Rate (ml/min) | % Solvent B |
|---|---|---|---|
| 0.00 | 0.00 | 48.19 | 20.0 |
| 18.08 | 19.80 | 48.19 | 20.0 |
| 26.91 | 9.67 | 48.19 | 35.0 (over 5.46 min) |
| 109.26 | 90.19 | 48.19 | 45.0 (over 23.61 min) |
| 130.00 | 22.72 | 48.19 | 95.0 (over 5.00 min) |
| 154.00 | 26.29 | 48.19 | 95.0 |

1 CV = 44 ml

Purification of SATP-AN2-AN2 was performed as follows using a Waters PrepLC 4000 with a BEH phenyl column (5 um, 19×150 mm, 135 Å). Solution A was 0.1% FA in $H_2O$; Solution B was 0.1% FA in MeOH with a flow rate of 13 ml/min and a gradient of 35-50% B. Purification results are shown in Table 10.

TABLE 10

Purification of SATP-AN2-AN2

| Time (min) | Column Volume (C.V.) | Flow Rate (ml/min) | % Solvent B |
|---|---|---|---|
| 0.00 | 0.00 | 13.00 | 35.0 |
| 5.12 | 1.51 | 13.00 | 35.0 |
| 28.75 | 6.98 | 13.00 | 50.0 (over 23.63 min) |
| 33.30 | 1.34 | 13.00 | 95.0 (over 4.55 min) |
| 40.00 | 1.98 | 13.00 | 95.0 |

1 C.V. = 44 ml

The conjugate was stored under nitrogen atmosphere, below −20° C.

EXAMPLE 3

Synthesis of an Angiopep-1 Dimer Using a Disulfide Bond

An Angiopep-1 dimer was prepared by incubating the Angiopep-1 peptide (SEQ ID NO:67) at 37° C. for 2 hours in phosphate buffered saline (PBS) at pH 8.5. This reaction resulted in formation of Angiopep-1 dimers joined by a disulfide bond through the cysteine amino acid on each protein (FIG. 5).

Figure 6:
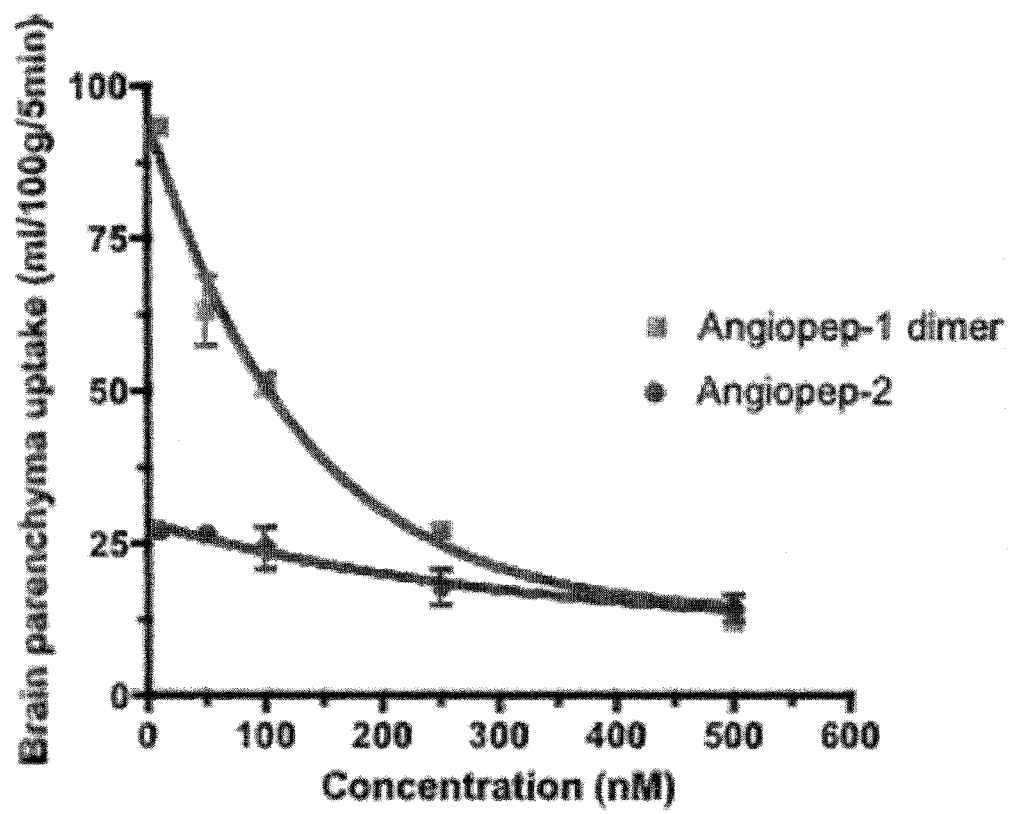
FIG. 6 is a graph showing apparent volume of parenchyma distribution measured by an in situ brain perfusion assay for the Angiopep-1 dimer and Angiopep-2.
Figure 7:
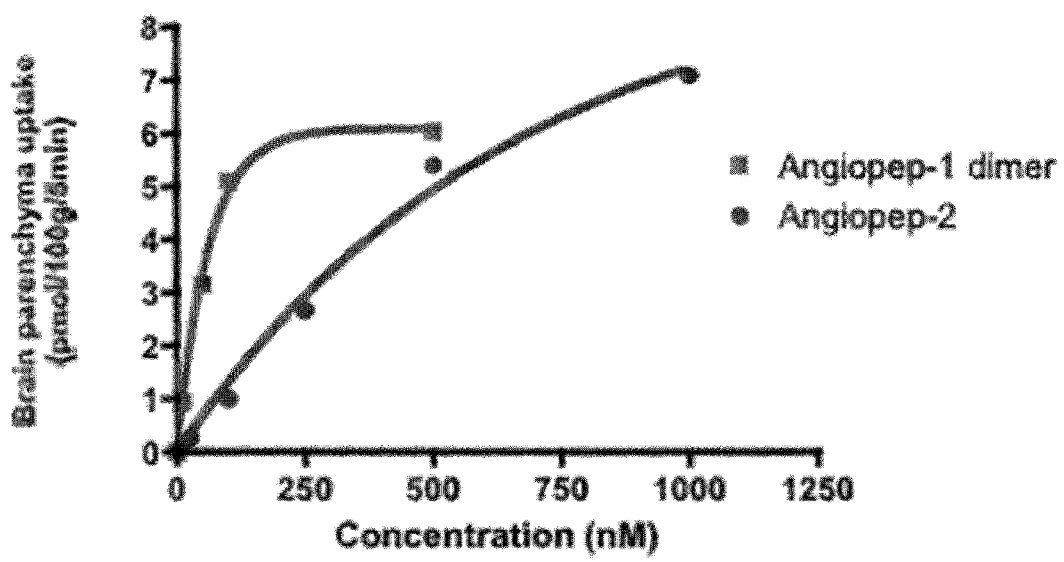
FIG. 7 is a graph showing parenchymal uptake (volume of parenchyma transformed to pmol uptake) using an in situ brain perfusion assay for the Angiopep-1 dimer and Angiopep-2.

Volume of brain parenchymal distribution was measured using the in situ brain perfusion assay (FIG. 6). Great uptake volumes using the Angiopep-1 dimer were observed, especially at lower concentrations, as compared to monomeric Angiopep-2. Parenchymal uptake of the Angiopep-1 dimer and Angiopep-2 was also measured at various concentrations in situ (FIG. 7). Here, the Angiopep-1 dimer, especially at lower concentrations (<500 nmol), exhibited higher transport than the Angiopep-2 monomer.

EXAMPLE 4

Transport of Angiopep-2 Dimers and Trimers

Figure 8:
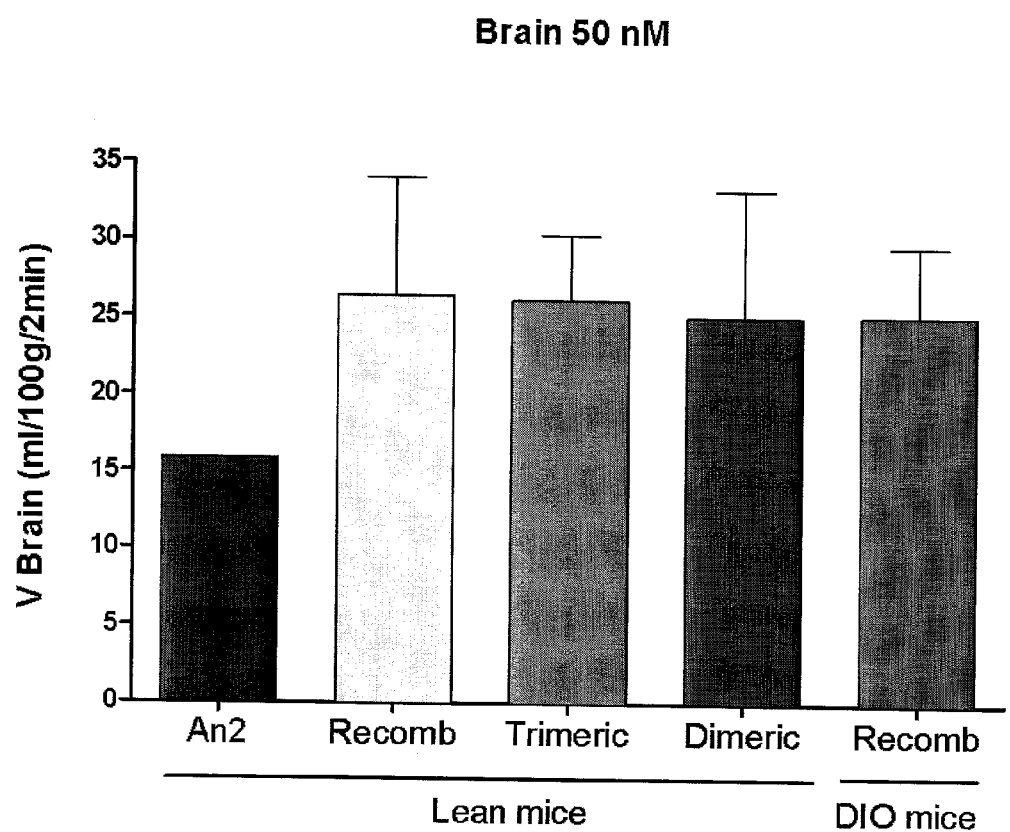
FIG. 8 is a graph showing uptake of Angiopep-2 monomers (synthetic and recombinant) as well as Angiopep-2 dimers and trimers in lean mice at 50 nM concentration using the in situ brain perfusion assay. A comparison using recombinant Angiopep-2 in diet-induced obese (DIO) mice is also shown.

Transport of Angiopep-2 (synthetic) as well as Angiopep-2 (recombinant) was compared to transport of Angiopep-2 dimers and Angiopep-2 trimers (e.g., prepared as described above) at 50 nM. Transport of recombinant Angiopep-2 into diet-induced obese mice (DIO) was also tested (FIG. 8). Transport of the dimers and trimers into brain was observed.

EXAMPLE 5

Generation of an Exendin-4-Angioep-2 Dimer Conjugate

Figure 9A:
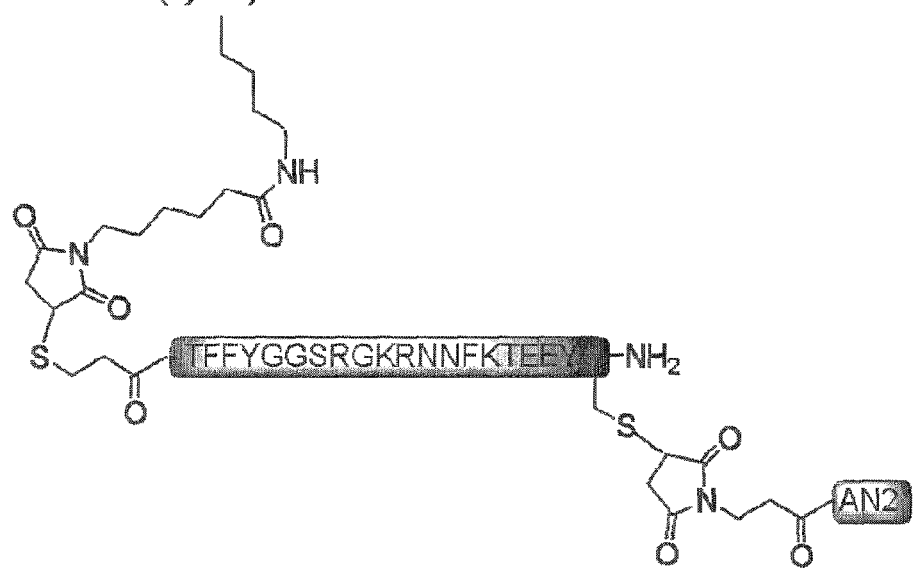
FIG. 9A is a schematic diagram showing the structure of an Exendin-4-Angiopep-2 dimmer conjugate (Ex4(Lys39 (MHA))-AN2-AN2). The compound has the structure HGEGTFTSDLSKQMEEEAVR-LFIEWLKNGGPSSGAPPPK (SEQ ID NO: 134)-(MHA)-TFFYGGSRGKRNNFKTEEYC-(MPA)-TFFYGGSRGKRNNFKTEEY (SEQ ID NO: 178)-OH, where MHA is maleimido hexanoic acid and MPA is maleimido propionic acid.
Figure 9B:
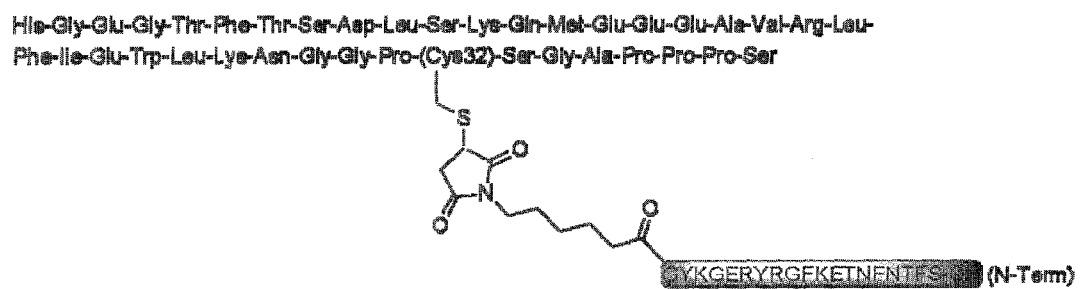
FIG. 9B is a schematic structure of an Exendin-4-scramble-Angiopep-2 (Ex4(Cys32)-ANS4 (N-Term) or Exen-S4) that was used a control. This compound has the structure HGEGTFTSDLSKQMEEEAVR-LFIEWLKNGGPCSGAPPPS-(MHA)-GYKGERYRG-FKETNFNTES-OH (SEQ ID NO: 123), where MHA is maleimido hexanoic acid.

Using the conjugation chemistry described herein or similar chemistry, an Exendin-4-Angiopep-2 dimer was generated having the structure shown in FIG. 9A. Briefly, the amine group in the C-terminal lysine of [Lys$^{39}$]Exendin-4 was conjugated to an Angiopep-2 dimer through an MHA linker at the N-terminal threonine of the first Angiopep-2 peptide. A N-succinimidyl-5-acetylthiopropionate (SATP) linker was attached to an Angiopep-2-Cys peptide at its N-terminus. Through this cysteine, the Angiopep-2-Cys peptide was conjugated to a second Angiopep-2 peptide, which had been modified to contain an MPA linker. The dimer was then linked to the [Lys$^{39}$]Exendin-4 through an MHA linker. A control molecule (Exen-S4) was also generated using a scrambed form of Angiopep-2 conjugated at its N-terminal to the cysteine of [Cys³²]Exendin-4 through an MHA linker (FIG. 9B). These conjugates were prepared as trifluoroacetate (TFA) salts.

EXAMPLE 6

Characterization of an Exendin-4-Angiopep-2 Dimer Conjugate

Brain uptake of the exemplary GLP-1 agonist, exendin-4, was measured in situ when unconjugated, conjugated to a single Angiopep-2 using variable linker lengths, conjugated to a scrambled Angiopep-2 (S4), or conjugated to a dimeric form of Angiopep-2. The experiments were performed as described in Example 2 above.

Figure 10:
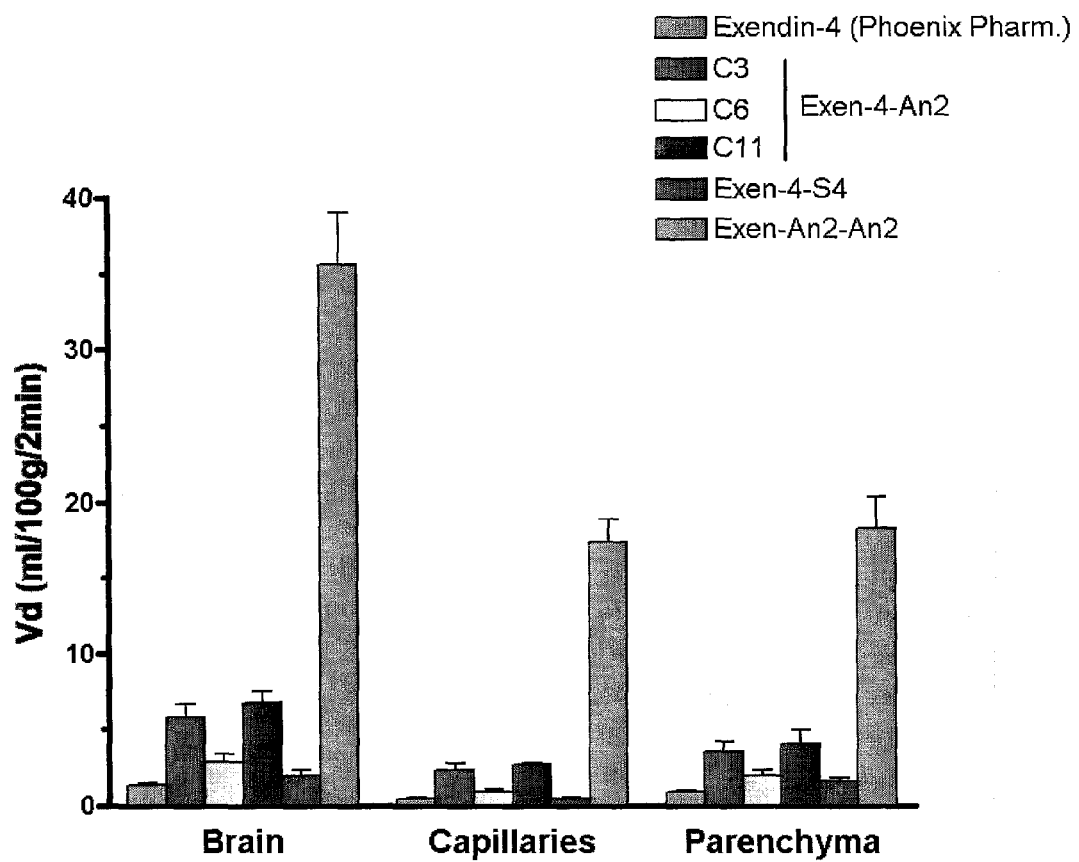
FIG. 10 is a graph showing the ability of, in order from left to right, Exendin-4, Exendin-4-Angiopep-2 conjugates C3, C6, and C11 (where the number indicates the length of the carbon chain connecting the Angiopep-2 and Exendin-4, as described in U.S. Provisional Application No. 61/105,618, filed Oct. 15, 2008), Exen-S4, and Exendin-4 when conjugated to a dimeric form of Angiopep-2, to cross the BBB.

From these results, we observed that conjugation of the exendin-4 analog to the dimeric form of Angiopep-2 results in a conjugate with a surprisingly greater ability to cross the BBB as compared to either the unconjugated exendin-4 or to the exendin-4 conjugated to a single Angiopep-2 (FIG. 10).

Figure 11:
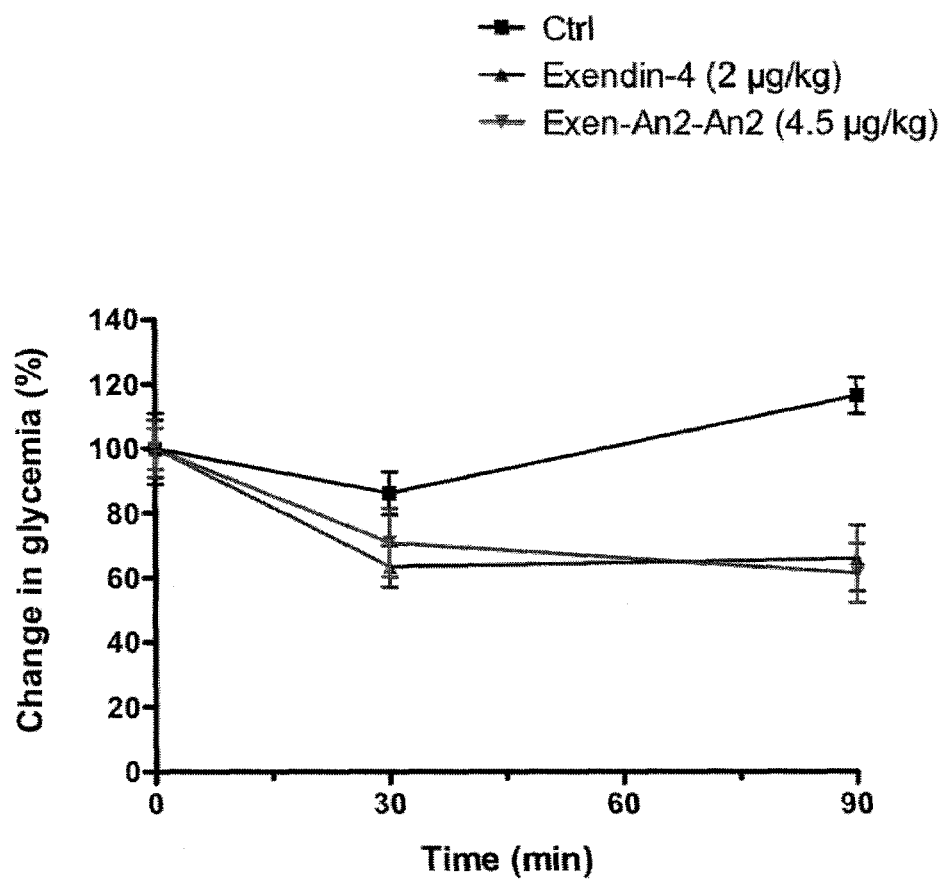
FIG. 11 is a graph showing the ability of Exendin-4 and Exen-An2-An2 to reduce glycemia in mice as compared to a control.

We also tested the ability of the exendin-4-Angiopep-2 dimer conjugate to reduce glycemia in DIO mice. Mice were injected with a bolus containing a control, exendin-4, or the exendin-4-Angiopep-2 dimer conjugate. Mice receiving either exendin-4 or the conjugate exhibited reduced glycemia as compared to mice receiving the control (FIG. 11).

Other Embodiments

All patents, patent applications including U.S. Provisional Application Nos. 61/222,785, filed Jul. 2, 2009, and 61/252,024, filed Oct. 15, 2009, and publications mentioned in this specification are herein incorporated by reference to the same extent as if each independent patent, patent application, or publication was specifically and individually indicated to be incorporated by reference.

What is claimed is:

1. A compound having a structure comprising the formula:

wherein $A^1$ is a peptide vector comprising the amino acid sequence of SEQ ID NO:114; $A^2$ is a peptide vector comprising the amino acid sequence of SEQ ID NO:97; and $X^1$ is a linker comprising a carbon-sulfur bond formed by reaction of a maleimido group of the linker and the sulfhydryl group of the Cys at position 20 of SEQ ID NO:114 of $A^1$.

2. The compound of claim 1, having a structure comprising the formula:

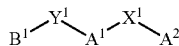

wherein $B^1$ is an agent; and $Y^1$ is a linker joining $A^1$ to $B^1$.

3. The compound of claim 1, wherein $X^1$ is a maleimido propionic acid linker.

4. The compound of claim 2, wherein $Y^1$ is a maleimido hexanoic acid linker.

5. The compound of claim 4, wherein said compound has the structure:

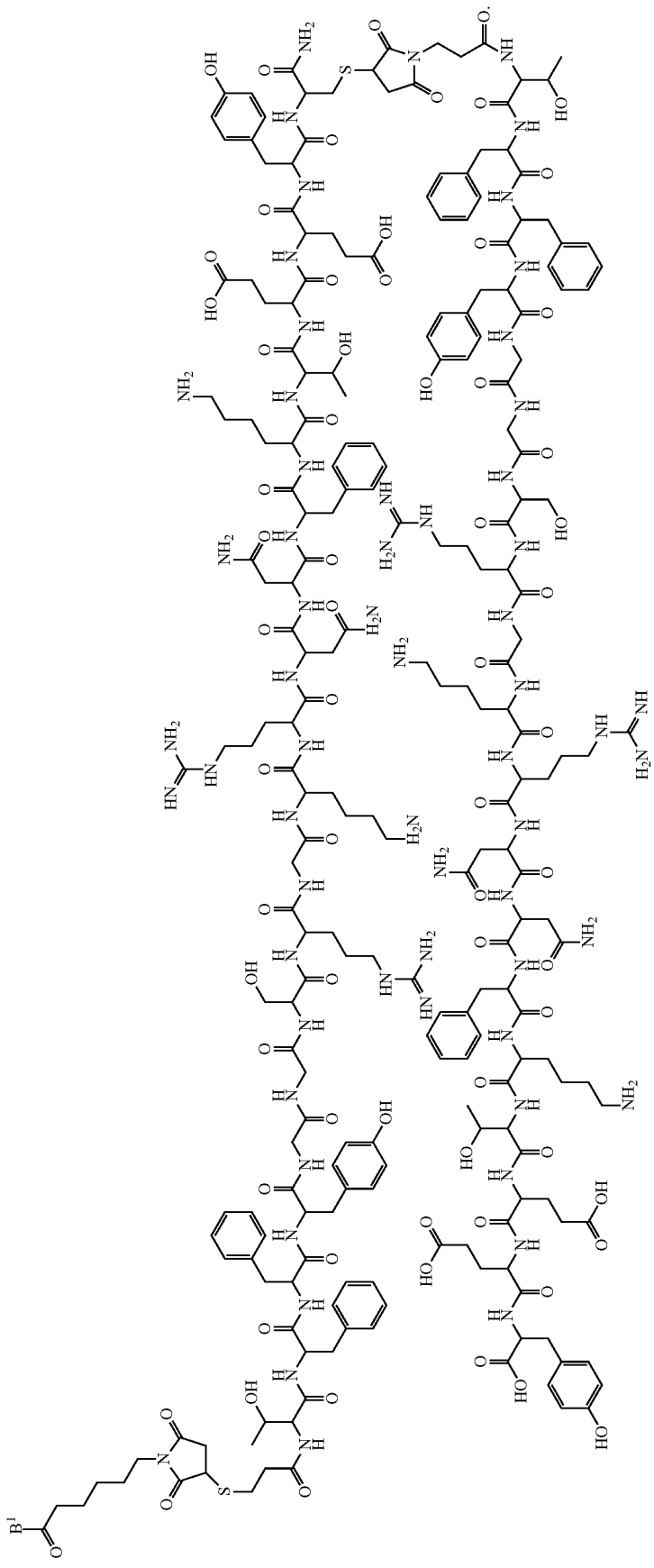

6. The compound of claim 2, wherein said agent is a therapeutic agent.

7. The compound of claim 6, wherein said therapeutic agent is selected from the group consisting of an anticancer agent, a therapeutic nucleic acid, a GLP-1 agonist, leptin, neurotensin, glial-derived neurotrophic factor (GDNF), brain-derived neurotrophic factor (BDNF), and an antibody.

8. The compound of claim 7, wherein said anticancer agent is selected from the group consisting of paclitaxel, vinblastine, vincristine, etoposide, doxorubicin, cyclophosphamide, docetaxel, melphalan, chlorambucil, abarelix, aldesleukin, alemtuzumab, alitretinoin, allopurinol, altretamine, amifostine, anakinra, anastrozole, arsenic trioxide, asparaginase, azacitidine, BCG Live, bevacuzimab, bexarotene, bleomycin, bortezombi, bortezomib, busulfan, calusterone, capecitabine, carboplatin, carmustine, celecoxib, cetuximab, cisplatin, cladribine, clofarabine, cytarabine, dacarbazine, dactinomycin, actinomycin D, dalteparin, darbepoetin alfa, dasatinib, daunorubicin, daunomycin, decitabine, denileukin, denileukin diftitox, dexrazoxane, dromostanolone propionate, eculizumab, epirubicin, epoetin alfa, erlotinib, estramustine, exemestane, fentany, filgrastim, floxuridine, fludarabine, fluorouracil, fulvestrant, gefitinib, gemcitabine, gemtuzumab ozogamicin, goserelin, histrelin, hydroxyurea, ibritumomab tiuxetan, idarubicin, ifosfamide, imatinib, Interferon alfa-2b, irinotecan, lapatinib ditosylate, lenalidomide, letrozole, leucovorin, leuprolide, levamisole, Iomustine, meclorethamine, megestrol, mercaptopurine, mesna, methotrexate, methoxsalen, mitomycin C, mitotane, mitoxantrone, nandrolone phenpropionate, nelarabine, nofetumomab, oprelvekin, oxaliplatin, palifermin, pamidronate, panitumumab, pegademase, pegaspargase, pegfilgrastim, peginterferon alfa-2b, pemetrexed, pentostatin, pipobroman, plicamycin, porfimer, procarbazine, quinacrine, rasburicase, rituximab, sargramostim, sorafenib, streptozocin, sunitinib, talc, tamoxifen, temozolomide, teniposide, testolactone, thalidomide, thioguanine, thiotepa, topotecan, toremifene, Tositumomab/I-131, trastuzumab, tretinoin, uracil mustard, valrubicin, vinorelbine, vorinostat, zoledronate, zoledronic acid and a pharmaceutically acceptable salt thereof.

9. The compound of claim 7, wherein said therapeutic nucleic acid is an RNAi agent capable of silencing EGFR or VEGF expression.

10. The compound of claim 7, where said therapeutic agent is a GLP-1 agonist, exendin-4 or a fragment thereof having GLP-1 agonist activity, [Lys$^{39}$]exendin-4, or [Cys$^{32}$] exendin-4.

11. The compound of claim 7, wherein said therapeutic agent is leptin, full-length human leptin, mature human leptin, or leptin$_{116-130}$.

12. The compound of claim 7, wherein said therapeutic agent is neurotensin, human neurotensin, human neurotensin (8-13), or pELYENKPRRPYIL-OH, where pE represents L-pyroglutamic acid.

13. The compound of claim 7, wherein said therapeutic agent is GDNF BDNF, a full length GDNF, a full length BDNF, a mature form of GDNF, a mature form of BDNF, or human GDNF$^{78-211}$.

14. The compound of claim 7, wherein said antibody is a monoclonal antibody, a monoclonal antibody that specifically binds to the amyloid-β protein or to a fragment thereof, or is selected from the group consisting of bapineuzumab and solanezumab.

* * * * *

```
                        SEQUENCE LISTING

<160> NUMBER OF SEQ ID NOS: 203

<210> SEQ ID NO 1
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Thr Phe Val Tyr Gly Gly Cys Arg Ala Lys Arg Asn Asn Phe Lys Ser
1               5                   10                  15

Ala Glu Asp

<210> SEQ ID NO 2
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Thr Phe Gln Tyr Gly Gly Cys Met Gly Asn Gly Asn Asn Phe Val Thr
1               5                   10                  15

Glu Lys Glu

<210> SEQ ID NO 3
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Pro Phe Phe Tyr Gly Gly Cys Gly Gly Asn Arg Asn Asn Phe Asp Thr
1               5                   10                  15

Glu Glu Tyr

<210> SEQ ID NO 4
<211> LENGTH: 19
<212> TYPE: PRT
<213> ORGANISM: Artificial Sequence
<220> FEATURE:
```

```
<223> OTHER INFORMATION: Description of Artificial Sequence: Synthetic
      peptide

<400> SEQUENCE: 4

Ser Phe Tyr Tyr Gly Gly Cys Leu Gly Asn Lys Asn Asn Tyr Leu Arg
1               5                   10                  15

Glu Glu Glu

<210> SEQ ID NO 5
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Thr Phe Phe Tyr Gly Gly Cys Arg Ala Lys Arg Asn Asn Phe Lys Arg
1               5                   10                  15

Ala Lys Tyr

<210> SEQ ID NO 6
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Thr Phe Phe Tyr Gly Gly Cys Arg Gly Lys Arg Asn Asn Phe Lys Arg
1               5                   10                  15

Ala Lys Tyr

<210> SEQ ID NO 7
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Thr Phe Phe Tyr Gly Gly Cys Arg Ala Lys Lys Asn Asn Tyr Lys Arg
1               5                   10                  15

Ala Lys Tyr

<210> SEQ ID NO 8
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Thr Phe Phe Tyr Gly Gly Cys Arg Gly Lys Lys Asn Asn Phe Lys Arg
1               5                   10                  15

Ala Lys Tyr

<210> SEQ ID NO 9
<211> LENGTH: 19
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 9

Thr Phe Gln Tyr Gly Gly Cys Arg Ala Lys Arg Asn Asn Phe Lys Arg
1               5                   10                  15

Ala Lys Tyr

<210> SEQ ID NO 10
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Thr Phe Gln Tyr Gly Gly Cys Arg Gly Lys Lys Asn Asn Phe Lys Arg
1               5                   10                  15

Ala Lys Tyr

<210> SEQ ID NO 11
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Thr Phe Phe Tyr Gly Gly Cys Leu Gly Lys Arg Asn Asn Phe Lys Arg
1               5                   10                  15

Ala Lys Tyr

<210> SEQ ID NO 12
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Thr Phe Phe Tyr Gly Gly Ser Leu Gly Lys Arg Asn Asn Phe Lys Arg
1               5                   10                  15

Ala Lys Tyr

<210> SEQ ID NO 13
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Pro Phe Phe Tyr Gly Gly Cys Gly Gly Lys Lys Asn Asn Phe Lys Arg
1               5                   10                  15

Ala Lys Tyr

<210> SEQ ID NO 14
<211> LENGTH: 19
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 14

Thr Phe Phe Tyr Gly Gly Cys Arg Gly Lys Gly Asn Asn Tyr Lys Arg
1               5                   10                  15

Ala Lys Tyr

<210> SEQ ID NO 15
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Pro Phe Phe Tyr Gly Gly Cys Arg Gly Lys Arg Asn Asn Phe Leu Arg
1               5                   10                  15

Ala Lys Tyr

<210> SEQ ID NO 16
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Thr Phe Phe Tyr Gly Gly Cys Arg Gly Lys Arg Asn Asn Phe Lys Arg
1               5                   10                  15

Glu Lys Tyr

<210> SEQ ID NO 17
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Pro Phe Phe Tyr Gly Gly Cys Arg Ala Lys Lys Asn Asn Phe Lys Arg
1               5                   10                  15

Ala Lys Glu

<210> SEQ ID NO 18
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Thr Phe Phe Tyr Gly Gly Cys Arg Gly Lys Arg Asn Asn Phe Lys Arg
1               5                   10                  15

Ala Lys Asp

<210> SEQ ID NO 19
<211> LENGTH: 19
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Thr Phe Phe Tyr Gly Gly Cys Arg Ala Lys Arg Asn Asn Phe Asp Arg
1               5                   10                  15

Ala Lys Tyr

<210> SEQ ID NO 20
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Thr Phe Phe Tyr Gly Gly Cys Arg Gly Lys Lys Asn Asn Phe Lys Arg
1               5                   10                  15

Ala Glu Tyr

<210> SEQ ID NO 21
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Pro Phe Phe Tyr Gly Gly Cys Gly Ala Asn Arg Asn Asn Phe Lys Arg
1               5                   10                  15

Ala Lys Tyr

<210> SEQ ID NO 22
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Thr Phe Phe Tyr Gly Gly Cys Gly Gly Lys Lys Asn Asn Phe Lys Thr
1               5                   10                  15

Ala Lys Tyr

<210> SEQ ID NO 23
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

Thr Phe Phe Tyr Gly Gly Cys Arg Gly Asn Arg Asn Asn Phe Leu Arg
1               5                   10                  15

Ala Lys Tyr

<210> SEQ ID NO 24
```

```
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

Thr Phe Phe Tyr Gly Gly Cys Arg Gly Asn Arg Asn Phe Lys Thr
1               5                   10                  15

Ala Lys Tyr

<210> SEQ ID NO 25
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

Thr Phe Phe Tyr Gly Gly Ser Arg Gly Asn Arg Asn Phe Lys Thr
1               5                   10                  15

Ala Lys Tyr

<210> SEQ ID NO 26
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26

Thr Phe Phe Tyr Gly Gly Cys Leu Gly Asn Gly Asn Asn Phe Lys Arg
1               5                   10                  15

Ala Lys Tyr

<210> SEQ ID NO 27
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 27

Thr Phe Phe Tyr Gly Gly Cys Leu Gly Asn Arg Asn Asn Phe Leu Arg
1               5                   10                  15

Ala Lys Tyr

<210> SEQ ID NO 28
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28

Thr Phe Phe Tyr Gly Gly Cys Leu Gly Asn Arg Asn Asn Phe Lys Thr
1               5                   10                  15

Ala Lys Tyr
```

```
<210> SEQ ID NO 29
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

Thr Phe Phe Tyr Gly Gly Cys Arg Gly Asn Gly Asn Asn Phe Lys Ser
1               5                   10                  15

Ala Lys Tyr

<210> SEQ ID NO 30
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 30

Thr Phe Phe Tyr Gly Gly Cys Arg Gly Lys Lys Asn Asn Phe Asp Arg
1               5                   10                  15

Glu Lys Tyr

<210> SEQ ID NO 31
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 31

Thr Phe Phe Tyr Gly Gly Cys Arg Gly Lys Arg Asn Asn Phe Leu Arg
1               5                   10                  15

Glu Lys Glu

<210> SEQ ID NO 32
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 32

Thr Phe Phe Tyr Gly Gly Cys Arg Gly Lys Gly Asn Asn Phe Asp Arg
1               5                   10                  15

Ala Lys Tyr

<210> SEQ ID NO 33
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 33

Thr Phe Phe Tyr Gly Gly Ser Arg Gly Lys Gly Asn Asn Phe Asp Arg
1               5                   10                  15

Ala Lys Tyr
```

<210> SEQ ID NO 34
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 34

Thr Phe Phe Tyr Gly Gly Cys Arg Gly Asn Gly Asn Asn Phe Val Thr
1               5                   10                  15

Ala Lys Tyr

<210> SEQ ID NO 35
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 35

Pro Phe Phe Tyr Gly Gly Cys Gly Gly Lys Gly Asn Asn Tyr Val Thr
1               5                   10                  15

Ala Lys Tyr

<210> SEQ ID NO 36
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 36

Thr Phe Phe Tyr Gly Gly Cys Leu Gly Lys Gly Asn Asn Phe Leu Thr
1               5                   10                  15

Ala Lys Tyr

<210> SEQ ID NO 37
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 37

Ser Phe Phe Tyr Gly Gly Cys Leu Gly Asn Lys Asn Asn Phe Leu Thr
1               5                   10                  15

Ala Lys Tyr

<210> SEQ ID NO 38
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 38

Thr Phe Phe Tyr Gly Gly Cys Gly Gly Asn Lys Asn Asn Phe Val Arg
1               5                   10                  15

Glu Lys Tyr

<210> SEQ ID NO 39
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 39

Thr Phe Phe Tyr Gly Gly Cys Met Gly Asn Lys Asn Asn Phe Val Arg
1               5                   10                  15

Glu Lys Tyr

<210> SEQ ID NO 40
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 40

Thr Phe Phe Tyr Gly Gly Ser Met Gly Asn Lys Asn Asn Phe Val Arg
1               5                   10                  15

Glu Lys Tyr

<210> SEQ ID NO 41
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 41

Pro Phe Phe Tyr Gly Gly Cys Leu Gly Asn Arg Asn Asn Tyr Val Arg
1               5                   10                  15

Glu Lys Tyr

<210> SEQ ID NO 42
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 42

Thr Phe Phe Tyr Gly Gly Cys Leu Gly Asn Arg Asn Asn Phe Val Arg
1               5                   10                  15

Glu Lys Tyr

<210> SEQ ID NO 43
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 43

Thr Phe Phe Tyr Gly Gly Cys Leu Gly Asn Lys Asn Asn Tyr Val Arg
1               5                   10                  15

Glu Lys Tyr

<210> SEQ ID NO 44
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 44

Thr Phe Phe Tyr Gly Gly Cys Gly Gly Asn Gly Asn Asn Phe Leu Thr
1               5                   10                  15

Ala Lys Tyr

<210> SEQ ID NO 45
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 45

Thr Phe Phe Tyr Gly Gly Cys Arg Gly Asn Arg Asn Asn Phe Leu Thr
1               5                   10                  15

Ala Glu Tyr

<210> SEQ ID NO 46
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 46

Thr Phe Phe Tyr Gly Gly Cys Arg Gly Asn Gly Asn Asn Phe Lys Ser
1               5                   10                  15

Ala Glu Tyr

<210> SEQ ID NO 47
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 47

Pro Phe Phe Tyr Gly Gly Cys Leu Gly Asn Lys Asn Asn Phe Lys Thr
1               5                   10                  15

Ala Glu Tyr

<210> SEQ ID NO 48
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 48

Thr Phe Phe Tyr Gly Gly Cys Arg Gly Asn Arg Asn Asn Phe Lys Thr
1               5                   10                  15

Glu Glu Tyr

```
<210> SEQ ID NO 49
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 49
```

Thr Phe Phe Tyr Gly Gly Cys Arg Gly Lys Arg Asn Asn Phe Lys Thr
1               5                   10                  15

Glu Glu Asp

```
<210> SEQ ID NO 50
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 50
```

Pro Phe Phe Tyr Gly Gly Cys Gly Gly Asn Gly Asn Asn Phe Val Arg
1               5                   10                  15

Glu Lys Tyr

```
<210> SEQ ID NO 51
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 51
```

Ser Phe Phe Tyr Gly Gly Cys Met Gly Asn Gly Asn Asn Phe Val Arg
1               5                   10                  15

Glu Lys Tyr

```
<210> SEQ ID NO 52
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 52
```

Pro Phe Phe Tyr Gly Gly Cys Gly Gly Asn Gly Asn Asn Phe Leu Arg
1               5                   10                  15

Glu Lys Tyr

```
<210> SEQ ID NO 53
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 53
```

Thr Phe Phe Tyr Gly Gly Cys Leu Gly Asn Gly Asn Asn Phe Val Arg

```
1               5                   10                  15

Glu Lys Tyr

<210> SEQ ID NO 54
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 54

Ser Phe Phe Tyr Gly Gly Cys Leu Gly Asn Gly Asn Asn Tyr Leu Arg
1               5                   10                  15

Glu Lys Tyr

<210> SEQ ID NO 55
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 55

Thr Phe Phe Tyr Gly Gly Ser Leu Gly Asn Gly Asn Asn Phe Val Arg
1               5                   10                  15

Glu Lys Tyr

<210> SEQ ID NO 56
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 56

Thr Phe Phe Tyr Gly Gly Cys Arg Gly Asn Gly Asn Asn Phe Val Thr
1               5                   10                  15

Ala Glu Tyr

<210> SEQ ID NO 57
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 57

Thr Phe Phe Tyr Gly Gly Cys Leu Gly Lys Gly Asn Asn Phe Val Ser
1               5                   10                  15

Ala Glu Tyr

<210> SEQ ID NO 58
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 58
```

Thr Phe Phe Tyr Gly Gly Cys Leu Gly Asn Arg Asn Asn Phe Asp Arg
1               5                   10                  15

Ala Glu Tyr

<210> SEQ ID NO 59
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 59

Thr Phe Phe Tyr Gly Gly Cys Leu Gly Asn Arg Asn Asn Phe Leu Arg
1               5                   10                  15

Glu Glu Tyr

<210> SEQ ID NO 60
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 60

Thr Phe Phe Tyr Gly Gly Cys Leu Gly Asn Lys Asn Asn Tyr Leu Arg
1               5                   10                  15

Glu Glu Tyr

<210> SEQ ID NO 61
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 61

Pro Phe Phe Tyr Gly Gly Cys Gly Gly Asn Arg Asn Asn Tyr Leu Arg
1               5                   10                  15

Glu Glu Tyr

<210> SEQ ID NO 62
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 62

Pro Phe Phe Tyr Gly Gly Ser Gly Gly Asn Arg Asn Asn Tyr Leu Arg
1               5                   10                  15

Glu Glu Tyr

<210> SEQ ID NO 63
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 63

```
Met Arg Pro Asp Phe Cys Leu Glu Pro Pro Tyr Thr Gly Pro Cys Val
1               5                   10                  15

Ala Arg Ile
```

<210> SEQ ID NO 64
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 64

```
Ala Arg Ile Ile Arg Tyr Phe Tyr Asn Ala Lys Ala Gly Leu Cys Gln
1               5                   10                  15

Thr Phe Val Tyr Gly
            20
```

<210> SEQ ID NO 65
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 65

```
Tyr Gly Gly Cys Arg Ala Lys Arg Asn Asn Tyr Lys Ser Ala Glu Asp
1               5                   10                  15

Cys Met Arg Thr Cys Gly
            20
```

<210> SEQ ID NO 66
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 66

```
Pro Asp Phe Cys Leu Glu Pro Pro Tyr Thr Gly Pro Cys Val Ala Arg
1               5                   10                  15

Ile Ile Arg Tyr Phe Tyr
            20
```

<210> SEQ ID NO 67
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 67

```
Thr Phe Phe Tyr Gly Gly Cys Arg Gly Lys Arg Asn Asn Phe Lys Thr
1               5                   10                  15

Glu Glu Tyr
```

<210> SEQ ID NO 68
<211> LENGTH: 19
<212> TYPE: PRT
<213> ORGANISM: Artificial Sequence
<220> FEATURE:

<223> OTHER INFORMATION: Description of Artificial Sequence: Synthetic
      peptide

<400> SEQUENCE: 68

Lys Phe Phe Tyr Gly Gly Cys Arg Gly Lys Arg Asn Asn Phe Lys Thr
1               5                   10                  15

Glu Glu Tyr

<210> SEQ ID NO 69
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 69

Thr Phe Tyr Tyr Gly Gly Cys Arg Gly Lys Arg Asn Asn Tyr Lys Thr
1               5                   10                  15

Glu Glu Tyr

<210> SEQ ID NO 70
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 70

Thr Phe Phe Tyr Gly Gly Ser Arg Gly Lys Arg Asn Asn Phe Lys Thr
1               5                   10                  15

Glu Glu Tyr

<210> SEQ ID NO 71
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 71

Cys Thr Phe Phe Tyr Gly Cys Cys Arg Gly Lys Arg Asn Asn Phe Lys
1               5                   10                  15

Thr Glu Glu Tyr
            20

<210> SEQ ID NO 72
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 72

Thr Phe Phe Tyr Gly Gly Cys Arg Gly Lys Arg Asn Asn Phe Lys Thr
1               5                   10                  15

Glu Glu Tyr Cys
            20

<210> SEQ ID NO 73
<211> LENGTH: 20

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 73

Cys Thr Phe Phe Tyr Gly Ser Cys Arg Gly Lys Arg Asn Asn Phe Lys
1               5                   10                  15

Thr Glu Glu Tyr
            20

<210> SEQ ID NO 74
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 74

Thr Phe Phe Tyr Gly Gly Ser Arg Gly Lys Arg Asn Asn Phe Lys Thr
1               5                   10                  15

Glu Glu Tyr Cys
            20

<210> SEQ ID NO 75
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 75

Pro Phe Phe Tyr Gly Gly Cys Arg Gly Lys Arg Asn Asn Phe Lys Thr
1               5                   10                  15

Glu Glu Tyr

<210> SEQ ID NO 76
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 76

Thr Phe Phe Tyr Gly Gly Cys Arg Gly Lys Arg Asn Asn Phe Lys Thr
1               5                   10                  15

Lys Glu Tyr

<210> SEQ ID NO 77
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 77

Thr Phe Phe Tyr Gly Gly Lys Arg Gly Lys Arg Asn Asn Phe Lys Thr
1               5                   10                  15

Glu Glu Tyr
```

<210> SEQ ID NO 78
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 78

Thr Phe Phe Tyr Gly Gly Cys Arg Gly Lys Arg Asn Asn Phe Lys Thr
1               5                   10                  15

Lys Arg Tyr

<210> SEQ ID NO 79
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 79

Thr Phe Phe Tyr Gly Gly Lys Arg Gly Lys Arg Asn Asn Phe Lys Thr
1               5                   10                  15

Ala Glu Tyr

<210> SEQ ID NO 80
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 80

Thr Phe Phe Tyr Gly Gly Lys Arg Gly Lys Arg Asn Asn Phe Lys Thr
1               5                   10                  15

Ala Gly Tyr

<210> SEQ ID NO 81
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 81

Thr Phe Phe Tyr Gly Gly Lys Arg Gly Lys Arg Asn Asn Phe Lys Arg
1               5                   10                  15

Glu Lys Tyr

<210> SEQ ID NO 82
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 82

Thr Phe Phe Tyr Gly Gly Lys Arg Gly Lys Arg Asn Asn Phe Lys Arg
1               5                   10                  15

Ala Lys Tyr

```
<210> SEQ ID NO 83
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 83

Thr Phe Phe Tyr Gly Gly Cys Leu Gly Asn Arg Asn Asn Phe Lys Thr
1               5                   10                  15

Glu Glu Tyr

<210> SEQ ID NO 84
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 84

Thr Phe Phe Tyr Gly Cys Gly Arg Gly Lys Arg Asn Asn Phe Lys Thr
1               5                   10                  15

Glu Glu Tyr

<210> SEQ ID NO 85
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 85

Thr Phe Phe Tyr Gly Gly Arg Cys Gly Lys Arg Asn Asn Phe Lys Thr
1               5                   10                  15

Glu Glu Tyr

<210> SEQ ID NO 86
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 86

Thr Phe Phe Tyr Gly Gly Cys Leu Gly Asn Gly Asn Asn Phe Asp Thr
1               5                   10                  15

Glu Glu Glu

<210> SEQ ID NO 87
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 87

Thr Phe Gln Tyr Gly Gly Cys Arg Gly Lys Arg Asn Asn Phe Lys Thr
1               5                   10                  15
```

```
Glu Glu Tyr

<210> SEQ ID NO 88
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 88

Tyr Asn Lys Glu Phe Gly Thr Phe Asn Thr Lys Gly Cys Glu Arg Gly
1               5                   10                  15

Tyr Arg Phe

<210> SEQ ID NO 89
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 89

Arg Phe Lys Tyr Gly Gly Cys Leu Gly Asn Met Asn Asn Phe Glu Thr
1               5                   10                  15

Leu Glu Glu

<210> SEQ ID NO 90
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 90

Arg Phe Lys Tyr Gly Gly Cys Leu Gly Asn Lys Asn Asn Phe Leu Arg
1               5                   10                  15

Leu Lys Tyr

<210> SEQ ID NO 91
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 91

Arg Phe Lys Tyr Gly Gly Cys Leu Gly Asn Lys Asn Asn Tyr Leu Arg
1               5                   10                  15

Leu Lys Tyr

<210> SEQ ID NO 92
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 92

Lys Thr Lys Arg Lys Arg Lys Lys Gln Arg Val Lys Ile Ala Tyr Glu
1               5                   10                  15
```

Glu Ile Phe Lys Asn Tyr
            20

<210> SEQ ID NO 93
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 93

Lys Thr Lys Arg Lys Arg Lys Lys Gln Arg Val Lys Ile Ala Tyr
1               5                   10                  15

<210> SEQ ID NO 94
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 94

Arg Gly Gly Arg Leu Ser Tyr Ser Arg Arg Phe Ser Thr Ser Thr Gly
1               5                   10                  15

Arg

<210> SEQ ID NO 95
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 95

Arg Arg Leu Ser Tyr Ser Arg Arg Arg Phe
1               5                   10

<210> SEQ ID NO 96
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 96

Arg Gln Ile Lys Ile Trp Phe Gln Asn Arg Arg Met Lys Trp Lys Lys
1               5                   10                  15

<210> SEQ ID NO 97
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 97

Thr Phe Phe Tyr Gly Gly Ser Arg Gly Lys Arg Asn Asn Phe Lys Thr
1               5                   10                  15

Glu Glu Tyr

```
<210> SEQ ID NO 98
<211> LENGTH: 59
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 98

Met Arg Pro Asp Phe Cys Leu Glu Pro Pro Tyr Thr Gly Pro Cys Val
1               5                   10                  15

Ala Arg Ile Ile Arg Tyr Phe Tyr Asn Ala Lys Ala Gly Leu Cys Gln
            20                  25                  30

Thr Phe Val Tyr Gly Gly Cys Arg Ala Lys Arg Asn Asn Phe Lys Ser
        35                  40                  45

Ala Glu Asp Cys Met Arg Thr Cys Gly Gly Ala
    50                  55

<210> SEQ ID NO 99
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 99

Thr Phe Phe Tyr Gly Gly Cys Arg Gly Lys Arg Asn Asn Phe Lys Thr
1               5                   10                  15

Lys Glu Tyr

<210> SEQ ID NO 100
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 100

Arg Phe Lys Tyr Gly Gly Cys Leu Gly Asn Lys Asn Asn Tyr Leu Arg
1               5                   10                  15

Leu Lys Tyr

<210> SEQ ID NO 101
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 101

Thr Phe Phe Tyr Gly Gly Cys Arg Ala Lys Arg Asn Asn Phe Lys Arg
1               5                   10                  15

Ala Lys Tyr

<210> SEQ ID NO 102
<211> LENGTH: 35
<212> TYPE: PRT
<213> ORGANISM: Artificial Sequence
<220> FEATURE:
<223> OTHER INFORMATION: Description of Artificial Sequence: Synthetic
      polypeptide
```

<400> SEQUENCE: 102

Asn Ala Lys Ala Gly Leu Cys Gln Thr Phe Val Tyr Gly Gly Cys Leu
1               5                   10                  15

Ala Lys Arg Asn Asn Phe Glu Ser Ala Glu Asp Cys Met Arg Thr Cys
            20                  25                  30

Gly Gly Ala
        35

<210> SEQ ID NO 103
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 103

Tyr Gly Gly Cys Arg Ala Lys Arg Asn Asn Phe Lys Ser Ala Glu Asp
1               5                   10                  15

Cys Met Arg Thr Cys Gly Gly Ala
            20

<210> SEQ ID NO 104
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 104

Gly Leu Cys Gln Thr Phe Val Tyr Gly Gly Cys Arg Ala Lys Arg Asn
1               5                   10                  15

Asn Phe Lys Ser Ala Glu
            20

<210> SEQ ID NO 105
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 105

Leu Cys Gln Thr Phe Val Tyr Gly Gly Cys Glu Ala Lys Arg Asn Asn
1               5                   10                  15

Phe Lys Ser Ala
            20

<210> SEQ ID NO 106
<211> LENGTH: 180
<212> TYPE: DNA
<213> ORGANISM: Artificial Sequence
<220> FEATURE:
<223> OTHER INFORMATION: Description of Artificial Sequence: Synthetic
      construct

<400> SEQUENCE: 106
atgagaccag atttctgcct cgagccgccg tacactgggc cctgcaaagc tcgtatcatc      60
cgttacttct acaatgcaaa ggcaggcctg tgtcagacct tcgtatacgg cggctgcaga     120
gctaagcgta acaacttcaa atccgcggaa gactgcatgc gtacttgcgg tggtgcttag     180

```
<210> SEQ ID NO 107
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 107

Thr Phe Phe Tyr Gly Gly Ser Arg Gly Lys Arg Asn Asn Phe Lys Thr
1               5                   10                  15

Glu Glu Tyr

<210> SEQ ID NO 108
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 108

Arg Phe Phe Tyr Gly Gly Ser Arg Gly Lys Arg Asn Asn Phe Lys Thr
1               5                   10                  15

Glu Glu Tyr

<210> SEQ ID NO 109
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 109

Arg Phe Phe Tyr Gly Gly Ser Arg Gly Lys Arg Asn Asn Phe Lys Thr
1               5                   10                  15

Glu Glu Tyr

<210> SEQ ID NO 110
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 110

Arg Phe Phe Tyr Gly Gly Ser Arg Gly Lys Arg Asn Asn Phe Arg Thr
1               5                   10                  15

Glu Glu Tyr

<210> SEQ ID NO 111
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 111

Thr Phe Phe Tyr Gly Gly Ser Arg Gly Lys Arg Asn Asn Phe Arg Thr
1               5                   10                  15

Glu Glu Tyr
```

<210> SEQ ID NO 112
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 112

Thr Phe Phe Tyr Gly Gly Ser Arg Gly Arg Arg Asn Asn Phe Arg Thr
1               5                   10                  15

Glu Glu Tyr

<210> SEQ ID NO 113
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 113

Cys Thr Phe Phe Tyr Gly Gly Ser Arg Gly Lys Arg Asn Asn Phe Lys
1               5                   10                  15

Thr Glu Glu Tyr
            20

<210> SEQ ID NO 114
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 114

Thr Phe Phe Tyr Gly Gly Ser Arg Gly Lys Arg Asn Asn Phe Lys Thr
1               5                   10                  15

Glu Glu Tyr Cys
            20

<210> SEQ ID NO 115
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 115

Cys Thr Phe Phe Tyr Gly Gly Ser Arg Gly Arg Arg Asn Asn Phe Arg
1               5                   10                  15

Thr Glu Glu Tyr
            20

<210> SEQ ID NO 116
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 116

```
Thr Phe Phe Tyr Gly Gly Ser Arg Gly Arg Arg Asn Asn Phe Arg Thr
1               5                   10                  15

Glu Glu Tyr Cys
            20

<210> SEQ ID NO 117
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 117

Tyr Glu Glu Thr Lys Phe Asn Asn Arg Lys Gly Arg Ser Gly Gly Tyr
1               5                   10                  15

Phe Phe Thr

<210> SEQ ID NO 118
<211> LENGTH: 19
<212> TYPE: RNA
<213> ORGANISM: Artificial Sequence
<220> FEATURE:
<223> OTHER INFORMATION: Description of Artificial Sequence: Synthetic
      construct

<400> SEQUENCE: 118
ggagcugccc augagaaau                                               19

<210> SEQ ID NO 119
<211> LENGTH: 19
<212> TYPE: RNA
<213> ORGANISM: Artificial Sequence
<220> FEATURE:
<223> OTHER INFORMATION: Description of Artificial Sequence: Synthetic
      construct

<400> SEQUENCE: 119
auuucucaug ggcagcucc                                               19

<210> SEQ ID NO 120
<211> LENGTH: 19
<212> TYPE: DNA
<213> ORGANISM: Artificial Sequence
<220> FEATURE:
<223> OTHER INFORMATION: Description of Artificial Sequence: Synthetic
      construct
<220> FEATURE:
<221> NAME/KEY: misc_feature
<222> LOCATION: (1)..(19)
<223> OTHER INFORMATION: synthetic construct for RNAi

<400> SEQUENCE: 120
ggagtaccct gatgagatc                                               19

<210> SEQ ID NO 121
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: L-pyroglutamic acid
<220> FEATURE:
<221> NAME/KEY: MOD_RES
```

```
<222> LOCATION: (13)..(13)
<223> OTHER INFORMATION: C-terminus hydroxylation

<400> SEQUENCE: 121

Xaa Leu Tyr Glu Asn Lys Pro Arg Arg Pro Tyr Ile Leu
1               5                   10

<210> SEQ ID NO 122
<211> LENGTH: 78
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MISC_FEATURE
<222> LOCATION: (39)..(40)
<223> OTHER INFORMATION: The linkage between Lys at position 39 and Thr
      at position 40 is maleimido hexanoic acid (MHA)
<220> FEATURE:
<221> NAME/KEY: MISC_FEATURE
<222> LOCATION: (59)..(60)
<223> OTHER INFORMATION: The linkage between Cys at position 59 and Thr
      at position 60 is maleimido propionic acid (MHA)
<220> FEATURE:
<221> NAME/KEY: MOD_RES
<222> LOCATION: (78)..(78)
<223> OTHER INFORMATION: C-terminus hydroxylation

<400> SEQUENCE: 122

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
                20                  25                  30

Ser Gly Ala Pro Pro Pro Lys Thr Phe Phe Tyr Gly Gly Ser Arg Gly
            35                  40                  45

Lys Arg Asn Asn Phe Lys Thr Glu Glu Tyr Cys Thr Phe Phe Tyr Gly
    50                  55                  60

Gly Ser Arg Gly Lys Arg Asn Asn Phe Lys Thr Glu Glu Tyr
65                  70                  75

<210> SEQ ID NO 123
<211> LENGTH: 58
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MISC_FEATURE
<222> LOCATION: (39)..(40)
<223> OTHER INFORMATION: The linkage between Ser at position 39 and Gly
      at position 40 is maleimido hexanoic acid (MHA)
<220> FEATURE:
<221> NAME/KEY: MOD_RES
<222> LOCATION: (58)..(58)
<223> OTHER INFORMATION: C-terminus hydroxylation

<400> SEQUENCE: 123

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Cys
                20                  25                  30

Ser Gly Ala Pro Pro Pro Ser Gly Tyr Lys Gly Glu Arg Tyr Arg Gly
            35                  40                  45

Phe Lys Glu Thr Asn Phe Asn Thr Phe Ser
    50                  55
```

```
<210> SEQ ID NO 124
<211> LENGTH: 30
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MISC_FEATURE
<222> LOCATION: (1)..(5)
<223> OTHER INFORMATION: This sequence may encompass 1-6 'Gly-Gly-Gly-
      Gly-Ser' repeating units

<400> SEQUENCE: 124

Gly Gly Gly Gly Ser Gly Gly Gly Ser Gly Gly Gly Gly Ser Gly
1               5                   10                  15

Gly Gly Gly Ser Gly Gly Gly Ser Gly Gly Gly Gly Ser
            20                  25                  30

<210> SEQ ID NO 125
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MISC_FEATURE
<222> LOCATION: (1)..(5)
<223> OTHER INFORMATION: This sequence may encompass 1-5 'Xaa-Xaa-Xaa-
      Xaa-Gly' repeating units.  See specification as filed for detailed
      description of substitutions and preferred embodiments
<220> FEATURE:
<221> NAME/KEY: MOD_RES
<222> LOCATION: (1)..(4)
<223> OTHER INFORMATION: Thr or Ser
<220> FEATURE:
<221> NAME/KEY: MOD_RES
<222> LOCATION: (6)..(9)
<223> OTHER INFORMATION: Thr or Ser
<220> FEATURE:
<221> NAME/KEY: MOD_RES
<222> LOCATION: (11)..(14)
<223> OTHER INFORMATION: Thr or Ser
<220> FEATURE:
<221> NAME/KEY: MOD_RES
<222> LOCATION: (16)..(19)
<223> OTHER INFORMATION: Thr or Ser
<220> FEATURE:
<221> NAME/KEY: MOD_RES
<222> LOCATION: (21)..(24)
<223> OTHER INFORMATION: Thr or Ser

<400> SEQUENCE: 125

Xaa Xaa Xaa Xaa Gly Xaa Xaa Xaa Xaa Gly Xaa Xaa Xaa Xaa Gly Xaa
1               5                   10                  15

Xaa Xaa Xaa Gly Xaa Xaa Xaa Xaa Gly
            20                  25

<210> SEQ ID NO 126
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MISC_FEATURE
<222> LOCATION: (1)..(5)
<223> OTHER INFORMATION: This sequence may encompass more than one 'Ser-
      Ser-Ser-Ser-Gly' repeating units
```

```
<400> SEQUENCE: 126

Ser Ser Ser Ser Gly
1               5

<210> SEQ ID NO 127
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 127

Pro Ala Pro Ala Pro
1               5

<210> SEQ ID NO 128
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MISC_FEATURE
<222> LOCATION: (1)..(2)
<223> OTHER INFORMATION: This sequence may encompass 1-7 'Pro-Thr'
      repeating units

<400> SEQUENCE: 128

Pro Thr Pro Thr Pro Thr Pro Thr Pro Thr Pro Thr Pro Thr Pro
1               5                   10                  15

<210> SEQ ID NO 129
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MISC_FEATURE
<222> LOCATION: (2)..(6)
<223> OTHER INFORMATION: This sequence may encompass 1-5 'Glu-Ala-Ala-
      Ala-Lys' repeating units

<400> SEQUENCE: 129

Ala Glu Ala Ala Ala Lys Glu Ala Ala Ala Lys Glu Ala Ala Ala Lys
1               5                   10                  15

Glu Ala Ala Ala Lys Glu Ala Ala Ala Lys Ala
            20                  25

<210> SEQ ID NO 130
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 130

Ala Leu Ala Leu
1

<210> SEQ ID NO 131
<211> LENGTH: 4
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 131

Gly Phe Leu Gly
1

<210> SEQ ID NO 132
<211> LENGTH: 39
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (39)..(39)
<223> OTHER INFORMATION: AMIDATION

<400> SEQUENCE: 132

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Ser
        35

<210> SEQ ID NO 133
<211> LENGTH: 39
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 133

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Cys
            20                  25                  30

Ser Gly Ala Pro Pro Pro Ser
        35

<210> SEQ ID NO 134
<211> LENGTH: 39
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 134

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Lys
        35

<210> SEQ ID NO 135
<211> LENGTH: 39
<212> TYPE: PRT
<213> ORGANISM: Artificial Sequence
```

```
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: His, Arg or Tyr
<220> FEATURE:
<221> NAME/KEY: MOD_RES
<222> LOCATION: (2)..(2)
<223> OTHER INFORMATION: Ser, Gly, Ala or Thr
<220> FEATURE:
<221> NAME/KEY: MOD_RES
<222> LOCATION: (3)..(3)
<223> OTHER INFORMATION: Asp or Glu
<220> FEATURE:
<221> NAME/KEY: MOD_RES
<222> LOCATION: (6)..(6)
<223> OTHER INFORMATION: Phe, Tyr or naphthylalanine (Nal)
<220> FEATURE:
<221> NAME/KEY: MOD_RES
<222> LOCATION: (7)..(7)
<223> OTHER INFORMATION: Thr or Ser
<220> FEATURE:
<221> NAME/KEY: MOD_RES
<222> LOCATION: (8)..(8)
<223> OTHER INFORMATION: Ser or Thr
<220> FEATURE:
<221> NAME/KEY: MOD_RES
<222> LOCATION: (9)..(9)
<223> OTHER INFORMATION: Asp or Glu
<220> FEATURE:
<221> NAME/KEY: MOD_RES
<222> LOCATION: (10)..(10)
<223> OTHER INFORMATION: Leu, Ile, Val, pentylglycine (pGly) or Met
<220> FEATURE:
<221> NAME/KEY: MOD_RES
<222> LOCATION: (14)..(14)
<223> OTHER INFORMATION: Leu, Ile, pentylglycine (pGly), Val or Met
<220> FEATURE:
<221> NAME/KEY: MOD_RES
<222> LOCATION: (22)..(22)
<223> OTHER INFORMATION: Phe, Tyr, or naphthylalanine (Nal)
<220> FEATURE:
<221> NAME/KEY: MOD_RES
<222> LOCATION: (23)..(23)
<223> OTHER INFORMATION: Ile, Val, Leu, pentylglycine (pGly), t-
      butylglycine (t-BuG) or Met
<220> FEATURE:
<221> NAME/KEY: MOD_RES
<222> LOCATION: (24)..(24)
<223> OTHER INFORMATION: Glu or Asp
<220> FEATURE:
<221> NAME/KEY: MOD_RES
<222> LOCATION: (25)..(25)
<223> OTHER INFORMATION: Trp, Phe, Tyr, or naphthylalanine (Nal)
<220> FEATURE:
<221> NAME/KEY: MOD_RES
<222> LOCATION: (31)..(31)
<223> OTHER INFORMATION: Pro, homoproline (HPro), 3Hyp, 4Hyp,
      thioproline (TPro), N-alkylglycine, N-alkyl-pentylglycine (N-
      alkyl-pGly) or N-alkylalanine
<220> FEATURE:
<221> NAME/KEY: MOD_RES
<222> LOCATION: (36)..(36)
<223> OTHER INFORMATION: Pro, homoproline (HPro), 3Hyp, 4Hyp,
      thioproline (TPro), N-alkylglycine, N-alkyl-pentylglycine
      (N-alkyl-pGly) or N-alkylalanine
<220> FEATURE:
<221> NAME/KEY: MOD_RES
<222> LOCATION: (37)..(37)
<223> OTHER INFORMATION: Pro, homoproline (HPro), 3Hyp, 4Hyp,
      thioproline (TPro), N-alkylglycine, N-alkyl-pentylglycine
      (N-alkyl-pGly) or N-alkylalanine
<220> FEATURE:
<221> NAME/KEY: MOD_RES
<222> LOCATION: (38)..(38)
<223> OTHER INFORMATION: Pro, homoproline (HPro), 3Hyp, 4Hyp,
      thioproline (TPro), N-alkylglycine, N-alkyl-pentylglycine
```

```
                (N-alkyl-pGly) or N-alkylalanine
<220> FEATURE:
<221> NAME/KEY: MOD_RES
<222> LOCATION: (39)..(39)
<223> OTHER INFORMATION: Ser, Thr, or Tyr
<220> FEATURE:
<221> NAME/KEY: MOD_RES
<222> LOCATION: (39)..(39)
<223> OTHER INFORMATION: C-terminus hydroxylation or amidation

<400> SEQUENCE: 135

Xaa Xaa Xaa Gly Thr Xaa Xaa Xaa Xaa Xaa Ser Lys Gln Xaa Glu Glu
1               5                   10                  15

Glu Ala Val Arg Leu Xaa Xaa Xaa Xaa Leu Lys Asn Gly Gly Xaa Ser
            20                  25                  30

Ser Gly Ala Xaa Xaa Xaa Xaa
        35

<210> SEQ ID NO 136
<211> LENGTH: 40
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (14)..(14)
<223> OTHER INFORMATION: Arg, Leu, Ile, or Met
<220> FEATURE:
<221> NAME/KEY: MOD_RES
<222> LOCATION: (20)..(20)
<223> OTHER INFORMATION: His, Arg, or Lys
<220> FEATURE:
<221> NAME/KEY: MOD_RES
<222> LOCATION: (40)..(40)
<223> OTHER INFORMATION: Arg, Lys, or absent
<220> FEATURE:
<221> NAME/KEY: MOD_RES
<222> LOCATION: (40)..(40)
<223> OTHER INFORMATION: C-terminus hydroxylation or amidation, where
      -NH2 is present when Arg or Lys is absent

<400> SEQUENCE: 136

His Gly Glu Gly Thr Phe Thr Ser Asp Leu Ser Lys Gln Xaa Glu Glu
1               5                   10                  15

Glu Ala Val Xaa Leu Phe Ile Glu Trp Leu Lys Asn Gly Gly Pro Ser
            20                  25                  30

Ser Gly Ala Pro Pro Pro Ser Xaa
        35                  40

<210> SEQ ID NO 137
<211> LENGTH: 32
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: Phe or Tyr
<220> FEATURE:
<221> NAME/KEY: MOD_RES
<222> LOCATION: (14)..(14)
<223> OTHER INFORMATION: Met, Ile or Leu
<220> FEATURE:
<221> NAME/KEY: MOD_RES
<222> LOCATION: (20)..(20)
<223> OTHER INFORMATION: Lys
<220> FEATURE:
```

```
<221> NAME/KEY: MOD_RES
<222> LOCATION: (30)..(30)
<223> OTHER INFORMATION: Gly or absent
<220> FEATURE:
<221> NAME/KEY: MOD_RES
<222> LOCATION: (32)..(32)
<223> OTHER INFORMATION: Arg or absent

<400> SEQUENCE: 137

His Gly Glu Gly Thr Xaa Thr Ser Asp Leu Ser Lys Gln Xaa Glu Glu
1               5                   10                  15

Glu Ala Val Xaa Leu Phe Ile Glu Trp Leu Lys Asn Gly Xaa Pro Xaa
                20                  25                  30

<210> SEQ ID NO 138
<211> LENGTH: 31
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (29)..(29)
<223> OTHER INFORMATION: Gly or absent, depending on indicated chain
      length
<220> FEATURE:
<221> NAME/KEY: MOD_RES
<222> LOCATION: (30)..(30)
<223> OTHER INFORMATION: Arg or absent, depending on indicated chain
      length
<220> FEATURE:
<221> NAME/KEY: MOD_RES
<222> LOCATION: (31)..(31)
<223> OTHER INFORMATION: Gly or absent, depending on indicated chain
      length

<400> SEQUENCE: 138

His Ala Glu Gly Thr Phe Thr Ser Asp Val Ser Ser Tyr Leu Glu Gly
1               5                   10                  15

Asn Ala Ala Lys Glu Phe Ile Ala Trp Leu Val Lys Xaa Xaa Xaa
                20                  25                  30

<210> SEQ ID NO 139
<211> LENGTH: 30
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(11)
<223> OTHER INFORMATION: Amino acids from positions 1 to 10
      (Ala-Glu-Gly-Thr-Phe-Thr-Ser-Asp-Val-Ser) may be absent, and Ser
      at position 11 may be amidated
<220> FEATURE:
<221> NAME/KEY: MOD_RES
<222> LOCATION: (1)..(10)
<223> OTHER INFORMATION: Amino acids from positions 1 to 9
      (Ala-Glu-Gly-Thr-Phe-Thr-Ser-Asp-Val) may be absent, and Ser at
      position 10 may be amidated
<220> FEATURE:
<221> NAME/KEY: MOD_RES
<222> LOCATION: (1)..(9)
<223> OTHER INFORMATION: Amino acids from positions 1 to 8
      (Ala-Glu-Gly-Thr-Phe-Thr-Ser-Asp) may be absent, and Val at
      position 9 may be amidated
<220> FEATURE:
<221> NAME/KEY: MOD_RES
<222> LOCATION: (1)..(8)
<223> OTHER INFORMATION: Amino acids from positions 1 to 7 (Ala-Glu-Gly-
      Thr-Phe-Thr-Ser) may be absent, and Asp at position 8 may be
```

```
        amidated
<220> FEATURE:
<221> NAME/KEY: MOD_RES
<222> LOCATION: (1)..(7)
<223> OTHER INFORMATION: Amino acids from positions 1 to 6 (Ala-Glu-Gly-
      Thr-Phe-Thr) may be absent, and Ser at position 7 may be amidated
<220> FEATURE:
<221> NAME/KEY: MOD_RES
<222> LOCATION: (1)..(6)
<223> OTHER INFORMATION: Amino acids from positions 1 to 5 (Ala-Glu-Gly-
      Thr-Phe) may be absent, and Thr at position 6 may be amidated
<220> FEATURE:
<221> NAME/KEY: MOD_RES
<222> LOCATION: (1)..(5)
<223> OTHER INFORMATION: Amino acids from positions 1 to 4 (Ala-Glu-Gly-
      Thr) may be absent, and Phe at position 5 may be amidated
<220> FEATURE:
<221> NAME/KEY: MOD_RES
<222> LOCATION: (1)..(4)
<223> OTHER INFORMATION: Amino acids from positions 1 to 3 (Ala-Glu-Gly)
      may be absent, and Thr at position 4 may be amidated
<220> FEATURE:
<221> NAME/KEY: MOD_RES
<222> LOCATION: (1)..(3)
<223> OTHER INFORMATION: Amino acids from positions 1 to 2 (Ala-Glu) may
      be absent, and Gly at position 3 may be amidated
<220> FEATURE:
<221> NAME/KEY: MOD_RES
<222> LOCATION: (1)..(2)
<223> OTHER INFORMATION: Amino acid at position 1 (Ala) may be absent,
      and Glu at position 2 may be amidated
<220> FEATURE:
<221> NAME/KEY: MOD_RES
<222> LOCATION: (1)..(1)
<223> OTHER INFORMATION: Ala at position 1 may be amidated
<220> FEATURE:
<221> NAME/KEY: MOD_RES
<222> LOCATION: (27)..(27)
<223> OTHER INFORMATION: Lys or Arg
<220> FEATURE:
<221> NAME/KEY: MOD_RES
<222> LOCATION: (29)..(29)
<223> OTHER INFORMATION: C-terminus hydroxylation or amidation when Gly
      at position 30 is absent
<220> FEATURE:
<221> NAME/KEY: MOD_RES
<222> LOCATION: (30)..(30)
<223> OTHER INFORMATION: Gly or absent
<220> FEATURE:
<221> NAME/KEY: MOD_RES
<222> LOCATION: (30)..(30)
<223> OTHER INFORMATION: C-terminus hydroxylation or amidation when Gly
      at position 30 is present

<400> SEQUENCE: 139

Ala Glu Gly Thr Phe Thr Ser Asp Val Ser Ser Tyr Leu Glu Gly Gln
1               5                   10                  15

Ala Ala Lys Glu Phe Ile Ala Trp Leu Val Xaa Gly Arg Xaa
            20                  25                  30

<210> SEQ ID NO 140
<211> LENGTH: 30
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (28)..(30)
<223> OTHER INFORMATION: The sequence Lys-Gly-Arg at positions 28 to 30
      may be absent
<220> FEATURE:
<221> NAME/KEY: MOD_RES
<222> LOCATION: (29)..(30)
<223> OTHER INFORMATION: The sequence Gly-Arg at positions 29 to 30 may
``` be absent
<220> FEATURE:
<221> NAME/KEY: MOD_RES
<222> LOCATION: (30)..(30)
<223> OTHER INFORMATION: The amino acid Arg at position 30 may be absent

<400> SEQUENCE: 140

His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg
            20                  25                  30

<210> SEQ ID NO 141
<211> LENGTH: 30
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: N-terminus amidation
<220> FEATURE:
<221> NAME/KEY: MOD_RES
<222> LOCATION: (30)..(30)
<223> OTHER INFORMATION: C-terminus modification with -OH, -OM, or
      -NR2R3, where M is a pharmaceutically acceptable cation or a lower
      branched or unbranched alkyl group; and R2 and 3 are independently
      hydrogen or a lower branched or unbranched alkyl group

<400> SEQUENCE: 141

His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg
            20                  25                  30

<210> SEQ ID NO 142
<211> LENGTH: 31
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: His, D-His, desamino-His, 2-amino-His, bis-
      hydroxy-His, homohistidine, alpha-fluoromethyl-His, or alpha-
      methyl-His
<220> FEATURE:
<221> NAME/KEY: MOD_RES
<222> LOCATION: (2)..(2)
<223> OTHER INFORMATION: Met, Asp, Lys, Thr, Leu, Asn, Gln, Phe, Val, or
      Tyr
<220> FEATURE:
<221> NAME/KEY: MOD_RES
<222> LOCATION: (15)..(15)
<223> OTHER INFORMATION: Glu, Gln, Ala, Thr, Ser, and Gly
<220> FEATURE:
<221> NAME/KEY: MOD_RES
<222> LOCATION: (21)..(21)
<223> OTHER INFORMATION: Glu, Gln, Ala, Thr, Ser, and Gly
<220> FEATURE:
<221> NAME/KEY: MOD_RES
<222> LOCATION: (31)..(31)
<223> OTHER INFORMATION: Gly or absent
<220> FEATURE:
<221> NAME/KEY: MOD_RES
<222> LOCATION: (31)..(31)
<223> OTHER INFORMATION: C-terminus hydroxylation, when Gly at position
      31 is present, or amidation, when Gly at position 31 is absent

<400> SEQUENCE: 142

Xaa Xaa Glu Gly Thr Phe Thr Ser Asp Val Ser Ser Tyr Leu Xaa Leu
1               5                   10                  15

Gln Ala Ala Lys Xaa Phe Ile Ala Trp Leu Val Lys Gly Arg Xaa
                20                  25                  30

<210> SEQ ID NO 143
<211> LENGTH: 31
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: 4-imidazopropionyl (des-amino-histidyl), 4-
      imidazoacetyl, or 4-imidazo-alpha,alpha-dimethyl-acetyl
<220> FEATURE:
<221> NAME/KEY: MOD_RES
<222> LOCATION: (20)..(20)
<223> OTHER INFORMATION: Lys or Arg
<220> FEATURE:
<221> NAME/KEY: MOD_RES
<222> LOCATION: (28)..(28)
<223> OTHER INFORMATION: R2, which is bound to the side chain of the Lys
      (e.g., through the sigma amino group), is C6-10 unbranched acyl or
      is absent
<220> FEATURE:
<221> NAME/KEY: MOD_RES
<222> LOCATION: (31)..(31)
<223> OTHER INFORMATION: Gly or absent
<220> FEATURE:
<221> NAME/KEY: MOD_RES
<222> LOCATION: (31)..(31)
<223> OTHER INFORMATION: C-terminus hydroxylation, when Gly at position
      31 is present, or amidation, when Gly at position 31 is absent

<400> SEQUENCE: 143

Xaa Ala Glu Gly Thr Phe Thr Ser Asp Val Ser Ser Tyr Leu Glu Gly
1               5                   10                  15

Gln Ala Ala Xaa Glu Phe Ile Ala Trp Leu Val Lys Gly Arg Xaa
                20                  25                  30

<210> SEQ ID NO 144
<211> LENGTH: 31
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Gly, Ala, Val, Leu, Ile, Ser, or Thr
<220> FEATURE:
<221> NAME/KEY: MOD_RES
<222> LOCATION: (5)..(5)
<223> OTHER INFORMATION: Asp, Glu, Arg, Thr, Ala, Lys, or His
<220> FEATURE:
<221> NAME/KEY: MOD_RES
<222> LOCATION: (6)..(6)
<223> OTHER INFORMATION: His, Trp, Phe, or Tyr
<220> FEATURE:
<221> NAME/KEY: MOD_RES
<222> LOCATION: (10)..(10)
<223> OTHER INFORMATION: Leu, Ser, Thr, Trp, His, Phe, Asp, Val, Tyr,
      Glu, or Ala
<220> FEATURE:
<221> NAME/KEY: MOD_RES
<222> LOCATION: (16)..(16)
<223> OTHER INFORMATION: Gly, Asp, Glu, Gln, Asn, Lys, Arg, Cys, or
      cysteic acid (Cya)

```
<220> FEATURE:
<221> NAME/KEY: MOD_RES
<222> LOCATION: (17)..(17)
<223> OTHER INFORMATION: His, Asp, Lys, Glu, or Gln
<220> FEATURE:
<221> NAME/KEY: MOD_RES
<222> LOCATION: (18)..(18)
<223> OTHER INFORMATION: Glu, His, Ala, or Lys
<220> FEATURE:
<221> NAME/KEY: MOD_RES
<222> LOCATION: (20)..(20)
<223> OTHER INFORMATION: Asp, Lys, Glu, or His
<220> FEATURE:
<221> NAME/KEY: MOD_RES
<222> LOCATION: (21)..(21)
<223> OTHER INFORMATION: Ala, Glu, His, Phe, Tyr, Trp, Arg, or Lys
<220> FEATURE:
<221> NAME/KEY: MOD_RES
<222> LOCATION: (25)..(25)
<223> OTHER INFORMATION: Ala, Glu, Asp, Ser, or His
<220> FEATURE:
<221> NAME/KEY: MOD_RES
<222> LOCATION: (27)..(27)
<223> OTHER INFORMATION: Asp, Arg, Val, Lys, Ala, Gly, or Glu
<220> FEATURE:
<221> NAME/KEY: MOD_RES
<222> LOCATION: (28)..(28)
<223> OTHER INFORMATION: Glu, Lys, or Asp
<220> FEATURE:
<221> NAME/KEY: MOD_RES
<222> LOCATION: (29)..(29)
<223> OTHER INFORMATION: Thr, Ser, Lys, Arg, Trp, Tyr, Phe, Asp, Gly,
     Pro, His, or Glu
<220> FEATURE:
<221> NAME/KEY: MOD_RES
<222> LOCATION: (30)..(30)
<223> OTHER INFORMATION: Arg, Glu, or His
<220> FEATURE:
<221> NAME/KEY: MOD_RES
<222> LOCATION: (31)..(31)
<223> OTHER INFORMATION: Lys, Arg, Thr, Ser, Glu, Asp, Trp, Tyr, Phe,
     His, -NH2, Gly, Gly-Pro, Gly-Pro-NH2, or absent

<400> SEQUENCE: 144

His Xaa Glu Gly Xaa Xaa Thr Ser Asp Xaa Ser Ser Tyr Leu Glu Xaa
1               5                   10                  15

Xaa Xaa Ala Xaa Xaa Phe Ile Ala Xaa Leu Xaa Xaa Xaa Xaa Xaa
            20                  25                  30

<210> SEQ ID NO 145
<211> LENGTH: 31
<212> TYPE: PRT
<213> ORGANISM: Artificial Sequence
<220> FEATURE:
<223> OTHER INFORMATION: Description of Artificial Sequence: Synthetic
     peptide
<220> FEATURE:
<221> NAME/KEY: MOD_RES
<222> LOCATION: (2)..(2)
<223> OTHER INFORMATION: Gly, Ala, Val, Leu, Ile, Ser, or Thr
<220> FEATURE:
<221> NAME/KEY: MOD_RES
<222> LOCATION: (6)..(6)
<223> OTHER INFORMATION: His, Trp, Phe, or Tyr
<220> FEATURE:
<221> NAME/KEY: MOD_RES
<222> LOCATION: (10)..(10)
<223> OTHER INFORMATION: Leu, Ser, Thr, Trp, His, Phe, Asp, Val, Glu, or
     Ala
<220> FEATURE:
<221> NAME/KEY: MOD_RES
<222> LOCATION: (16)..(16)
<223> OTHER INFORMATION: Gly, Asp, Glu, Gln, Asn, Lys, Arg, Cys, or
     cysteic acid (Cya)
<220> FEATURE:
<221> NAME/KEY: MOD_RES
```

```
<222> LOCATION: (17)..(17)
<223> OTHER INFORMATION: His, Asp, Lys, Glu, or Gln
<220> FEATURE:
<221> NAME/KEY: MOD_RES
<222> LOCATION: (20)..(20)
<223> OTHER INFORMATION: Asp, Lys, Glu, or His
<220> FEATURE:
<221> NAME/KEY: MOD_RES
<222> LOCATION: (24)..(24)
<223> OTHER INFORMATION: Ala, Glu, Asp, Ser, or His
<220> FEATURE:
<221> NAME/KEY: MOD_RES
<222> LOCATION: (29)..(29)
<223> OTHER INFORMATION: Thr, Ser, Lys, Arg, Trp, Tyr, Phe, Asp, Gly,
      Pro, His, or Glu
<220> FEATURE:
<221> NAME/KEY: MOD_RES
<222> LOCATION: (31)..(31)
<223> OTHER INFORMATION: Lys, Arg, Thr, Ser, Glu, Asp, Trp, Tyr, Phe,
      His, -NH2, Gly, Gly-Pro, Gly-Pro-NH2, or absent

<400> SEQUENCE: 145

His Xaa Glu Gly Thr Xaa Thr Ser Asp Xaa Ser Ser Tyr Leu Glu Xaa
1               5                   10                  15

Xaa Ala Ala Xaa Glu Phe Ile Xaa Trp Leu Val Lys Xaa Arg Xaa
            20                  25                  30

<210> SEQ ID NO 146
<211> LENGTH: 31
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Gly, Ala, Val, Leu, Ile, Ser, or Thr
<220> FEATURE:
<221> NAME/KEY: MOD_RES
<222> LOCATION: (16)..(16)
<223> OTHER INFORMATION: Gly, Asp, Glu, Gln, Asn, Lys, Arg, Cys, or
      cysteic acid (Cya)
<220> FEATURE:
<221> NAME/KEY: MOD_RES
<222> LOCATION: (17)..(17)
<223> OTHER INFORMATION: His, Asp, Lys, Glu, or Gln
<220> FEATURE:
<221> NAME/KEY: MOD_RES
<222> LOCATION: (21)..(21)
<223> OTHER INFORMATION: Ala, Glu, His, Phe, Tyr, Trp, Arg, or Lys
<220> FEATURE:
<221> NAME/KEY: MOD_RES
<222> LOCATION: (24)..(24)
<223> OTHER INFORMATION: Ala, Glu, Asp, Ser, or His
<220> FEATURE:
<221> NAME/KEY: MOD_RES
<222> LOCATION: (31)..(31)
<223> OTHER INFORMATION: Lys, Arg, Thr, Ser, Glu, Asp, Trp, Tyr, Phe,
      His, -NH2, Gly, Gly-Pro, Gly-Pro-NH2, or absent

<400> SEQUENCE: 146

His Xaa Glu Gly Thr Phe Thr Ser Asp Val Ser Ser Tyr Leu Glu Xaa
1               5                   10                  15

Xaa Ala Ala Lys Xaa Phe Ile Xaa Trp Leu Val Lys Gly Arg Xaa
            20                  25                  30

<210> SEQ ID NO 147
<211> LENGTH: 31
<212> TYPE: PRT
<213> ORGANISM: Artificial Sequence
<220> FEATURE:
<223> OTHER INFORMATION: Description of Artificial Sequence: Synthetic
```

```
                                                  -continued peptide
<220> FEATURE:
<221> NAME/KEY: MOD_RES
<222> LOCATION: (1)..(1)
<223> OTHER INFORMATION: L-His, D-His, desamino-His, 2amino-His, beta-
      hydroxy-His, homo-His, alpha-fluoromethyl-His or alpha-methyl-His
<220> FEATURE:
<221> NAME/KEY: MOD_RES
<222> LOCATION: (2)..(2)
<223> OTHER INFORMATION: Gly, Ala, Val, Leu, Ile, Ser or Thr
<220> FEATURE:
<221> NAME/KEY: MOD_RES
<222> LOCATION: (16)..(16)
<223> OTHER INFORMATION: Asp, Glu, Gln, Asn, Lys, Arg, Cys, or cysteic
      acid (Cya)
<220> FEATURE:
<221> NAME/KEY: MOD_RES
<222> LOCATION: (16)..(16)
<223> OTHER INFORMATION: Asp, Glu, Gln, Asn, Lys, Arg, Cys, or cysteic
      acid (Cya)
<220> FEATURE:
<221> NAME/KEY: MOD_RES
<222> LOCATION: (31)..(31)
<223> OTHER INFORMATION: Gly or absent
<220> FEATURE:
<221> NAME/KEY: MOD_RES
<222> LOCATION: (31)..(31)
<223> OTHER INFORMATION: C-termimus hydroxylation, when Gly at position
      31 is present, or amidation, when Gly at position 31 is absent

<400> SEQUENCE: 147

Xaa Xaa Glu Gly Thr Phe Thr Ser Asp Val Asp Asp Tyr Leu Glu Xaa
 1               5                  10                  15

Gln Ala Ala Lys Glu Phe Ile Ala Trp Leu Val Lys Gly Arg Xaa
            20                  25                  30

<210> SEQ ID NO 148
<211> LENGTH: 31
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: L-His, D-His, desamino-His, 2-amino-His, beta-
      hydroxy-His, homohistidine, alpha-fluoromethyl-His, or alpha-
      methyl-His
<220> FEATURE:
<221> NAME/KEY: MOD_RES
<222> LOCATION: (2)..(2)
<223> OTHER INFORMATION: Ala, Gly, Val, Leu, Ile, Ser, or Thr
<220> FEATURE:
<221> NAME/KEY: MOD_RES
<222> LOCATION: (6)..(6)
<223> OTHER INFORMATION: Phe, Trp, or Tyr
<220> FEATURE:
<221> NAME/KEY: MOD_RES
<222> LOCATION: (10)..(10)
<223> OTHER INFORMATION: Val, Trp, Ile, Leu, Phe, or Tyr
<220> FEATURE:
<221> NAME/KEY: MOD_RES
<222> LOCATION: (12)..(12)
<223> OTHER INFORMATION: Ser, Trp, Tyr, Phe, Lys, Ile, Leu, or Val
<220> FEATURE:
<221> NAME/KEY: MOD_RES
<222> LOCATION: (13)..(13)
<223> OTHER INFORMATION: Tyr, Trp, or Phe
<220> FEATURE:
<221> NAME/KEY: MOD_RES
<222> LOCATION: (14)..(14)
<223> OTHER INFORMATION: Leu, Phe, Tyr, or Trp
<220> FEATURE:
<221> NAME/KEY: MOD_RES
<222> LOCATION: (16)..(16)
```

```
<223> OTHER INFORMATION: Gly, Glu, Asp, or Lys
<220> FEATURE:
<221> NAME/KEY: MOD_RES
<222> LOCATION: (19)..(19)
<223> OTHER INFORMATION: Ala, Val, Ile, or Leu
<220> FEATURE:
<221> NAME/KEY: MOD_RES
<222> LOCATION: (21)..(21)
<223> OTHER INFORMATION: Glu, Ile, or Ala
<220> FEATURE:
<221> NAME/KEY: MOD_RES
<222> LOCATION: (24)..(24)
<223> OTHER INFORMATION: Ala or Glu
<220> FEATURE:
<221> NAME/KEY: MOD_RES
<222> LOCATION: (27)..(27)
<223> OTHER INFORMATION: Val, or Ile
<220> FEATURE:
<221> NAME/KEY: MOD_RES
<222> LOCATION: (31)..(31)
<223> OTHER INFORMATION: Gly, His, or absent
<220> FEATURE:
<221> NAME/KEY: MOD_RES
<222> LOCATION: (31)..(31)
<223> OTHER INFORMATION: C-terminus amidation, when Gly at position 31
      is absent

<400> SEQUENCE: 148

Xaa Xaa Glu Gly Thr Xaa Thr Ser Asp Xaa Ser Xaa Xaa Xaa Glu Xaa
1               5                   10                  15

Gln Ala Xaa Lys Xaa Phe Ile Xaa Trp Leu Xaa Lys Gly Arg Xaa
            20                  25                  30

<210> SEQ ID NO 149
<211> LENGTH: 31
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: L-His, D-His, desamino-His, 2-amino-His, beta-
      hydroxy-His, homohistidine, alpha-fluoromethyl-His, or alpha-
      methyl-His
<220> FEATURE:
<221> NAME/KEY: MOD_RES
<222> LOCATION: (2)..(2)
<223> OTHER INFORMATION: Gly, Ala, Val, Leu, Ile, Ser, or Thr
<220> FEATURE:
<221> NAME/KEY: MOD_RES
<222> LOCATION: (10)..(10)
<223> OTHER INFORMATION: Val, Phe, Tyr, or Trp
<220> FEATURE:
<221> NAME/KEY: MOD_RES
<222> LOCATION: (12)..(12)
<223> OTHER INFORMATION: Ser, Tyr, Trp, Phe, Lys, Ile, Leu, or Val
<220> FEATURE:
<221> NAME/KEY: MOD_RES
<222> LOCATION: (16)..(16)
<223> OTHER INFORMATION: Gly, Glu, Asp, or Lys
<220> FEATURE:
<221> NAME/KEY: MOD_RES
<222> LOCATION: (19)..(19)
<223> OTHER INFORMATION: Ala, Val, Ile, or Leu
<220> FEATURE:
<221> NAME/KEY: MOD_RES
<222> LOCATION: (27)..(27)
<223> OTHER INFORMATION: Val or Ile
<220> FEATURE:
<221> NAME/KEY: MOD_RES
<222> LOCATION: (31)..(31)
<223> OTHER INFORMATION: Gly or absent
<220> FEATURE:
<221> NAME/KEY: MOD_RES
```

```
<222> LOCATION: (31)..(31)
<223> OTHER INFORMATION: C-terminus amidation, when Gly at position 31
      is absent

<400> SEQUENCE: 149

Xaa Xaa Glu Gly Thr Phe Thr Ser Asp Xaa Ser Xaa Tyr Leu Glu Xaa
1               5                   10                  15

Gln Ala Xaa Lys Glu Phe Ile Ala Trp Leu Xaa Lys Gly Arg Xaa
            20                  25                  30

<210> SEQ ID NO 150
<211> LENGTH: 13
<212> TYPE: PRT
<213> ORGANISM: Homo sapiens

<400> SEQUENCE: 150

Gln Leu Tyr Glu Asn Lys Pro Arg Arg Pro Tyr Ile Leu
1               5                   10

<210> SEQ ID NO 151
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 151

Phe Pro Leu Pro Ala Gly Lys Arg
1               5

<210> SEQ ID NO 152
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: Ala, Leu, Ile, or Val
<220> FEATURE:
<221> NAME/KEY: MOD_RES
<222> LOCATION: (6)..(6)
<223> OTHER INFORMATION: Gly, any amino acid residue of the D
      configuration, or absent
<220> FEATURE:
<221> NAME/KEY: MOD_RES
<222> LOCATION: (7)..(7)
<223> OTHER INFORMATION: Lys, Arg, His, or absent
<220> FEATURE:
<221> NAME/KEY: MOD_RES
<222> LOCATION: (8)..(8)
<223> OTHER INFORMATION: Arg, Lys, His, or absent

<400> SEQUENCE: 152

Phe Pro Leu Pro Xaa Xaa Xaa Xaa
1               5

<210> SEQ ID NO 153
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
```

<223> OTHER INFORMATION: Leu, Ala, Ile, or Val
<220> FEATURE:
<221> NAME/KEY: MOD_RES
<222> LOCATION: (6)..(6)
<223> OTHER INFORMATION: Gly, any amino acid residue of the D
      configuration, or absent
<220> FEATURE:
<221> NAME/KEY: MOD_RES
<222> LOCATION: (7)..(7)
<223> OTHER INFORMATION: Lys, Arg, His, or absent
<220> FEATURE:
<221> NAME/KEY: MOD_RES
<222> LOCATION: (8)..(8)
<223> OTHER INFORMATION: Arg, Lys, His, or absent

<400> SEQUENCE: 153

Phe Pro Xaa Pro Ala Xaa Xaa Xaa
1               5

<210> SEQ ID NO 154
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: Gly, any amino acid residue of the D
      configuration, or absent
<220> FEATURE:
<221> NAME/KEY: MOD_RES
<222> LOCATION: (7)..(7)
<223> OTHER INFORMATION: Lys, Arg, His, or absent
<220> FEATURE:
<221> NAME/KEY: MOD_RES
<222> LOCATION: (8)..(8)
<223> OTHER INFORMATION: Arg, Lys, His, or absent

<400> SEQUENCE: 154

Phe Pro Leu Pro Ala Xaa Xaa Xaa
1               5

<210> SEQ ID NO 155
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Leu, Ala, Ile, or Val
<220> FEATURE:
<221> NAME/KEY: MOD_RES
<222> LOCATION: (5)..(5)
<223> OTHER INFORMATION: Ala, Leu, Ile, or Val
<220> FEATURE:
<221> NAME/KEY: MOD_RES
<222> LOCATION: (7)..(7)
<223> OTHER INFORMATION: Lys, Arg, His, or absent
<220> FEATURE:
<221> NAME/KEY: MOD_RES
<222> LOCATION: (8)..(8)
<223> OTHER INFORMATION: Arg, Lys, His, or absent

<400> SEQUENCE: 155

Phe Pro Xaa Pro Xaa Gly Xaa Xaa
1               5

<210> SEQ ID NO 156

```
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: Ala, Leu, Ile, or Val
<220> FEATURE:
<221> NAME/KEY: MOD_RES
<222> LOCATION: (7)..(7)
<223> OTHER INFORMATION: Lys, Arg, His, or absent
<220> FEATURE:
<221> NAME/KEY: MOD_RES
<222> LOCATION: (8)..(8)
<223> OTHER INFORMATION: Arg, Lys, His, or absent

<400> SEQUENCE: 156

Phe Pro Leu Pro Xaa Gly Xaa Xaa
1               5

<210> SEQ ID NO 157
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (7)..(7)
<223> OTHER INFORMATION: Lys, Arg, His, or absent
<220> FEATURE:
<221> NAME/KEY: MOD_RES
<222> LOCATION: (8)..(8)
<223> OTHER INFORMATION: Arg, Lys, His, or absent

<400> SEQUENCE: 157

Phe Pro Phe Pro Ala Gly Xaa Xaa
1               5

<210> SEQ ID NO 158
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Leu, Ala, Ile, or Val
<220> FEATURE:
<221> NAME/KEY: MOD_RES
<222> LOCATION: (5)..(5)
<223> OTHER INFORMATION: Ala, Leu, Ile, or Val
<220> FEATURE:
<221> NAME/KEY: MOD_RES
<222> LOCATION: (6)..(6)
<223> OTHER INFORMATION: Gly, any amino acid residue of the D
      configuration, or absent
<220> FEATURE:
<221> NAME/KEY: MOD_RES
<222> LOCATION: (8)..(8)
<223> OTHER INFORMATION: Arg, Lys, His, or absent

<400> SEQUENCE: 158

Phe Pro Xaa Pro Xaa Xaa Lys Xaa
1               5

<210> SEQ ID NO 159
```

```
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: Ala, Leu, Ile, or Val
<220> FEATURE:
<221> NAME/KEY: MOD_RES
<222> LOCATION: (6)..(6)
<223> OTHER INFORMATION: Gly, any amino acid residue of the D
      configuration, or absent
<220> FEATURE:
<221> NAME/KEY: MOD_RES
<222> LOCATION: (8)..(8)
<223> OTHER INFORMATION: Arg, Lys, His, or absent

<400> SEQUENCE: 159

Phe Pro Leu Pro Xaa Xaa Lys Xaa
1               5

<210> SEQ ID NO 160
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: Gly, any amino acid residue of the D
      configuration, or absent
<220> FEATURE:
<221> NAME/KEY: MOD_RES
<222> LOCATION: (8)..(8)
<223> OTHER INFORMATION: Arg, Lys, His, or absent

<400> SEQUENCE: 160

Phe Pro Leu Pro Ala Xaa Lys Xaa
1               5

<210> SEQ ID NO 161
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (8)..(8)
<223> OTHER INFORMATION: Arg, Lys, His, or absent

<400> SEQUENCE: 161

Phe Pro Leu Pro Ala Gly Lys Xaa
1               5

<210> SEQ ID NO 162
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Leu, Ala, Ile, or Val
<220> FEATURE:
```

```
<221> NAME/KEY: MOD_RES
<222> LOCATION: (5)..(5)
<223> OTHER INFORMATION: Ala, Leu, Ile, or Val
<220> FEATURE:
<221> NAME/KEY: MOD_RES
<222> LOCATION: (6)..(6)
<223> OTHER INFORMATION: Gly, any amino acid residue of the D
      configuration, or absent
<220> FEATURE:
<221> NAME/KEY: MOD_RES
<222> LOCATION: (7)..(7)
<223> OTHER INFORMATION: Lys, Arg, His, or absent

<400> SEQUENCE: 162

Phe Pro Xaa Pro Xaa Xaa Xaa Arg
1               5

<210> SEQ ID NO 163
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: Ala, Leu, Ile, or Val
<220> FEATURE:
<221> NAME/KEY: MOD_RES
<222> LOCATION: (6)..(6)
<223> OTHER INFORMATION: Gly, any amino acid residue of the D
      configuration, or absent
<220> FEATURE:
<221> NAME/KEY: MOD_RES
<222> LOCATION: (7)..(7)
<223> OTHER INFORMATION: Lys, Arg, His, or absent

<400> SEQUENCE: 163

Phe Pro Leu Pro Xaa Xaa Xaa Arg
1               5

<210> SEQ ID NO 164
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: Gly, any amino acid residue of the D
      configuration, or absent
<220> FEATURE:
<221> NAME/KEY: MOD_RES
<222> LOCATION: (7)..(7)
<223> OTHER INFORMATION: Lys, Arg, His, or absent

<400> SEQUENCE: 164

Phe Pro Leu Pro Ala Xaa Xaa Arg
1               5

<210> SEQ ID NO 165
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (7)..(7)
```

```
<223> OTHER INFORMATION: Lys, Arg, His, or absent

<400> SEQUENCE: 165

Phe Pro Leu Pro Ala Gly Xaa Arg
1               5

<210> SEQ ID NO 166
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 166

Pro Pro Glu Ala Pro Ala Glu Asp Arg Ser Leu Gly Arg Arg
1               5                   10

<210> SEQ ID NO 167
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 167

Arg Arg Glu Arg Asn Arg Gln Ala Ala Ala Ala Asn Pro Glu Asn Ser
1               5                   10                  15

Arg Gly Lys Gly Arg Arg
            20

<210> SEQ ID NO 168
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (17)..(17)
<223> OTHER INFORMATION: C-terminus amidation

<400> SEQUENCE: 168

Glu Arg Asn Arg Gln Ala Ala Ala Ala Asn Pro Glu Asn Ser Arg Gly
1               5                   10                  15

Lys

<210> SEQ ID NO 169
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: C-terminus amidation

<400> SEQUENCE: 169

Phe Pro Leu Pro Ala
1               5

<210> SEQ ID NO 170
<211> LENGTH: 11
```

<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (11)..(11)
<223> OTHER INFORMATION: C-terminus amidation

<400> SEQUENCE: 170

Pro Pro Glu Ala Pro Ala Glu Asp Arg Ser Leu
1               5                   10

<210> SEQ ID NO 171
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (11)..(11)
<223> OTHER INFORMATION: C-terminus amidation

<400> SEQUENCE: 171

Leu Leu Glu Ala Pro Ala Glu Asp His Ser Leu
1               5                   10

<210> SEQ ID NO 172
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 172

Ser Pro Asp Lys Gln Met Ala Val Leu Pro
1               5                   10

<210> SEQ ID NO 173
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 173

Ser Pro Asp Lys Gln Ala Ala Ala Leu Pro
1               5                   10

<210> SEQ ID NO 174
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 174

Ser Pro Asp Lys Gln Thr Pro Ile Phe Ser
1               5                   10

<210> SEQ ID NO 175
<211> LENGTH: 17
<212> TYPE: PRT

```
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (17)..(17)
<223> OTHER INFORMATION: C-terminus amidation

<400> SEQUENCE: 175

Glu Arg Asn Arg Gln Ala Ala Ala Ala Ser Pro Glu Asn Ser Arg Gly
1               5                   10                  15

Lys

<210> SEQ ID NO 176
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (17)..(17)
<223> OTHER INFORMATION: C-terminus amidation

<400> SEQUENCE: 176

Glu Arg Asn Arg Gln Ser Ala Ala Thr Asn Val Glu Asn Ser Ser Lys
1               5                   10                  15

Lys

<210> SEQ ID NO 177
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: N-terminus modification with N-succinimidyl
      S-acetylthiopropionate
<220> FEATURE:
<221> NAME/KEY: MOD_RES
<222> LOCATION: (20)..(20)
<223> OTHER INFORMATION: C-terminus amidation

<400> SEQUENCE: 177

Thr Phe Phe Tyr Gly Gly Ser Arg Gly Lys Arg Asn Asn Phe Lys Thr
1               5                   10                  15

Glu Glu Tyr Cys
            20

<210> SEQ ID NO 178
<211> LENGTH: 39
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: N-terminus modification with N-succinimidyl
      S-acetylthiopropionate
<220> FEATURE:
<221> NAME/KEY: MOD_RES
<222> LOCATION: (20)..(20)
<223> OTHER INFORMATION: C-terminus amidation
```

```
<220> FEATURE:
<221> NAME/KEY: MOD_RES
<222> LOCATION: (20)..(21)
<223> OTHER INFORMATION: The linkage between Cys at position 20 and Thr
      at position 21 is maleimido propionic acid (MPA)

<400> SEQUENCE: 178

Thr Phe Phe Tyr Gly Gly Ser Arg Gly Lys Arg Asn Asn Phe Lys Thr
1               5                   10                  15

Glu Glu Tyr Cys Thr Phe Phe Tyr Gly Gly Ser Arg Gly Lys Arg Asn
            20                  25                  30

Asn Phe Lys Thr Glu Glu Tyr
35

<210> SEQ ID NO 179
<211> LENGTH: 39
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Xaa is His, Arg, or Tyr
<220> FEATURE:
<221> NAME/KEY: MOD_RES
<222> LOCATION: (2)..(2)
<223> OTHER INFORMATION: Xaa is Ser, Gly, Ala, or Thr
<220> FEATURE:
<221> NAME/KEY: MOD_RES
<222> LOCATION: (3)..(3)
<223> OTHER INFORMATION: Xaa is Asp or Glu
<220> FEATURE:
<221> NAME/KEY: MOD_RES
<222> LOCATION: (5)..(5)
<223> OTHER INFORMATION: Xaa is Ala or Thr
<220> FEATURE:
<221> NAME/KEY: MOD_RES
<222> LOCATION: (6)..(6)
<223> OTHER INFORMATION: Xaa is Ala, Phe, Tyr, or Nal
<220> FEATURE:
<221> NAME/KEY: MOD_RES
<222> LOCATION: (7)..(7)
<223> OTHER INFORMATION: Xaa is Thr or Ser
<220> FEATURE:
<221> NAME/KEY: MOD_RES
<222> LOCATION: (8)..(8)
<223> OTHER INFORMATION: Xaa is Ala, Ser, or Thr
<220> FEATURE:
<221> NAME/KEY: MOD_RES
<222> LOCATION: (9)..(9)
<223> OTHER INFORMATION: Xaa is Asp or Glu
<220> FEATURE:
<221> NAME/KEY: MOD_RES
<222> LOCATION: (10)..(10)
<223> OTHER INFORMATION: Xaa is Ala, Leu, Ile, Val, pGly, or Met
<220> FEATURE:
<221> NAME/KEY: MOD_RES
<222> LOCATION: (11)..(11)
<223> OTHER INFORMATION: Xaa is Ala or Ser
<220> FEATURE:
<221> NAME/KEY: MOD_RES
<222> LOCATION: (12)..(12)
<223> OTHER INFORMATION: Xaa is Ala or Lys
<220> FEATURE:
<221> NAME/KEY: MOD_RES
<222> LOCATION: (13)..(13)
<223> OTHER INFORMATION: Xaa is Ala or Gln
<220> FEATURE:
<221> NAME/KEY: MOD_RES
<222> LOCATION: (14)..(14)
<223> OTHER INFORMATION: Xaa is Ala, Leu, Ile, pGly, Val, or Met
<220> FEATURE:
<221> NAME/KEY: MOD_RES
```

```
<222> LOCATION: (15)..(17)
<223> OTHER INFORMATION: Xaa are independently Ala or Glu
<220> FEATURE:
<221> NAME/KEY: MOD_RES
<222> LOCATION: (19)..(19)
<223> OTHER INFORMATION: Xaa is Ala or Val
<220> FEATURE:
<221> NAME/KEY: MOD_RES
<222> LOCATION: (20)..(20)
<223> OTHER INFORMATION: Xaa is Ala or Arg
<220> FEATURE:
<221> NAME/KEY: MOD_RES
<222> LOCATION: (21)..(21)
<223> OTHER INFORMATION: Xaa is Ala or Leu
<220> FEATURE:
<221> NAME/KEY: MOD_RES
<222> LOCATION: (22)..(22)
<223> OTHER INFORMATION: Xaa is Phe, Tyr, or Nal
<220> FEATURE:
<221> NAME/KEY: MOD_RES
<222> LOCATION: (23)..(23)
<223> OTHER INFORMATION: Xaa is Ile, Val, Leu, pGly, t-BuG, or Met
<220> FEATURE:
<221> NAME/KEY: MOD_RES
<222> LOCATION: (24)..(24)
<223> OTHER INFORMATION: Xaa is Ala, Glu, or Asp
<220> FEATURE:
<221> NAME/KEY: MOD_RES
<222> LOCATION: (25)..(25)
<223> OTHER INFORMATION: Xaa is Ala, Trp, Phe, Tyr, or Nal
<220> FEATURE:
<221> NAME/KEY: MOD_RES
<222> LOCATION: (26)..(26)
<223> OTHER INFORMATION: Xaa is Ala or Leu
<220> FEATURE:
<221> NAME/KEY: MOD_RES
<222> LOCATION: (27)..(27)
<223> OTHER INFORMATION: Xaa is Ala or Lys
<220> FEATURE:
<221> NAME/KEY: MOD_RES
<222> LOCATION: (28)..(28)
<223> OTHER INFORMATION: Xaa is Ala or Asn
<220> FEATURE:
<221> NAME/KEY: MOD_RES
<222> LOCATION: (29)..(30)
<223> OTHER INFORMATION: Xaa is independently Gly or absent
<220> FEATURE:
<221> NAME/KEY: MOD_RES
<222> LOCATION: (31)..(31)
<223> OTHER INFORMATION: Xaa is Pro, HPro, 3Hyp, 4Hyp, TPro, N-
     alkylglycine, N-alkyl-pGly or N-alkylalanine or absent
<220> FEATURE:
<221> NAME/KEY: MOD_RES
<222> LOCATION: (32)..(33)
<223> OTHER INFORMATION: Xaa is independently Ser or absent
<220> FEATURE:
<221> NAME/KEY: MOD_RES
<222> LOCATION: (34)..(34)
<223> OTHER INFORMATION: Xaa is Gly or absent
<220> FEATURE:
<221> NAME/KEY: MOD_RES
<222> LOCATION: (35)..(35)
<223> OTHER INFORMATION: Xaa is Ala or absent
<220> FEATURE:
<221> NAME/KEY: MOD_RES
<222> LOCATION: (36)..(38)
<223> OTHER INFORMATION: Xaa are independently Pro, HPro, 3Hyp, 4Hyp,
     TPro, N-alkylglycine, N-alkyl-pGly or N-alkylalanine or absent
<220> FEATURE:
<221> NAME/KEY: MOD_RES
<222> LOCATION: (39)..(39)
<223> OTHER INFORMATION: Xaa is OH or NH2

<400> SEQUENCE: 179

Xaa Xaa Xaa Gly Xaa Xaa Xaa Xaa Xaa Xaa Xaa Xaa Xaa Xaa Xaa Xaa
1               5                   10                  15

Xaa Ala Xaa Xaa Xaa Xaa Xaa Xaa Xaa Xaa Xaa Xaa Xaa Xaa Xaa Xaa
```

```
            20                  25                  30
Xaa Xaa Xaa Xaa Xaa Xaa Xaa
        35

<210> SEQ ID NO 180
<211> LENGTH: 40
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Xaa is His, Arg, Tyr, Ala, Norval, Val, or
      Norleu
<220> FEATURE:
<221> NAME/KEY: MOD_RES
<222> LOCATION: (2)..(2)
<223> OTHER INFORMATION: Xaa is Ser, Gly, Ala, or Thr
<220> FEATURE:
<221> NAME/KEY: MOD_RES
<222> LOCATION: (3)..(3)
<223> OTHER INFORMATION: Xaa is Ala, Asp, or Glu
<220> FEATURE:
<221> NAME/KEY: MOD_RES
<222> LOCATION: (4)..(4)
<223> OTHER INFORMATION: Xaa is Ala, Norval, Val, Norleu, or Gly
<220> FEATURE:
<221> NAME/KEY: MOD_RES
<222> LOCATION: (5)..(5)
<223> OTHER INFORMATION: Xaa is Ala or Thr
<220> FEATURE:
<221> NAME/KEY: MOD_RES
<222> LOCATION: (6)..(6)
<223> OTHER INFORMATION: Xaa is Phe, Tyr or Nal
<220> FEATURE:
<221> NAME/KEY: MOD_RES
<222> LOCATION: (7)..(7)
<223> OTHER INFORMATION: Xaa is Thr or Ser
<220> FEATURE:
<221> NAME/KEY: MOD_RES
<222> LOCATION: (8)..(8)
<223> OTHER INFORMATION: Xaa is Ala, Ser or Thr
<220> FEATURE:
<221> NAME/KEY: MOD_RES
<222> LOCATION: (9)..(9)
<223> OTHER INFORMATION: Xaa is Ala, Norval, Val, Norleu, Asp, or Glu
<220> FEATURE:
<221> NAME/KEY: MOD_RES
<222> LOCATION: (10)..(10)
<223> OTHER INFORMATION: Xaa is Ala, Leu, Ile, Val, pGly, or Met
<220> FEATURE:
<221> NAME/KEY: MOD_RES
<222> LOCATION: (11)..(11)
<223> OTHER INFORMATION: Xaa is Ala or Ser
<220> FEATURE:
<221> NAME/KEY: MOD_RES
<222> LOCATION: (12)..(12)
<223> OTHER INFORMATION: Xaa is Ala or Lys
<220> FEATURE:
<221> NAME/KEY: MOD_RES
<222> LOCATION: (13)..(13)
<223> OTHER INFORMATION: Xaa is Ala or Gln
<220> FEATURE:
<221> NAME/KEY: MOD_RES
<222> LOCATION: (14)..(14)
<223> OTHER INFORMATION: Xaa is Ala, Leu, Ile, pGly, Val, or Met
<220> FEATURE:
<221> NAME/KEY: MOD_RES
<222> LOCATION: (15)..(17)
<223> OTHER INFORMATION: Xaa are independently Ala or Glu
<220> FEATURE:
<221> NAME/KEY: MOD_RES
<222> LOCATION: (19)..(19)
<223> OTHER INFORMATION: Xaa is Ala or Val
<220> FEATURE:
```

```
<221> NAME/KEY: MOD_RES
<222> LOCATION: (20)..(20)
<223> OTHER INFORMATION: Xaa is Ala or Arg
<220> FEATURE:
<221> NAME/KEY: MOD_RES
<222> LOCATION: (21)..(21)
<223> OTHER INFORMATION: Xaa is Ala or Leu
<220> FEATURE:
<221> NAME/KEY: MOD_RES
<222> LOCATION: (22)..(22)
<223> OTHER INFORMATION: Xaa is Phe, Tyr, or Nal
<220> FEATURE:
<221> NAME/KEY: MOD_RES
<222> LOCATION: (23)..(23)
<223> OTHER INFORMATION: Xaa is Ile, Val, Leu, pGly, t-BuG, or Met
<220> FEATURE:
<221> NAME/KEY: MOD_RES
<222> LOCATION: (24)..(24)
<223> OTHER INFORMATION: Xaa is Ala, Glu, or Asp
<220> FEATURE:
<221> NAME/KEY: MOD_RES
<222> LOCATION: (25)..(25)
<223> OTHER INFORMATION: Xaa is Ala, Trp, Phe, Tyr, or Nal
<220> FEATURE:
<221> NAME/KEY: MOD_RES
<222> LOCATION: (26)..(26)
<223> OTHER INFORMATION: Xaa is Ala or Leu
<220> FEATURE:
<221> NAME/KEY: MOD_RES
<222> LOCATION: (27)..(27)
<223> OTHER INFORMATION: Xaa is Ala or Lys
<220> FEATURE:
<221> NAME/KEY: MOD_RES
<222> LOCATION: (28)..(28)
<223> OTHER INFORMATION: Xaa is Ala or Asn
<220> FEATURE:
<221> NAME/KEY: MOD_RES
<222> LOCATION: (29)..(30)
<223> OTHER INFORMATION: Xaa are independently Gly or absent
<220> FEATURE:
<221> NAME/KEY: MOD_RES
<222> LOCATION: (31)..(31)
<223> OTHER INFORMATION: Xaa is Pro, HPro, 3Hyp, 4Hyp, TPro, N-
      alkylglycine, N-alkyl-pGly, or N-alkylalanine or absent
<220> FEATURE:
<221> NAME/KEY: MOD_RES
<222> LOCATION: (32)..(33)
<223> OTHER INFORMATION: Xaa are independently Ser or absent
<220> FEATURE:
<221> NAME/KEY: MOD_RES
<222> LOCATION: (34)..(34)
<223> OTHER INFORMATION: Xaa is Gly or absent
<220> FEATURE:
<221> NAME/KEY: MOD_RES
<222> LOCATION: (35)..(35)
<223> OTHER INFORMATION: Xaa is Ala or absent
<220> FEATURE:
<221> NAME/KEY: MOD_RES
<222> LOCATION: (36)..(38)
<223> OTHER INFORMATION: Xaa are independently Pro, HPro, 3Hyp, 4Hyp,
      TPro, N-alkylglycine, N-alkyl-pGly, or N-alkylalanine or absent
<220> FEATURE:
<221> NAME/KEY: MOD_RES
<222> LOCATION: (39)..(39)
<223> OTHER INFORMATION: Xaa is any naturally accuring amino acid
<220> FEATURE:
<221> NAME/KEY: MOD_RES
<222> LOCATION: (40)..(40)
<223> OTHER INFORMATION: Xaa is OH or NH2

<400> SEQUENCE: 180

Xaa Xaa Xaa Xaa Xaa Xaa Xaa Xaa Xaa Xaa Xaa Xaa Xaa Xaa Xaa
1               5                   10                  15

Xaa Ala Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa
```

```
                    35                  40

<210> SEQ ID NO 181
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Xaa is H2N; H2N-Ser; H2N-Val-Ser; H2N-Asp-Val-
      Ser; H2N-Ser-Asp-Val-Ser; H2N-Thr-Ser-Asp-Val-Ser;
      H2N-Phe-Thr-Ser-Asp-Val-Ser; H2N-Thr-Phe-Thr-Ser-Asp-Val-Ser;
      H2N-Gly-Thr-Phe-Thr-Ser-Asp-Val-Ser
<220> FEATURE:
<221> NAME/KEY: MOD_RES
<222> LOCATION: (18)..(18)
<223> OTHER INFORMATION: Xaa is Lys or Arg
<220> FEATURE:
<221> NAME/KEY: MOD_RES
<222> LOCATION: (21)..(21)
<223> OTHER INFORMATION: Xaa is NH2, OH, Gly-NH2, or Gly-OH

<400> SEQUENCE: 181

Xaa Ser Tyr Leu Glu Gly Gln Ala Ala Lys Glu Phe Ile Ala Trp Leu
1               5                   10                  15

Val Xaa Gly Arg Xaa
            20

<210> SEQ ID NO 182
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Xaa is Phe, Trp, or Tyr
<220> FEATURE:
<221> NAME/KEY: MOD_RES
<222> LOCATION: (3)..(3)
<223> OTHER INFORMATION: Xaa is Leu, Ala, Ile, or Val
<220> FEATURE:
<221> NAME/KEY: MOD_RES
<222> LOCATION: (5)..(5)
<223> OTHER INFORMATION: Xaa is Ala, Leu, Ile, or Val
<220> FEATURE:
<221> NAME/KEY: MOD_RES
<222> LOCATION: (6)..(6)
<223> OTHER INFORMATION: Xaa is Gly, is any amino acid residue of the D
      configuration or is absent
<220> FEATURE:
<221> NAME/KEY: MOD_RES
<222> LOCATION: (7)..(7)
<223> OTHER INFORMATION: Xaa is Lys, Arg, or His or is absent
<220> FEATURE:
<221> NAME/KEY: MOD_RES
<222> LOCATION: (8)..(8)
<223> OTHER INFORMATION: Xaa is Arg, Lys, or His or is absent

<400> SEQUENCE: 182

Xaa Pro Xaa Pro Xaa Xaa Xaa Xaa
1               5

<210> SEQ ID NO 183
<211> LENGTH: 8
<212> TYPE: PRT
<213> ORGANISM: Artificial Sequence
<220> FEATURE:
```

```
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Xaa is Leu, Ala, Ile, or Val
<220> FEATURE:
<221> NAME/KEY: MOD_RES
<222> LOCATION: (5)..(5)
<223> OTHER INFORMATION: Xaa is Ala, Leu, Ile, or Val
<220> FEATURE:
<221> NAME/KEY: MOD_RES
<222> LOCATION: (6)..(6)
<223> OTHER INFORMATION: Xaa is Gly, is any amino acid residue of the D
      configuration or is absent
<220> FEATURE:
<221> NAME/KEY: MOD_RES
<222> LOCATION: (7)..(7)
<223> OTHER INFORMATION: Xaa is Lys, Arg, or His or is absent
<220> FEATURE:
<221> NAME/KEY: MOD_RES
<222> LOCATION: (8)..(8)
<223> OTHER INFORMATION: Xaa is Arg, Lys, or His or is absent

<400> SEQUENCE: 183

Phe Pro Xaa Pro Xaa Xaa Xaa Xaa
1               5

<210> SEQ ID NO 184
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Xaa is Phe, Trp, or Tyr
<220> FEATURE:
<221> NAME/KEY: MOD_RES
<222> LOCATION: (5)..(5)
<223> OTHER INFORMATION: Xaa is Ala, Leu, Ile, or Val
<220> FEATURE:
<221> NAME/KEY: MOD_RES
<222> LOCATION: (6)..(6)
<223> OTHER INFORMATION: Xaa is Gly, is any amino acid residue of the D
      configuration or is absent
<220> FEATURE:
<221> NAME/KEY: MOD_RES
<222> LOCATION: (7)..(7)
<223> OTHER INFORMATION: Xaa is Lys, Arg, or His or is absent
<220> FEATURE:
<221> NAME/KEY: MOD_RES
<222> LOCATION: (8)..(8)
<223> OTHER INFORMATION: Xaa is Arg, Lys, or His or is absent

<400> SEQUENCE: 184

Xaa Pro Leu Pro Xaa Xaa Xaa Xaa
1               5

<210> SEQ ID NO 185
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Xaa is Phe, Trp, or Tyr
<220> FEATURE:
<221> NAME/KEY: MOD_RES
<222> LOCATION: (3)..(3)
```

```
<223> OTHER INFORMATION: Xaa is Leu, Ala, Ile, or Val
<220> FEATURE:
<221> NAME/KEY: MOD_RES
<222> LOCATION: (6)..(6)
<223> OTHER INFORMATION: Xaa is Gly, is any amino acid residue of the D
      configuration or is absent
<220> FEATURE:
<221> NAME/KEY: MOD_RES
<222> LOCATION: (7)..(7)
<223> OTHER INFORMATION: Xaa is Lys, Arg, or His or is absent
<220> FEATURE:
<221> NAME/KEY: MOD_RES
<222> LOCATION: (8)..(8)
<223> OTHER INFORMATION: Xaa is Arg, Lys, or His or is absent

<400> SEQUENCE: 185

Xaa Pro Xaa Pro Ala Xaa Xaa Xaa
1               5

<210> SEQ ID NO 186
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Xaa is Phe, Trp, or Tyr
<220> FEATURE:
<221> NAME/KEY: MOD_RES
<222> LOCATION: (3)..(3)
<223> OTHER INFORMATION: Xaa is Leu, Ala, Ile, or Val
<220> FEATURE:
<221> NAME/KEY: MOD_RES
<222> LOCATION: (5)..(5)
<223> OTHER INFORMATION: Xaa is Ala, Leu, Ile, or Val
<220> FEATURE:
<221> NAME/KEY: MOD_RES
<222> LOCATION: (7)..(7)
<223> OTHER INFORMATION: Xaa is Lys, Arg, or His or is absent
<220> FEATURE:
<221> NAME/KEY: MOD_RES
<222> LOCATION: (8)..(8)
<223> OTHER INFORMATION: Xaa is Arg, Lys, or His or is absent

<400> SEQUENCE: 186

Xaa Pro Xaa Pro Xaa Gly Xaa Xaa
1               5

<210> SEQ ID NO 187
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Xaa is Phe, Trp, or Tyr
<220> FEATURE:
<221> NAME/KEY: MOD_RES
<222> LOCATION: (3)..(3)
<223> OTHER INFORMATION: Xaa is Leu, Ala, Ile, or Val
<220> FEATURE:
<221> NAME/KEY: MOD_RES
<222> LOCATION: (5)..(5)
<223> OTHER INFORMATION: Xaa is Ala, Leu, Ile, or Val
<220> FEATURE:
<221> NAME/KEY: MOD_RES
<222> LOCATION: (6)..(6)
<223> OTHER INFORMATION: Xaa is Gly, is any amino acid residue of the D
      configuration or is absent
```

```
<220> FEATURE:
<221> NAME/KEY: MOD_RES
<222> LOCATION: (8)..(8)
<223> OTHER INFORMATION: Xaa is Arg, Lys, or His or is absent

<400> SEQUENCE: 187

Xaa Pro Xaa Pro Xaa Xaa Lys Xaa
1               5

<210> SEQ ID NO 188
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Xaa is Phe, Trp, or Tyr
<220> FEATURE:
<221> NAME/KEY: MOD_RES
<222> LOCATION: (3)..(3)
<223> OTHER INFORMATION: Xaa is Leu, Ala, Ile, or Val
<220> FEATURE:
<221> NAME/KEY: MOD_RES
<222> LOCATION: (5)..(5)
<223> OTHER INFORMATION: Xaa is Ala, Leu, Ile, or Val
<220> FEATURE:
<221> NAME/KEY: MOD_RES
<222> LOCATION: (6)..(6)
<223> OTHER INFORMATION: Xaa is Gly, is any amino acid residue of the D
      configuration or is absent
<220> FEATURE:
<221> NAME/KEY: MOD_RES
<222> LOCATION: (7)..(7)
<223> OTHER INFORMATION: Xaa is Lys, Arg, or His or is absent

<400> SEQUENCE: 188

Xaa Pro Xaa Pro Xaa Xaa Xaa Arg
1               5

<210> SEQ ID NO 189
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Xaa is Glu or Asp
<220> FEATURE:
<221> NAME/KEY: MOD_RES
<222> LOCATION: (4)..(4)
<223> OTHER INFORMATION: Xaa is Ala, Gly, Ile, Leu, Met, or Val
<220> FEATURE:
<221> NAME/KEY: MOD_RES
<222> LOCATION: (6)..(6)
<223> OTHER INFORMATION: Xaa is Ala, Gly, Ile, Leu, Met, or Val
<220> FEATURE:
<221> NAME/KEY: MOD_RES
<222> LOCATION: (7)..(7)
<223> OTHER INFORMATION: Xaa is Glu or Asp
<220> FEATURE:
<221> NAME/KEY: MOD_RES
<222> LOCATION: (8)..(8)
<223> OTHER INFORMATION: Xaa is Asp or Glu
<220> FEATURE:
<221> NAME/KEY: MOD_RES
<222> LOCATION: (9)..(9)
<223> OTHER INFORMATION: Xaa is Arg, His, or Lys
<220> FEATURE:
<221> NAME/KEY: MOD_RES
```

```
<222> LOCATION: (10)..(10)
<223> OTHER INFORMATION: Xaa is Ser, Asn, Gln, or Thr
<220> FEATURE:
<221> NAME/KEY: MOD_RES
<222> LOCATION: (11)..(11)
<223> OTHER INFORMATION: Xaa is Leu, Ala, Gly, Ile, Leu, Met or Val
<220> FEATURE:
<221> NAME/KEY: MOD_RES
<222> LOCATION: (12)..(12)
<223> OTHER INFORMATION: Xaa is Gly, is any amino acid residue of the D-
      configuration, or is not present
<220> FEATURE:
<221> NAME/KEY: MOD_RES
<222> LOCATION: (13)..(14)
<223> OTHER INFORMATION: Xaa are indepndtly Arg, His, or Lys or is not
      present

<400> SEQUENCE: 189

Pro Pro Xaa Xaa Pro Xaa Xaa Xaa Xaa Xaa Xaa Xaa Xaa Xaa
1               5                   10

<210> SEQ ID NO 190
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 190

Pro Pro Glu Ala Pro Ala Glu Asp Arg Ser Leu Gly Arg Arg
1               5                   10

<210> SEQ ID NO 191
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(2)
<223> OTHER INFORMATION: Xaa are, independently, Arg, Lys, or H is or
      are absent
<220> FEATURE:
<221> NAME/KEY: MOD_RES
<222> LOCATION: (3)..(3)
<223> OTHER INFORMATION: Xaa is Glu or Asp
<220> FEATURE:
<221> NAME/KEY: MOD_RES
<222> LOCATION: (4)..(4)
<223> OTHER INFORMATION: Xaa is Arg, Lys, or His
<220> FEATURE:
<221> NAME/KEY: MOD_RES
<222> LOCATION: (5)..(5)
<223> OTHER INFORMATION: Xaa is Asn, Gln, Ser, or Thr
<220> FEATURE:
<221> NAME/KEY: MOD_RES
<222> LOCATION: (6)..(6)
<223> OTHER INFORMATION: Xaa is Arg, Lys, or His
<220> FEATURE:
<221> NAME/KEY: MOD_RES
<222> LOCATION: (7)..(7)
<223> OTHER INFORMATION: Xaa is Gln, Asn, Ser, or Thr
<220> FEATURE:
<221> NAME/KEY: MOD_RES
<222> LOCATION: (8)..(11)
<223> OTHER INFORMATION: Xaa are, independently, Ala, Gly, Ile, Leu,
      Met, or Val
<220> FEATURE:
<221> NAME/KEY: MOD_RES
<222> LOCATION: (12)..(12)
<223> OTHER INFORMATION: Xaa is Asn, Gln, Ser, or Thr
<220> FEATURE:
```

```
<221> NAME/KEY: MOD_RES
<222> LOCATION: (13)..(13)
<223> OTHER INFORMATION: Xaa is Pro or Ser
<220> FEATURE:
<221> NAME/KEY: MOD_RES
<222> LOCATION: (14)..(14)
<223> OTHER INFORMATION: Xaa is Glu or Asp
<220> FEATURE:
<221> NAME/KEY: MOD_RES
<222> LOCATION: (15)..(15)
<223> OTHER INFORMATION: Xaa is Asn, Gln, Ser, or Thr
<220> FEATURE:
<221> NAME/KEY: MOD_RES
<222> LOCATION: (16)..(16)
<223> OTHER INFORMATION: Xaa is Ser, Asn, Gln, or Thr
<220> FEATURE:
<221> NAME/KEY: MOD_RES
<222> LOCATION: (17)..(17)
<223> OTHER INFORMATION: Xaa is Lys, Arg, or His
<220> FEATURE:
<221> NAME/KEY: MOD_RES
<222> LOCATION: (18)..(18)
<223> OTHER INFORMATION: Xaa is Gly, Ala, Ile, Leu, Met, or Val
<220> FEATURE:
<221> NAME/KEY: MOD_RES
<222> LOCATION: (19)..(19)
<223> OTHER INFORMATION: Xaa is Lys, Arg, or His
<220> FEATURE:
<221> NAME/KEY: MOD_RES
<222> LOCATION: (20)..(20)
<223> OTHER INFORMATION: Xaa is Gly, is any amino acid residue of the D-
      configuration, or is not present
<220> FEATURE:
<221> NAME/KEY: MOD_RES
<222> LOCATION: (21)..(22)
<223> OTHER INFORMATION: Xaa are, independently, Arg, Lys, His, or are
      not present

<400> SEQUENCE: 191

Xaa Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa
            20

<210> SEQ ID NO 192
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 192

Arg Arg Glu Arg Asn Arg Gln Ala Ala Ala Ala Asn Pro Glu Asn Ser
1               5                   10                  15

Arg Gly Lys Gly Arg Arg
            20

<210> SEQ ID NO 193
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Xaa is D, E, A or G
<220> FEATURE:
<221> NAME/KEY: MOD_RES
<222> LOCATION: (2)..(2)
<223> OTHER INFORMATION: Xaa is a sequence of 2-3 amino acid residues or
```

```
        a single amino acid residue selected from the group consisting of
        amino acid residues A, D, E, G, I, K, L, P, Q, S, T and V
<220> FEATURE:
<221> NAME/KEY: MOD_RES
<222> LOCATION: (3)..(3)
<223> OTHER INFORMATION: Xaa is amino acid residue Y or H, or a
        hydrophobic amino acid residue
<220> FEATURE:
<221> NAME/KEY: MOD_RES
<222> LOCATION: (4)..(6)
<223> OTHER INFORMATION: At least one of Xaa is a charged or
        hydrophobic amino acid residue

<400> SEQUENCE: 193

Xaa Xaa Xaa Xaa Xaa Xaa
1               5

<210> SEQ ID NO 194
<211> LENGTH: 5
<212> TYPE: PRT
<213> ORGANISM: Artificial Sequence
<220> FEATURE:
<223> OTHER INFORMATION: Description of Artificial Sequence: Synthetic
        peptide
<220> FEATURE:
<221> NAME/KEY: MOD_RES
<222> LOCATION: (5)..(5)
<223> OTHER INFORMATION: C-terminus amidation

<400> SEQUENCE: 194

Phe Pro Leu Pro Ala
1               5

<210> SEQ ID NO 195
<211> LENGTH: 11
<212> TYPE: PRT
<213> ORGANISM: Artificial Sequence
<220> FEATURE:
<223> OTHER INFORMATION: Description of Artificial Sequence: Synthetic
        peptide
<220> FEATURE:
<221> NAME/KEY: MOD_RES
<222> LOCATION: (11)..(11)
<223> OTHER INFORMATION: C-terminus amidation

<400> SEQUENCE: 195

Pro Pro Glu Ala Pro Ala Glu Asp Arg Ser Leu
1               5                   10

<210> SEQ ID NO 196
<211> LENGTH: 11
<212> TYPE: PRT
<213> ORGANISM: Artificial Sequence
<220> FEATURE:
<223> OTHER INFORMATION: Description of Artificial Sequence: Synthetic
        peptide
<220> FEATURE:
<221> NAME/KEY: MOD_RES
<222> LOCATION: (11)..(11)
<223> OTHER INFORMATION: C-terminus amidation

<400> SEQUENCE: 196

Leu Leu Glu Ala Pro Ala Glu Asp His Ser Leu
1               5                   10

<210> SEQ ID NO 197
<211> LENGTH: 10
<212> TYPE: PRT
<213> ORGANISM: Artificial Sequence
<220> FEATURE:
<223> OTHER INFORMATION: Description of Artificial Sequence: Synthetic
``` peptide

<400> SEQUENCE: 197

Ser Pro Asp Lys Gln Met Ala Val Leu Pro
1               5                   10

<210> SEQ ID NO 198
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 198

Ser Pro Asp Lys Gln Ala Ala Ala Leu Pro
1               5                   10

<210> SEQ ID NO 199
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 199

Ser Pro Asp Lys Gln Thr Pro Ile Phe Ser
1               5                   10

<210> SEQ ID NO 200
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (17)..(17)
<223> OTHER INFORMATION: C-terminus amidation

<400> SEQUENCE: 200

Glu Arg Asn Arg Gln Ala Ala Ala Ala Asn Pro Glu Asn Ser Arg Gly
1               5                   10                  15

Lys

<210> SEQ ID NO 201
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (17)..(17)
<223> OTHER INFORMATION: C-terminus amidation

<400> SEQUENCE: 201

Glu Arg Asn Arg Gln Ala Ala Ala Ala Ser Pro Glu Asn Ser Arg Gly
1               5                   10                  15

Lys

<210> SEQ ID NO 202
<211> LENGTH: 17
<212> TYPE: PRT

```
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (17)..(17)
<223> OTHER INFORMATION: C-terminus amidation

<400> SEQUENCE: 202

Glu Arg Asn Arg Gln Ser Ala Ala Thr Asn Val Glu Asn Ser Ser Lys
1               5                   10                  15

Lys

<210> SEQ ID NO 203
<211> LENGTH: 30
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 203

His Ala Glu Gly Thr Phe Thr Ser Asp Val Ser Ser Thr Leu Glu Gly
1               5                   10                  15

Gln Ala Ala Lys Glu Phe Ile Ala Trp Leu Val Lys Gly Arg
            20                  25                  30
```